United States Patent
Natoli et al.

(10) Patent No.: US 11,065,308 B2
(45) Date of Patent: *Jul. 20, 2021

(54) METHODS AND COMPOSITIONS FOR CNS DELIVERY OF HEPARAN N-SULFATASE

(71) Applicant: Shire Human Genetic Therapies, Inc., Lexington, MA (US)

(72) Inventors: Farah Natoli, Georgetown, MA (US); Gaozhong Zhu, Weston, MA (US); Jennifer Terew, Concord, MA (US); Yuan Jiang, Londonderry, NH (US); Jamie Tsung, Wellesley, MA (US); Zahra Shahrokh, Weston, MA (US); Brian Vernaglia, Winchester, MA (US); Jing Pan, Boxborough, MA (US); Richard Pfeifer, North Granby, CT (US); Pericles Calias, Melrose, MA (US)

(73) Assignee: Shire Human Genetic Therapies, Inc., Lexington, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/036,584

(22) Filed: Jul. 16, 2018

(65) Prior Publication Data

US 2019/0183984 A1   Jun. 20, 2019

Related U.S. Application Data

(60) Continuation of application No. 15/077,046, filed on Mar. 22, 2016, now abandoned, which is a division of application No. 13/168,957, filed on Jun. 25, 2011, now Pat. No. 9,320,711.

(60) Provisional application No. 61/495,268, filed on Jun. 9, 2011, provisional application No. 61/476,210, filed on Apr. 15, 2011, provisional application No. 61/442,115, filed on Feb. 11, 2011, provisional application No. 61/435,710, filed on Jan. 24, 2011, provisional application No. 61/387,862, filed on Sep. 29, 2010, provisional application No. 61/360,786, filed on Jul. 1, 2010, provisional application No. 61/358,857, filed on Jun. 25, 2010.

(51) Int. Cl.
| | |
|---|---|
| A61K 38/47 | (2006.01) |
| A61K 35/76 | (2015.01) |
| A61K 35/761 | (2015.01) |
| A61K 9/19 | (2006.01) |
| C12N 9/24 | (2006.01) |
| A61K 9/00 | (2006.01) |
| A61K 38/46 | (2006.01) |
| C07K 14/65 | (2006.01) |
| C12N 9/42 | (2006.01) |
| A61K 9/08 | (2006.01) |
| A61K 47/02 | (2006.01) |
| A61K 47/26 | (2006.01) |

(52) U.S. Cl.
CPC ............ *A61K 38/47* (2013.01); *A61K 9/0019* (2013.01); *A61K 9/0085* (2013.01); *A61K 9/08* (2013.01); *A61K 9/19* (2013.01); *A61K 35/76* (2013.01); *A61K 35/761* (2013.01); *A61K 38/46* (2013.01); *A61K 38/465* (2013.01); *A61K 47/02* (2013.01); *A61K 47/26* (2013.01); *C07K 14/65* (2013.01); *C12N 9/2402* (2013.01); *C12N 9/2437* (2013.01); *C12Y 301/06008* (2013.01); *C12Y 301/06013* (2013.01); *C12Y 302/0105* (2013.01); *C12Y 302/01045* (2013.01); *C12Y 302/01046* (2013.01); *C12Y 310/01001* (2013.01)

(58) Field of Classification Search
CPC ...... A61K 35/76; A61K 35/761; A61K 38/46; A61K 38/465; A61K 38/47; A61K 47/02; A61K 47/26; A61K 9/0019; A61K 9/0085; A61K 9/08; A61K 9/19; A61P 13/00; A61P 13/12; A61P 19/00; A61P 1/08; A61P 1/16; A61P 21/00; A61P 25/00; A61P 25/02; A61P 25/08
See application file for complete search history.

(56) References Cited

U.S. PATENT DOCUMENTS

| | | | |
|---|---|---|---|
| 4,743,265 | A | 5/1988 | Whitehouse et al. |
| 5,972,333 | A | 10/1999 | Hopwood et al. |
| 6,118,045 | A | 9/2000 | Reuser et al. |
| 6,217,552 | B1 | 4/2001 | Barbut et al. |
| 6,534,300 | B1 | 3/2003 | Canfield |

(Continued)

FOREIGN PATENT DOCUMENTS

| | | |
|---|---|---|
| JP | 2005-506340 | 3/2005 |
| JP | 2007-504166 | 3/2007 |

(Continued)

OTHER PUBLICATIONS

Kroin JS, Clin Pharmacokinet, 22(5):319-326 (1992).

(Continued)

*Primary Examiner* — Blaine Lankford
(74) *Attorney, Agent, or Firm* — Proskauer Rose LLP; Fangli Chen

(57) ABSTRACT

The present invention provides, among other things, compositions and methods for CNS delivery of lysosomal enzymes for effective treatment of lysosomal storage diseases. In some embodiments, the present invention includes a stable formulation for direct CNS intrathecal administration comprising a heparan N-sulfatase (HNS) protein, salt, and a polysorbate surfactant for the treatment of Sanfilippo Syndrome Type A.

5 Claims, 40 Drawing Sheets

Specification includes a Sequence Listing.

(56) References Cited

U.S. PATENT DOCUMENTS

| | | |
|---|---|---|
| 6,537,785 B1 | 3/2003 | Canfield |
| 7,351,410 B2 | 4/2008 | van Bree et al. |
| 7,396,811 B2 | 7/2008 | LeBowitz et al. |
| 7,442,372 B2 | 10/2008 | Kakkis |
| 7,560,424 B2 | 7/2009 | LeBowitz et al. |
| 7,629,309 B2 | 12/2009 | LeBowitz et al. |
| 8,545,837 B2 | 10/2013 | Zhu et al. |
| 9,320,711 B2 * | 4/2016 | Natoli ............... A61P 25/00 |
| 2002/0052311 A1 | 5/2002 | Solomon et al. |
| 2002/0099025 A1 | 7/2002 | Heywood |
| 2003/0072761 A1 | 4/2003 | LeBowitz |
| 2003/0082176 A1 | 5/2003 | LeBowitz et al. |
| 2004/0005309 A1 | 1/2004 | LeBowitz et al. |
| 2004/0006008 A1 | 1/2004 | LeBowitz et al. |
| 2004/0172665 A1 | 9/2004 | Reuser et al. |
| 2004/0243058 A1 | 12/2004 | Barbut et al. |
| 2004/0248262 A1 | 12/2004 | Koeberl et al. |
| 2005/0042227 A1 | 2/2005 | Zankel et al. |
| 2005/0048047 A1 | 3/2005 | Kakkis |
| 2005/0208090 A1 | 9/2005 | Keimel et al. |
| 2005/0244400 A1 | 11/2005 | LeBowitz et al. |
| 2005/0281805 A1 | 12/2005 | LeBowitz et al. |
| 2006/0029656 A1 | 2/2006 | O'Donnell et al. |
| 2006/0177433 A1 | 8/2006 | Treco et al. |
| 2008/0003211 A1 | 1/2008 | Fogh et al. |
| 2008/0299640 A1 | 12/2008 | LeBowitz et al. |
| 2009/0017005 A1 | 1/2009 | Kakkis |
| 2009/0041741 A1 | 2/2009 | Sly et al. |
| 2009/0130079 A1 | 5/2009 | Dodge et al. |
| 2009/0191178 A1 | 7/2009 | Zankel et al. |
| 2009/0246187 A1 | 10/2009 | Nilsson |
| 2009/0291062 A1 | 11/2009 | Fraunhofer et al. |
| 2009/0297592 A1 | 12/2009 | Sakuraba et al. |
| 2010/0068195 A1 | 3/2010 | Vellard et al. |
| 2010/0260706 A1 | 10/2010 | Bogin et al. |
| 2011/0105560 A1 | 5/2011 | Wustman |
| 2011/0318323 A1 | 12/2011 | Zhu et al. |
| 2011/0318324 A1 | 12/2011 | Salamat-Miller et al. |
| 2011/0318327 A1 | 12/2011 | Concino et al. |
| 2012/0003202 A1 | 1/2012 | Calias et al. |
| 2012/0009171 A1 | 1/2012 | Salamat-Miller et al. |
| 2012/0148558 A1 | 6/2012 | Kakkis |
| 2012/0213762 A1 | 8/2012 | LeBowitz et al. |
| 2013/0168961 A1 | 7/2013 | Stahlkopf et al. |
| 2013/0295071 A1 | 11/2013 | Salamat-Miller et al. |
| 2013/0295077 A1 | 11/2013 | Concino et al. |
| 2014/0271598 A1 | 9/2014 | Zhu et al. |

FOREIGN PATENT DOCUMENTS

| | | |
|---|---|---|
| RU | 2209080 C2 | 7/2003 |
| WO | WO 2002/087510 | 11/2002 |
| WO | WO 2003/032727 | 4/2003 |
| WO | WO 2003/032913 | 4/2003 |
| WO | WO 2003/102583 | 12/2003 |
| WO | WO 2004/043373 | 5/2004 |
| WO | WO 2005/002515 A2 | 1/2005 |
| WO | WO 2005/021064 A2 | 3/2005 |
| WO | WO 2005/078077 | 8/2005 |
| WO | WO 2007/141346 A2 | 12/2007 |
| WO | WO 2008/070769 A1 | 6/2008 |
| WO | WO 2009/017005 A1 | 2/2009 |
| WO | WO 2009/131698 | 10/2009 |
| WO | WO 2009/137721 | 11/2009 |
| WO | WO 2011/163647 | 12/2011 |
| WO | WO 2011/163648 | 12/2011 |
| WO | WO 2011/163649 | 12/2011 |
| WO | WO 2011/163650 | 12/2011 |
| WO | WO 2011/163651 | 12/2011 |
| WO | WO 2011/163652 | 12/2011 |
| WO | WO-2012/023623 A2 | 2/2012 |

OTHER PUBLICATIONS

Altschul et al., "Basic logic alignment search tool," J. Mol. Biol., 215(3): 403-410, 1990.
Altschul et al., "Gapped BLAST and PSI-BLAST: A new generation of protein database search programs," Nucleic Acids Res. 25: 3389-3402, 1997.
Altschul et al., "Local alignment statistics," 266:460-80, Methods in Enzymology., 1996.
Ammaya et al., "Subcutaneous Reservoir and Pump for Sterile Access to Ventricular Cerebrospinal Fluid," Lancet 2(7315): 983-984, 1963.
Anonymous, TKT to Present Research on Intrathecal Delivery of I2S for Hunter Syndrome at ASHG, PRNewswire, 1 (2004).
Anonymous, TKT's Research Findings on Intrathecal Delivery of I2S Presented at ASHG, Evaluate Ltd, 1 (2004).
Baskin, G. et al., "Genetic galactocerebrosidase deficiency (globoid cell leukodystrophy, Krabbe disease) in rhesus monkeys (*Macaca mulatta*)," Lab Anim. Sci., 48(5): 476-482, 1998.
Baum, H. et al., "The assay of arylsulphatases A and B in human urine," Clin Chim Acta. 4(3): 453-455, 1959.
Begley et al., "Lysosomal storage diseases and the blood-brain barrier," Curr Pharm Des 14(16): 1566-1580, 2008.
Belichenko et al., Penetration, diffusion, and uptake of recombinant human alpha-L-iduronidase after intraventricular injection into the rat brain, Mol. Genet. Metab., 86(1-2): 141-149, 2005.
Beniaminovitz et al., "Prevention of rejection in cardiac transplantation by blockage of the interleukin-2 receptor with a monoclonal antibody," N. Engl. J. Med. 342(9): 613-619, 2000.
Berard et al., "A review of interleukin-2 receptor antagonists in solid organ transplantation," Pharmacotherapy 19(10): 1127-1137, 1999.
Bielicki et al., "Recombinant human sulphamidase: expression, amplification, purification and characterization," Journal of Biochemistry, 329(Pt 1): 145-150, 1998.
Biswas S. et al., "Substrate reduction intervention by L-cycloserine in twitcher mice (globoid cell leukodystrophy) on a B6; CAST/Ei background," Neurosci. Lett., 347(1): 33-36, 2003.
Blasberg, R.G. et al., "Intrathecal chemotherapy: brain tissue profiles after ventriculocisternal perfusion," J Pharmacol Exp Ther. 195(1): 73-83, 1975.
Bobo et al., "Convection-enhanced delivery of macromolecules in the brain," Proc. Natl. Acad. Sci. U.S.A. 91(6), 2076-2080, 1994.
Bowman, R.H., "Inhibition of citrate metabolism by sodium fluoroacetate in the perfused rat heart and the effect on phosphofructokinase activity and glucose utilization," 93(2): 13C-15C, 1964.
Branco et al., "Selective deletion of antigen-specific, activated T cells by a humanized MAB to CD2 (MEDI-507) is mediated by NK cells," Transplantation 68(10): 1588-1596, 1999.
Burrow, T. Andrew and Leslie, Nancy D., Review of the use of idursulfase in the treatment of mucopolysaccharidosis II, Biologics: Targets and Therapy, 2(2):311-320 (2008).
Butt MT, "Morphologic changes associated with intrathecal catheters for direct delivery to the central nervous system im preclinical studies," Toxicol. Pathol., 39(1): 213-219, 2011.
Cabrera-Salazar, M.A. et al., "Intracerebroventricular delivery of glucocerebrosidase reduces substrates and increases lifespan in a mouse model of neuronopathic Gaucher disease," Exp Neurol. 225(2): 436-444, 2010.
Champion K. J. et al., Identification and characterization of a novel homozygous deletion in the x-N-acetylglucosaminidase gene in a patient with Sanfilippo type B syndrome (mucopolysaccharidosis IIIB), Molecular Genetics and Metabolism, 100: 51-56 (2010).
Chirmule et al., "Readministration of adenovirus vector in nonhuman primate lungs by blockage of CD40-CD40 ligand interactions," J. Virol. 74(7): 3345-3352, 2000.
Chiro et al., "Spinal descent of cerebrospinal fluid in man," Neurology 26(1): 1-8, 1976.
Clarke, L. A., Idursulfase for the treatment of mucopolysaccharidosis II, Expert Opin. Pharmacother., 9(2):311-317 (2008).
Cressent, A. et al., Improved Behavior and Neuropathology in the Mouse Model of Sanfilippo Type IIIb Disease after Adeno-Associated Virus-Mediated Gene Transfer in the Striatum, The Journal of Neuroscience, 24(45): 10229-10239 (2004).

(56) References Cited

OTHER PUBLICATIONS

Dekaban AS., "Changes in brain weights during the span of human life: relation of brain weights to body heights and body weights," Ann Neurol 4: 345-356, 1978.
Descartes, M. et al., Enzyme Replacement Therapy for MPS II: Developing a Pre-Medication Protocol, University of Alabama and Children's Hospital of Alambama, 1 (2007).
Desnick, R.J., "Enzyme replacement and enhancement therapies for lysosomal diseases," J. Inherit. Metab. Dis., 27(3): 385-410, 2004.
Dickson, P. et al., Intrathecal enzyme replacement therapy: Successful treatment of brain disease via the cerebrospinal fluid, Molecular Genetics & Metabolism, 91(1):61-68 (2007).
Dickson, P.I., Novel Treatments and Future Perspectives: Outcomes of Intrathecal Drug Delivery, International Journal of Clinical Pharmacology and Therapeutics, 47:1 S124-127 (2009).
Eckhoff et al., "The safety and efficacy of a two-dose daclizumab (zenapax) induction therapy in liver transplant recipients," Transplantation 69(9): 1867-1872, 2000.
Ekberg et al., "Daclizumab prevents acute rejection and improves patient survival post transplantation: 1 year pooled analysis," Transpl. Int. 13(2): 151-159, 2000.
Elaprase (idursulfase), http://www.elaprase.com/pdf/Elaprase_Overview_Sheet110811.pdf, REV 5, 2011.
Elaprase idursulface, European Medicines Agency—Science, Medicines, Health, XP-002716697, pp. 1-3 (2007).
Esposito, S. et al, Heparan N-sulfatase gene: two novel mutations and transient expression of 15 defects, Biochimica et Biophysica Acta 1501, 1-11: 1 (2000).
Extended European Search Report for EP11799035.8, 7 pages, dated Dec. 16, 2013.
Extended European Search Report for 11799039.0, 12 pages (dated Jun. 10, 2014).
Fenstermacher et al., "Drug "diffusion" within the brain," Ann NY Acad Sci 531: 29-39, 1988.
Ficko-Blean E, et al., "Structural and mechanistic insight into the basis of mucopolysaccharidosis IIIB," PNAS, 105(18): 6560-6565, 2008.
Fishwild et al., "Differential effects of administration of a human anti-CD4 monoclonal antibody, HM6G, in nonhuman primates," Clin. Immunol. 92(2): 138-152, 1999.
Fu, H. et al., Restoration of Central Nervous System a-N-Acetylglucosaminidase Activity and Therapeutic Benefits in Mucopolysaccharidosis IIIB Mice by a Single Intracisternal Recombinant Adeno-Associated Viral Type 2 Vector Delivery, The Journal of Gene Medicine, 12:624-633 (2010).
Fu, H. et al., Significantly Increased Lifespan and Improved Behavioral Performances by rAAV Gene Delivery in Adult Mucopolysaccharidosis IIIB Mice, Gene Therapy 14:1065-1077 (2007).
Garbuzova-Davis, S. et al., Transplantation of Human Umbilical Cord Blood Cells Benefits an Animal Model of Sanfilippo Syndrome Type B, Stem Cells and Development, 14:384-394 (2005).
Garcia, A.R. et al., Intrathecal Delivery of Iduronate 2-Sulfatase to the CNS of Cynomolgous Monkeys, Shire Human Genetic Therapies, 1 (2007).
Gaziev et al., "Chronic graft-versus-host disease: is there an alternative to the conventional treatment?," Bone Marrow Transplant, 25(7): 689-696, 2000.
GenBank accession No. NM000263, *Homo sapiens* N-Acetylglucosaminidase, Alpha (NAGLU) mRNA, 1-4 (accessed May 3, 2014).
GeneCards, Galactosylceramidase, http://www.genecards.org/cgi-bin-carddisp.pl?gene=GALC&search=Galactocerebrosidase, 2012.
Ghersi-Egea, J.F. et al., "Rapid distribution of intraventricularly administered sucrose into cerebrospinal fluid cisterns via subarachnoid velae in rat," Neuroscience 75(4): 1271-1288, 1996.
Greene, H.L. et al. "Metachromatic leukodystrophy. Treatment with arylsulfatase-A" Feb. 1969, Arch Neurol vol. 20, pp. 147-153.
Graham et al., "Characteristics of a human cell line transformed by DNA from human adenovirus type 5," J. Gen Virol., 36(1): 59-74, 1977.

Grubb JH et al., "New strategies for enzyme replacement therapy for lysosomal storage diseases," Rejuvenation Research 13(2-3): 229-236, 2010.
Gummert et al., "Newer immunosuppressive drugs: a review," J. Am. Soc. Nephrol, 10(6): 1366-1380, 1999.
Hashimoto R, "N-terminal deletion mutants of insulin-like growth factor-II (IGF-II) show Thr7 and Leu8 important for binding to insulin and IGF-I receptors and Leu8 critical for all IGF-II functions," J Biol Chem., 270(30); 18013-18018, 1995.
Hemsley, Kim M. et al., "Injection of recombinant human sulfamidase into the CSF via the cerebellomedullary cistern in MPS IIIA mice," Mol Genet Metab. 90(3): 313-328, 2007.
Henry ML, "Cyclosporine and tacrolimus (FK506): a comparison of efficacy and safety profiles," Clin. Transplant, 13(3): 209-220, 1999.
Hong et al., "Immunosuppressive agents in organ transplantation: past, present, and future," Semin. Nephrol. 20(2): 108-125, 2000.
Hood RD, Development and Reproductive Toxicology: A practical approach, 276, 2006.
Hoogerbrugge, P.M., et al., "Effect of bone marrow transplantation on enzyme levels and clinical course in the neurologically affected," J. Clin. Invest., 81(6): 1790-1794, 1988.
Hovland DN, et al., "Six-month continuous intraputamenal infusion toxicity study of recombinant methionyl human glial cell line-derived neurotrophic factor (r-metHuGDNF in rhesus monkeys," Toxicol. Pathol., 35(7): 1013-1029, 2007.
Ideguchi et al., "Local adenovirus-mediated CFLA40immunoglobulin expression suppresses the immune responses to adenovirus vectors in the brain," Neuroscience 95(1): 217-226, 2000.
International Preliminary Report on Patentability for PCT/US11/41928, 36 pages (dated Mar. 29, 2013).
International Search Report for PCT/US11/41922, dated Feb. 14, 2012.
International Search Report for PCT/US2011/41928,4 pages (dated Sep. 26, 2012).
International Search Report for PCT/US11/41924, dated Nov. 7, 2011.
International Search Report for PCT/US11/41925, dated Feb. 14, 2012.
International Search Report for PCT/US11/41927, dated Mar. 9, 2012.
International Search Report for PCT/US11/41926, 5 pages (dated May 13, 2013).
Ito et al., "Induction of CTL responses by simultaneous administration of liposomal peptide vaccine with anti-CD40 and anti-CTLA-4 mAb," J. Immunol. 164(3): 1230-1235, 2000.
Johanson CE, et al., "Multiplicity of cerebrospinal fluid functions: New challenges in health and disease," Cerebrospinal Fluid Res., 14(5): 10, 2008.
Johnson, K., "Globoid leukodystrophy in the cat," J. Am. Vet. Med. Assoc., 157(12): 2057-2064, 1970.
Joshi S. et al., "Targeting the brain: rationalizing the novel methods of drug delivery to the central nervous system," Neurocrit Care 6(3): 200-212, 2007.
Kakkis, E. et al., Intrathecal enzyme replacement therapy reduces lysosomal storage in the brain and meninges of the canine model of MPS I, Molecular Genetics and Metabolism 83:163-174 (2004).
Kang, H. et al., Significantly increased lifespan and improved behavioral performances by rAAV gene delivery in adult mucopolysaccharidosis IIIB mice, Gene Therapy, 14:1066-1077 (2007).
Kerwin, Bruce A., Polysorbates 20 and 80 Used in the Formulation of Protein Biotherapeutics: Structure and Degradation Pathways, Journal of Pharmaceutical Sciences, 97: 2924-2935 (2008).
Kobayashi T. et al., "The Twitcher mouse: an enzymatically authentic model of human globoid cell leukodystrophy (Krabbe disease)," Brain Res., 202(2): 479-483, 1980.
Krewson, CE et al., "Distribution of nerve growth factor following direct delivery to brain interstitium," Brain Res. 680(1-2): 196-206, 1995.
Kurlberg et al., "Blockage of the B7-CD28 pathway by CTLA4-Ig counteracts rejection and prolongs survival in small bowel transplantation," Scand. J. Immunol, 51(3): 224-230, 2000.

(56) References Cited

OTHER PUBLICATIONS

Lamsa, J.C et al., Delivery of I2S to the Canine CNS: Comparison of Intracisternal, Intralumbar and Intraventricular Dose Routes as Potential Treatents for Severe MPS II, Shire HGT, 1 (2006).
Lamsa, J.C. et al., Intrathecal Delivery of Iduronate 2-Sulfatase for MPS II to the Canine CNS, ASHG Annual Meeting, 1 (2004).
Lazorthes et al., Advances in Drug Delivery Systems and Application in Neurosurgery, 18: 143-192, 1991.
Lee, et al., "Single-dose intracerebroventricular administration of galactocerebrosidase improves survival in a mouse model of globoid cell leukodystrophy," FASEB Journal, 21(10): 2520-2527, 2007.
LeVine S. et al., "L-cycloserine slows the clinical and pathological course in mice with globoid cell leukodystrophy (twitcher mice)," J. Neurosci. Res., 60(2): 231-236, 2000.
Li HH, et al., "Mouse model of Sanfilippo syndrome type B produced by targeted disruption of the gene encoding alpha-N-acetylglucosaminidase," PNAS 96(25): 14505-14510, 1999.
Li, et al., "Attenuated plasticity in neurons and astrocytes in the mouse model of Sanfilippo syndrome type B," J Neurosci Res, 69(1): 30-8, 2002.
Lin, D., et al., "Central nervous system-directed AAV2/5-mediated gene therapy synergizes with bone marrow transplantation in the murine model of globoid-cell leukodystrophy," Mol. Ther., 15(1): 44-52, 2007.
Lu, Y. et al., Direct Brain Delivery of Iduronate 2-Sulfastase Reduces Glycosaminoglycan Accumulation and Improves Histopathology in the CNS and Peripheral Tissue of Hunter Mice, Shire HGT, 1 (2007).
Luca, Tonia, "Axons mediate the distribution of arylsulfatase A within the mouse hippocampus upon gene delivery," Mol Ther. 12(4): 669-679, 2005.
Marinova-Mutafchieva et al., "A comparative study into the mechanisms of action of anti-tumor necrosis factor alpha, anti-CD4, and combined anti-tumor necrosis factor alpha/anti-CD4 treatment in early collagen-induced arthritis," Arthritis Rheum 43: 638-644, 2000.
Mather et al., "Culture of testicular cells in hormone-supplemented serum-free medium," Ann N.Y. Acad. Sci., 383: 44-68, 1982.
Mather, "Establishment and characterization of two distinct mouse testicular epithelial cell lines," Biol. Reprod., 23: 243-251, 1980.
Matheus, MG et al., "Brain MRI findings in patients with mucopolysaccharidosis types I and Ii and mild clinical presentation," Neuroradiology 46(8): 666-672, 2004.
Matzner, U. et al., Enzyme replacement improves nervous system pathology and function in a mouse model for metachromatic leukodystrophy, Human Molecular Genetics, 14(9):1139-1152 (2005).
Meikle et al., "Diagnosis of lysosomal storage disorders: evaluation of lysosome-associated membrane protein LAMP-1 as a diagnostic marker," Clin Chem., 43(8 Pt 1): 1325-1335, 1997.
Middaugh et al., "Determination of the apparent thermodynamic activities of saturated protein solutions," J. Biol. Chem. 254(2): 367-370, 1979.
Moder, KG., "New medications for use in patients with rheumatoid arthritis," Ann. Allergy Asthma Immunol. 84(3): 280-284, 2000.
Nagaraja, TN et al., "In normal rat, intraventricularly administered insulin-like growth factor-1 is rapidly cleared from CSF with limited distribution into brain," Cerebrospinal Fluid Res. 2: 1-15, 2005.
Nail S.L. et al., "Fundamentals of freeze-drying, in Development and manufacture of protein pharmaceuticals," Nail S.L. editor New York: Kluwer Academic/Plenum Publishers, 281-353, 2002.
Neufeld EF, Muenzer J., "The mucopolysaccharidoses," In: Scriver CR, Beaudet Al, Sly WS, et al, eds. The Metabolic and Molecular Bases of Inherited Disease. www.ommbid.com 8th ed. New York, NY: McGraw-Hill; 2001:3421-3452.
Neufeld, E.F., Enzyme Replacement therapy. Lysosomal disorders of the Brain, ed. F.M.A.W. Platt, S.V. 2004: Oxford University Press: 327-338, 2004.
Nevins, TE., "Overview of new immunosuppressive therapies," Curr. Opin. Pediatr. 12(2): 146-150, 2000.

Nguyen et al., "Convective distribution of macromolecules in the primate brain demonstrated using computerized tomography and magnetic resonance imaging," J. Neurosurg. 98(3), 584-590, 2003.
Ohmi, et al., "Activated microglia in cortex of mouse models of mucopolysaccharidoses I and IIIB," Proc Natl Acad Sci, 100(4): 1902-7, 2002.
Ommaya et al., "Implantable devices for chronic access and drug delivery to the central nervous system," Cancer Drug Delivery, 1(2): 169-179, 1984.
Okuyama, T. et al., Japan Elaprase® Treatment (JET) study: Idursulfase enzyme replacement therapy in adult patients with attenuated Hunter syndrome (Mucopolysaccharidosis II, MPS II), Molecular Genetics and Metabolism, 99:18-25 (2010).
Pardridge WM., "Drug transport in brain via the cerebrospinal fluid," Fluids Barriers CNS, 8(1): 7, 2011.
Passini, MA et al., "Distribution of a lysosomal enzyme in the adult brain by axonal transport and by cells of the rostral migratory stream," J Neurosci 22(15): 6437-6446, 2002.
Penn, RD et al., "Intrathecal ciliary neurotrophic factor delivery for treatment of amyotrophic lateral sclerosis (phase I trial)," Neurosurgery 40(1): 94-99, 1997.
Phosphate Buffer Calculation, http://www.egr.msu.edu/biofuelcell/tools/phosphate/phosphate.html, Dec. 31, 2000, accessed Aug. 28, 2012.
Ponce RP, et al., "Immunogenicity of biologically-derived therapeutics: assessment and interpretation of nonclinical safety studies," Regul. Toxicol. Pharmacol., 54(2): 164-182, 2009.
Ponticelli et al., "Promising new agents in the prevention of transplant rejection," Drugs R.D. 1(1), 55-60, 1999.
Potter et al., "Review—the use of immunosuppressive agents to prevent neutralizing antibodies against a transgene product," Ann. N.Y. Acad. Sci. 875: 159-174, 1999.
Pritchard, D. et al., "Globoid cell leucodystrophy in polled Dorset sheet," Vet. Pathol., 17(4): 399-405, 1980.
Przepiorka et al., "A phase II study of BTI-322, a monoclonal anti-CD2 antibody, for treatment of steroid-resistant acute graft-versus-host disease," Blood 92(11): 4066-4071, 1998.
Qi et al., "Effect of tacrolimus (FK506) and sirolimus (rapamycin) mono- and combination therapy in prolongation of renal allograft survival in the monkey," Transplantation 69(7), 1275-1283, 2000.
Rieselbach RE et al., "Subarachnoid distribution of drugs after lumbar injection," N Engl J Med. 267(25): 1273-1278, 1962.
Savas, et al., "Intracerebral injection of sulfamidase delays neuropathology in murine MPS-IIIA," Mol Genet Metab., 82(4): 273-285, 2004.
Schlessingerman, A., Mass of an Adult, obtained from hypertextbook.com/facts/2003/AlexSchlessingerman.shtml, 2003, 2 pages.
Scientific Discussion—Elaprase, XP00271916, pp. 1-43 (2007).
Shahrokh et al., "Intrathecal delivery of protein therapeutics to treat genetic diseases involving the CNS, in: Injectable Drug Delivery 2010: Formulations Focus," ONdrugDelivery, pp. 16-20, 2010.
Shire Human Genetic Therapies, Intrathecal Delivery of Protein Therapeutics to Treat Genetic Diseases Involving the CNS, www.ondrugdelivery.com, pp. 16-20, (Publically available on Jun. 30, 2010).
Simard JM et al., "Brain oedema in focal ischaemia: molecular pathophysiology and theoretical implications," Lancet Neurol. 6(3): 258-268, 2007.
Sinow, C.S., Construction of an IGF-NAGLU Fusion Protein for Treatment of Sanfilippo B Syndrome, California State Sciene Fair, 1 (2008).
Sjoberg, M. et al., Long-term Intrathecal Morphine and Bupivacaine in Patients with Refractory Cancer Pain, Anesthesiology, 80:284-297 (1994).
Slavik et al., "CD28/CTLA-4 and CD80/CD86 families: signaling and function," Immunol Res. 19(1): 1-24, 1999.
Stamatovic SM, et al., "Brain endothelial cell-cell junctions: how to "open" the blood brain barrier," Curr. Neuropharmacol., 6(3): 179-192, 2008.
Stroobants S. et al., "Intracerebroventricular enzyme infusion corrects central nervous system pathology and dysfunction in a mouse model of metachromatic leukodystrophy," Hum Mol Genet. 20(14): 2760-2769, 2011.

(56) References Cited

OTHER PUBLICATIONS

Sturk, et al., "Combined Intracerebroventricular Intraperitoneal Enzyme Replacement Therapy Improves Survival and Reduces Brain Psychosine in a Mouse Model of Krabbe Disease," European Task Force on Brain and Neurogenerative Lysosomal Storage Diseases, http://www.brains4brain.eu/assets/files/abstract-francoforte-2009.pdf_pg._42, 2009.

Tang, X. et al., "Design of freeze-drying processes for pharmaceuticals: Practical advice," Pharm. Res., 21(2): 191-200, 2004.

Tippin, B. et al., Insulin-like Growth Factor-2 Peptide Fusion Enables Uptake and Lysosomal Delivery of N-Acetylglucosamindidase to Mucopolysaccharidosis IIIB Fibrboblasts, MPS Scientific Program: Plenary Papers, entire document: p. 100 (Jun. 26, 2010).

Toyoshima, E. et al., "Nerve conduction studies in the Twitcher mouse (murine globoid cell leukodystrophy)," J. Neurol. Sci., 74(2-3): 307-318, 1986.

Urlaub and Chasin, "Isolation of Chinese hamster cell mutants deficient in dihydrofolate reductase activity," Proc. Natl. Acad. Sci. USA, 77(7): 4216-4220, 1980.

Vedolin, L. et al., "Correlation of MR imaging and MR spectroscopy findings with cognitive impairment in mucopolysaccharidosis II," AJNR Am J Neuroradial 28(6): 1029-1033, 2007.

Vertemati, T. et al., Multidisciplinary Evaluation in 12 Mucopolysaccharidose Type II or Hunter Syndrome Patients Prior Enzyme Replacement Therapy, CREIM, UNIFESP, 1 (2007).

Vite, Charles H. et al., "Biodistribution and pharmacodynamics of recombinant human alpha-L-iduronidase (rhIDU) in mucopolysaccharidosis type I-affected cats following multiple intrathecal administrations," Mol Genet Metab 103(3): 268-274, 2011.

Vogler, C. et al., "Overcoming the blood-brain barrier with high-dose enzyme replacement therapy in murine mucopolysaccharidosis VII," Proc Natl Acad Sci USA 102(41): 14777-14782, 2005.

Waheed, A et al., "Purification of mammalian arylsulfatase A enzymes by subunit affinity chromatography," Int J Pept Protein Res., 26(4): 362-372, 1985.

Walkley, "Cell Pathology of lysosomal storage disorders," Brain Pathol., 8, 175-93, 1998.

Wang, W. and Roberts, C., Aggregation of Therapeutic Proteins, published by John Wiley & Sons, Inc., Hoboken, New Jersey (2010).

Wang et al., "Lyophilization and development of solid protein pharmaceuticals," Int. J. Pharm., 203(1-2): 1-60, 2000.

Wang et al., "Treatment reduces or stabilizes brain imaging abnormalities in patients with MPS I and II," Molecular Genetics and Metabolism, 98(4): 406-11, 2009.

Watson et al., "Intrathecal administration of AAV vectors for the treatment of lysosomal storage in the brains of MPS I mice," Gene Ther., 13(11): 917-925, 2006.

Weber, B. et al., Novel Mutations in Sanfilippo A syndrome: Implications for Enzyme function, Hum. Mol. Genet., 6(9): 1573-1579 (1997).

Wenger, D.A. et al., Galactosylceramide Lipidosis: Globoid Cell Leukodystrophy (Krabbe Disease), in the Metabolic and Molecular Bases of Inherited Disease, C.R. Scriver, Beaudet, A., Sly, W.S. and Valle, D. Editor 2001 McGraw-Hill, 3669-3687, 2001.

Wenger, D.A., "Murine, canine and non-human primate models of Krabbe disease," Mol. Med. Today, 6(11): 449-451, 2000.

Williams N.A. et al., "The lyophilization of pharmaceuticals; A literature review." J. Parenter Sci. Technol., 38(2): 48-59, 1984.

Wiseman et al., "Daclizumab: a review of its use in the prevention of acute rejection in renal transplant recipients," Drugs 58(6): 1029-1042, 1999.

Won, C., Stabilizers against heat-induced aggregation of RPR 114849, an acidic fibroblast growth factor (aFGF), International Journal of Pharmaceutics, 167:25-36 (1998).

Wraith, J.E. et al., Mucopolysaccharidosis type II (Hunter syndrome): a clinical review and recommendations for treatment in the era of enzyme replacement therapy, Eur. J. Pediatr., 167: 247-277 (2008).

Written Opinion for PCT/US11/41922, dated Feb. 14, 2012.
Written Opinion for PCT/US2011/041928,13 pages dated Sep. 26, 2012.
Written Opinion for PCT/US11/41924, dated Nov. 7, 2011.
Written Opinion for PCT/US11/41925, dated Feb. 14, 2012.
Written Opinion for PCT/US11/41927, dated Mar. 9, 2012.
Written Opinion for PCT/US11/41926, 8 pages (dated May 13, 2013).

Yan Q et al., "Distribution of intracerebral ventricularly administered neurotrophins in rat brain and its correlation with trk receptor expression," Exp Neurol. 127(1): 23-36, 1994.

Yeager A. et al., "Prolonged survival and remyelination after hematopoietic cell transplantation in the twitcher mouse," Science, 225(4666): 1052-1054, 1984.

Felice, B.R. et al., Safety Evaluation of Chronic Intrathecal Administration of Idursulfase-IT in Cynomolgus Monkeys, Toxicology Pathology, 39:879-893 (2011).

* cited by examiner

1%

1.5%

VirTis

LyoStar meltback

| | |
|---|---|
| Figure | 2A |
| Animal | 080 |
| Group | 3F |
| Slide | 6 |
| Mag. | 40X  Stain  HE |
| Tissue | Brain |
| Note | The Arrow Indicates an Eosinophil in the Perivascular Space of a Low Dose Female |

| | |
|---|---|
| Figure | 2C |
| Animal | 023 |
| Group | 3M |
| Slide | 2 |
| Mag. | 40X  Stain  HE |
| Tissue | Brain |
| Note | Eosinophils in the Perivascular Space and the Adjacent Parenchyma of the Brain in a Low Dose Male |

Comparison of non-compartmental PK parameters in the brain

| | Parameter | Unit | IT Mean | IT SD | IV Mean | IV SD | Ratio IT/IV |
|---|---|---|---|---|---|---|---|
| 1 mg/kg | $\lambda z$ | 1/hr | 0.016 | 0.003 | 0.011 | 0.005 | |
| | $t_{1/2}$ | hr | 45 | 7 | 71 | 23 | |
| | $C_{max}$ | ug/g | 257 | 90 | 0.1 | 0.0 | 3212 |
| | $AUC_{0-192hr}$ | hr*ug/g | 8393 | 2457 | 7 | 2 | 1136 |
| 10 mg/kg | $\lambda z$ | 1/hr | 0.014 | 0.001 | 0.102 | 0.180 | |
| | $t_{1/2}$ | hr | 49 | 4 | 60 | 53 | |
| | $C_{max}$ | ug/g | 2628 | 265 | 1.8 | 0.2 | 1501 |
| | $AUC_{0-192hr}$ | hr*ug/g | 83962 | 10083 | 86 | 66 | 978 |

Comparison of non-compartmental PK parameters in the liver

| | Parameter | Unit | IT Mean | IT SD | IV Mean | IV SD | Ratio IT/IV |
|---|---|---|---|---|---|---|---|
| 1 mg/kg | λz | 1/hr | 0.030 | 0.011 | 0.015 | 0.003 | |
| | $t_{1/2}$ | hr | 28 | 16 | 47 | 10 | |
| | $C_{max}$ | ug/g | 4.9 | 1.3 | 9.6 | 0.5 | 0.5 |
| | $AUC_{0-192hr}$ | hr*ug/g | 204 | 50 | 525 | 104 | 0.4 |
| 10 mg/kg | λz | 1/hr | 0.017 | 0.000 | 0.021 | 0.012 | |
| | $t_{1/2}$ | hr | 42 | 1 | 38 | 13 | |
| | $C_{max}$ | ug/g | 105 | 41 | 131.6 | 27 | 0.8 |
| | $AUC_{0-192hr}$ | hr*ug/g | 7987 | 3276 | 6747 | 2837 | 1.2 |

Port-A-Cath Low Profile Intrathecal Implantable Access System

SEQUENCE LISTING

<160> NUMBER OF SEQ ID NOS: 2

<210> SEQ ID NO 1
<211> LENGTH: 482
<212> TYPE: PRT
<213> ORGANISM: Homo sapiens

<400> SEQUENCE: 1

Arg Pro Arg Asn Ala Leu Leu Leu Ala Asp Asp Gly Gly Phe Glu
1               5                   10                  15

Ser Gly Ala Tyr Asn Asn Ser Ala Ile Ala Thr Pro His Leu Asp Ala
            20                  25                  30

Leu Ala Arg Arg Ser Leu Leu Phe Arg Asn Ala Phe Thr Ser Val Ser
        35                  40                  45

Ser Cys Ser Pro Ser Arg Ala Ser Leu Leu Thr Gly Leu Pro Gln His
    50                  55                  60

Gln Asn Gly Met Tyr Gly Leu His Gln Asp Val His His Phe Asn Ser
65                  70                  75                  80

Phe Asp Lys Val Arg Ser Leu Pro Leu Leu Ser Gln Ala Gly Val
                85                  90                  95

Arg Thr Gly Ile Ile Gly Lys Lys His Val Gly Pro Glu Thr Val Tyr
                100                 105                 110

Pro Phe Asp Phe Ala Tyr Thr Glu Glu Asn Gly Ser Val Leu Gln Val
                115                 120                 125

Gly Arg Asn Ile Thr Arg Ile Lys Leu Leu Val Arg Lys Phe Leu Gln
130                 135                 140

Thr Gln Asp Asp Arg Pro Phe Phe Leu Tyr Val Ala Phe His Asp Pro
145                 150                 155                 160

His Arg Cys Gly His Ser Gln Pro Gln Tyr Gly Thr Phe Cys Glu Lys
                165                 170                 175

Phe Gly Asn Gly Glu Ser Gly Met Gly Arg Ile Pro Asp Trp Thr Pro
                180                 185                 190

Gln Ala Tyr Asp Pro Leu Asp Val Leu Val Pro Tyr Phe Val Pro Asn
                195                 200                 205

Thr Pro Ala Ala Arg Ala Asp Leu Ala Ala Gln Tyr Thr Thr Val Gly
                210                 215                 220

Arg Met Asp Gln Gly Val Gly Leu Val Leu Gln Glu Leu Arg Asp Ala
225                 230                 235                 240

Gly Val Leu Asn Asp Thr Leu Val Ile Phe Thr Ser Asp Asn Gly Ile
                245                 250                 255

Pro Phe Pro Ser Gly Arg Thr Asn Leu Tyr Trp Pro Gly Thr Ala Glu
                260                 265                 270

Pro Leu Leu Val Ser Ser Pro Glu His Pro Lys Arg Trp Gly Gln Val
                275                 280                 285

Ser Glu Ala Tyr Val Ser Leu Leu Asp Leu Thr Pro Thr Ile Leu Asp
            290                 295                 300

Trp Phe Ser Ile Pro Tyr Pro Ser Tyr Ala Ile Phe Gly Ser Lys Thr
305                 310                 315                 320

Ile His Leu Thr Gly Arg Ser Leu Leu Pro Ala Leu Glu Ala Glu Pro
                325                 330                 335

Leu Trp Ala Thr Val Phe Gly Ser Gln Ser His His Glu Val Thr Met
                340                 345                 350

Ser Tyr Pro Met Arg Ser Val Gln His Arg His Phe Arg Leu Val His
                355                 360                 365

```
Asn Leu Asn Phe Lys Met Pro Phe Pro Ile Asp Gln Asp Phe Tyr Val
    370                 375                 380

Ser Pro Thr Phe Gln Asp Leu Leu Asn Arg Thr Thr Ala Gly Gln Pro
385                 390                 395                 400

Thr Gly Trp Tyr Lys Asp Leu Arg His Tyr Tyr Arg Ala Arg Trp
                405                 410                 415

Glu Leu Tyr Asp Arg Ser Arg Asp Pro His Glu Thr Gln Asn Leu Ala
                420                 425                 430

Thr Asp Pro Arg Phe Ala Gln Leu Leu Glu Met Leu Arg Asp Gln Leu
            435                 440                 445

Ala Lys Trp Gln Trp Glu Thr His Asp Pro Trp Val Cys Ala Pro Asp
450                 455                 460

Gly Val Leu Glu Glu Lys Leu Ser Pro Gln Cys Gln Pro Leu His Asn
465                 470                 475                 480

Glu Leu

<210> SEQ ID NO 2
<211> LENGTH: 502
<212> TYPE: PRT
<213> ORGANISM: Homo sapiens

<400> SEQUENCE: 2

Met Ser Cys Pro Val Pro Ala Cys Cys Ala Leu Leu Leu Val Leu Gly
1               5                   10                  15

Leu Cys Arg Ala Arg Pro Arg Asn Ala Leu Leu Leu Leu Ala Asp Asp
                20                  25                  30

Gly Gly Phe Glu Ser Gly Ala Tyr Asn Asn Ser Ala Ile Ala Thr Pro
            35                  40                  45

His Leu Asp Ala Leu Ala Arg Arg Ser Leu Leu Phe Arg Asn Ala Phe
    50                  55                  60

Thr Ser Val Ser Ser Cys Ser Pro Ser Arg Ala Ser Leu Leu Thr Gly
65                  70                  75                  80

Leu Pro Gln His Gln Asn Gly Met Tyr Gly Leu His Gln Asp Val His
                85                  90                  95

His Phe Asn Ser Phe Asp Lys Val Arg Ser Leu Pro Leu Leu Leu Ser
                100                 105                 110

Gln Ala Gly Val Arg Thr Gly Ile Ile Gly Lys Lys His Val Gly Pro
            115                 120                 125

Glu Thr Val Tyr Pro Phe Asp Phe Ala Tyr Thr Glu Glu Asn Gly Ser
    130                 135                 140

Val Leu Gln Val Gly Arg Asn Ile Thr Arg Ile Lys Leu Leu Val Arg
145                 150                 155                 160

Lys Phe Leu Gln Thr Gln Asp Asp Arg Pro Phe Phe Leu Tyr Val Ala
                165                 170                 175

Phe His Asp Pro His Arg Cys Gly His Ser Gln Pro Gln Tyr Gly Thr
            180                 185                 190

Phe Cys Glu Lys Phe Gly Asn Gly Glu Ser Gly Met Gly Arg Ile Pro
    195                 200                 205

Asp Trp Thr Pro Gln Ala Tyr Asp Pro Leu Asp Val Leu Val Pro Tyr
210                 215                 220

Phe Val Pro Asn Thr Pro Ala Ala Arg Ala Asp Leu Ala Ala Gln Tyr
225                 230                 235                 240

Thr Thr Val Gly Arg Met Asp Gln Gly Val Gly Leu Val Leu Gln Glu
                245                 250                 255
```

-continued

```
Leu Arg Asp Ala Gly Val Leu Asn Asp Thr Leu Val Ile Phe Thr Ser
            260                 265                 270
Asp Asn Gly Ile Pro Phe Pro Ser Gly Arg Thr Asn Leu Tyr Trp Pro
            275                 280                 285
Gly Thr Ala Glu Pro Leu Leu Val Ser Ser Pro Glu His Pro Lys Arg
            290                 295                 300
Trp Gly Gln Val Ser Glu Ala Tyr Val Ser Leu Leu Asp Leu Thr Pro
305                 310                 315                 320
Thr Ile Leu Asp Trp Phe Ser Ile Pro Tyr Pro Ser Tyr Ala Ile Phe
                325                 330                 335
Gly Ser Lys Thr Ile His Leu Thr Gly Arg Ser Leu Leu Pro Ala Leu
            340                 345                 350
Glu Ala Glu Pro Leu Trp Ala Thr Val Phe Gly Ser Gln Ser His His
            355                 360                 365
Glu Val Thr Met Ser Tyr Pro Met Arg Ser Val Gln His Arg His Phe
            370                 375                 380
Arg Leu Val His Asn Leu Asn Phe Lys Met Pro Phe Pro Ile Asp Gln
385                 390                 395                 400
Asp Phe Tyr Val Ser Pro Thr Phe Gln Asp Leu Leu Asn Arg Thr Thr
                405                 410                 415
Ala Gly Gln Pro Thr Gly Trp Tyr Lys Asp Leu Arg His Tyr Tyr Tyr
                420                 425                 430
Arg Ala Arg Trp Glu Leu Tyr Asp Arg Ser Arg Asp Pro His Glu Thr
            435                 440                 445
Gln Asn Leu Ala Thr Asp Pro Arg Phe Ala Gln Leu Leu Glu Met Leu
450                 455                 460
Arg Asp Gln Leu Ala Lys Trp Gln Trp Glu Thr His Asp Pro Trp Val
465                 470                 475                 480
Cys Ala Pro Asp Gly Val Leu Glu Glu Lys Leu Ser Pro Gln Cys Gln
                485                 490                 495
Pro Leu His Asn Glu Leu
            500
```

METHODS AND COMPOSITIONS FOR CNS DELIVERY OF HEPARAN N-SULFATASE

CROSS REFERENCE TO RELATED APPLICATIONS

This application is a continuation application of U.S. application Ser. No. 15/077,046, filed Mar. 22, 2016, which is a divisional application of issued U.S. Pat. No. 9,320,711, filed Jun. 25, 2011 which claims priority to U.S. Provisional Patent Application Ser. Nos. 61/358,857 filed Jun. 25, 2010; 61/360,786, filed Jul. 1, 2010; 61/387,862, filed Sep. 29, 2010; 61/435,710, filed Jan. 24, 2011; 61/442,115, filed Feb. 11, 2011; 61/476,210, filed Apr. 15, 2011; and 61/495,268 filed on Jun. 9, 2011; the entirety of each of which is hereby incorporated by reference. This application relates to US applications entitled "CNS Delivery of Therapeutic Agents;" filed on even date; "Methods and Compositions for CNS Delivery of Iduronate-2-Sulfatase," filed on even date; "Methods and Compositions for CNS Delivery of β-Galactocerebrosidase," filed on even date; "Methods and Compositions for CNS Delivery of Arylsulfatase A," filed on even date; "Treatment of Sanfilippo Syndrome Type B," filed on even date; the entirety of each of which is hereby incorporated by reference.

SEQUENCE LISTING

The present specification makes reference to a Sequence Listing (submitted electronically as a .txt file named 200688-1336_SL.txt on Jul. 16, 2018). The .txt file was generated on Jul. 16, 2018 and is 9,135 bytes in size. The entire contents of the Sequence Listing are herein incorporated by reference.

BACKGROUND

Enzyme replacement therapy (ERT) involves the systemic administration of natural or recombinantly-derived proteins and/or enzymes to a subject. Approved therapies are typically administered to subjects intravenously and are generally effective in treating the somatic symptoms of the underlying enzyme deficiency. As a result of the limited distribution of the intravenously administered protein and/or enzyme into the cells and tissues of the central nervous system (CNS), the treatment of diseases having a CNS etiology has been especially challenging because the intravenously administered proteins and/or enzymes do not adequately cross the blood-brain barrier (BBB).

The blood-brain barrier (BBB) is a structural system comprised of endothelial cells that functions to protect the central nervous system (CNS) from deleterious substances in the blood stream, such as bacteria, macromolecules (e.g., proteins) and other hydrophilic molecules, by limiting the diffusion of such substances across the BBB and into the underlying cerebrospinal fluid (CSF) and CNS.

There are several ways of circumventing the BBB to enhance brain delivery of a therapeutic agent including direct intra-cranial injection, transient permeabilization of the BBB, and modification of the active agent to alter tissue distribution. Direct injection of a therapeutic agent into brain tissue bypasses the vasculature completely, but suffers primarily from the risk of complications (infection, tissue damage, immune responsive) incurred by intra-cranial injections and poor diffusion of the active agent from the site of administration. To date, direct administration of proteins into the brain substance has not achieved significant therapeutic effect due to diffusion barriers and the limited volume of therapeutic that can be administered. Convection-assisted diffusion has been studied via catheters placed in the brain parenchyma using slow, long-term infusions (Bobo, et al., Proc. Natl. Acad. Sci. U.S.A 91, 2076-2080 (1994); Nguyen, et al. J. Neurosurg. 98, 584-590 (2003)), but no approved therapies currently use this approach for long-term therapy. In addition, the placement of intracerebral catheters is very invasive and less desirable as a clinical alternative.

Intrathecal (IT) injection, or the administration of proteins to the cerebrospinal fluid (CSF), has also been attempted but has not yet yielded therapeutic success. A major challenge in this treatment has been the tendency of the active agent to bind the ependymal lining of the ventricle very tightly which prevented subsequent diffusion. Currently, there are no approved products for the treatment of brain genetic disease by administration directly to the CSF.

In fact, many believed that the barrier to diffusion at the brain's surface, as well as the lack of effective and convenient delivery methods, were too great an obstacle to achieve adequate therapeutic effect in the brain for any disease.

Many lysosomal storage disorders affect the nervous system and thus demonstrate unique challenges in treating these diseases with traditional therapies. There is often a large build-up of glycosaminoglycans (GAGs) in neurons and meninges of affected individuals, leading to various forms of CNS symptoms. To date, no CNS symptoms resulting from a lysosomal disorder has successfully been treated by any means available.

Thus, there remains a great need to effectively deliver therapeutic agents to the brain. More particularly, there is a great need for more effective delivery of active agents to the central nervous system for the treatment of lysosomal storage disorders.

SUMMARY OF THE INVENTION

The present invention provides an effective and less invasive approach for direct delivery of therapeutic agents to the central nervous system (CNS). The present invention is, in part, based on unexpected discovery that a replacement enzyme (e.g., heparan N-sulfatase (HNS)) for a lysosomal storage disease (e.g., Sanfilippo A Syndrome) can be directly introduced into the cerebrospinal fluid (CSF) of a subject in need of treatment at a high concentration (e.g., greater than about 3 mg/ml, 4 mg/ml, 5 mg/ml, 10 mg/ml or more) such that the enzyme effectively and extensively diffuses across various surfaces and penetrates various regions across the brain, including deep brain regions. More surprisingly, the present inventors have demonstrated that such high protein concentration delivery can be done using simple saline or buffer-based formulations and without inducing substantial adverse effects, such as severe immune response, in the subject. Therefore, the present invention provides a highly efficient, clinically desirable and patient-friendly approach for direct CNS delivery for the treatment various diseases and disorders that have CNS components, in particular, lysosomal storage diseases. The present invention represents a significant advancement in the field of CNS targeting and enzyme replacement therapy.

As described in detail below, the present inventors have successfully developed stable formulations for effective intrathecal (IT) administration of an heparan N-sulfatase (HNS) protein. It is contemplated, however, that various stable formulations described herein are generally suitable for CNS delivery of therapeutic agents, including various other lysosomal enzymes. Indeed, stable formulations according to the present invention can be used for CNS delivery via various techniques and routes including, but not limited to, intraparenchymal, intracerebral, intravetricular cerebral (ICV), intrathecal (e.g., IT-Lumbar, IT-cisterna magna) administrations and any other techniques and routes for injection directly or indirectly to the CNS and/or CSF.

It is also contemplated that various stable formulations described herein are generally suitable for CNS delivery of other therapeutic agents, such as therapeutic proteins including various replacement enzymes for lysosomal storage diseases. In some embodiments, a replacement enzyme can be a synthetic, recombinant, gene-activated or natural enzyme.

In one aspect, the present invention provides stable formulations for intrathecal administration comprising a heparan N-sulfatase (HNS) protein, salt, a buffering agent and a polysorbate surfactant. In some embodiments, the HNS protein is present at a concentration ranging from approximately 1-300 mg/ml (e.g., 1-250 mg/ml, 1-200 mg/ml, 1-150 mg/ml, 1-100 mg/ml, 1-50 mg/ml). In some embodiments, the HNS protein is present at or up to a concentration selected from 2 mg/ml, 3 mg/ml, 4 mg/ml, 5 mg/ml, 10 mg/ml, 15 mg/ml, 20 mg/ml, 25 mg/ml, 30 mg/ml, 35 mg/ml, 40 mg/ml, 45 mg/ml, 50 mg/ml, 60 mg/ml, 70 mg/ml, 80 mg/ml, 90 mg/ml, 100 mg/ml, 150 mg/ml, 200 mg/ml, 250 mg/ml, or 300 mg/ml.

In various embodiments, the present invention includes a stable formulation of any of the embodiments described herein, wherein the HNS protein comprises an amino acid sequence of SEQ ID NO:1. In some embodiments, the HNS protein comprises an amino acid sequence at least 60%, 65%, 70%, 75%, 80%, 85%, 90%, 95%, or 98% identical to SEQ ID NO:1. In some embodiments, the stable formulation of any of the embodiments described herein includes a salt. In some embodiments, the salt is NaCl. In some embodiments, the NaCl is present as a concentration ranging from approximately 0-300 mM (e.g., 0-250 mM, 0-200 mM, 0-150 mM, 0-100 mM, 0-75 mM, 0-50 mM, or 0-30 mM). In some embodiments, the NaCl is present at a concentration ranging from approximately 135-155 mM. In some embodiments, the NaCl is present at a concentration of approximately 145 mM.

In various embodiments, the present invention includes a stable formulation of any of the embodiments described herein, wherein the polysorbate surfactant is selected from the group consisting of polysorbate 20, polysorbate 40, polysorbate 60, polysorbate 80 and combination thereof. In some embodiments, the polysorbate surfactant is polysorbate 20. In some embodiments, the polysorbate 20 is present at a concentration ranging approximately 0-0.02%. In some embodiments, the polysorbate 20 is present at a concentration of approximately 0.005%. In some embodiments, the polysorbate 20 is present at a concentration of approximately 0.02%.

In various embodiments, the present invention includes a stable formulation of any of the embodiments described herein, wherein the formulation further comprises a buffering agent. In some embodiments, the buffering agent is selected from the group consisting of phosphate, acetate, histidine, succinate, Tris, and combinations thereof. In some embodiments, the buffering agent is phosphate. In some embodiments, the phosphate is present at a concentration no greater than 50 mM (e.g., no greater than 45 mM, 40 mM, 35 mM, 30 mM, 25 mM, 20 mM, 15 mM, 10 mM, or 5 mM). In some embodiments, the phosphate is present at a concentration no greater than 20 mM. In certain embodiments, the phosphate is present at a concentration of approximately 5 mM. In various aspects the invention includes a stable formulation of any of the embodiments described herein, wherein the formulation has a pH of approximately 3-8 (e.g., approximately 4-7.5, 5-8, 5-7.5, 5-6.5, 5-7.5, 5.5-8.0, 5.5-7.7, 5.5-6.5, 6-7.5, 6-7.0, or 6.5-7.5). In some embodiments, the formulation has a pH of approximately 6.5-7.5 (e.g., 6.5, 6.7, 6.9, 7.0, 7.2, 7.3, or 7.5). In some embodiments, the formulation has a pH of approximately 7.0.

In some embodiments, the formulation further comprises a stabilizing agent. In certain embodiments, the stabilizing agent is selected from the group consisting of sucrose, glucose, mannitol, sorbitol, PEG 4000, histidine, arginine, lysine, phospholipids and combination thereof. In certain embodiments, the stabilizing agent is sucrose. In some embodiments, the sucrose is present at a concentration ranging from approximately 0-10%. In some embodiments, the sucrose is present at a concentration ranging from approximately 0.5-2.0%. In certain embodiments, the stabilizing agent is glucose. In some embodiments, the glucose is present at a concentration ranging from approximately 0.5-1.0%.

In various embodiments, the present invention includes stable formulations of any of the embodiments described herein, wherein the formulation is a liquid formulation. In various embodiments, the present invention includes stable formulation of any of the embodiments described herein, wherein the formulation is formulated as lyophilized dry powder.

In some embodiments, the present invention includes a stable formulation for intrathecal administration comprising a heparan N-sulfatase (HNS) protein at a concentration up to approximately 30 mg/ml, NaCl at a concentration of approximately 100-200 mM, polysorbate 20 at a concentration of approximately 0.02%, phosphate at a concentration of approximately 5 mM, and a pH of approximately 7.0. In some embodiments, the HNS protein is at a concentration of approximately 15 mg/ml. In some embodiments, the HNS protein is at a concentration of approximately 30 mg/ml, 40 mg/ml, 50 mg/ml, 100 mg/ml, 150 mg/ml, 200 mg/ml, 250 mg/ml, or 300 mg/ml. In some embodiments, the NaCl is at a concentration of approximately 145 mM. In some embodiments, the formulation further comprises sucrose at a concentration of approximately 0-10% (e.g., approximately 0-5%, 1-7%, 1-2.5%. 1-1.5%, or 0.5-1.5%).

In some embodiments, the present invention includes a stable formulation for intrathecal administration comprising a heparan N-sulfatase (HNS) protein at a concentration up to approximately 30 mg/ml, NaCl at a concentration of approximately 145 mM, polysorbate 20 at a concentration of approximately 0.02%, phosphate at a concentration of approximately 5 mM, sucrose at a concentration of approximately 0.5-2%, and a pH of approximately 7.0.

In some embodiments, the present invention includes a stable formulation for intrathecal administration comprising a heparan N-sulfatase (HNS) protein at a concentration up to approximately 30 mg/ml, NaCl at a concentration of approximately 145 mM, polysorbate 20 at a concentration of approximately 0.02%, phosphate at a concentration of approximately 5 mM, glucose at a concentration of approximately 0.5-1.0%, and a pH of approximately 7.0.

In various aspects, the present invention includes a container comprising a single dosage form of a stable formulation in various embodiments described herein. In some embodiments, the container is selected from an ampule, a vial, a bottle, a cartridge, a reservoir, a lyo-ject, or a pre-filled syringe. In some embodiments, the container is a pre-filled syringe. In some embodiments, the pre-filled syringe is selected from borosilicate glass syringes with baked silicone coating, borosilicate glass syringes with sprayed silicone, or plastic resin syringes without silicone. In some embodiments, the stable formulation is present in a volume of less than about 50 mL (e.g., less than about 45 ml, 40 ml, 35 ml, 30 ml, 25 ml, 20 ml, 15 ml, 10 ml, 5 ml, 4 ml, 3 ml, 2.5 ml, 2.0 ml, 1.5 ml, 1.0 ml, or 0.5 ml). In some embodiments, the stable formulation is present in a volume of less than about 3.0 mL.

In various aspects, the present invention includes methods of treating Sanfilippo A Syndrome including the step of administering intrathecally to a subject in need of treatment a formulation according to any of the embodiments described herein.

In some embodiments, the present invention includes a method of treating Sanfilippo A Syndrome including a step of administering intrathecally to a subject in need of treatment a formulation comprising an HNS protein at a concentration ranging from approximately 1-300 mg/ml, NaCl at a concentration of approximately 145 mM, polysorbate 20 at a concentration of approximately 0.02%, and a pH of approximately 7.

In some embodiments, the intrathecal administration results in no substantial adverse effects (e.g., severe immune response) in the subject. In some embodiments, the intrathecal administration results in no substantial adaptive T cell-mediated immune response in the subject.

In some embodiments, the intrathecal administration of the formulation results in delivery of the HNS protein to various target tissues in the brain, the spinal cord, and/or peripheral organs. In some embodiments, the intrathecal administration of the formulation results in delivery of the HNS protein to target brain tissues. In certain embodiments, the one or more target brain tissues are selected from the group consisting of tissues from gray matter, white matter, periventricular areas, pia-arachnoid, meninges, neocortex, cerebellum, deep tissues in cerebral cortex, molecular layer, caudate/putamen region, midbrain, deep regions of the pons or medulla, and combinations thereof. In certain embodiments, the HNS protein is delivered to neurons, glial cells, perivascular cells and/or meningeal cells. In some embodiments, the HNS protein is further delivered to the neurons in the spinal cord.

In some embodiments, the intrathecal administration of the formulation further results in systemic delivery of the HNS protein in peripheral target tissues. In some embodiments, the peripheral target tissues are selected from liver, kidney, spleen and/or heart.

In some embodiments, the intrathecal administration of the formulation results in lysosomal localization in brain target tissues, spinal cord neurons and/or peripheral target tissues. In some embodiments, the intrathecal administration of the formulation results in reduction of GAG storage in the brain target tissues, spinal cord neurons and/or peripheral target tissues. In some embodiments, the GAG storage is reduced by at least 10%, 20%, 30%, 40%, 50%, 60%, 70%, 80%, 90%, 1-fold, 1.5-fold, or 2-fold as compared to a control (e.g., the pre-treatment GAG storage in the subject). In some embodiments, the intrathecal administration of the formulation results in reduced vacuolization in neurons (e.g., by at least 20%, 40%, 50%, 60%, 80%, 90%, 1-fold, 1.5-fold, or 2-fold as compared to a control). In some embodiments, the neurons comprises Purkinje cells.

In some embodiments, the intrathecal administration of the formulation results in increased HNS enzymatic activity in the brain target tissues, spinal cord neurons and/or peripheral target tissues. In some embodiments, the HNS enzymatic activity is increased by at least 1-fold, 2-fold, 3-fold, 4-fold, 5-fold, 6-fold, 7-fold, 8-fold, 9-fold or 10-fold as compared to a control (e.g., the pre-treatment endogenous enzymatic activity in the subject). In some embodiments, the increased HNS enzymatic activity is at least approximately 10 nmol/hr/mg, 20 nmol/hr/mg, 40 nmol/hr/mg, 50 nmol/hr/mg, 60 nmol/hr/mg, 70 nmol/hr/mg, 80 nmol/hr/mg, 90 nmol/hr/mg, 100 nmol/hr/mg, 150 nmol/hr/mg, 200 nmol/hr/mg, 250 nmol/hr/mg, 300 nmol/hr/mg, 350 nmol/hr/mg, 400 nmol/hr/mg, 450 nmol/hr/mg, 500 nmol/hr/mg, 550 nmol/hr/mg or 600 nmol/hr/mg.

In some embodiments, the HNS enzymatic activity is increased in the lumbar region. In some embodiments, the increased HNS enzymatic activity in the lumbar region is at least approximately 2000 nmol/hr/mg, 3000 nmol/hr/mg, 4000 nmol/hr/mg, 5000 nmol/hr/mg, 6000 nmol/hr/mg, 7000 nmol/hr/mg, 8000 nmol/hr/mg, 9000 nmol/hr/mg, or 10,000 nmol/hr/mg.

In some embodiments, the intrathecal administration of the formulation results in reduced intensity, severity, or frequency, or delayed onset of at least one symptom or feature of the Sanfilippo A Syndrome. In some embodiments, the at least one symptom or feature of the Sanfilippo A Syndrome is hearing loss, delayed speech development, deficits in motor skills, hyperactivity, mental retardation, aggressiveness and/or sleep disturbances.

In some embodiments, the intrathecal administration takes place once every two weeks. In some embodiments, the intrathecal administration takes place once every month. In some embodiments, the intrathecal administration takes place once every two months. In some embodiments, the intrathecal administration is used in conjunction with intravenous administration. In some embodiments, the intravenous administration is no more frequent than once every week. In some embodiments, the intravenous administration is no more frequent than once every two weeks. In some embodiments, the intravenous administration is no more frequent than once every month. In some embodiments, the intravenous administration is no more frequent than once every two months. In certain embodiments, the intraveneous administration is more frequent than monthly administration, such as twice weekly, weekly, every other week, or twice monthly.

In some embodiments, intraveneous and intrathecal administrations are performed on the same day. In some embodiments, the intraveneous and intrathecal administrations are not performed within a certain amount of time of each other, such as not within at least 2 days, within at least 3 days, within at least 4 days, within at least 5 days, within at least 6 days, within at least 7 days, or within at least one week. In some embodiments, intraveneous and intrathecal administrations are performed on an alternating schedule, such as alternating administrations weekly, every other week, twice monthly, or monthly. In some embodiments, an intrathecal administration replaces an intravenous administration in an administration schedule, such as in a schedule of intraveneous administration weekly, every other week, twice monthly, or monthly, every third or fourth or fifth administration in that schedule can be replaced with an intrathecal administration in place of an intraveneous administration.

In some embodiments, intraveneous and intrathecal administrations are performed sequentially, such as performing intraveneous administrations first (e.g., weekly, every other week, twice monthly, or monthly dosing for two weeks, a month, two months, three months, four months, five months, six months, a year or more) followed by IT administrations (e.g., weekly, every other week, twice monthly, or monthly dosing for more than two weeks, a month, two months, three months, four months, five months, six months, a year or more). In some embodiments, intrathecal administrations are performed first (e.g., weekly, every other week, twice monthly, monthly, once every two months, once every three months dosing for two weeks, a month, two months, three months, four months, five months, six months, a year or more) followed by intravenous administrations (e.g., weekly, every other week, twice monthly, or monthly dosing for more than two weeks, a month, two months, three months, four months, five months, six months, a year or more).

In some embodiments, the intrathecal administration is used in absence of intravenous administration.

In some embodiments, the intrathecal administration is used in absence of concurrent immunosuppressive therapy.

BRIEF DESCRIPTION OF THE DRAWINGS

The drawings are for illustration purposes only, not for limitation.

FIG. 1A Profile of 2 mg/ml rhHNS 20 mM Citrate, pH 7.0; FIG. 1B Scaled chromatogram of 2 mg/ml rhHNS 20 mM Citrate, pH 7.0, baseline (ilc); FIG. 1C Scaled chromatogram of 2 mg/ml rhHNS 20 mM Citrate, pH 7.0 after 7 days at 50° C.; FIG. 1D Overlay of the wavelength scan of the 16 min peak and 26 min dimer peak of 2 mg/ml Citrate, pH 7.0 after 7 days at 50° C.

FIG. 7A Effect of pH on rhHNS solubility; FIG. 7B Effect of salt concentration on rhHNS solubility. Increasing pH and sodium chloride appear to increase rhHNS solubility.

FIG. 8A Effect of 145 mM salt; FIG. 8B Effect of 300 mM salt.

FIG. 9A VirTis lyo unit; upper panel, 1% sucrose; lower panel 1.5% sucrose; FIG. 9B 1.5% sucrose; upper panel, VirTis lyo unit; lower panel LyoStar lyo unit.

FIG. 13A depicts an exemplary result illustrating a low-power view of neutrophilic infiltrates local to the IT catheter in a DC monkey. FIG. 13B depicts an exemplary result illustrating a high-power view of eosinophilic infiltrates in the meninges of a high-dose (8.3 mg/dose) monkey; the overall severity of infiltrates was similar to the mid-dose (4.5 mg/dose) group (not shown). FIG. 13C depicts an exemplary result illustrating a high-power view of a low-dose (1.5 mg/dose) monkey showing eosinophils in the perivascular space (brain parenchyma). FIG. 13D depicts an exemplary result illustrating a low-dose monkey (1.5 mg/dose) showing eosinophils in the perivascular space and adjoining parenchyma. FIG. 13E depicts an exemplary result illustrating eosinophils in the spinal cord parenchyma (indicated by arrows) of a low-dose group animal; neurons in the area are normal. FIG. 13F depicts an exemplary result illustrating eosinophils and an area of microgliosis (arrows indicate eosinophils; the box indicates an area of microgliosis) in a low-dose (1.5 mg/dose) monkey. There are several large neurons in the area, all of which are normal. Scale bars: 200 μm.

FIGS. 14A and 14B depict an exemplary result illustrating activity in the spinal cords of (A) male and (B) female monkeys. Slice—3=lumbar, slices 3, 6=thoracic, and slice 9=cervical; 0=catheter tip. FIGS. 14C and 14D depicts an exemplary result illustrating rhHNS activity in the brains of (C) male and (D) female monkeys. Slices are numbered rostral to caudal (3 to 15). All tissue samples were collected approximately 24 hours after the last dose or 4 weeks after the last dose for the recovery animals. DC, device control. The data represent mean±SEM for n=4 monkeys per treatment group.

FIG. 15A depicts an exemplary result illustrating rhHNS activity distribution in the high-dose (8.3 mg/dose) group monkey brain. The fold-change in activity for surface, deep, and very deep (periventricular) areas of the brain compared with endogenous levels (DC group) is shown. All tissue samples were collected approximately 24 hours after the last dose or 4 weeks after the last dose for the recovery animals. The data represent mean±SEM for n=6 monkeys (both sexes), brain slices 6 and 9. Data for two monkeys were not included; at necropsy the catheters were not found to be patent. FIG. 15B shows rhHNS activity in monkey liver. All tissue samples were collected approximately 24 hours after the last dose or 4 weeks after the last dose for the recovery animals. DC, device control. Rec, recovery. The data represent mean±SEM for n=4 monkeys per treatment group except for the low-dose (4.5 mg/dose) female group (n=3).

FIG. 16A depicts an exemplary result illustrating cerebellum of a vehicle control animal (0 mg/dose) negative for rhHNS immunostaining; 20× magnification. FIG. 16B depicts an exemplary result illustrating cerebellum of a low-dose (1.5 mg/dose) animal showing minimal positive staining limited to the molecular layer; 20× magnification. FIG. 16C depicts an exemplary result illustrating cerebellum of a mid-dose (4.5 mg/dose) animal showing minimal staining in the outer granular layer; 20× magnification. FIG. 16D depicts an exemplary result illustrating moderate staining in the cerebellum of a high-dose (8.3 mg/dose) animal including molecular, outer granular layer, and Purkinje cells; 20× magnification.

DEFINITIONS

Figure 1A:
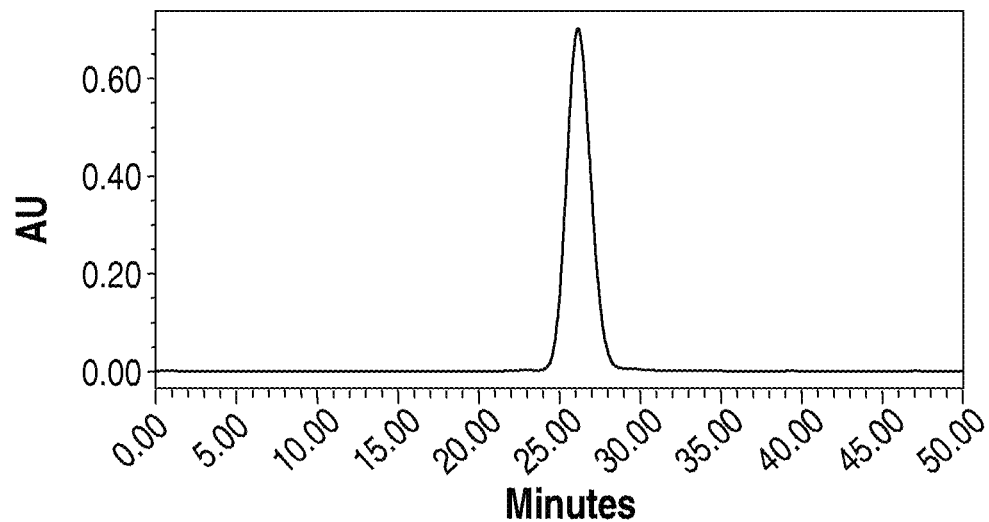
FIG. 1A-D depicts exemplary chromatograms of SEC-HPLC elution profiles for HNS.

In order for the present invention to be more readily understood, certain terms are first defined below. Additional definitions for the following terms and other terms are set forth throughout the specification.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Amelioration: As used herein, the term "amelioration" is meant the prevention, reduction or palliation of a state, or improvement of the state of a subject. Amelioration includes, but does not require complete recovery or complete prevention of a disease condition. In some embodiments, amelioration includes increasing levels of relevant protein or its activity that is deficient in relevant disease tissues.

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active. In particular embodiments, where a protein or polypeptide is biologically active, a portion of that protein or polypeptide that shares at least one biological activity of the protein or polypeptide is typically referred to as a "biologically active" portion.

Bulking agent: As used herein, the term "bulking agent" refers to a compound which adds mass to the lyophilized mixture and contributes to the physical structure of the lyophilized cake (e.g., facilitates the production of an essentially uniform lyophilized cake which maintains an open pore structure). Exemplary bulking agents include mannitol, glycine, sodium chloride, hydroxyethyl starch, lactose, sucrose, trehalose, polyethylene glycol and dextran.

Cation-independent mannose-6-phosphate receptor (CI-MPR): As used herein, the term "cation-independent mannose-6-phosphate receptor (CI-MPR)" refers to a cellular receptor that binds mannose-6-phosphate (M6P) tags on acid hydrolase precursors in the Golgi apparatus that are destined for transport to the lysosome. In addition to mannose-6-phosphates, the CI-MPR also binds other proteins including IGF-II. The CI-MPR is also known as "M6P/IGF-II receptor," "CI-MPR/IGF-II receptor," "IGF-II receptor" or "IGF2 Receptor." These terms and abbreviations thereof are used interchangeably herein.

Concurrent immunosuppressant therapy: As used herein, the term "concurrent immunosuppressant therapy" includes any immunosuppressant therapy used as pre-treatment, pre-conditioning or in parallel to a treatment method.

Diluent: As used herein, the term "diluent" refers to a pharmaceutically acceptable (e.g., safe and non-toxic for administration to a human) diluting substance useful for the preparation of a reconstituted formulation. Exemplary diluents include sterile water, bacteriostatic water for injection (BWFI), a pH buffered solution (e.g. phosphate-buffered saline), sterile saline solution, Ringer's solution or dextrose solution.

Dosage form: As used herein, the terms "dosage form" and "unit dosage form" refer to a physically discrete unit of a therapeutic protein for the patient to be treated. Each unit contains a predetermined quantity of active material calculated to produce the desired therapeutic effect. It will be understood, however, that the total dosage of the composition will be decided by the attending physician within the scope of sound medical judgment.

Enzyme replacement therapy (ERT): As used herein, the term "enzyme replacement therapy (ERT)" refers to any therapeutic strategy that corrects an enzyme deficiency by providing the missing enzyme. In some embodiments, the missing enzyme is provided by intrathecal administration. In some embodiments, the missing enzyme is provided by infusing into bloodstream. Once administered, enzyme is taken up by cells and transported to the lysosome, where the enzyme acts to eliminate material that has accumulated in the lysosomes due to the enzyme deficiency. Typically, for lysosomal enzyme replacement therapy to be effective, the therapeutic enzyme is delivered to lysosomes in the appropriate cells in target tissues where the storage defect is manifest.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control individual (or multiple control individuals) in the absence of the treatment described herein. A "control individual" is an individual afflicted with the same form of lysosomal storage disease as the individual being treated, who is about the same age as the individual being treated (to ensure that the stages of the disease in the treated individual and the control individual(s) are comparable).

Individual, subject, patient: As used herein, the terms "subject," "individual" or "patient" refer to a human or a non-human mammalian subject. The individual (also referred to as "patient" or "subject") being treated is an individual (fetus, infant, child, adolescent, or adult human) suffering from a disease.

Intrathecal administration: As used herein, the term "intrathecal administration" or "intrathecal injection" refers to an injection into the spinal canal (intrathecal space surrounding the spinal cord). Various techniques may be used including, without limitation, lateral cerebroventricular injection through a burrhole or cisternal or lumbar puncture or the like. In some embodiments, "intrathecal administration" or "intrathecal delivery" according to the present invention refers to IT administration or delivery via the lumbar area or region, i.e., lumbar IT administration or delivery. As used herein, the term "lumbar region" or "lumbar area" refers to the area between the third and fourth lumbar (lower back) vertebrae and, more inclusively, the L2-S1 region of the spine.

Linker: As used herein, the term "linker" refers to, in a fusion protein, an amino acid sequence other than that appearing at a particular position in the natural protein and is generally designed to be flexible or to interpose a structure, such as an a-helix, between two protein moieties. A linker is also referred to as a spacer.

Lyoprotectant: As used herein, the term "lyoprotectant" refers to a molecule that prevents or reduces chemical and/or physical instability of a protein or other substance upon lyophilization and subsequent storage. Exemplary lyoprotectants include sugars such as sucrose or trehalose; an amino acid such as monosodium glutamate or histidine; a methylamine such as betaine; a lyotropic salt such as magnesium sulfate: a polyol such as trihydric or higher sugar alcohols, e.g. glycerin, erythritol, glycerol, arabitol, xylitol, sorbitol, and mannitol; propylene glycol; polyethylene glycol; Pluronics; and combinations thereof. In some embodiments, a lyoprotectant is a non-reducing sugar, such as trehalose or sucrose.

Lysosomal enzyme: As used herein, the term "lysosomal enzyme" refers to any enzyme that is capable of reducing accumulated materials in mammalian lysosomes or that can rescue or ameliorate one or more lysosomal storage disease symptoms. Lysosomal enzymes suitable for the invention include both wild-type or modified lysosomal enzymes and can be produced using recombinant and synthetic methods or purified from nature sources. Exemplary lysosomal enzymes are listed in Table 1.

Lysosomal enzyme deficiency: As used herein, "lysosomal enzyme deficiency" refers to a group of genetic disorders that result from deficiency in at least one of the enzymes that are required to break macromolecules (e.g., enzyme substartes) down to peptides, amino acids, monosaccharides, nucleic acids and fatty acids in lysosomes. As a result, individuals suffering from lysosomal enzyme deficiencies have accumulated materials in various tissues (e.g., CNS, liver, spleen, gut, blood vessel walls and other organs).

Lysosomal Storage Disease: As used herein, the term "lysosomal storage disease" refers to any disease resulting from the deficiency of one or more lysosomal enzymes necessary for metabolizing natural macromolecules. These diseases typically result in the accumulation of un-degraded molecules in the lysosomes, resulting in increased numbers of storage granules (also termed storage vesicles). These diseases and various examples are described in more detail below.

Polypeptide: As used herein, a "polypeptide", generally speaking, is a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides sometimes include "non-natural" amino acids or other entities that nonetheless are capable of integrating into a polypeptide chain, optionally.

Replacement enzyme: As used herein, the term "replacement enzyme" refers to any enzyme that can act to replace at least in part the deficient or missing enzyme in a disease to be treated. In some embodiments, the term "replacement enzyme" refers to any enzyme that can act to replace at least in part the deficient or missing lysosomal enzyme in a lysosomal storage disease to be treated. In some embodiments, a replacement enzyme is capable of reducing accumulated materials in mammalian lysosomes or that can rescue or ameliorate one or more lysosomal storage disease symptoms. Replacement enzymes suitable for the invention include both wild-type or modified lysosomal enzymes and can be produced using recombinant and synthetic methods or purified from nature sources. A replacement enzyme can be a recombinant, synthetic, gene-activated or natural enzyme.

Soluble: As used herein, the term "soluble" refers to the ability of a therapeutic agent to form a homogenous solution. In some embodiments, the solubility of the therapeutic agent in the solution into which it is administered and by which it is transported to the target site of action (e.g., the cells and tissues of the brain) is sufficient to permit the delivery of a therapeutically effective amount of the therapeutic agent to the targeted site of action. Several factors can impact the solubility of the therapeutic agents. For example, relevant factors which may impact protein solubility include ionic strength, amino acid sequence and the presence of other co-solubilizing agents or salts (e.g., calcium salts). In some embodiments, the pharmaceutical compositions are formulated such that calcium salts are excluded from such compositions. In some embodiments, therapeutic agents in accordance with the present invention are soluble in its corresponding pharmaceutical composition. It will be appreciated that, while isotonic solutions are generally preferred for parenterally administered drugs, the use of isotonic solutions may limit adequate solubility for some therapeutic agents and, in particular some proteins and/or enzymes. Slightly hypertonic solutions (e.g., up to 175 mM sodium chloride in 5 mM sodium phosphate at pH 7.0) and sugar-containing solutions (e.g., up to 2% sucrose in 5 mM sodium phosphate at pH 7.0) have been demonstrated to be well tolerated in monkeys. For example, the most common approved CNS bolus formulation composition is saline (150 mM NaCl in water).

Stability: As used herein, the term "stable" refers to the ability of the therapeutic agent (e.g., a recombinant enzyme) to maintain its therapeutic efficacy (e.g., all or the majority of its intended biological activity and/or physiochemical integrity) over extended periods of time. The stability of a therapeutic agent, and the capability of the pharmaceutical composition to maintain stability of such therapeutic agent, may be assessed over extended periods of time (e.g., for at least 1, 3, 6, 12, 18, 24, 30, 36 months or more). In general, pharmaceutical compositions described herein have been formulated such that they are capable of stabilizing, or alternatively slowing or preventing the degradation, of one or more therapeutic agents formulated therewith (e.g., recombinant proteins). In the context of a formulation a stable formulation is one in which the therapeutic agent therein essentially retains its physical and/or chemical integrity and biological activity upon storage and during processes (such as freeze/thaw, mechanical mixing and lyophilization). For protein stability, it can be measure by formation of high molecular weight (HMW) aggregates, loss of enzyme activity, generation of peptide fragments and shift of charge profiles.

Subject: As used herein, the term "subject" means any mammal, including humans. In certain embodiments of the present invention the subject is an adult, an adolescent or an infant. Also contemplated by the present invention are the administration of the pharmaceutical compositions and/or performance of the methods of treatment in-utero.

Substantial homology: The phrase "substantial homology" is used herein to refer to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains Substitution of one amino acid for another of the same type may often be considered a "homologous" substitution.

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul, et al., "Gapped BLAST and PSI-BLAST: a new generation of protein database search programs", *Nucleic Acids Res.* 25:3389-3402, 1997; Baxevanis, et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying homologous sequences, the programs mentioned above typically provide an indication of the degree of homology. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding residues are homologous over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Substantial identity: The phrase "substantial identity" is used herein to refer to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul et al., *Nucleic Acids Res.* 25:3389-3402, 1997; Baxevanis et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Synthetic CSF: As used herein, the term "synthetic CSF" refers to a solution that has pH, electrolyte composition, glucose content and osmolarity consistent with the cerebrospinal fluid. Synthetic CSF is also referred to as artificial CSF. In some embodiments, synthetic CSF is an Elliott's B solution.

Suitable for CNS delivery: As used herein, the phrase "suitable for CNS delivery" or "suitable for intrathecal delivery" as it relates to the pharmaceutical compositions of the present invention generally refers to the stability, tolerability, and solubility properties of such compositions, as well as the ability of such compositions to deliver an effective amount of the therapeutic agent contained therein to the targeted site of delivery (e.g., the CSF or the brain).

Target tissues: As used herein, the term "target tissues" refers to any tissue that is affected by the lysosomal storage disease to be treated or any tissue in which the deficient lysosomal enzyme is normally expressed. In some embodiments, target tissues include those tissues in which there is a detectable or abnormally high amount of enzyme substrate, for example stored in the cellular lysosomes of the tissue, in patients suffering from or susceptible to the lysosomal storage disease. In some embodiments, target tissues include those tissues that display disease-associated pathology, symptom, or feature. In some embodiments, target tissues include those tissues in which the deficient lysosomal enzyme is normally expressed at an elevated level. As used herein, a target tissue may be a brain target tissue, a spinal cord target tissue an/or a peripheral target tissue. Exemplary target tissues are described in detail below.

Therapeutic moiety: As used herein, the term "therapeutic moiety" refers to a portion of a molecule that renders the therapeutic effect of the molecule. In some embodiments, a therapeutic moiety is a polypeptide having therapeutic activity.

Therapeutically effective amount: As used herein, the term "therapeutically effective amount" refers to an amount of a therapeutic protein (e.g., replacement enzyme) which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). In particular, the "therapeutically effective amount" refers to an amount of a therapeutic protein or composition effective to treat, ameliorate, or prevent a desired disease or condition, or to exhibit a detectable therapeutic or preventative effect, such as by ameliorating symptoms associated with the disease, preventing or delaying the onset or progression of the disease, and/or also lessening the severity or frequency of symptoms of the disease. A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific fusion protein employed; the duration of the treatment; and like factors as is well known in the medical arts.

Tolerable: As used herein, the terms "tolerable" and "tolerability" refer to the ability of the pharmaceutical compositions of the present invention to not elicit an adverse reaction in the subject to whom such composition is administered, or alternatively not to elicit a serious adverse reaction in the subject to whom such composition is administered. In some embodiments, the pharmaceutical compositions of the present invention are well tolerated by the subject to whom such compositions is administered.

Treatment: As used herein, the term "treatment" (also "treat" or "treating") refers to any administration of a therapeutic protein (e.g., lysosomal enzyme) that partially or completely alleviates, ameliorates, relieves, inhibits, delays onset of, reduces severity of and/or reduces incidence of one or more symptoms or features of a particular disease, disorder, and/or condition (e.g., Hunters syndrome, Sanfilippo A syndrome, Sanfilippo B syndrome). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition.

DETAILED DESCRIPTION OF THE INVENTION

The present invention provides, among other things, improved methods and compositions for effective direct delivery of a therapeutic agent to the central nervous system (CNS). As discussed above, the present invention is based on unexpected discovery that a replacement enzyme (e.g., an HNS protein) for a lysosomal storage disease (e.g., Sanfilippo A Syndrome) can be directly introduced into the cerebrospinal fluid (CSF) of a subject in need of treatment at a high concentration without inducing substantial adverse effects in the subject. More surprisingly, the present inventors found that the replacement enzyme may be delivered in a simple saline or buffer-based formulation, without using synthetic CSF. Even more unexpectedly, intrathecal delivery according to the present invention does not result in substantial adverse effects, such as severe immune response, in the subject. Therefore, in some embodiments, intrathecal delivery according to the present invention may be used in absence of concurrent immunosuppressant therapy (e.g., without induction of immune tolerance by pre-treatment or pre-conditioning).

In some embodiments, intrathecal delivery according to the present invention permits efficient diffusion across various brain tissues resulting in effective delivery of the replacement enzyme in various target brain tissues in surface, shallow and/or deep brain regions. In some embodiments, intrathecal delivery according to the present invention resulted in sufficient amount of replacement enzymes entering the peripheral circulation. As a result, in some cases, intrathecal delivery according to the present invention resulted in delivery of the replacement enzyme in peripheral tissues, such as liver, heart, spleen and kidney. This discovery is unexpected and can be particular useful for the treatment of lysosomal storage diseases that have both CNS and peripheral components, which would typically require both regular intrathecal administration and intravenous administration. It is contemplated that intrathecal delivery according to the present invention may allow reduced dosing and/or frequency of iv injection without compromising therapeutic effects in treating peripheral symptoms.

The present invention provides various unexpected and beneficial features that allow efficient and convenient delivery of replacement enzymes to various brain target tissues, resulting in effective treatment of lysosomal storage diseases that have CNS indications.

Various aspects of the invention are described in detail in the following sections. The use of sections is not meant to limit the invention. Each section can apply to any aspect of the invention. In this application, the use of "or" means "and/or" unless stated otherwise.

Replacement Enzymes

Heparan-N-Sulfatase (HNS) Protein

In some embodiments, inventive methods and compositions provided by the present invention are used to deliver an Heparan-N-Sulfatase (HNS) protein to the CNS for treatment of Sanfilippo A. A suitable HNS protein can be any molecule or a portion of a molecule that can substitute for naturally-occurring Heparan-N-Sulfatase (HNS) protein activity or rescue one or more phenotypes or symptoms associated with HNS-deficiency. In some embodiments, a replacement enzyme suitable for the invention is a polypeptide having an N-terminus and a C-terminus and an amino acid sequence substantially similar or identical to mature human HNS protein.

Typically, human HNS is produced as a precursor molecule that is processed to a mature form. This process generally occurs by removing the 20 amino acid signal peptide. Typically, the precursor form is also referred to as full-length precursor or full-length HNS protein, which contains 502 amino acids. The N-terminal 20 amino acids are cleaved, resulting in a mature form that is 482 amino acids in length. Thus, it is contemplated that the N-terminal 20 amino acids is generally not required for the HNS protein activity. The amino acid sequences of the mature form (SEQ ID NO:1) and full-length precursor (SEQ ID NO:2) of a typical wild-type or naturally-occurring human HNS protein are shown in Table 1.

TABLE 1

| Human Heparan-N-Sulfatase | |
|---|---|
| Mature Form | RPRNALLLLA DDGGFESGAY NNSAIATPHL DALARRSLLF RNAFTSVSSC SPSRASLLTG LPQHQNGMYG LHQDVHHFNS FDKVRSLPLL LSQAGVRTGI IGKKHVGPET VYPFDFAYTE ENGSVLQVGR NITRIKLLVR KFLQTQDDRP FFLYVAFHDP HRCGHSQPQY GTFCEKFGNG ESGMGRIPDW TPQAYDPLDV LVPYFVPNTP AARADLAAQY TTVGRMDQGV GLVLQELRDA GVLNDTLVIF TSDNGIPFPS GRTNLYWPGT AEPLLVSSPE HPKRWGQVSE AYVSLLDLTP TILDWFSIPY PSYAIFGSKT IHLTGRSLLP ALEAEPLWAT VFGSQSHHEV TMSYPMRSVQ HRHFRLVHNL NFKMPFPIDQ DFYVSPTFQD LLNRTTAGQP TGWYKDLRHY YYRARWELYD RSRDPHETQN LATDPRFAQL LEMLRDQLAK WQWETHDPWV CAPDGVLEEK LSPQCQPLHN EL (SEQ ID NO: 1) |
| Full-Length Precursor | MSCPVPACCA LLLVLGLCRA RPRNALLLLA DDGGFESGAY NNSAIATPHL DALARRSLLF RNAFTSVSSC SPSRASLLTG LPQHQNGMYG LHQDVHHFNS FDKVRSLPLL LSQAGVRTGI IGKKHVGPET VYPFDFAYTE ENGSVLQVGR NITRIKLLVR KFLQTQDDRP FFLYVAFHDP HRCGHSQPQY GTFCEKFGNG ESGMGRIPDW TPQAYDPLDV LVPYFVPNTP AARADLAAQY TTVGRMDQGV GLVLQELRDA GVLNDTLVIF TSDNGIPFPS GRTNLYWPGT AEPLLVSSPE HPKRWGQVSE AYVSLLDLTP TILDWFSIPY PSYAIFGSKT IHLTGRSLLP ALEAEPLWAT VFGSQSHHEV TMSYPMRSVQ HRHFRLVHNL NFKMPFPIDQ DFYVSPTFQD LLNRTTAGQP TGWYKDLRHY YYRARWELYD RSRDPHETQN LATDPRFAQL LEMLRDQLAK WQWETHDPWV CAPDGVLEEK LSPQCQPLHN EL (SEQ ID NO: 2) |

Thus, in some embodiments, a therapeutic moiety suitable for the present invention is mature human HNS protein (SEQ ID NO:1). In some embodiments, a suitable therapeutic moiety may be a homologue or an analogue of mature human HNS protein. For example, a homologue or an analogue of mature human HNS protein may be a modified mature human HNS protein containing one or more amino acid substitutions, deletions, and/or insertions as compared to a wild-type or naturally-occurring HNS protein (e.g., SEQ ID NO:1), while retaining substantial HNS protein activity. Thus, in some embodiments, a therapeutic moiety suitable for the present invention is substantially homologous to mature human HNS protein (SEQ ID NO:1). In some embodiments, a therapeutic moiety suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:1. In some embodiments, a therapeutic moiety suitable for the present invention is substantially identical to mature human HNS protein (SEQ ID NO:1). In some embodiments, a therapeutic moiety suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:1. In some embodiments, a therapeutic moiety suitable for the present invention contains a fragment or a portion of mature human HNS protein.

Alternatively, a therapeutic moiety suitable for the present invention is full-length HNS protein. In some embodiments, a suitable therapeutic moiety may be a homologue or an analogue of full-length human HNS protein. For example, a homologue or an analogue of full-length human HNS protein may be a modified full-length human HNS protein containing one or more amino acid substitutions, deletions, and/or insertions as compared to a wild-type or naturally-occurring full-length HNS protein (e.g., SEQ ID NO:2), while retaining substantial HNS protein activity. Thus, In some embodiments, a therapeutic moiety suitable for the present invention is substantially homologous to full-length human HNS protein (SEQ ID NO:2). In some embodiments, a therapeutic moiety suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:2. In some embodiments, a therapeutic moiety suitable for the present invention is substantially identical to SEQ ID NO:2. In some embodiments, a therapeutic moiety suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:2. In some embodiments, a therapeutic moiety suitable for the present invention contains a fragment or a portion of full-length HNS protein. As used herein, a full-length HNS protein typically contains signal peptide sequence.

Other Lysosomal Storage Diseases and Replacement Enzymes

It is contemplated that inventive methods and compositions according to the present invention can be used to treat other lysosomal storage diseases, in particular those lysosomal storage diseases having CNS etiology and/or symptoms, including, but are not limited to, aspartylglucosaminuria, cholesterol ester storage disease, Wolman disease, cystinosis, Danon disease, Fabry disease, Farber lipogranulomatosis, Farber disease, fucosidosis, galactosialidosis types I/II, Gaucher disease types I/II/III, globoid cell leukodystrophy, Krabbe disease, glycogen storage disease II, Pompe disease, GM1-gangliosidosis types I/II/III, GM2-gangliosidosis type I, Tay Sachs disease, GM2-gangliosidosis type II, Sandhoff disease, GM2-gangliosidosis, α-mannosidosis types I/II, .beta.-mannosidosis, metachromatic leukodystrophy, mucolipidosis type I, sialidosis types I/II, mucolipidosis types II/III, I-cell disease, mucolipidosis type IIIC pseudo-Hurler polydystrophy, mucopolysaccharidosis type I, mucopolysaccharidosis type II, mucopolysaccharidosis type IIIA, Sanfilippo syndrome (e.g., types A, B, C, D), mucopolysaccharidosis type IIIB, mucopolysaccharidosis type IIIC, mucopolysaccharidosis type IIID, mucopolysaccharidosis type IVA, Morquio syndrome, mucopolysaccharidosis type IVB, mucopolysaccharidosis type VI, mucopolysaccharidosis type VII, Sly syndrome, mucopolysaccharidosis type IX, multiple sulfatase deficiency, neuronal ceroid lipofuscinosis, CLN1 Batten disease, CLN2 Batten disease, Niemann-Pick disease types A/B, Niemann-Pick disease type C1, Niemann-Pick disease type C2, pycnodysostosis, Schindler disease types I/II, Gaucher disease and sialic acid storage disease.

A detailed review of the genetic etiology, clinical manifestations, and molecular biology of the lysosomal storage diseases are detailed in Scriver et al., eds., The Metabolic and Molecular Basis of Inherited Disease, 7.sup.th Ed., Vol. II, McGraw Hill, (1995). Thus, the enzymes deficient in the above diseases are known to those of skill in the art, some of these are exemplified in the Table below:

TABLE 2

| Disease Name | Enzyme Deficiency | Substance Stored |
|---|---|---|
| Pompe Disease | Acid-α1, 4-Glucosidase | Glycogen α 1-4 linked Oligosaccharides |
| GM1 Gangliodsidosis | β-Galactosidase | GM$_1$ Gangliosides |
| Tay-Sachs Disease | β-Hexosaminidase A | GM$_2$ Ganglioside |
| GM2 Gangliosidosis: AB Variant | GM$_2$ Activator Protein | GM$_2$ Ganglioside |
| Sandhoff Disease | β-Hexosaminidase A&B | GM$_2$ Ganglioside |
| Fabry Disease | α-Galactosidase A | Globosides |
| Gaucher Disease | Glucocerebrosidase | Glucosylceramide |
| Metachromatic Leukodystrophy | Arylsulfatase A | Sulphatides |
| Krabbe Disease | Galactosylceramidase | Galactocerebroside |
| Niemann Pick, Types A & B | Acid Sphingomyelinase | Sphingomyelin |
| Niemann-Pick, Type C | Cholesterol Esterification Defect | Sphingomyelin |
| Niemann-Pick, Type D | Unknown | Sphingomyelin |
| Farber Disease | Acid Ceramidase | Ceramide |
| Wolman Disease | Acid Lipase | Cholesteryl Esters |
| Hurler Syndrome (MPS IH) | α-L-Iduronidase | Heparan & Dermatan Sulfates |
| Scheie Syndrome (MPS IS) | α-L-Iduronidase | Heparan & Dermatan, Sulfates |
| Hurler-Scheie (MPS IH/S) | α-L-Iduronidase | Heparan & Dermatan Sulfates |
| Hunter Syndrome (MPS II) | Iduronate Sulfatase | Heparan & Dermatan Sulfates |
| Sanfilippo A (MPS IIIA) | Heparan N-Sulfatase | Heparan Sulfate |
| Sanfilippo B (MPS IIIB) | α-N-Acetylglucosaminidase | Heparan Sulfate |
| Sanfilippo C (MPS IIIC) | Acetyl-CoA-Glucosaminide Acetyltransferase | Heparan Sulfate |
| Sanfilippo D (MPS IIID) | N-Acetylglucosamine-6-Sulfatase | Heparan Sulfate |
| Morquio B (MPS IVB) | β-Galactosidase | Keratan Sulfate |
| Maroteaux-Lamy (MPS VI) | Arylsulfatase B | Dermatan Sulfate |
| Sly Syndrome (MPS VII) | β-Glucuronidase | |
| α-Mannosidosis | α-Mannosidase | Mannose/Oligosaccharides |
| β-Mannosidosis | β-Mannosidase | Mannose/Oligosaccharides |
| Fucosidosis | α-L-Fucosidase | Fucosyl Oligosaccharides |
| Aspartylglucosaminuria | N-Aspartyl-β-Glucosaminidase | Aspartylglucosamine Asparagines |
| Sialidosis (Mucolipidosis I) | α-Neuraminidase | Sialyloligosaccharides |
| Galactosialidosis (Goldberg Syndrome) | Lysosomal Protective Protein Deficiency | Sialyloligosaccharides |
| Schindler Disease | α-N-Acetyl-Galactosaminidase | |
| Mucolipidosis II (I-Cell Disease) | N-Acetylglucosamine-1-Phosphotransferase | Heparan Sulfate |
| Mucolipidosis III (Pseudo-Hurler Polydystrophy) | Same as ML II | |
| Cystinosis | Cystine Transport Protein | Free Cystine |
| Salla Disease | Sialic Acid Transport Protein | Free Sialic Acid and Glucuronic Acid |
| Infantile Sialic Acid Storage Disease | Sialic Acid Transport Protein | Free Sialic Acid and Glucuronic Acid |

TABLE 2-continued

| Disease Name | Enzyme Deficiency | Substance Stored |
|---|---|---|
| Infantile Neuronal Ceroid Lipofuscinosis | Palmitoyl-Protein Thioesterase | Lipofuscins |
| Mucolipidosis IV | Unknown | Gangliosides & Hyaluronic Acid |
| Prosaposin | Saposins A, B, C or D | |

Inventive methods according to the present invention may be used to deliver various other replacement enzymes. As used herein, replacement enzymes suitable for the present invention may include any enzyme that can act to replace at least partial activity of the deficient or missing lysosomal enzyme in a lysosomal storage disease to be treated. In some embodiments, a replacement enzyme is capable of reducing accumulated substance in lysosomes or that can rescue or ameliorate one or more lysosomal storage disease symptoms.

In some embodiments, a suitable replacement enzyme may be any lysosomal enzyme known to be associated with the lysosomal storage disease to be treated. In some embodiments, a suitable replacement enzyme is an enzyme selected from the enzyme listed in Table 2 above.

In some embodiments, a replacement enzyme suitable for the invention may have a wild-type or naturally occurring sequence. In some embodiments, a replacement enzyme suitable for the invention may have a modified sequence having substantial homology or identify to the wild-type or naturally-occurring sequence (e.g., having at least 50%, 55%, 60%, 65%, 70%, 75%, 80%, 85%, 90%, 95%, 98% sequence identity to the wild-type or naturally-occurring sequence).

A replacement enzyme suitable for the present invention may be produced by any available means. For example, replacement enzymes may be recombinantly produced by utilizing a host cell system engineered to express a replacement enzyme-encoding nucleic acid. Alternatively or additionally, replacement enzymes may be produced by activating endogenous genes. Alternatively or additionally, replacement enzymes may be partially or fully prepared by chemical synthesis. Alternatively or additionally, replacements enzymes may also be purified from natural sources.

Where enzymes are recombinantly produced, any expression system can be used. To give but a few examples, known expression systems include, for example, egg, baculovirus, plant, yeast, or mammalian cells.

In some embodiments, enzymes suitable for the present invention are produced in mammalian cells. Non-limiting examples of mammalian cells that may be used in accordance with the present invention include BALB/c mouse myeloma line (NSO/1, ECACC No: 85110503); human retinoblasts (PER.C6, CruCell, Leiden, The Netherlands); monkey kidney CV1 line transformed by SV40 (COS-7, ATCC CRL 1651); human embryonic kidney line (293 or 293 cells subcloned for growth in suspension culture, Graham et al., J. Gen Virol., 36:59, 1977); human fibrosarcoma cell line (e.g., HT1080); baby hamster kidney cells (BHK, ATCC CCL 10); Chinese hamster ovary cells +/−DHFR (CHO, Urlaub and Chasin, Proc. Natl. Acad. Sci. USA, 77:4216, 1980); mouse sertoli cells (TM4, Mather, Biol. Reprod., 23:243-251, 1980); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68, 1982); MRC 5 cells; FS4 cells; and a human hepatoma line (Hep G2).

In some embodiments, inventive methods according to the present invention are used to deliver replacement enzymes produced from human cells. In some embodiments, inventive methods according to the present invention are used to deliver replacement enzymes produced from CHO cells.

In some embodiments, replacement enzymes delivered using a method of the invention contain a moiety that binds to a receptor on the surface of brain cells to facilitate cellular uptake and/or lysosomal targeting. For example, such a receptor may be the cation-independent mannose-6-phosphate receptor (CI-MPR) which binds the mannose-6-phosphate (M6P) residues. In addition, the CI-MPR also binds other proteins including IGF-II. In some embodiments, a replacement enzyme suitable for the present invention contains M6P residues on the surface of the protein. In some embodiments, a replacement enzyme suitable for the present invention may contain bis-phosphorylated oligosaccharides which have higher binding affinity to the CI-MPR. In some embodiments, a suitable enzyme contains up to about an average of about at least 20% bis-phosphorylated oligosaccharides per enzyme. In other embodiments, a suitable enzyme may contain about 10%, 15%, 18%, 20%, 25%, 30%, 35%, 40%, 45%, 50%, 55%, 60% bis-phosphorylated oligosaccharides per enzyme. While such bis-phosphorylated oligosaccharides may be naturally present on the enzyme, it should be noted that the enzymes may be modified to possess such oligosaccharides. For example, suitable replacement enzymes may be modified by certain enzymes which are capable of catalyzing the transfer of N-acetylglucosamine-L-phosphate from UDP-GlcNAc to the 6' position of α-1,2-linked mannoses on lysosomal enzymes. Methods and compositions for producing and using such enzymes are described by, for example, Canfield et al. in U.S. Pat. Nos. 6,537,785, and 6,534,300, each incorporated herein by reference.

In some embodiments, replacement enzymes for use in the present invention may be conjugated or fused to a lysosomal targeting moiety that is capable of binding to a receptor on the surface of brain cells. A suitable lysosomal targeting moiety can be IGF-I, IGF-II, RAP, p97, and variants, homologues or fragments thereof (e.g., including those peptide having a sequence at least 70%, 75%, 80%, 85%, 90%, or 95% identical to a wild-type mature human IGF-I, IGF-II, RAP, p97 peptide sequence).

In some embodiments, replacement enzymes suitable for the present invention have not been modified to enhance delivery or transport of such agents across the BBB and into the CNS.

In some embodiments, a therapeutic protein includes a targeting moiety (e.g., a lysosome targeting sequence) and/or a membrane-penetrating peptide. In some embodiments, a targeting sequence and/or a membrane-penetrating peptide is an intrinsic part of the therapeutic moiety (e.g., via a chemical linkage, via a fusion protein). In some embodiments, a targeting sequence contains a mannose-6-phosphate moiety. In some embodiments, a targeting sequence contains an IGF-I moiety. In some embodiments, a targeting sequence contains an IGF-II moiety.

Formulations

In some embodiments, desired enzymes are delivered in stable formulations for intrathecal delivery. Certain embodiments of the invention are based, at least in part, on the discovery that various formulations disclosed herein facilitate the effective delivery and distribution of one or more therapeutic agents (e.g., an HNS enzyme) to targeted tissues, cells and/or organelles of the CNS. Among other things, formulations described herein are capable of solubilizing high concentrations of therapeutic agents (e.g., an HNS enzyme) and are suitable for the delivery of such therapeutic agents to the CNS of subjects for the treatment of diseases having a CNS component and/or etiology (e.g., Sanfilippo A Syndrome). The compositions described herein are further characterized by improved stability and improved tolerability when administered to the CNS of a subject (e.g., intrathecally) in need thereof.

Before the present invention, traditional unbuffered isotonic saline and Elliott's B solution, which is artificial CSF, were typically used for intrathecal delivery. A comparison depicting the compositions of CSF relative to Elliott's B solution is included in Table 3 below. As shown in Table 3, the concentration of Elliot's B Solution closely parallels that of the CSF. Elliott's B Solution, however contains a very low buffer concentration and accordingly may not provide the adequate buffering capacity needed to stabilize therapeutic agents (e.g., proteins), especially over extended periods of time (e.g., during storage conditions). Furthermore, Elliott's B Solution contains certain salts which may be incompatible with the formulations intended to deliver some therapeutic agents, and in particular proteins or enzymes. For example, the calcium salts present in Elliott's B Solution are capable of mediating protein precipitation and thereby reducing the stability of the formulation.

Stability of the therapeutic agent is of particular importance. Stability of the therapeutic agent may be further assessed relative to the biological activity or physiochemical integrity of the therapeutic agent over extended periods of time. For example, stability at a given time point may be compared against stability at an earlier time point (e.g., upon formulation day 0) or against unformulated therapeutic agent and the results of this comparison expressed as a percentage. Preferably, the pharmaceutical compositions of the present invention maintain at least 100%, at least 99%, at least 98%, at least 97% at least 95%, at least 90%, at least 85%, at least 80%, at least 75%, at least 70%, at least 65%, at least 60%, at least 55% or at least 50% of the therapeutic agent's biological activity or physiochemical integrity over an extended period of time (e.g., as measured over at least about 6-12 months, at room temperature or under accelerated storage conditions).

In some embodiments, therapeutic agents (e.g., desired enzymes) are soluble in formulations of the present invention. The term "soluble" as it relates to the therapeutic agents of the present invention refer to the ability of such therapeutic agents to form a homogenous solution. Preferably the solubility of the therapeutic agent in the solution into which it is administered and by which it is transported to the target site of action (e.g., the cells and tissues of the brain) is sufficient to permit the delivery of a therapeutically effective amount of the therapeutic agent to the targeted site of action. Several factors can impact the solubility of the therapeutic agents. For example, relevant factors which may impact protein solubility include ionic strength, amino acid sequence and the presence of other co-solubilizing agents or salts (e.g., calcium salts.) In some embodiments, the pharmaceutical compositions are formulated such that calcium salts are excluded from such compositions.

TABLE 3

| Solution | Na$^+$ mEq/L | K$^+$ mEq/L | Ca$^{++}$ mEq/L | Mg$^{++}$ mEq/L | HCO3$^-$ mEq/L | Cl$^-$ mEq/L | pH | Phosphorous mg/L | Glucose mg/L |
|---|---|---|---|---|---|---|---|---|---|
| CSF | 117-137 | 2.3 | 2.2 | 2.2 | 22.9 | 113-127 | 7.31 | 1.2-2.1 | 45-80 |
| Elliott's B Sol'n | 149 | 2.6 | 2.7 | 2.4 | 22.6 | 132 | 6.0-7.5 | 2.3 | 80 |

Thus, in some embodiments, formulations suitable for CNS delivery according to the present invention are not synthetic or artificial CSF.

In some embodiments, formulations for CNS delivery have been formulated such that they are capable of stabilizing, or alternatively slowing or preventing the degradation, of a therapeutic agent formulated therewith (e.g., an HNS enzyme). As used herein, the term "stable" refers to the ability of the therapeutic agent (e.g., an HNS enzyme) to maintain its therapeutic efficacy (e.g., all or the majority of its intended biological activity and/or physiochemical integrity) over extended periods of time. The stability of a therapeutic agent, and the capability of the pharmaceutical composition to maintain stability of such therapeutic agent, may be assessed over extended periods of time (e.g., preferably for at least 1, 3, 6, 12, 18, 24, 30, 36 months or more). In the context of a formulation a stable formulation is one in which the therapeutic agent therein essentially retains its physical and/or chemical integrity and biological activity upon storage and during processes (such as freeze/thaw, mechanical mixing and lyophilization). For protein stability, it can be measure by formation of high molecular weight (HMW) aggregates, loss of enzyme activity, generation of peptide fragments and shift of charge profiles.

Suitable formulations, in either aqueous, pre-lyophilized, lyophilized or reconstituted form, may contain a therapeutic agent of interest at various concentrations. In some embodiments, formulations may contain a protein or therapeutic agent of interest at a concentration in the range of about 0.1 mg/ml to 100 mg/ml (e.g., about 0.1 mg/ml to 80 mg/ml, about 0.1 mg/ml to 60 mg/ml, about 0.1 mg/ml to 50 mg/ml, about 0.1 mg/ml to 40 mg/ml, about 0.1 mg/ml to 30 mg/ml, about 0.1 mg/ml to 25 mg/ml, about 0.1 mg/ml to 20 mg/ml, about 0.1 mg/ml to 60 mg/ml, about 0.1 mg/ml to 50 mg/ml, about 0.1 mg/ml to 40 mg/ml, about 0.1 mg/ml to 30 mg/ml, about 0.1 mg/ml to 25 mg/ml, about 0.1 mg/ml to 20 mg/ml, about 0.1 mg/ml to 15 mg/ml, about 0.1 mg/ml to 10 mg/ml, about 0.1 mg/ml to 5 mg/ml, about 1 mg/ml to 10 mg/ml, about 1 mg/ml to 20 mg/ml, about 1 mg/ml to 40 mg/ml, about 5 mg/ml to 100 mg/ml, about 5 mg/ml to 50 mg/ml, or about 5 mg/ml to 25 mg/ml). In some embodiments, formulations according to the invention may contain a therapeutic agent at a concentration of approximately 1 mg/ml, 5 mg/ml, 10 mg/ml, 15 mg/ml, 20 mg/ml, 25 mg/ml, 30 mg/ml, 40 mg/ml, 50 mg/ml, 60 mg/ml, 70 mg/ml, 80 mg/ml, 90 mg/ml, or 100 mg/ml.

The formulations of the present invention are characterized by their tolerability either as aqueous solutions or as reconstituted lyophilized solutions. As used herein, the terms "tolerable" and "tolerability" refer to the ability of the pharmaceutical compositions of the present invention to not elicit an adverse reaction in the subject to whom such composition is administered, or alternatively not to elicit a serious adverse reaction in the subject to whom such composition is administered. In some embodiments, the pharmaceutical compositions of the present invention are well tolerated by the subject to whom such compositions is administered.

Many therapeutic agents, and in particular the proteins and enzymes of the present invention, require controlled pH and specific excipients to maintain their solubility and stability in the pharmaceutical compositions of the present invention. Table 4 below identifies typical exemplary aspects of protein formulations considered to maintain the solubility and stability of the protein therapeutic agents of the present invention.

TABLE 4

| Parameter | Typical Range/Type | Rationale |
|---|---|---|
| pH | 5 to 7.5 | For stability<br>Sometimes also for solubility |
| Buffer type | acetate, succinate, citrate, histidine, phosphate or Tris | To maintain optimal pH<br>May also affect stability |
| Buffer concentration | 5-50 mM | To maintain pH<br>May also stabilize or add ionic strength |
| Tonicifier | NaCl, sugars, mannitol | To render iso-osmotic or isotonic solutions |
| Surfactant | Polysorbate 20, polysorbate 80 | To stabilize against interfaces and shear |
| Other | Amino acids (e.g. arginine) at tens to hundreds of mM | For enhanced solubility or stability |

Buffers

The pH of the formulation is an additional factor which is capable of altering the solubility of a therapeutic agent (e.g., an enzyme or protein) in an aqueous formulation or for a pre-lyophilization formulation. Accordingly the formulations of the present invention preferably comprise one or more buffers. In some embodiments the aqueous formulations comprise an amount of buffer sufficient to maintain the optimal pH of said composition between about 4.0-8.0 (e.g., about 4.0, 4.5, 5.0, 5.5, 6.0, 6.2, 6.4, 6.5, 6.6, 6.8, 7.0, 7.5, or 8.0). In some embodiments, the pH of the formulation is between about 5.0-7.5, between about 5.5-7.0, between about 6.0-7.0, between about 5.5-6.0, between about 5.5-6.5, between about 5.0-6.0, between about 5.0-6.5 and between about 6.0-7.5. Suitable buffers include, for example acetate, citrate, histidine, phosphate, succinate, tris(hydroxymethyl) aminomethane ("Tris") and other organic acids. The buffer concentration and pH range of the pharmaceutical compositions of the present invention are factors in controlling or adjusting the tolerability of the formulation. In some embodiments, a buffering agent is present at a concentration ranging between about 1 mM to about 150 mM, or between about 10 mM to about 50 mM, or between about 15 mM to about 50 mM, or between about 20 mM to about 50 mM, or between about 25 mM to about 50 mM. In some embodiments, a suitable buffering agent is present at a concentration of approximately 1 mM, 5 mM, 10 mM, 15 mM, 20 mM, 25 mM, 30 mM, 35 mM, 40 mM, 45 mM 50 mM, 75 mM, 100 mM, 125 mM or 150 mM.

Tonicity

In some embodiments, formulations, in either aqueous, pre-lyophilized, lyophilized or reconstituted form, contain an isotonicity agent to keep the formulations isotonic. Typically, by "isotonic" is meant that the formulation of interest has essentially the same osmotic pressure as human blood. Isotonic formulations will generally have an osmotic pressure from about 240 mOsm/kg to about 350 mOsm/kg. Isotonicity can be measured using, for example, a vapor pressure or freezing point type osmometers. Exemplary isotonicity agents include, but are not limited to, glycine, sorbitol, mannitol, sodium chloride and arginine. In some embodiments, suitable isotonic agents may be present in aqueous and/or pre-lyophilized formulations at a concentration from about 0.01-5% (e.g., 0.05, 0.1, 0.15, 0.2, 0.3, 0.4, 0.5, 0.75, 1.0, 1.25, 1.5, 2.0, 2.5, 3.0, 4.0 or 5.0%) by weight. In some embodiments, formulations for lyophilization contain an isotonicity agent to keep the pre-lyophilization formulations or the reconstituted formulations isotonic.

While generally isotonic solutions are preferred for parenterally administered drugs, the use of isotonic solutions may change solubility for some therapeutic agents and in particular some proteins and/or enzymes. Slightly hypertonic solutions (e.g., up to 175 mM sodium chloride in 5 mM sodium phosphate at pH 7.0) and sugar-containing solutions (e.g., up to 2% sucrose in 5 mM sodium phosphate at pH 7.0) have been demonstrated to be well tolerated. The most common approved CNS bolus formulation composition is saline (about 150 mM NaCl in water).

Stabilizing Agents

In some embodiments, formulations may contain a stabilizing agent, or lyoprotectant, to protect the protein. Typically, a suitable stabilizing agent is a sugar, a non-reducing sugar and/or an amino acid. Exemplary sugars include, but are not limited to, dextran, lactose, mannitol, mannose, sorbitol, raffinose, sucrose and trehalose. Exemplary amino acids include, but are not limited to, arginine, glycine and methionine. Additional stabilizing agents may include sodium chloride, hydroxyethyl starch and polyvinylpyrolidone. The amount of stabilizing agent in the lyophilized formulation is generally such that the formulation will be isotonic. However, hypertonic reconstituted formulations may also be suitable. In addition, the amount of stabilizing agent must not be too low such that an unacceptable amount of degradation/aggregation of the therapeutic agent occurs. Exemplary stabilizing agent concentrations in the formulation may range from about 1 mM to about 400 mM (e.g., from about 30 mM to about 300 mM, and from about 50 mM to about 100 mM), or alternatively, from 0.1% to 15% (e.g., from 1% to 10%, from 5% to 15%, from 5% to 10%) by weight. In some embodiments, the ratio of the mass amount of the stabilizing agent and the therapeutic agent is about 1:1. In other embodiments, the ratio of the mass amount of the stabilizing agent and the therapeutic agent can be about 0.1:1, 0.2:1, 0.25:1, 0.4:1, 0.5:1, 1:1, 2:1, 2.6:1, 3:1, 4:1, 5:1, 10:1, or 20:1. In some embodiments, suitable for lyophilization, the stabilizing agent is also a lyoprotectant.

In some embodiments, liquid formulations suitable for the present invention contain amorphous materials. In some embodiments, liquid formulations suitable for the present invention contain a substantial amount of amorphous materials (e.g., sucrose-based formulations). In some embodiments, liquid formulations suitable for the present invention contain partly crystalline/partly amorphous materials.

Bulking Agents

In some embodiments, suitable formulations for lyophilization may further include one or more bulking agents. A "bulking agent" is a compound which adds mass to the lyophilized mixture and contributes to the physical structure of the lyophilized cake. For example, a bulking agent may improve the appearance of lyophilized cake (e.g., essentially uniform lyophilized cake). Suitable bulking agents include, but are not limited to, sodium chloride, lactose, mannitol, glycine, sucrose, trehalose, hydroxyethyl starch. Exemplary concentrations of bulking agents are from about 1% to about 10% (e.g., 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, and 10.0%).

Surfactants

In some embodiments, it is desirable to add a surfactant to formulations. Exemplary surfactants include nonionic surfactants such as Polysorbates (e.g., Polysorbates 20 or 80); poloxamers (e.g., poloxamer 188); Triton; sodium dodecyl sulfate (SDS); sodium laurel sulfate; sodium octyl glycoside; lauryl-, myristyl-, linoleyl-, or stearyl-sulfo-betaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g., lauroamidopropyl); myristamidopropyl-, palmidopropyl-, or isostearamidopropyl-dimethylamine; sodium methyl cocoyl-, or disodium methyl ofeyl-taurate; and the MONAQUAT™ series (Mona Industries, Inc., Paterson, N.J.), polyethyl glycol, polypropyl glycol, and copolymers of ethylene and propylene glycol (e.g., Pluronics, PF68, etc). Typically, the amount of surfactant added is such that it reduces aggregation of the protein and minimizes the formation of particulates or effervescences. For example, a surfactant may be present in a formulation at a concentration from about 0.001-0.5% (e.g., about 0.005-0.05%, or 0.005-0.01%). In particular, a surfactant may be present in a formulation at a concentration of approximately 0.005%, 0.01%, 0.02%, 0.1%, 0.2%, 0.3%, 0.4%, or 0.5%, etc. Alternatively, or in addition, the surfactant may be added to the lyophilized formulation, pre-lyophilized formulation and/or the reconstituted formulation.

Other pharmaceutically acceptable carriers, excipients or stabilizers such as those described in Remington's Pharmaceutical Sciences 16th edition, Osol, A. Ed. (1980) may be included in the formulation (and/or the lyophilized formulation and/or the reconstituted formulation) provided that they do not adversely affect the desired characteristics of the formulation. Acceptable carriers, excipients or stabilizers are nontoxic to recipients at the dosages and concentrations employed and include, but are not limited to, additional buffering agents; preservatives; co-solvents; antioxidants including ascorbic acid and methionine; chelating agents such as EDTA; metal complexes (e.g., Zn-protein complexes); biodegradable polymers such as polyesters; and/or salt-forming counterions such as sodium.

Formulations, in either aqueous, pre-lyophilized, lyophilized or reconstituted form, in accordance with the present invention can be assessed based on product quality analysis, reconstitution time (if lyophilized), quality of reconstitution (if lyophilized), high molecular weight, moisture, and glass transition temperature. Typically, protein quality and product analysis include product degradation rate analysis using methods including, but not limited to, size exclusion HPLC (SE-HPLC), cation exchange-HPLC (CEX-HPLC), X-ray diffraction (XRD), modulated differential scanning calorimetry (mDSC), reversed phase HPLC (RP-HPLC), multi-angle light scattering (MALS), fluorescence, ultraviolet absorption, nephelometry, capillary electrophoresis (CE), SDS-PAGE, and combinations thereof. In some embodiments, evaluation of product in accordance with the present invention may include a step of evaluating appearance (either liquid or cake appearance).

Generally, formulations (lyophilized or aqueous) can be stored for extended periods of time at room temperature. Storage temperature may typically range from 0° C. to 45° C. (e.g., 4° C., 20° C., 25° C., 45° C. etc.). Formulations may be stored for a period of months to a period of years. Storage time generally will be 24 months, 12 months, 6 months, 4.5 months, 3 months, 2 months or 1 month. Formulations can be stored directly in the container used for administration, eliminating transfer steps.

Formulations can be stored directly in the lyophilization container (if lyophilized), which may also function as the reconstitution vessel, eliminating transfer steps. Alternatively, lyophilized product formulations may be measured into smaller increments for storage. Storage should generally avoid circumstances that lead to degradation of the proteins, including but not limited to exposure to sunlight, UV radiation, other forms of electromagnetic radiation, excessive heat or cold, rapid thermal shock, and mechanical shock.

Lyophilization

Inventive methods in accordance with the present invention can be utilized to lyophilize any materials, in particular, therapeutic agents. Typically, a pre-lyophilization formulation further contains an appropriate choice of excipients or other components such as stabilizers, buffering agents, bulking agents, and surfactants to prevent compound of interest from degradation (e.g., protein aggregation, deamidation, and/or oxidation) during freeze-drying and storage. The formulation for lyophilization can include one or more additional ingredients including lyoprotectants or stabilizing agents, buffers, bulking agents, isotonicity agents and surfactants.

After the substance of interest and any additional components are mixed together, the formulation is lyophilized. Lyophilization generally includes three main stages: freezing, primary drying and secondary drying. Freezing is necessary to convert water to ice or some amorphous formulation components to the crystalline form. Primary drying is the process step when ice is removed from the frozen product by direct sublimation at low pressure and temperature. Secondary drying is the process step when bounded water is removed from the product matrix utilizing the diffusion of residual water to the evaporation surface. Product temperature during secondary drying is normally higher than during primary drying. See, Tang X. et al. (2004) "Design of freeze-drying processes for pharmaceuticals: Practical advice," *Pharm. Res.*, 21:191-200; Nail S. L. et al. (2002) "Fundamentals of freeze-drying," in Development and manufacture of protein pharmaceuticals. Nail S. L. editor New York: Kluwer Academic/Plenum Publishers, pp 281-353; Wang et al. (2000) "Lyophilization and development of solid protein pharmaceuticals," *Int. J. Pharm.*, 203:1-60; Williams N. A. et al. (1984) "The lyophilization of pharmaceuticals; A literature review." *J. Parenteral Sci. Technol.*, 38:48-59. Generally, any lyophilization process can be used in connection with the present invention.

In some embodiments, an annealing step may be introduced during the initial freezing of the product. The annealing step may reduce the overall cycle time. Without wishing to be bound by any theories, it is contemplated that the annealing step can help promote excipient crystallization and formation of larger ice crystals due to re-crystallization of small crystals formed during supercooling, which, in turn, improves reconstitution. Typically, an annealing step includes an interval or oscillation in the temperature during freezing. For example, the freeze temperature may be −40° C., and the annealing step will increase the temperature to, for example, −10° C. and maintain this temperature for a set period of time. The annealing step time may range from 0.5 hours to 8 hours (e.g., 0.5, 1.0 1.5, 2.0, 2.5, 3, 4, 6, and 8 hours). The annealing temperature may be between the freezing temperature and 0° C.

Lyophilization may be performed in a container, such as a tube, a bag, a bottle, a tray, a vial (e.g., a glass vial), syringe or any other suitable containers. The containers may be disposable. Lyophilization may also be performed in a large scale or small scale. In some instances, it may be desirable to lyophilize the protein formulation in the container in which reconstitution of the protein is to be carried out in order to avoid a transfer step. The container in this instance may, for example, be a 3, 4, 5, 10, 20, 50 or 100 cc vial.

Many different freeze-dryers are available for this purpose such as Hull pilot scale dryer (SP Industries, USA), Genesis (SP Industries) laboratory freeze-dryers, or any freeze-dryers capable of controlling the given lyophilization process parameters. Freeze-drying is accomplished by freezing the formulation and subsequently subliming ice from the frozen content at a temperature suitable for primary drying. Initial freezing brings the formulation to a temperature below about −20° C. (e.g., −50° C., −45° C., −40° C., −35° C., −30° C., −25° C., etc.) in typically not more than about 4 hours (e.g., not more than about 3 hours, not more than about 2.5 hours, not more than about 2 hours). Under this condition, the product temperature is typically below the eutectic point or the collapse temperature of the formulation. Typically, the shelf temperature for the primary drying will range from about −30 to 25° C. (provided the product remains below the melting point during primary drying) at a suitable pressure, ranging typically from about 20 to 250 mTorr. The formulation, size and type of the container holding the sample (e.g., glass vial) and the volume of liquid will mainly dictate the time required for drying, which can range from a few hours to several days. A secondary drying stage is carried out at about 0-60° C., depending primarily on the type and size of container and the type of therapeutic agent employed. Again, volume of liquid will mainly dictate the time required for drying, which can range from a few hours to several days.

As a general proposition, lyophilization will result in a lyophilized formulation in which the moisture content thereof is less than about 5%, less than about 4%, less than about 3%, less than about 2%, less than about 1%, and less than about 0.5%.

Reconstitution

While the pharmaceutical compositions of the present invention are generally in an aqueous form upon administration to a subject, in some embodiments the pharmaceutical compositions of the present invention are lyophilized. Such compositions must be reconstituted by adding one or more diluents thereto prior to administration to a subject. At the desired stage, typically at an appropriate time prior to administration to the patient, the lyophilized formulation may be reconstituted with a diluent such that the protein concentration in the reconstituted formulation is desirable.

Various diluents may be used in accordance with the present invention. In some embodiments, a suitable diluent for reconstitution is water. The water used as the diluent can be treated in a variety of ways including reverse osmosis, distillation, deionization, filtrations (e.g., activated carbon, microfiltration, nanofiltration) and combinations of these treatment methods. In general, the water should be suitable for injection including, but not limited to, sterile water or bacteriostatic water for injection.

Additional exemplary diluents include a pH buffered solution (e.g., phosphate-buffered saline), sterile saline solution, Elliot's solution, Ringer's solution or dextrose solution. Suitable diluents may optionally contain a preservative. Exemplary preservatives include aromatic alcohols such as benzyl or phenol alcohol. The amount of preservative employed is determined by assessing different preservative concentrations for compatibility with the protein and preservative efficacy testing. For example, if the preservative is an aromatic alcohol (such as benzyl alcohol), it can be present in an amount from about 0.1-2.0%, from about 0.5-1.5%, or about 1.0-1.2%.

Diluents suitable for the invention may include a variety of additives, including, but not limited to, pH buffering agents, (e.g. Tris, histidine) salts (e.g., sodium chloride) and other additives (e.g., sucrose) including those described above (e.g. stabilizing agents, isotonicity agents).

According to the present invention, a lyophilized substance (e.g., protein) can be reconstituted to a concentration of at least 25 mg/ml (e.g., at least 50 mg/ml, at least 75 mg/ml, at least 100 mg/) and in any ranges therebetween. In some embodiments, a lyophilized substance (e.g., protein) may be reconstituted to a concentration ranging from about 1 mg/ml to 100 mg/ml (e.g., from about 1 mg/ml to 50 mg/ml, from 1 mg/ml to 100 mg/ml, from about 1 mg/ml to about 5 mg/ml, from about 1 mg/ml to about 10 mg/ml, from about 1 mg/ml to about 25 mg/ml, from about 1 mg/ml to about 75 mg/ml, from about 10 mg/ml to about 30 mg/ml, from about 10 mg/ml to about 50 mg/ml, from about 10 mg/ml to about 75 mg/ml, from about 10 mg/ml to about 100 mg/ml, from about 25 mg/ml to about 50 mg/ml, from about 25 mg/ml to about 75 mg/ml, from about 25 mg/ml to about 100 mg/ml, from about 50 mg/ml to about 75 mg/ml, from about 50 mg/ml to about 100 mg/ml). In some embodiments, the concentration of protein in the reconstituted formulation may be higher than the concentration in the pre-lyophilization formulation. High protein concentrations in the reconstituted formulation are considered to be particularly useful where subcutaneous or intramuscular delivery of the reconstituted formulation is intended. In some embodiments, the protein concentration in the reconstituted formulation may be about 2-50 times (e.g., about 2-20, about 2-10 times, or about 2-5 times) of the pre-lyophilized formulation. In some embodiments, the protein concentration in the reconstituted formulation may be at least about 2 times (e.g., at least about 3, 4, 5, 10, 20, 40 times) of the pre-lyophilized formulation.

Reconstitution according to the present invention may be performed in any container. Exemplary containers suitable for the invention include, but are not limited to, such as tubes, vials, syringes (e.g., single-chamber or dual-chamber), bags, bottles, and trays. Suitable containers may be made of any materials such as glass, plastics, metal. The containers may be disposable or reusable. Reconstitution may also be performed in a large scale or small scale.

In some instances, it may be desirable to lyophilize the protein formulation in the container in which reconstitution of the protein is to be carried out in order to avoid a transfer step. The container in this instance may, for example, be a 3, 4, 5, 10, 20, 50 or 100 cc vial. In some embodiments, a suitable container for lyophilization and reconstitution is a dual chamber syringe (e.g., Lyo-Ject,® (Vetter) syringes). For example, a dual chamber syringe may contain both the lyophilized substance and the diluent, each in a separate chamber, separated by a stopper (see Example 5). To reconstitute, a plunger can be attached to the stopper at the diluent side and pressed to move diluent into the product chamber so that the diluent can contact the lyophilized substance and reconstitution may take place as described herein (see Example 5).

The pharmaceutical compositions, formulations and related methods of the invention are useful for delivering a variety of therapeutic agents to the CNS of a subject (e.g., intrathecally, intraventricularly or intracisternally) and for the treatment of the associated diseases. The pharmaceutical compositions of the present invention are particularly useful for delivering proteins and enzymes (e.g., enzyme replacement therapy) to subjects suffering from lysosomal storage disorders. The lysosomal storage diseases represent a group of relatively rare inherited metabolic disorders that result from defects in lysosomal function. The lysosomal diseases are characterized by the accumulation of undigested macromolecules within the lysosomes, which results in an increase in the size and number of such lysosomes and ultimately in cellular dysfunction and clinical abnormalities.

CNS Delivery

It is contemplated that various stable formulations described herein are generally suitable for CNS delivery of therapeutic agents. Stable formulations according to the present invention can be used for CNS delivery via various techniques and routes including, but not limited to, intraparenchymal, intracerebral, intravetricular cerebral (ICV), intrathecal (e.g., IT-Lumbar, IT-cisterna magna) administrations and any other techniques and routes for injection directly or indirectly to the CNS and/or CSF.

Intrathecal Delivery

In some embodiments, a replacement enzyme is delivered to the CNS in a formulation described herein. In some embodiments, a replacement enzyme is delivered to the CNS by administering into the cerebrospinal fluid (CSF) of a subject in need of treatment. In some embodiments, intrathecal administration is used to deliver a desired replacement enzyme (e.g., an HNS protein) into the CSF. As used herein, intrathecal administration (also referred to as intrathecal injection) refers to an injection into the spinal canal (intrathecal space surrounding the spinal cord). Various techniques may be used including, without limitation, lateral cerebroventricular injection through a burrhole or cisternal or lumbar puncture or the like. Exemplary methods are described in Lazorthes et al. Advances in Drug Delivery Systems and Applications in Neurosurgery, 143-192 and Omaya et al., Cancer Drug Delivery, 1: 169-179, the contents of which are incorporated herein by reference.

According to the present invention, an enzyme may be injected at any region surrounding the spinal canal. In some embodiments, an enzyme is injected into the lumbar area or the cisterna magna or intraventricularly into a cerebral ventricle space. As used herein, the term "lumbar region" or "lumbar area" refers to the area between the third and fourth lumbar (lower back) vertebrae and, more inclusively, the L2-S1 region of the spine. Typically, intrathecal injection via the lumbar region or lumber area is also referred to as "lumbar IT delivery" or "lumbar IT administration." The term "cisterna magna" refers to the space around and below the cerebellum via the opening between the skull and the top of the spine. Typically, intrathecal injection via cisterna magna is also referred to as "cisterna magna delivery." The term "cerebral ventricle" refers to the cavities in the brain that are continuous with the central canal of the spinal cord. Typically, injections via the cerebral ventricle cavities are referred to as intravetricular Cerebral (ICV) delivery.

In some embodiments, "intrathecal administration" or "intrathecal delivery" according to the present invention refers to lumbar IT administration or delivery, for example, delivered between the third and fourth lumbar (lower back) vertebrae and, more inclusively, the L2-S1 region of the spine. It is contemplated that lumbar IT administration or delivery distinguishes over cisterna magna delivery in that lumbar IT administration or delivery according to our invention provides better and more effective delivery to the distal spinal canal, while cisterna magna delivery, among other things, typically does not deliver well to the distal spinal canal.

Device for Intrathecal Delivery

Figure 36:
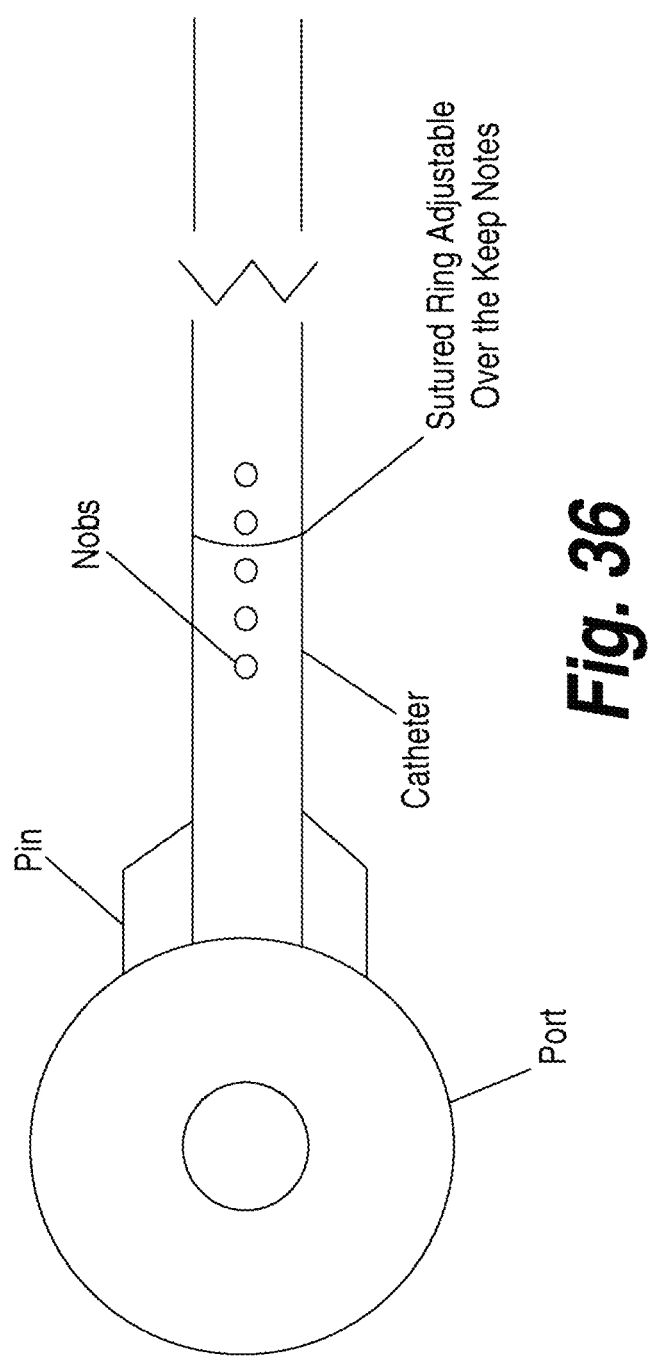
FIG. 36 illustrates an exemplary diagram of an intrathecal drug delivery device (IDDD) with a securing mechanism.
Figure 37A:
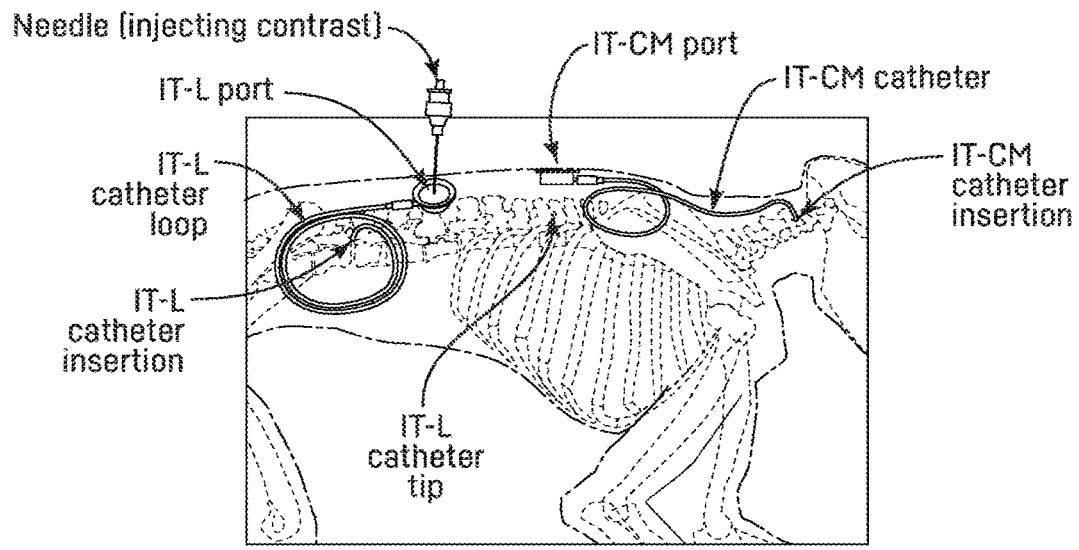
FIG. 37A depicts exemplary locations within a patient's body where an IDDD may be placed.
Figure 37B:
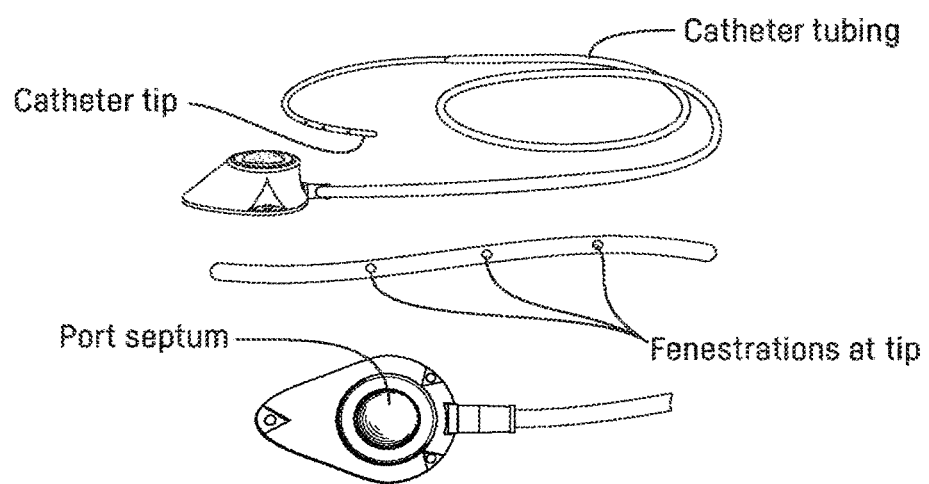
FIG. 37B depicts various components of an intrathecal drug delivery device (IDDD)
Figure 37C:
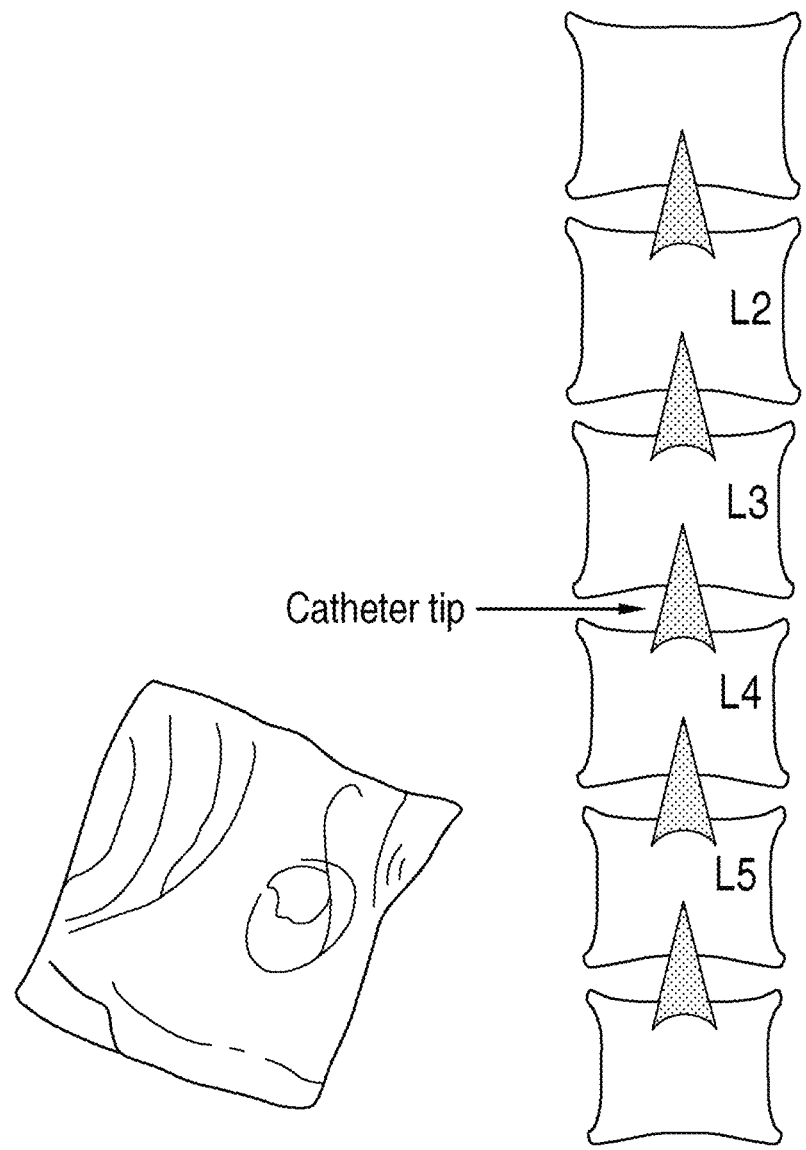
FIG. 37C depicts an exemplary insertion location within a patient's body for IT-lumbar injection.

Various devices may be used for intrathecal delivery according to the present invention. In some embodiments, a device for intrathecal administration contains a fluid access port (e.g., injectable port); a hollow body (e.g., catheter) having a first flow orifice in fluid communication with the fluid access port and a second flow orifice configured for insertion into spinal cord; and a securing mechanism for securing the insertion of the hollow body in the spinal cord. As a non-limiting example shown in FIG. 36, a suitable securing mechanism contains one or more nobs mounted on the surface of the hollow body and a sutured ring adjustable over the one or more nobs to prevent the hollow body (e.g., catheter) from slipping out of the spinal cord. In various embodiments, the fluid access port comprises a reservoir. In some embodiments, the fluid access port comprises a mechanical pump (e.g., an infusion pump). In some embodiments, an implanted catheter is connected to either a reservoir (e.g., for bolus delivery), or an infusion pump. The fluid access port may be implanted or external In some embodiments, intrathecal administration may be performed by either lumbar puncture (i.e., slow bolus) or via a port-catheter delivery system (i.e., infusion or bolus). In some embodiments, the catheter is inserted between the laminae of the lumbar vertebrae and the tip is threaded up the thecal space to the desired level (generally L3-L4) (FIG. 37A-C).

Relative to intravenous administration, a single dose volume suitable for intrathecal administration is typically small. Typically, intrathecal delivery according to the present invention maintains the balance of the composition of the CSF as well as the intracranial pressure of the subject. In some embodiments, intrathecal delivery is performed absent the corresponding removal of CSF from a subject. In some embodiments, a suitable single dose volume may be e.g., less than about 10 ml, 8 ml, 6 ml, 5 ml, 4 ml, 3 ml, 2 ml, 1.5 ml, 1 ml, or 0.5 ml. In some embodiments, a suitable single dose volume may be about 0.5-5 ml, 0.5-4 ml, 0.5-3 ml, 0.5-2 ml, 0.5-1 ml, 1-3 ml, 1-5 ml, 1.5-3 ml, 1-4 ml, or 0.5-1.5 ml. In some embodiments, intrathecal delivery according to the present invention involves a step of removing a desired amount of CSF first. In some embodiments, less than about 10 ml (e.g., less than about 9 ml, 8 ml, 7 ml, 6 ml, 5 ml, 4 ml, 3 ml, 2 ml, 1 ml) of CSF is first removed before IT administration. In those cases, a suitable single dose volume may be e.g., more than about 3 ml, 4 ml, 5 ml, 6 ml, 7 ml, 8 ml, 9 ml, 10 ml, 15 ml, or 20 ml.

Various other devices may be used to effect intrathecal administration of a therapeutic composition. For example, formulations containing desired enzymes may be given using an Ommaya reservoir which is in common use for intrathecally administering drugs for meningeal carcinomatosis (Lancet 2: 983-84, 1963). More specifically, in this method, a ventricular tube is inserted through a hole formed in the anterior horn and is connected to an Ommaya reservoir installed under the scalp, and the reservoir is subcutaneously punctured to intrathecally deliver the particular enzyme being replaced, which is injected into the reservoir.

Other devices for intrathecal administration of therapeutic compositions or formulations to an individual are described in U.S. Pat. No. 6,217,552, incorporated herein by reference. Alternatively, the drug may be intrathecally given, for example, by a single injection, or continuous infusion. It should be understood that the dosage treatment may be in the form of a single dose administration or multiple doses.

For injection, formulations of the invention can be formulated in liquid solutions. In addition, the enzyme may be formulated in solid form and re-dissolved or suspended immediately prior to use. Lyophilized forms are also included. The injection can be, for example, in the form of a bolus injection or continuous infusion (e.g., using infusion pumps) of the enzyme.

In one embodiment of the invention, the enzyme is administered by lateral cerebro ventricular injection into the brain of a subject. The injection can be made, for example, through a burr hole made in the subject's skull. In another embodiment, the enzyme and/or other pharmaceutical formulation is administered through a surgically inserted shunt into the cerebral ventricle of a subject. For example, the injection can be made into the lateral ventricles, which are larger. In some embodiments, injection into the third and fourth smaller ventricles can also be made.

In yet another embodiment, the pharmaceutical compositions used in the present invention are administered by injection into the cisterna magna, or lumbar area of a subject.

In another embodiment of the method of the invention, the pharmaceutically acceptable formulation provides sustained delivery, e.g., "slow release" of the enzyme or other pharmaceutical composition used in the present invention, to a subject for at least one, two, three, four weeks or longer periods of time after the pharmaceutically acceptable formulation is administered to the subject.

As used herein, the term "sustained delivery" refers to continual delivery of a pharmaceutical formulation of the invention in vivo over a period of time following administration, preferably at least several days, a week or several weeks. Sustained delivery of the composition can be demonstrated by, for example, the continued therapeutic effect of the enzyme over time (e.g., sustained delivery of the enzyme can be demonstrated by continued reduced amount of storage granules in the subject). Alternatively, sustained delivery of the enzyme may be demonstrated by detecting the presence of the enzyme in vivo over time.

Delivery to Target Tissues

As discussed above, one of the surprising and important features of the present invention is that therapeutic agents, in particular, replacement enzymes administered using inventive methods and compositions of the present invention are able to effectively and extensively diffuse across the brain surface and penetrate various layers or regions of the brain, including deep brain regions. In addition, inventive methods and compositions of the present invention effectively deliver therapeutic agents (e.g., an HNS enzyme) to various tissues, neurons or cells of spinal cord, including the lumbar region, which is hard to target by existing CNS delivery methods such as ICV injection. Furthermore, inventive methods and compositions of the present invention deliver sufficient amount of therapeutic agents (e.g., an HNS enzyme) to blood stream and various peripheral organs and tissues.

Thus, in some embodiments, a therapeutic protein (e.g., an HNS enzyme) is delivered to the central nervous system of a subject. In some embodiments, a therapeutic protein (e.g., an HNS enzyme) is delivered to one or more of target tissues of brain, spinal cord, and/or peripheral organs. As used herein, the term "target tissues" refers to any tissue that is affected by the lysosomal storage disease to be treated or any tissue in which the deficient lysosomal enzyme is normally expressed. In some embodiments, target tissues include those tissues in which there is a detectable or abnormally high amount of enzyme substrate, for example stored in the cellular lysosomes of the tissue, in patients suffering from or susceptible to the lysosomal storage disease. In some embodiments, target tissues include those tissues that display disease-associated pathology, symptom, or feature. In some embodiments, target tissues include those tissues in which the deficient lysosomal enzyme is normally expressed at an elevated level. As used herein, a target tissue may be a brain target tissue, a spinal cord target tissue and/or a peripheral target tissue. Exemplary target tissues are described in detail below.

Brain Target Tissues

In general, the brain can be divided into different regions, layers and tissues. For example, meningeal tissue is a system of membranes which envelops the central nervous system, including the brain. The meninges contain three layers, including dura matter, arachnoid matter, and pia matter. In general, the primary function of the meninges and of the cerebrospinal fluid is to protect the central nervous system. In some embodiments, a therapeutic protein in accordance with the present invention is delivered to one or more layers of the meninges.

The brain has three primary subdivisions, including the cerebrum, cerebellum, and brain stem. The cerebral hemispheres, which are situated above most other brain structures and are covered with a cortical layer. Underneath the cerebrum lies the brainstem, which resembles a stalk on which the cerebrum is attached. At the rear of the brain, beneath the cerebrum and behind the brainstem, is the cerebellum.

The diencephalon, which is located near the midline of the brain and above the mesencephalon, contains the thalamus, metathalamus, hypothalamus, epithalamus, prethalamus, and pretectum. The mesencephalon, also called the midbrain, contains the tectum, tegumentum, ventricular mesocoelia, and cerebral peduncels, the red nucleus, and the cranial nerve III nucleus. The mesencephalon is associated with vision, hearing, motor control, sleep/wake, alertness, and temperature regulation.

Regions of tissues of the central nervous system, including the brain, can be characterized based on the depth of the tissues. For example, CNS (e.g., brain) tissues can be characterized as surface or shallow tissues, mid-depth tissues, and/or deep tissues.

According to the present invention, a therapeutic protein (e.g., a replacement enzyme) may be delivered to any appropriate brain target tissue(s) associated with a particular disease to be treated in a subject. In some embodiments, a therapeutic protein (e.g., a replacement enzyme) in accordance with the present invention is delivered to surface or shallow brain target tissue. In some embodiments, a therapeutic protein in accordance with the present invention is delivered to mid-depth brain target tissue. In some embodiments, a therapeutic protein in accordance with the present invention is delivered to deep brain target tissue. In some embodiments, a therapeutic protein in accordance with the present invention is delivered to a combination of surface or shallow brain target tissue, mid-depth brain target tissue, and/or deep brain target tissue. In some embodiments, a therapeutic protein in accordance with the present invention is delivered to a deep brain tissue at least 4 mm, 5 mm, 6 mm, 7 mm, 8 mm, 9 mm, 10 mm or more below (or internal to) the external surface of the brain.

In some embodiments, therapeutic agents (e.g., enzymes) are delivered to one or more surface or shallow tissues of cerebrum. In some embodiments, the targeted surface or shallow tissues of the cerebrum are located within 4 mm from the surface of the cerebrum. In some embodiments, the targeted surface or shallow tissues of the cerebrum are selected from pia mater tissues, cerebral cortical ribbon tissues, hippocampus, Virchow Robin space, blood vessels within the VR space, the hippocampus, portions of the hypothalamus on the inferior surface of the brain, the optic nerves and tracts, the olfactory bulb and projections, and combinations thereof.

In some embodiments, therapeutic agents (e.g., enzymes) are delivered to one or more deep tissues of the cerebrum. In some embodiments, the targeted surface or shallow tissues of the cerebrum are located 4 mm (e.g., 5 mm, 6 mm, 7 mm, 8 mm, 9 mm, or 10 mm) below (or internal to) the surface of the cerebrum. In some embodiments, targeted deep tissues of the cerebrum include the cerebral cortical ribbon. In some embodiments, targeted deep tissues of the cerebrum include one or more of the diencephalon (e.g., the hypothalamus, thalamus, prethalamus, subthalamus, etc.), metencephalon, lentiform nuclei, the basal ganglia, caudate, putamen, amygdala, globus pallidus, and combinations thereof.

In some embodiments, therapeutic agents (e.g., enzymes) are delivered to one or more tissues of the cerebellum. In certain embodiments, the targeted one or more tissues of the cerebellum are selected from the group consisting of tissues of the molecular layer, tissues of the Purkinje cell layer, tissues of the Granular cell layer, cerebellar peduncles, and combination thereof. In some embodiments, therapeutic agents (e.g., enzymes) are delivered to one or more deep tissues of the cerebellum including, but not limited to, tissues of the Purkinje cell layer, tissues of the Granular cell layer, deep cerebellar white matter tissue (e.g., deep relative to the Granular cell layer), and deep cerebellar nuclei tissue.

In some embodiments, therapeutic agents (e.g., enzymes) are delivered to one or more tissues of the brainstem. In some embodiments, the targeted one or more tissues of the brainstem include brain stem white matter tissue and/or brain stem nuclei tissue.

In some embodiments, therapeutic agents (e.g., enzymes) are delivered to various brain tissues including, but not limited to, gray matter, white matter, periventricular areas, pia-arachnoid, meninges, neocortex, cerebellum, deep tissues in cerebral cortex, molecular layer, caudate/putamen region, midbrain, deep regions of the pons or medulla, and combinations thereof.

In some embodiments, therapeutic agents (e.g., enzymes) are delivered to various cells in the brain including, but not limited to, neurons, glial cells, perivascular cells and/or meningeal cells. In some embodiments, a therapeutic protein is delivered to oligodendrocytes of deep white matter.

Spinal Cord

In general, regions or tissues of the spinal cord can be characterized based on the depth of the tissues. For example, spinal cord tissues can be characterized as surface or shallow tissues, mid-depth tissues, and/or deep tissues.

In some embodiments, therapeutic agents (e.g., enzymes) are delivered to one or more surface or shallow tissues of the spinal cord. In some embodiments, a targeted surface or shallow tissue of the spinal cord is located within 4 mm from the surface of the spinal cord. In some embodiments, a targeted surface or shallow tissue of the spinal cord contains pia matter and/or the tracts of white matter.

In some embodiments, therapeutic agents (e.g., enzymes) are delivered to one or more deep tissues of the spinal cord. In some embodiments, a targeted deep tissue of the spinal cord is located internal to 4 mm from the surface of the spinal cord. In some embodiments, a targeted deep tissue of the spinal cord contains spinal cord grey matter and/or ependymal cells.

In some embodiments, therapeutic agents (e.g., enzymes) are delivered to neurons of the spinal cord.

Peripheral Target Tissues

As used herein, peripheral organs or tissues refer to any organs or tissues that are not part of the central nervous system (CNS). Peripheral target tissues may include, but are not limited to, blood system, liver, kidney, heart, endothelium, bone marrow and bone marrow derived cells, spleen, lung, lymph node, bone, cartilage, ovary and testis. In some embodiments, a therapeutic protein (e.g., a replacement enzyme) in accordance with the present invention is delivered to one or more of the peripheral target tissues.

Biodistribution and Bioavailability

In various embodiments, once delivered to the target tissue, a therapeutic agent (e.g., an HNS enzyme) is localized intracellularly. For example, a therapeutic agent (e.g., enzyme) may be localized to exons, axons, lysosomes, mitochondria or vacuoles of a target cell (e.g., neurons such as Purkinje cells). For example, in some embodiments intrathecally-administered enzymes demonstrate translocation dynamics such that the enzyme moves within the perivascular space (e.g., by pulsation-assisted convective mechanisms). In addition, active axonal transport mechanisms relating to the association of the administered protein or enzyme with neurofilaments may also contribute to or otherwise facilitate the distribution of intrathecally-administered proteins or enzymes into the deeper tissues of the central nervous system.

In some embodiments, a therapeutic agent (e.g., an HNS enzyme) delivered according to the present invention may achieve therapeutically or clinically effective levels or activities in various targets tissues described herein. As used herein, a therapeutically or clinically effective level or activity is a level or activity sufficient to confer a therapeutic effect in a target tissue. The therapeutic effect may be objective (i.e., measurable by some test or marker) or subjective (i.e., subject gives an indication of or feels an effect). For example, a therapeutically or clinically effective level or activity may be an enzymatic level or activity that is sufficient to ameliorate symptoms associated with the disease in the target tissue (e.g., GAG storage).

In some embodiments, a therapeutic agent (e.g., a replacement enzyme) delivered according to the present invention may achieve an enzymatic level or activity that is at least 5%, 10%, 20%, 30%, 40%, 50%, 60%, 70%, 80%, 90%, 95% of the normal level or activity of the corresponding lysosomal enzyme in the target tissue. In some embodiments, a therapeutic agent (e.g., a replacement enzyme) delivered according to the present invention may achieve an enzymatic level or activity that is increased by at least 1-fold, 2-fold, 3-fold, 4-fold, 5-fold, 6-fold, 7-fold, 8-fold, 9-fold or 10-fold as compared to a control (e.g., endogenous levels or activities without the treatment). In some embodiments, a therapeutic agent (e.g., a replacement enzyme) delivered according to the present invention may achieve an increased enzymatic level or activity at least approximately 10 nmol/hr/mg, 20 nmol/hr/mg, 40 nmol/hr/mg, 50 nmol/hr/mg, 60 nmol/hr/mg, 70 nmol/hr/mg, 80 nmol/hr/mg, 90 nmol/hr/mg, 100 nmol/hr/mg, 150 nmol/hr/mg, 200 nmol/hr/mg, 250 nmol/hr/mg, 300 nmol/hr/mg, 350 nmol/hr/mg, 400 nmol/hr/mg, 450 nmol/hr/mg, 500 nmol/hr/mg, 550 nmol/hr/mg or 600 nmol/hr/mg in a target tissue.

In some embodiments, inventive methods according to the present invention are particularly useful for targeting the lumbar region. In some embodiments, a therapeutic agent (e.g., a replacement enzyme) delivered according to the present invention may achieve an increased enzymatic level or activity in the lumbar region of at least approximately 500 nmol/hr/mg, 600 nmol/hr/mg, 700 nmol/hr/mg, 800 nmol/hr/mg, 900 nmol/hr/mg, 1000 nmol/hr/mg, 1500 nmol/hr/mg, 2000 nmol/hr/mg, 3000 nmol/hr/mg, 4000 nmol/hr/mg, 5000 nmol/hr/mg, 6000 nmol/hr/mg, 7000 nmol/hr/mg, 8000 nmol/hr/mg, 9000 nmol/hr/mg, or 10,000 nmol/hr/mg.

In general, therapeutic agents (e.g., replacement enzymes) delivered according to the present invention have sufficiently long half time in CSF and target tissues of the brain, spinal cord, and peripheral organs. In some embodiments, a therapeutic agent (e.g., a replacement enzyme) delivered according to the present invention may have a half-life of at least approximately 30 minutes, 45 minutes, 60 minutes, 90 minutes, 2 hours, 3 hours, 4 hours, 5 hours, 6 hours, 7 hours, 8 hours, 9 hours, 10 hours, 12 hours, 16 hours, 18 hours, 20 hours, 25 hours, 30 hours, 35 hours, 40 hours, up to 3 days, up to 7 days, up to 14 days, up to 21 days or up to a month. In some embodiments, In some embodiments, a therapeutic agent (e.g., a replacement enzyme) delivered according to the present invention may retain detectable level or activity in CSF or bloodstream after 12 hours, 24 hours, 30 hours, 36 hours, 42 hours, 48 hours, 54 hours, 60 hours, 66 hours, 72 hours, 78 hours, 84 hours, 90 hours, 96 hours, 102 hours, or a week following administration. Detectable level or activity may be determined using various methods known in the art.

In certain embodiments, a therapeutic agent (e.g., a replacement enzyme) delivered according to the present invention achieves a concentration of at least 30 µg/ml in the CNS tissues and cells of the subject following administration (e.g., one week, 3 days, 48 hours, 36 hours, 24 hours, 18 hours, 12 hours, 8 hours, 6 hours, 4 hours, 3 hours, 2 hours, 1 hour, 30 minutes, or less, following intrathecal administration of the pharmaceutical composition to the subject). In certain embodiments, a therapeutic agent (e.g., a replacement enzyme) delivered according to the present invention achieves a concentration of at least 20 µg/ml, at least 15 µg/ml, at least 10 µg/ml, at least 7.5 µg/ml, at least 5 µg/ml, at least 2.5 µg/ml, at least 1.0 µg/ml or at least 0.5 µg/ml in the targeted tissues or cells of the subject (e.g., brain tissues or neurons) following administration to such subject (e.g., one week, 3 days, 48 hours, 36 hours, 24 hours, 18 hours, 12 hours, 8 hours, 6 hours, 4 hours, 3 hours, 2 hours, 1 hour, 30 minutes, or less following intrathecal administration of such pharmaceutical compositions to the subject).

Treatment of Sanfilippo a Syndrome and Other Lysosomal Storage Diseases

The lysosomal storage diseases represent a group of relatively rare inherited metabolic disorders that result from defects in lysosomal function. The lysosomal diseases are characterized by the accumulation of undigested macromolecules, including those enzyme substrates, within the lysosomes (see Table 1), which results in an increase in the size and number of such lysosomes and ultimately in cellular dysfunction and clinical abnormalities.

Inventive methods described herein can advantageously facilitate the delivery of one or more therapeutic agents (e.g., one or more replacement enzymes) to targeted organelles. For example, because lysosomal storage disorders such as Sanfilippo syndrome Type A are characterized by an accumulation of glycosaminoglycans (GAG) in the lysosomes of affected cells, the lysosomes represent an desired target organelle for the treatment of the lysosomal storage disorders.

Inventive methods and compositions of the present invention are particularly useful for treating those diseases having a CNS etiology or component. Lysosomal storage diseases having a CNS etiology or component, include for example and without limitation Sanfilippo syndrome Type A, Sanfilippo syndrome type B, Hunter syndrome, metachromatic leukodystrophy and globoid cell leukodystrophy. Prior to the present invention, traditional therapies are limited in that they are administered to subjects intravenously, and are generally only effective in treating the somatic symptoms of the underlying enzyme deficiency. The compositions and methods of the present invention may advantageously be administered directly into the CNS of a subject suffering from a disease having such a CNS etiology thereby achieving a therapeutic concentration within the affected cells and tissues of the CNS (e.g., the brain), thus overcoming the limitations associated with traditional systemic administration of such therapeutic agents.

In some embodiments, inventive methods and compositions of the invention are useful for treating both the neurologic and the somatic sequelae or symptoms of lysosomal storage disorders. For example, some embodiments of the invention relate to compositions and methods of delivering one or more therapeutic agents to the CNS of a subject (e.g., intrathecally, intraventricularly or intracisternally) for the treatment of the CNS or neurologic sequelae and manifestations of a lysosomal storage disease, while also treating the systemic or somatic manifestations of that lysosomal storage disease. For example, some compositions of the present invention may be administered to a subject intrathecally, thereby delivering one or more therapeutic agents to the CNS of the subject and treating the neurological sequelae, coupled with the intravenous administration of one or more therapeutic agents to deliver such therapeutic agents to both the cells and tissues of the systemic circulation (e.g., cells and tissues of heart, lungs, liver, kidney or lymph nodes) to thereby treat the somatic sequelae. For example, a subject having or otherwise affected by a lysosomal storage disease (e.g., Sanfilippo Syndrome Type A) may be administered a pharmaceutical composition comprising one or more therapeutic agents (e.g., HNS) intrathecally at least once per week, biweekly, monthly, bimonthly or more to treat the neurologic sequelae, while a different therapeutic agent is administered to the subject intravenously on a more frequent basis (e.g., once per day, every other day, three times a week or weekly) to treat the systemic or somatic manifestations of the disease.

Sanfilippo syndrome, or mucopolysaccharidosis III (MPS III), is a rare genetic disorder characterized by the deficiency of enzymes involved in the degradation of glycosaminoglycans (GAG). In the absence of enzyme, partially degraded GAG molecules cannot be cleared from the body and accumulate in lysosomes of various tissues, resulting in progressive widespread somatic dysfunction (Neufeld and Muenzer, 2001).

Four distinct forms of MPS III, designated MPS IIIA, B, C, and D, have been identified. Each represents a deficiency in one of four enzymes involved in the degradation of the GAG heparan sulfate. All forms include varying degrees of the same clinical symptoms, including coarse facial features, hepatosplenomegaly, corneal clouding and skeletal deformities. Most notably, however, is the severe and progressive loss of cognitive ability, which is tied not only to the accumulation of heparan sulfate in neurons, but also the subsequent elevation of the gangliosides GM2, GM3 and GD2 caused by primary GAG accumulation (Walkley 1998).

Mucopolysaccharidosis type IIIA (MPS IIIA; Sanfilippo Syndrome Type A) is the most severe form of Sanfilippo syndrome and affects approximately 1 in 100,000 people worldwide. Sanfilippo Syndrome Type A (SanA) is characterized by a deficiency of the enzyme heparan N-sulfatase (HNS), an exosulfatase involved in the lysosomal catabolism of glycosaminoglycan (GAG) heparan sulfate (Neufeld E F, et al. The Metabolic and Molecular Bases of Inherited Disease (2001) pp. 3421-3452). In the absence of this enzyme, GAG heparan sulfate accumulates in lysosomes of neurons and glial cells, with lesser accumulation outside the brain.

A defining clinical feature of this disorder is central nervous system (CNS) degeneration, which results in loss of, or failure to attain, major developmental milestones. The progressive cognitive decline culminates in dementia and premature mortality. The disease typically manifests itself in young children, and the lifespan of an affected individual generally does not extend beyond late teens to early twenties.

Compositions and methods of the present invention may be used to effectively treat individuals suffering from or susceptible to Sanfilippo Syndrome Type A. The terms, "treat" or "treatment," as used herein, refers to amelioration of one or more symptoms associated with the disease, prevention or delay of the onset or progression of one or more symptoms of the disease, and/or lessening of the severity or frequency of one or more symptoms of the disease.

In some embodiments, treatment refers to partially or complete alleviation, amelioration, relief, inhibition, delaying onset, reducing severity and/or incidence of neurological impairment in a SanA patient. As used herein, the term "neurological impairment" includes various symptoms associated with impairment of the central nervous system (e.g., the brain and spinal cord). Symptoms of neurological impairment may include, for example, developmental delay, progressive cognitive impairment, hearing loss, impaired speech development, deficits in motor skills, hyperactivity, aggressiveness and/or sleep disturbances, among others.

In some embodiments, treatment refers to decreased lysosomal storage (e.g., of GAG) in various tissues. In some embodiments, treatment refers to decreased lysosomal storage in brain target tissues, spinal cord neurons, and/or peripheral target tissues. In certain embodiments, lysosomal storage is decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to a control. In some embodiments, lysosomal storage is decreased by at least 1-fold, 2-fold, 3-fold, 4-fold, 5-fold, 6-fold, 7-fold, 8-fold, 9-fold or 10-fold as compared to a control. In some embodiments, lysosomal storage is measured by the presence of lysosomal storage granules (e.g., zebra-striped morphology).

In some embodiments, treatment refers to reduced vacuolization in neurons (e.g., neurons containing Purkinje cells). In certain embodiments, vacuolization in neurons is decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to a control. In some embodiments, vacuolization is decreased by at least 1-fold, 2-fold, 3-fold, 4-fold, 5-fold, 6-fold, 7-fold, 8-fold, 9-fold or 10-fold as compared to a control.

In some embodiments, treatment refers to increased HNS enzyme activity in various tissues. In some embodiments, treatment refers to increased HNS enzyme activity in brain target tissues, spinal cord neurons and/or peripheral target tissues. In some embodiments, HNS enzyme activity is increased by about 5%, 10%, 15%, 20%, 25%, 30%, 35%, 40%, 45%, 50%, 55%, 60%, 65%, 70%, 75%, 80%, 85%, 90%, 95%, 100%, 200%, 300%, 400%, 500%, 600%, 700%, 800%, 900% 1000% or more as compared to a control. In some embodiments, HNS enzyme activity is increased by at least 1-fold, 2-fold, 3-fold, 4-fold, 5-fold, 6-fold, 7-fold, 8-fold, 9-fold or 10-fold as compared to a control. In some embodiments, increased HNS enzymatic activity is at least approximately 10 nmol/hr/mg, 20 nmol/hr/mg, 40 nmol/hr/mg, 50 nmol/hr/mg, 60 nmol/hr/mg, 70 nmol/hr/mg, 80 nmol/hr/mg, 90 nmol/hr/mg, 100 nmol/hr/mg, 150 nmol/hr/mg, 200 nmol/hr/mg, 250 nmol/hr/mg, 300 nmol/hr/mg, 350 nmol/hr/mg, 400 nmol/hr/mg, 450 nmol/hr/mg, 500 nmol/hr/mg, 550 nmol/hr/mg, 600 nmol/hr/mg or more. In some embodiments, HNS enzymatic activity is increased in the lumbar region. In some embodiments, increased HNS enzymatic activity in the lumbar region is at least approximately 2000 nmol/hr/mg, 3000 nmol/hr/mg, 4000 nmol/hr/mg, 5000 nmol/hr/mg, 6000 nmol/hr/mg, 7000 nmol/hr/mg, 8000 nmol/hr/mg, 9000 nmol/hr/mg, 10,000 nmol/hr/mg, or more.

In some embodiments, treatment refers to decreased progression of loss of cognitive ability. In certain embodiments, progression of loss of cognitive ability is decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to a control. In some embodiments, treatment refers to decreased developmental delay. In certain embodiments, developmental delay is decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to a control.

In some embodiments, treatment refers to increased survival (e.g. survival time). For example, treatment can result in an increased life expectancy of a patient. In some embodiments, treatment according to the present invention results in an increased life expectancy of a patient by more than about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 105%, about 110%, about 115%, about 120%, about 125%, about 130%, about 135%, about 140%, about 145%, about 150%, about 155%, about 160%, about 165%, about 170%, about 175%, about 180%, about 185%, about 190%, about 195%, about 200% or more, as compared to the average life expectancy of one or more control individuals with similar disease without treatment. In some embodiments, treatment according to the present invention results in an increased life expectancy of a patient by more than about 6 month, about 7 months, about 8 months, about 9 months, about 10 months, about 11 months, about 12 months, about 2 years, about 3 years, about 4 years, about 5 years, about 6 years, about 7 years, about 8 years, about 9 years, about 10 years or more, as compared to the average life expectancy of one or more control individuals with similar disease without treatment. In some embodiments, treatment according to the present invention results in long term survival of a patient. As used herein, the term "long term survival" refers to a survival time or life expectancy longer than about 40 years, 45 years, 50 years, 55 years, 60 years, or longer.

The terms, "improve," "increase" or "reduce," as used herein, indicate values that are relative to a control. In some embodiments, a suitable control is a baseline measurement, such as a measurement in the same individual prior to initiation of the treatment described herein, or a measurement in a control individual (or multiple control individuals) in the absence of the treatment described herein. A "control individual" is an individual afflicted with Sanfilippo Syndrome Type A, who is about the same age and/or gender as the individual being treated (to ensure that the stages of the disease in the treated individual and the control individual(s) are comparable).

The individual (also referred to as "patient" or "subject") being treated is an individual (fetus, infant, child, adolescent, or adult human) having Sanfilippo Syndrome Type A or having the potential to develop Sanfilippo Syndrome Type A. The individual can have residual endogenous HNS expression and/or activity, or no measurable activity. For example, the individual having Sanfilippo Syndrome Type A may have HNS expression levels that are less than about 30-50%, less than about 25-30%, less than about 20-25%, less than about 15-20%, less than about 10-15%, less than about 5-10%, less than about 0.1-5% of normal HNS expression levels.

In some embodiments, the individual is an individual who has been recently diagnosed with the disease. Typically, early treatment (treatment commencing as soon as possible after diagnosis) is important to minimize the effects of the disease and to maximize the benefits of treatment.

Immune Tolerance

Generally, intrathecal administration of a therapeutic agent (e.g., a replacement enzyme) according to the present invention does not result in severe adverse effects in the subject. As used herein, severe adverse effects induce, but are not limited to, substantial immune response, toxicity, or death. As used herein, the term "substantial immune response" refers to severe or serious immune responses, such as adaptive T-cell immune responses.

Thus, in many embodiments, inventive methods according to the present invention do not involve concurrent immunosuppressant therapy (i.e., any immunosuppressant therapy used as pre-treatment/pre-conditioning or in parallel to the method). In some embodiments, inventive methods according to the present invention do not involve an immune tolerance induction in the subject being treated. In some embodiments, inventive methods according to the present invention do not involve a pre-treatment or preconditioning of the subject using T-cell immunosuppressive agent.

In some embodiments, intrathecal administration of therapeutic agents can mount an immune response against these agents. Thus, in some embodiments, it may be useful to render the subject receiving the replacement enzyme tolerant to the enzyme replacement therapy. Immune tolerance may be induced using various methods known in the art. For example, an initial 30-60 day regimen of a T-cell immunosuppressive agent such as cyclosporin A (CsA) and an antiproliferative agent, such as, azathioprine (Aza), combined with weekly intrathecal infusions of low doses of a desired replacement enzyme may be used.

Any immunosuppressant agent known to the skilled artisan may be employed together with a combination therapy of the invention. Such immunosuppressant agents include but are not limited to cyclosporine, FK506, rapamycin, CTLA4-Ig, and anti-TNF agents such as etanercept (see e.g. Moder, 2000, Ann. Allergy Asthma Immunol. 84, 280-284; Nevins, 2000, Curr. Opin. Pediatr. 12, 146-150; Kurlberg et al., 2000, Scand. J. Immunol. 51, 224-230; Ideguchi et al., 2000, Neuroscience 95, 217-226; Potter et al., 1999, Ann. N.Y. Acad. Sci. 875, 159-174; Slavik et al., 1999, Immunol. Res. 19, 1-24; Gaziev et al., 1999, Bone Marrow Transplant. 25, 689-696; Henry, 1999, Clin. Transplant. 13, 209-220; Gummert et al., 1999, J. Am. Soc. Nephrol. 10, 1366-1380; Qi et al., 2000, Transplantation 69, 1275-1283). The anti-IL2 receptor (.alpha.-subunit) antibody daclizumab (e.g. Zenapax™), which has been demonstrated effective in transplant patients, can also be used as an immunosuppressant agent (see e.g. Wiseman et al., 1999, Drugs 58, 1029-1042; Beniaminovitz et al., 2000, N. Engl J. Med. 342, 613-619; Ponticelli et al., 1999, Drugs R. D. 1, 55-60; Berard et al., 1999, Pharmacotherapy 19, 1127-1137; Eckhoff et al., 2000, Transplantation 69, 1867-1872; Ekberg et al., 2000, Transpl. Int. 13, 151-159). Additional immunosuppressant agents include but are not limited to anti-CD2 (Branco et al., 1999, Transplantation 68, 1588-1596; Przepiorka et al., 1998, Blood 92, 4066-4071), anti-CD4 (Marinova-Mutafchieva et al., 2000, Arthritis Rheum. 43, 638-644; Fishwild et al., 1999, Clin. Immunol. 92, 138-152), and anti-CD40 ligand (Hong et al., 2000, Semin. Nephrol. 20, 108-125; Chirmule et al., 2000, J. Virol. 74, 3345-3352; Ito et al., 2000, J. Immunol. 164, 1230-1235).

Administration

Inventive methods of the present invention contemplate single as well as multiple administrations of a therapeutically effective amount of the therapeutic agents (e.g., replacement enzymes) described herein. Therapeutic agents (e.g., replacement enzymes) can be administered at regular intervals, depending on the nature, severity and extent of the subject's condition (e.g., a lysosomal storage disease). In some embodiments, a therapeutically effective amount of the therapeutic agents (e.g., replacement enzymes) of the present invention may be administered intrathecally periodically at regular intervals (e.g., once every year, once every six months, once every five months, once every three months, bimonthly (once every two months), monthly (once every month), biweekly (once every two weeks), weekly).

In some embodiments, intrathecal administration may be used in conjunction with other routes of administration (e.g., intravenous, subcutaneously, intramuscularly, parenterally, transdermally, or transmucosally (e.g., orally or nasally)). In some embodiments, those other routes of administration (e.g., intravenous administration) may be performed no more frequent than biweekly, monthly, once every two months, once every three months, once every four months, once every five months, once every six months, annually administration.

As used herein, the term "therapeutically effective amount" is largely determined base on the total amount of the therapeutic agent contained in the pharmaceutical compositions of the present invention. Generally, a therapeutically effective amount is sufficient to achieve a meaningful benefit to the subject (e.g., treating, modulating, curing, preventing and/or ameliorating the underlying disease or condition). For example, a therapeutically effective amount may be an amount sufficient to achieve a desired therapeutic and/or prophylactic effect, such as an amount sufficient to modulate lysosomal enzyme receptors or their activity to thereby treat such lysosomal storage disease or the symptoms thereof (e.g., a reduction in or elimination of the presence or incidence of "zebra bodies" or cellular vacuolization following the administration of the compositions of the present invention to a subject). Generally, the amount of a therapeutic agent (e.g., a recombinant lysosomal enzyme) administered to a subject in need thereof will depend upon the characteristics of the subject. Such characteristics include the condition, disease severity, general health, age, sex and body weight of the subject. One of ordinary skill in the art will be readily able to determine appropriate dosages depending on these and other related factors. In addition, both objective and subjective assays may optionally be employed to identify optimal dosage ranges.

A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific fusion protein employed; the duration of the treatment; and like factors as is well known in the medical arts.

In some embodiments, the therapeutically effective dose ranges from about 0.005 mg/kg brain weight to 500 mg/kg brain weight, e.g., from about 0.005 mg/kg brain weight to 400 mg/kg brain weight, from about 0.005 mg/kg brain weight to 300 mg/kg brain weight, from about 0.005 mg/kg brain weight to 200 mg/kg brain weight, from about 0.005 mg/kg brain weight to 100 mg/kg brain weight, from about 0.005 mg/kg brain weight to 90 mg/kg brain weight, from about 0.005 mg/kg brain weight to 80 mg/kg brain weight, from about 0.005 mg/kg brain weight to 70 mg/kg brain weight, from about 0.005 mg/kg brain weight to 60 mg/kg brain weight, from about 0.005 mg/kg brain weight to 50 mg/kg brain weight, from about 0.005 mg/kg brain weight to 40 mg/kg brain weight, from about 0.005 mg/kg brain weight to 30 mg/kg brain weight, from about 0.005 mg/kg brain weight to 25 mg/kg brain weight, from about 0.005 mg/kg brain weight to 20 mg/kg brain weight, from about 0.005 mg/kg brain weight to 15 mg/kg brain weight, from about 0.005 mg/kg brain weight to 10 mg/kg brain weight.

In some embodiments, the therapeutically effective dose is greater than about 0.1 mg/kg brain weight, greater than about 0.5 mg/kg brain weight, greater than about 1.0 mg/kg brain weight, greater than about 3 mg/kg brain weight, greater than about 5 mg/kg brain weight, greater than about 10 mg/kg brain weight, greater than about 15 mg/kg brain weight, greater than about 20 mg/kg brain weight, greater than about 30 mg/kg brain weight, greater than about 40 mg/kg brain weight, greater than about 50 mg/kg brain weight, greater than about 60 mg/kg brain weight, greater than about 70 mg/kg brain weight, greater than about 80 mg/kg brain weight, greater than about 90 mg/kg brain weight, greater than about 100 mg/kg brain weight, greater than about 150 mg/kg brain weight, greater than about 200 mg/kg brain weight, greater than about 250 mg/kg brain weight, greater than about 300 mg/kg brain weight, greater than about 350 mg/kg brain weight, greater than about 400 mg/kg brain weight, greater than about 450 mg/kg brain weight, greater than about 500 mg/kg brain weight.

In some embodiments, the therapeutically effective dose may also be defined by mg/kg body weight. As one skilled in the art would appreciate, the brain weights and body weights can be correlated. Dekaban A S. "Changes in brain weights during the span of human life: relation of brain weights to body heights and body weights," Ann Neurol 1978; 4:345-56. Thus, in some embodiments, the dosages can be converted as shown in Table 5.

TABLE 5

Correlation between Brain Weights, body weights and ages of males

| Age (year) | Brain weight (kg) | Body weight (kg) |
|---|---|---|
| 3 (31-43 months) | 1.27 | 15.55 |
| 4-5 | 1.30 | 19.46 |

In some embodiments, the therapeutically effective dose may also be defined by mg/15 cc of CSF. As one skilled in the art would appreciate, therapeutically effective doses based on brain weights and body weights can be converted to mg/15 cc of CSF. For example, the volume of CSF in adult humans is approximately 150 mL (Johanson C E, et al. "Multiplicity of cerebrospinal fluid functions: New challenges in health and disease," Cerebrospinal Fluid Res. 2008 May 14; 5:10). Therefore, single dose injections of 0.1 mg to 50 mg protein to adults would be approximately 0.01 mg/15 cc of CSF (0.1 mg) to 5.0 mg/15 cc of CSF (50 mg) doses in adults.

It is to be further understood that for any particular subject, specific dosage regimens should be adjusted over time according to the individual need and the professional judgment of the person administering or supervising the administration of the enzyme replacement therapy and that dosage ranges set forth herein are exemplary only and are not intended to limit the scope or practice of the claimed invention.

Kits

The present invention further provides kits or other articles of manufacture which contains the formulation of the present invention and provides instructions for its reconstitution (if lyophilized) and/or use. Kits or other articles of manufacture may include a container, an IDDD, a catheter and any other articles, devices or equipment useful in interthecal administration and associated surgery. Suitable containers include, for example, bottles, vials, syringes (e.g., pre-filled syringes), ampules, cartridges, reservoirs, or lyojects. The container may be formed from a variety of materials such as glass or plastic. In some embodiments, a container is a pre-filled syringe. Suitable pre-filled syringes include, but are not limited to, borosilicate glass syringes with baked silicone coating, borosilicate glass syringes with sprayed silicone, or plastic resin syringes without silicone.

Typically, the container may holds formulations and a label on, or associated with, the container that may indicate directions for reconstitution and/or use. For example, the label may indicate that the formulation is reconstituted to protein concentrations as described above. The label may further indicate that the formulation is useful or intended for, for example, IT administration. In some embodiments, a container may contain a single dose of a stable formulation containing a therapeutic agent (e.g., a replacement enzyme). In various embodiments, a single dose of the stable formulation is present in a volume of less than about 15 ml, 10 ml, 5.0 ml, 4.0 ml, 3.5 ml, 3.0 ml, 2.5 ml, 2.0 ml, 1.5 ml, 1.0 ml, or 0.5 ml. Alternatively, a container holding the formulation may be a multi-use vial, which allows for repeat administrations (e.g., from 2-6 administrations) of the formulation. Kits or other articles of manufacture may further include a second container comprising a suitable diluent (e.g., BWFI, saline, buffered saline). Upon mixing of the diluent and the formulation, the final protein concentration in the reconstituted formulation will generally be at least 1 mg/ml (e.g., at least 5 mg/ml, at least 10 mg/ml, at least 25 mg/ml, at least 50 mg/ml, at least 75 mg/ml, at least 100 mg/ml). Kits or other articles of manufacture may further include other materials desirable from a commercial and user standpoint, including other buffers, diluents, filters, needles, IDDDs, catheters, syringes, and package inserts with instructions for use.

The invention will be more fully understood by reference to the following examples. They should not, however, be construed as limiting the scope of the invention. All literature citations are incorporated by reference.

EXAMPLES

Example 1: HNS Formulation

The experiments in the present example were designed as part of the pre-formulation study to examine the stability of Heparan-N-Sulfatase (HNS) in various formulation conditions including pH, ionic strength, and buffer type intended for intrathecal delivery.

HNS is generally found to be a dimer in its native state (Bielicki et al., Journal of Biochemistry, 1998, 329, 145-150). The molecular weight of the HNS dimer is 115 kDa. HNS typically elutes as a dimer during size exclusion chromatography (SEC). When run on SDS-PAGE gels, HNS appears as a dimer unless the sample is heated to 100° C. prior to loading on the gel, in which case it appears as a monomer (62 kDa). The full length and mature sequences of HNS are shown below in Table 6 and Table 7, respectively. The mature HNS sequence contains 5 cysteine residues (underlined), which could allow for two internal disulfide bonds and one free cysteine.

TABLE 6

Sequence of Full Length HNS

MSCPVPACCA LLLVLGLCRA RPRNALLLLA DDGGFESGAY
NNSAIATPHL DALARRSLLF RNAFTSVSSC SPSRASLLTG
LPQHQNGMYG LHQDVHHFNS FDKVRSLPLL LSQAGVRTGI
IGKKHVGPET VYPFDFAYTE ENGSVLQVGR NITRIKLLVR
KFLQTQDDRP FFLYVAFHDP HRCGHSQPQY GTFCEKFGNG
ESGMGRIPDW TPQAYDPLDV LVPYFVPNTP AARADLAAQY
TTVGRMDQGV GLVLQELRDA GVLNDTLVIF TSDNGIPFPS
GRTNLYWPGT AEPLLVSSPE HPKRWGQVSE AYVSLLDLTP
TILDWFSIPY PSYAIFGSKT IHLTGRSLLP ALEAEPLWAT
VFGSQSHHEV TMSYPMRSVQ HRHFRLVHNL NFKMPFPIDQ
DFYVSPTFQD LLNRTTAGQP TGWYKDLRHY YYRARWELYD
RSRDPHETQN LATDPRFAQL LEMLRDQLAK WQWETHDPWV
CAPDGVLEEK LSPQCQPLHN EL (SEQ ID NO: 2)

TABLE 7

Sequence of Mature HNS (rhHNS)

RPRNALLLLA DDGGFESGAY NNSAIATPHL DALARRSLLF
RNAFTSVSSC SPSRASLLTG LPQHQNGMYG LHQDVHHFNS
FDKVRSLPLL LSQAGVRTGI IGKKHVGPET VYPFDFAYTE
ENGSVLQVGR NITRIKLLVR KFLQTQDDRP FFLYVAFHDP
HRCGHSQPQY GTFCEKFGNG ESGMGRIPDW TPQAYDPLDV
LVPYFVPNTP AARADLAAQY TTVGRMDQGV GLVLQELRDA
GVLNDTLVIF TSDNGIPFPS GRTNLYWPGT AEPLLVSSPE
HPKRWGQVSE AYVSLLDLTP TILDWFSIPY PSYAIFGSKT
IHLTGRSLLP ALEAEPLWAT VFGSQSHHEV TMSYPMRSVQ
HRHFRLVHNL NFKMPFPIDQ DFYVSPTFQD LLNRTTAGQP
TGWYKDLRHY YYRARWELYD RSRDPHETQN LATDPRFAQL
LEMLRDQLAK WQWETHDPWV CAPDGVLEEK LSPQCQPLHN
EL (SEQ ID NO: 1)

In this example, the following formulation parameters were examined: (1) pH in citrate formulations of pH 3-8 and in phosphate formulations of pH 5-8; (2) Buffers: sodium citrate buffer (pH 3.0-8.0) and sodium phosphate buffer (pH 5.0-8.0), all at 20 mM concentration; and (3) Ionic strength: NaCl (0-300 mM).

All pre-formulation studies described in this example were conducted at low protein concentrations of 1-2 mg/mL.

In order to analyze formulation products and degradation products generated under various stresses, SEC-HPLC, SDS-PAGE, Differential Scanning Calorimetry (DSC), turbidity (OD 320) and enzymatic activity assays were used.

Generally, SDS-PAGE results showed fragmentation of the formulation at low pH (pH 3), while higher pH formulations showed little fragmentation. Evaluation of melting temperature by DSC showed rhHNS formulations containing citrate and phosphate have greatest thermal stability at a pH range of 6-7. Enzymatic activity results showed that rhHNS formulations containing citrate at all pH values evaluated became inactive after storage at 50° C. for 7 days. rhHNS formulations containing phosphate at pH 6-7 retained significant activity after storage at 50° C. for 7 days. However, a high molecular weight peak ("16 minute peak", as seen by SEC) is maximal at pH 7-8, although this peak was not consistently observed in separate preparations of the same formulation.

The effects of ionic strength, 0-300 mM NaCl, on rhHNS formulation stability were also evaluated. SDS-PAGE gels of samples stored at accelerated stability conditions of 50° C. for 7 days showed no greater fragmentation than of the internal lot control. rhHNS formulations containing citrate showed a complete loss in activity after 7 days at 50° C. regardless of the ionic strength. rhHNS formulations containing phosphate retained significant activity in 50-300 mM NaCl. However, the 16 minute peak (by SEC) is maximal in the 50-150 mM NaCl range.

Methods

Effect of pH on rhHNS Stability rhHNS (9.2 mg/ml in 10 mM sodium phosphate, 138 mM sodium chloride, pH 7.0) was buffer-exchanged using dialysis (Piece Slide-A-Lyzer, PN #66383, lot #HK107537) into 20 mM sodium citrate with a pH range of 3.0 to 8.0, and 20 mM sodium phosphate with a pH range of 6.0 to 8.0. The final protein concentration in each exchanged buffer was targeted to 2.0 mg/mL. These solutions were aliquoted at 0.5 mL each into 2.0 ml glass vials (West Pharmeuticals, Cat #: 6800-0314, lot #: 30809A2001), and then incubated in 50° C., 25° C. and 2-8° C. chambers. After 7, 14 and 28 days, samples were pulled for analysis of aggregation (SEC-HPLC), fragmentation (SDS-PAGE), turbidity (OD320) and enzymatic activity.

The subsequent pH study in phosphate buffer was repeated following the same procedures as above, however, rhHNS lot #SS10 was used. The pH range for the initial phosphate study was narrow, so the study was repeated to incorporate a wider pH range.

OD320

Turbidity of rhHNS samples was determined by performing OD320 measurements. Samples were measured in the Molecular Devices SpectraMax Plus 384 at 2 mg/ml in a 0.2 cm pathlength cuvette. Total volume used was 30 µl for each testing.

SEC-HPLC

For SEC-HPLC analysis of rhHNS, a Superdex column 200 (10/300 GL, PN: 17-5175-01, GE Healthcare) was used. The mobile phase was phosphate buffered saline (25 mM sodium phosphate, 150 mM sodium chloride, pH 6) running at a flow rate of 0.5 ml/min. The injection volume was 30 μl of 1 mg/ml (diluted from 2 mg/ml in respective buffer). The run time of each injection was 50 minutes and a detection wavelength of 214 nm.

SDS-PAGE

This method evaluates fragmentation and aggregation of rhHNS under reduced and denaturing conditions. rhHNS samples were mixed with SDS buffer (final concentration=0.5 mg/ml), and DTT was added (reduced samples only). Samples were heated to 100° C. for 5 minutes. Boiling samples for longer than 5 minutes resulted in fragmentation of rhHNS. Each lane was loaded with 10 μg of rhHNS samples on 8-16% gradient acrylamide gels (Cat #: EC6045BOX). The gel was run at 150V and then incubated overnight (with shaking) with Gel Code Blue Coomassie stain. The gels were destained with water for 1 hour prior to scanning.

Activity Assay

The activity assay for rhHNS is a two step reaction. In the first reaction, heparan-N-sulfatase desulfates the substrate. Further hydrolysis occurs in the second reaction with the addition of alpha-glucosidase enzyme that releases 4-MU, which can then be measured. rhHNS was diluted 1:210 for a final assay concentration of 10 μg/ml. For the Phosphate Buffer pH Study, the assay was modified and rhHNS was diluted 1:24 for a final assay concentration of ~100 μg/mL.

DSC

Differential scanning calorimetry (DSC) measurements were made on the Microcalorimeter instrument (MicroCal VP-DSC). rhHNS samples tested were 0.5 mg/ml. The temperature was equilibrated to 10° C., and then ramped to 100° C. at 1° per minute.

Ionic Strength Effect on HNS Stability rhHNS was buffer-exchanged using dialysis (Piece Slide-A-Lyzer lot #HK107537) into 20 mM citrate buffer of pH 6.0 with sodium chloride in the range of 0-300 mM, and 20 mM phosphate buffer of pH 7.0 with sodium chloride in the range of 0-300 mM. The final protein concentration in each exchanged buffer was targeted to 2.0 mg/mL. These solutions were aliquoted at 0.5 mL each into 2.0 ml glass vials (West Pharmaceuticals, Cat #6800-0314, lot #30809A2001), and then incubated in 50° C., 25° C. and 2-8° C. chambers. After 7, 14 and 28 days, samples were pulled for analysis of aggregation (SEC-HPLC), fragmentation (SDS-PAGE), turbidity (OD 320), and enzymatic activity.

Results pH Effect on HNS Stability

OD320 and Appearance

The results of the OD 320 values to measure turbidity are shown below in Table 8. There were no significant changes in turbidity under accelerated stability conditions of the rhHNS formulations containing phosphate at pH 7 or citrate at pH 3-6. However, the samples at pH 8.0 in both phosphate and citrate formulations, and the citrate at pH 7.0 showed increased turbidity after 7 days at 50° C. Appearance check was performed under a light box (M.W. Technologies, INC, Model #: MIH-DX) and all formulations appeared to remain clear, colorless and free of visible particulates.

TABLE 8

OD320 Summary of pH Study

| Storage Condition | Formulation | OD 320 |
|---|---|---|
| ILC | 2 mg/ml HNS 20 mM Citrate, pH 3.0 | 0.005 |
| 50° C. 7 day | 2 mg/ml HNS 20 mM Citrate, pH 3.0 | 0.006 |

TABLE 8-continued

OD320 Summary of pH Study

| Storage Condition | Formulation | OD 320 |
|---|---|---|
| 25° C. 14 day | 2 mg/ml HNS 20 mM Citrate, pH 3.0 | 0.007 |
| 5° C. 28 day | 2 mg/ml HNS 20 mM Citrate, pH 3.0 | 0.003 |
| ILC | 2 mg/ml HNS 20 mM Citrate, pH 4.0 | 0.002 |
| 50° C. 7 day | 2 mg/ml HNS 20 mM Citrate, pH 4.0 | 0.006 |
| 25° C. 14 day | 2 mg/ml HNS 20 mM Citrate, pH 4.0 | 0.009 |
| 5° C. 28 day | 2 mg/ml HNS 20 mM Citrate, pH 4.0 | 0.000 |
| ILC | 2 mg/ml HNS 20 mM Citrate, pH 5.0 | 0.002 |
| 50° C. 7 day | 2 mg/ml HNS 20 mM Citrate, pH 5.0 | 0.004 |
| 25° C. 14 day | 2 mg/ml HNS 20 mM Citrate, pH 5.0 | 0.004 |
| 5° C. 28 day | 2 mg/ml HNS 20 mM Citrate, pH 5.0 | 0.004 |
| ILC | 2 mg/ml HNS 20 mM Citrate, pH 6.0 | 0.000 |
| 50° C. 7 day | 2 mg/ml HNS 20 mM Citrate, pH 6.0 | 0.002 |
| 25° C. 14 day | 2 mg/ml HNS 20 mM Citrate, pH 6.0 | 0.001 |
| 5° C. 28 day | 2 mg/ml HNS 20 mM Citrate, pH 6.0 | 0.000 |
| ILC | 2 mg/ml HNS 20 mM Citrate, pH 7.0 | 0.001 |
| 50° C. 7 day | 2 mg/ml HNS 20 mM Citrate, pH 7.0 | 0.017 |
| 25° C. 14 day | 2 mg/ml HNS 20 mM Citrate, pH 7.0 | 0.002 |
| 5° C. 28 day | 2 mg/ml HNS 20 mM Citrate, pH 7.0 | −0.001 |
| ILC | 2 mg/ml HNS 20 mM Citrate, pH 8.0 | 0.000 |
| 50° C. 7 day | 2 mg/ml HNS 20 mM Citrate, pH 8.0 | 0.018 |
| 25° C. 14 day | 2 mg/ml HNS 20 mM Citrate, pH 8.0 | 0.002 |
| 5° C. 28 day | 2 mg/ml HNS 20 mM Citrate, pH 8.0 | −0.001 |
| ILC | 2 mg/ml HNS 20 mM Phosphate, pH 7.0 | 0.000 |
| 50° C. 7 day | 2 mg/ml HNS 20 mM Phosphate, pH 7.0 | 0.005 |
| 25° C. 14 day | 2 mg/ml HNS 20 mM Phosphate, pH 7.0 | 0.000 |
| 5° C. 28 day | 2 mg/ml HNS 20 mM Phosphate, pH 7.0 | 0.001 |
| ILC | 2 mg/ml HNS 20 mM Phosphate, pH 8.0 | 0.002 |
| 50° C. 7 day | 2 mg/ml HNS 20 mM Phosphate, pH 8.0 | 0.023 |
| 25° C. 14 day | 2 mg/ml HNS 20 mM Phosphate, pH 8.0 | 0.002 |
| 5° C. 28 day | 2 mg/ml HNS 20 mM Phosphate, pH 8.0 | 0.001 |

SEC-HPLC

Figure 1B:
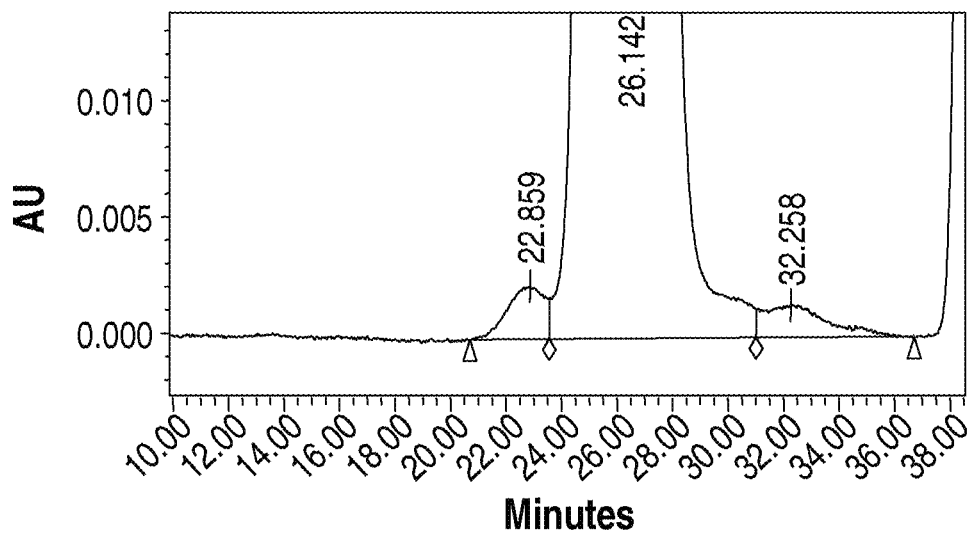
Figure 1C:
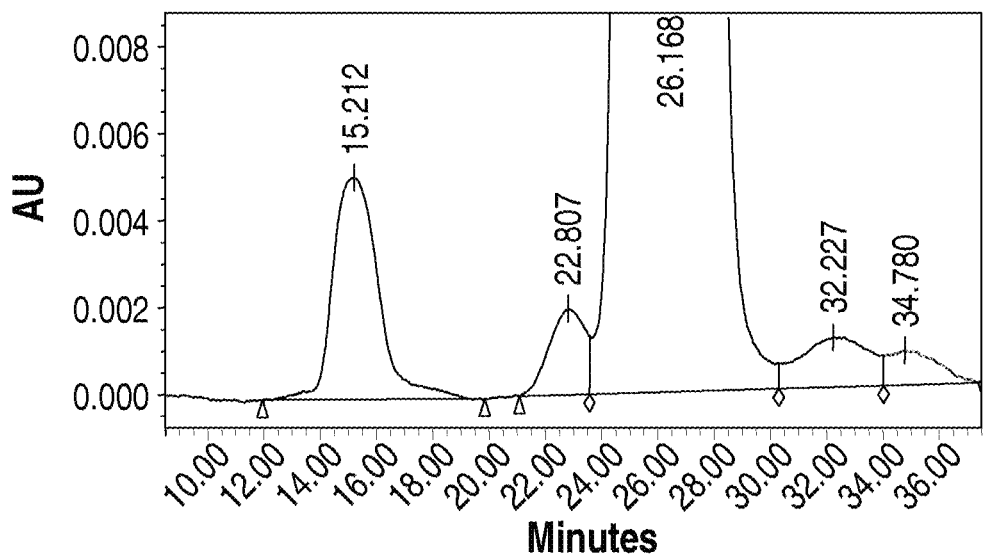

Representative chromatograms of SEC elution profiles of rhHNS are shown in FIGS. 1A-1C. The baseline sample mainly contains three peaks with retention times of ~22 min, ~26 min, and ~32 min, respectively. Occasionally, it also has a peak at ~34 min. The main peak at ~26 min, was confirmed as a dimer by SEC-LS. The natures of other peaks are unknown.

The SEC data from the first pH study are summarized below in Table 9. Overall, all the formulations essentially had little change under the stressed conditions (50° C.) as well as accelerated (25° C.) and real time storage condition (2-8° C.). However, after 7 days at 50° C., rhHNS formulations containing citrate or phosphate at pH 6-8 generated a high molecular weight peak with a retention time of 16 min. In the rhHNS formulation containing phosphate pH 7.0, the 16 min peak accounts for ~2% of the total area. However, the same formulation prepared in the ionic strength study only contained about 0.1%.

TABLE 9

SEC-HPLC Data Summary from pH Study

| Storage Condition | Formulation Description | % 16 Min Peak | % Dimer |
|---|---|---|---|
| ILC | 20 mM Citrate pH 3.0 | 0 | 99.8 |
| 7 day 50° C. | 20 mM Citrate pH 3.0 | 0 | 99.9 |
| 14 day 25° C. | 20 mM Citrate pH 3.0 | 0 | 99.7 |
| 1 mo 5° C. | 20 mM Citrate pH 3.0 | 0 | 99.7 |
| ILC | 20 mM Citrate pH 4.0 | 0 | 99.8 |
| 7 day 50° C. | 20 mM Citrate pH 4.0 | 0 | 99.8 |
| 14 day 25° C. | 20 mM Citrate pH 4.0 | 0 | 99.6 |
| 1 mo 5° C. | 20 mM Citrate pH 4.0 | 0 | 99.5 |
| ILC | 20 mM Citrate pH 5.0 | 0 | 99.8 |
| 7 day 50° C. | 20 mM Citrate pH 5.0 | 0 | 99.8 |
| 14 day 25° C. | 20 mM Citrate pH 5.0 | 0 | 99.6 |
| 1 mo 5° C. | 20 mM Citrate pH 5.0 | 0 | 99.5 |

TABLE 9-continued

SEC-HPLC Data Summary from pH Study

| Storage Condition | Formulation Description | % 16 Min Peak | % Dimer |
|---|---|---|---|
| ILC | 20 mM Citrate pH 6.0 | 0 | 99.8 |
| 7 day 50° C. | 20 mM Citrate pH 6.0 | 0.3 | 99.0 |
| 14 day 25° C. | 20 mM Citrate pH 6.0 | 0 | 99.6 |
| 1 mo 5° C. | 20 mM Citrate pH 6.0 | 0 | 99.3 |
| ILC | 20 mM Citrate pH 7.0 | 0 | 99.8 |
| 7 day 50° C. | 20 mM Citrate pH 7.0 | 0.9 | 98.6 |
| 14 day 25° C. | 20 mM Citrate pH 7.0 | 0 | 99.6 |
| 1 mo 5° C. | 20 mM Citrate pH 7.0 | 0 | 99.2 |
| ILC | 20 mM Citrate pH 8.0 | 0 | 99.8 |
| 7 day 50° C. | 20 mM Citrate pH 8.0 | 0.5 | 98.7 |
| 14 day 25° C. | 20 mM Citrate pH 8.0 | 0 | 99.6 |
| 1 mo 5° C. | 20 mM Citrate pH 8.0 | 0 | 99.4 |
| ILC | 20 mM phosphate pH 7.0 | 0 | 99.8 |
| 7 day 50° C. | 20 mM phosphate pH 7.0 | 2.0 | 97.2 |
| 14 day 25° C. | 20 mM phosphate pH 7.0 | 0 | 99.6 |
| 1 mo 5° C. | 20 mM phosphate pH 7.0 | 0 | 99.5 |
| ILC | 20 mM phosphate pH 8.0 | 0 | 99.8 |
| 7 day 50° C. | 20 mM phosphate pH 8.0 | 1.0 | 98.8 |
| 14 day 25° C. | 20 mM phosphate pH 8.0 | 0 | 99.7 |
| 1 mo 5° C. | 20 mM phosphate pH 8.0 | 0 | 99.4 |

In order to verify this phenomenon, the pH study in phosphate buffer was repeated over a wider range of pHs and the SEC data are summarized below in Table 10. In this study, the 16 minute peak was not present in the pH 5 buffer after 7 days at 50° C., but indeed existed in the formulations of pH 6-8, which increases with increasing pH. Addition of polysorbate 20 (0.05%) did not significantly affect the size of the 16 minute peak. Interestingly, although the pH 5 formulation did not contain this peak in the stability samples, during the preparation of dialyzing from saline solution into pH 5, a significant amount of rhHNS precipitated.

TABLE 10

SEC-HPLC Data Summary from Repeat Phosphate Buffer pH Study

| Storage Condition | Formulation Description | % 16 mm peak | % Dimer |
|---|---|---|---|
| 5° C. 7 days | 2 mg/ml HNS 20 mM Phosphate, pH 5.0 | 0.0 | 98.4 |
| 50° C. 7 days | 2 mg/ml HNS 20 mM Phosphate, pH 5.0 | 0.0 | 99.3 |
| 5° C. 7 days | 2 mg/ml HNS 20 mM Phosphate, pH 6.0 | 0.0 | 99.0 |
| 50° C. 7 days | 2 mg/ml HNS 20 mM Phosphate, pH 6.0 | 0.2 | 99.1 |
| 5° C. 7 days | 2 mg/ml HNS 20 mM Phosphate, pH 7.0 | 0.0 | 98.8 |
| 50° C. 7 days | 2 mg/ml HNS 20 mM Phosphate, pH 7.0 | 0.6 | 98.8 |
| 5° C. 7 days | 2 mg/ml HNS 20 mM Phosphate, pH 7.0, 0.05% polysorbate 20 | 0.0 | 98.9 |
| 50° C. 7 days | 2 mg/ml HNS 20 mM Phosphate, pH 7.0, 0.05% polysorbate 20 | 0.8 | 98.0 |
| 5° C. 7 days | 2 mg/ml HNS 20 mM Phosphate, pH 8.0 | 0.0 | 99.1 |
| 50° C. 7 days | 2 mg/ml HNS 20 mM Phosphate, pH 8.0 | 1.6 | 97.6 |

Figure 1D:
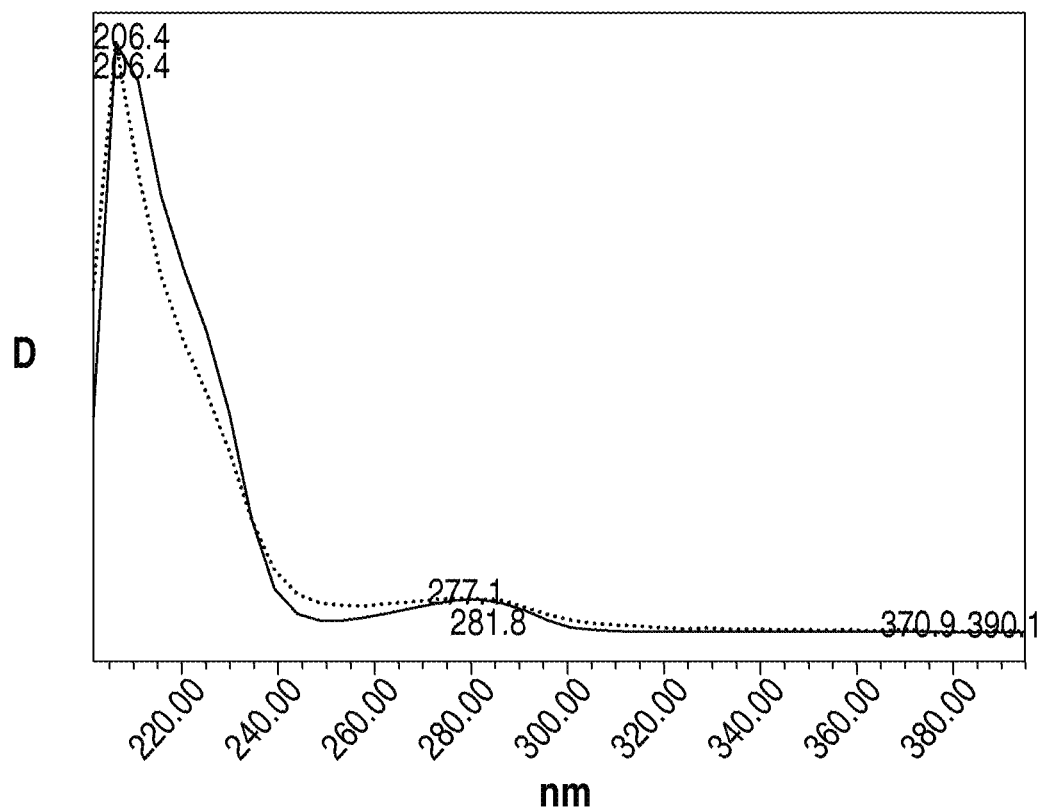

Preliminary characterization results confirm that the 16 minute peak has a spectrum indicative of protein which, when scaled, superimposes well with the spectrum of rhHNS dimer peak (FIG. 1D). When examined by SEC-LS, the 16 minute peak displays an apparent molecular weight of >1 MDa. Further characterization may be needed to understand the nature of this peak.

Enzyme Activity

The activity data summary from the first pH study is shown below in Table 5. Under accelerated stability conditions of 50° C. for 7 days, rhHNS lost most of the enzymatic activity in all citrate containing formulations, pH 3-8, while the rhHNS formulations containing phosphate, pH 7-8, retain activity. At 25° C. and 5° C., all rhHNS formulations in both citrate and phosphate buffers retained most of the activity. rhHNS formulations containing citrate pH 3.0 appear to have lower overall activity values. The activity data from the repeat pH study in phosphate are summarized in Tables 11 and 12. All rhHNS formulations in pH 5-7 retain 84-100% of enzyme activity after 7 days at 50° C., except that the rhHNS formulation at pH 8.0 lost 65% activity.

TABLE 11

Activity Summary from the First pH Study

| Storage Condition | Formulation Description | Activity nmol/mg/hr |
|---|---|---|
| ILC | 20 mM Citrate pH 3.0 | 639 |
| 7 day 50° C. | 20 mM Citrate pH 3.0 | 29 |
| 14 day 25° C. | 20 mM Citrate pH 3.0 | 920 |
| 1 mo. 5° C. | 20 mM Citrate pH 3.0 | 794 |
| ILC | 20 mM Citrate pH 4.0 | 2178 |
| 7 day 50° C. | 20 mM Citrate pH 4.0 | 43 |
| 14 day 25° C. | 20 mM Citrate pH 4.0 | 1998 |
| 1 mo. 5° C. | 20 mM Citrate pH 4.0 | 2123 |
| ILC | 20 mM Citrate pH 5.0 | 1901 |
| 7 day 50° C. | 20 mM Citrate pH 5.0 | 72 |
| 14 day 25° C. | 20 mM Citrate pH 5.0 | 1779 |
| 1 mo. 5° C. | 20 mM Citrate pH 5.0 | 2194 |
| ILC | 20 mM Citrate pH 6.0 | 2316 |
| 7 day 50° C. | 20 mM Citrate pH 6.0 | 80 |
| 14 day 25° C. | 20 mM Citrate pH 6.0 | 2026 |
| 1 mo. 5° C. | 20 mM Citrate pH 6.0 | 2122 |
| ILC | 20 mM Citrate pH 7.0 | 2312 |
| 7 day 50° C. | 20 mM Citrate pH 7.0 | 115 |
| 14 day 25° C. | 20 mM Citrate pH 7.0 | 2009 |
| 1 mo. 5° C. | 20 mM Citrate pH 7.0 | 2205 |
| ILC | 20 mM Citrate pH 8.0 | 2221 |
| 7 day 50° C. | 20 mM Citrate pH 8.0 | 44 |
| 14 day 25° C. | 20 mM Citrate pH 8.0 | 2071 |
| 1 mo. 5° C. | 20 mM Citrate pH 8.0 | 2505 |
| ILC | 20 mM phosphate pH 7.0 | 640 |
| 7 day 50° C. | 20 mM phosphate pH 7.0 | 1200 |

TABLE 11-continued

Activity Summary from the First pH Study

| Storage Condition | Formulation Description | Activity nmol/mg/hr |
|---|---|---|
| 14 day 25° C. | 20 mM phosphate pH 7.0 | 1749 |
| 1 mo. 5° C. | 20 mM phosphate pH 7.0 | 1391 |
| ILC | 20 mM phosphate pH 8.0 | 1451 |
| 7 day 50° C. | 20 mM phosphate pH 8.0 | 1125 |
| 14 day 25° C. | 20 mM phosphate pH 8.0 | 1620 |
| 1 mo. 5° C. | 20 mM phosphate pH 8.0 | 1492 |

TABLE 12

Activity Summary from the Repeat pH Study

| Storage Condition | Formulation Description | Activity nmol/mg/hr |
|---|---|---|
| ° C. 7 days | 2 mg/ml HNS 20 mM Phosphate, pH 5.0 | 4201 |
| 50° C. 7 days | 2 mg/ml HNS 20 mM Phosphate, pH 5.0 | 3952 |
| 5° C. 7 days | 2 mg/ml HNS 20 mM Phosphate, pH 6.0 | 3923 |
| 50° C. 7 days | 2 mg/ml HNS 20 mM Phosphate, pH 6.0 | 4131 |
| 5° C. 7 days | 2 mg/ml HNS 20 mM Phosphate, pH 7.0 | 4107 |
| 50° C. 7 days | 2 mg/ml HNS 20 mM Phosphate, pH 7.0 | 3841 |
| 5° C. 7 days | 2 mg/ml HNS 20 mM Phosphate, pH 7.0, 0.05% polysorbate 20 | 4952 |
| 50° C. 7 days | 2 mg/ml HNS 20 mM Phosphate, pH 7.0, 0.05% polysorbate 20 | 4173 |
| 5° C. 7 days | 2 mg/ml HNS 20 mM Phosphate, pH 8.0 | 4729 |
| 50° C. 7 days | 2 mg/ml HNS 20 mM Phosphate, pH 8.0 | 1590 |

SDS-PAGE Gels of HNS Formulations from pH Study

Figure 2A:
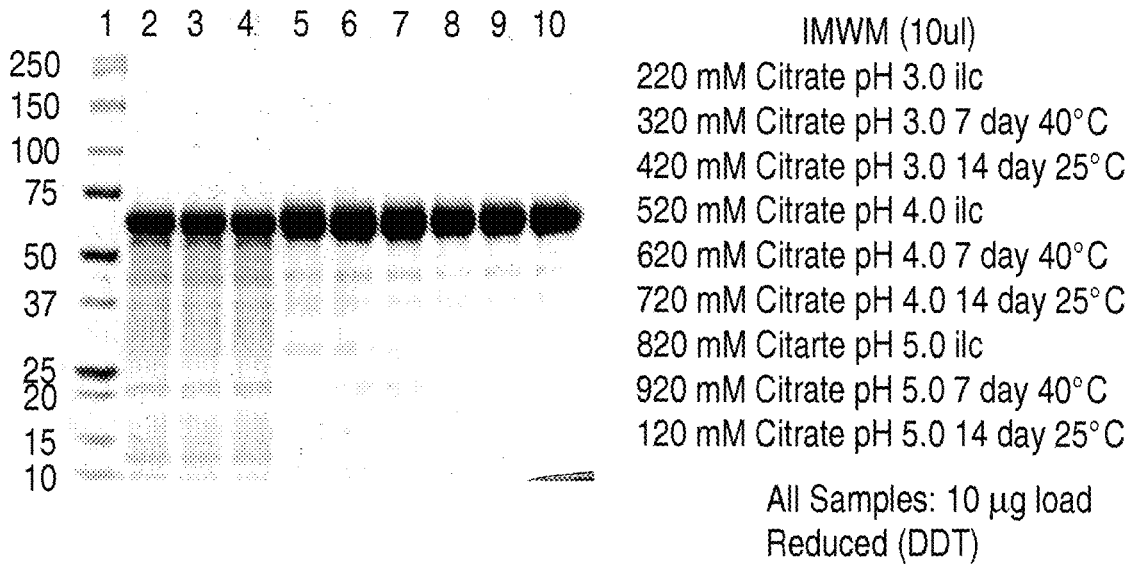
FIG. 2A-C depicts exemplary reduced SDS-PAGE gels from pH studies for rhHNS in various buffers and at various pH.
Figure 2B:
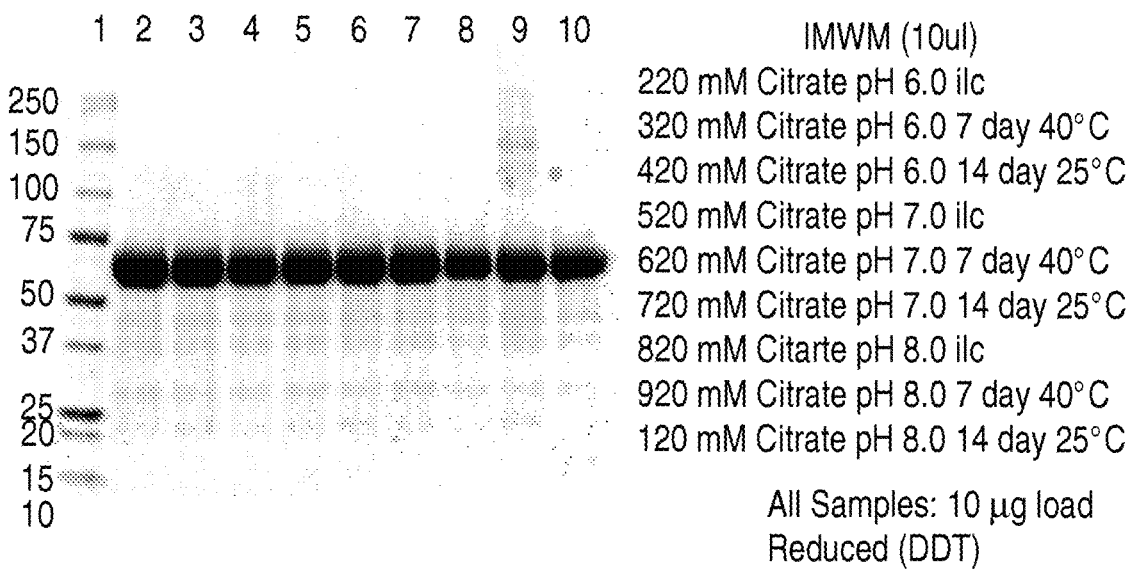
Figure 2C:
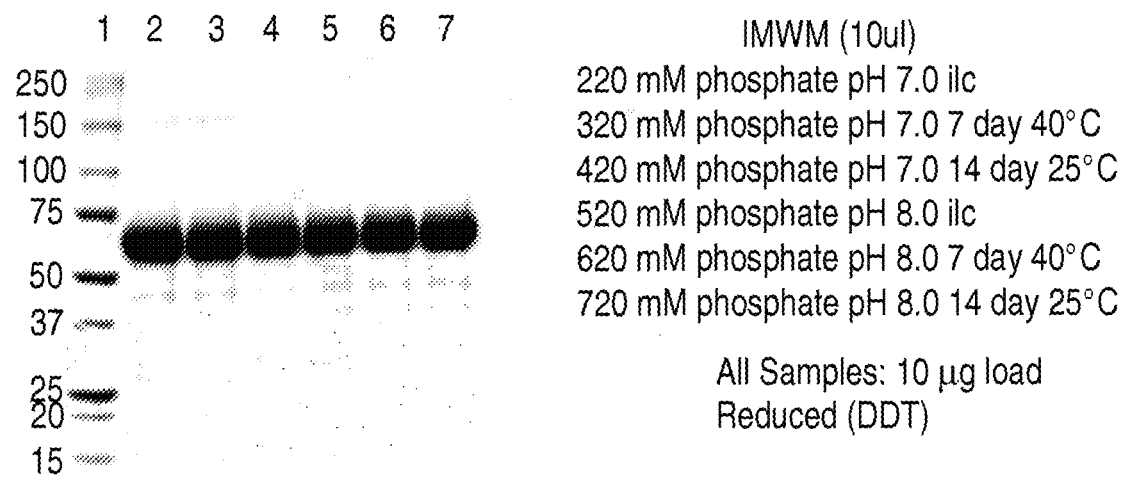
Figure 3A:
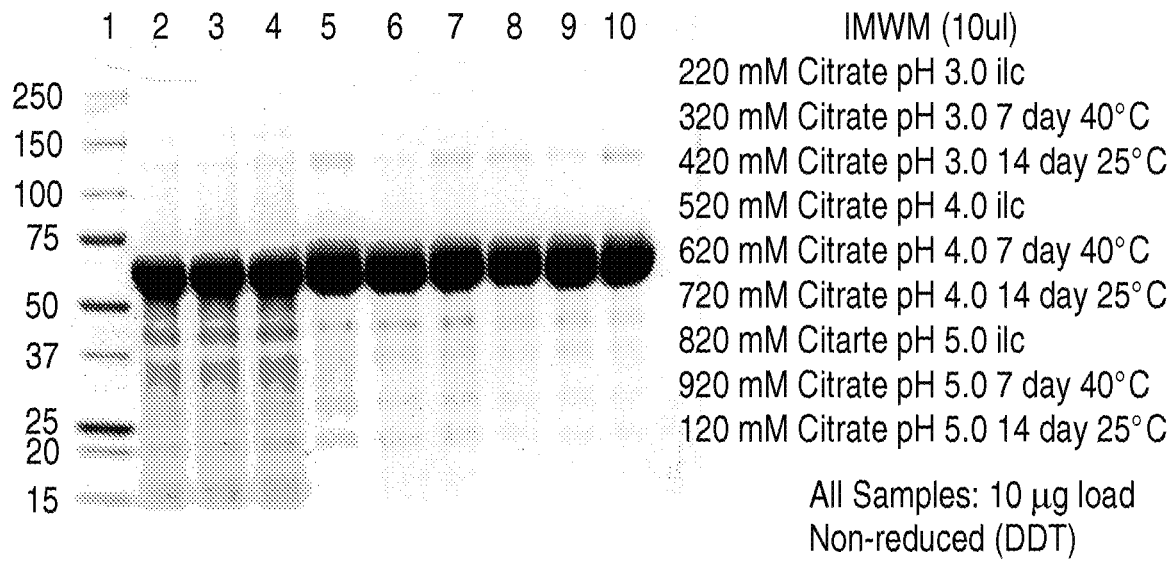
FIG. 3A-C depicts exemplary non-reduced SDS-PAGE gels from pH studies for rhHNS in various buffers and at various pH.
Figure 3B:
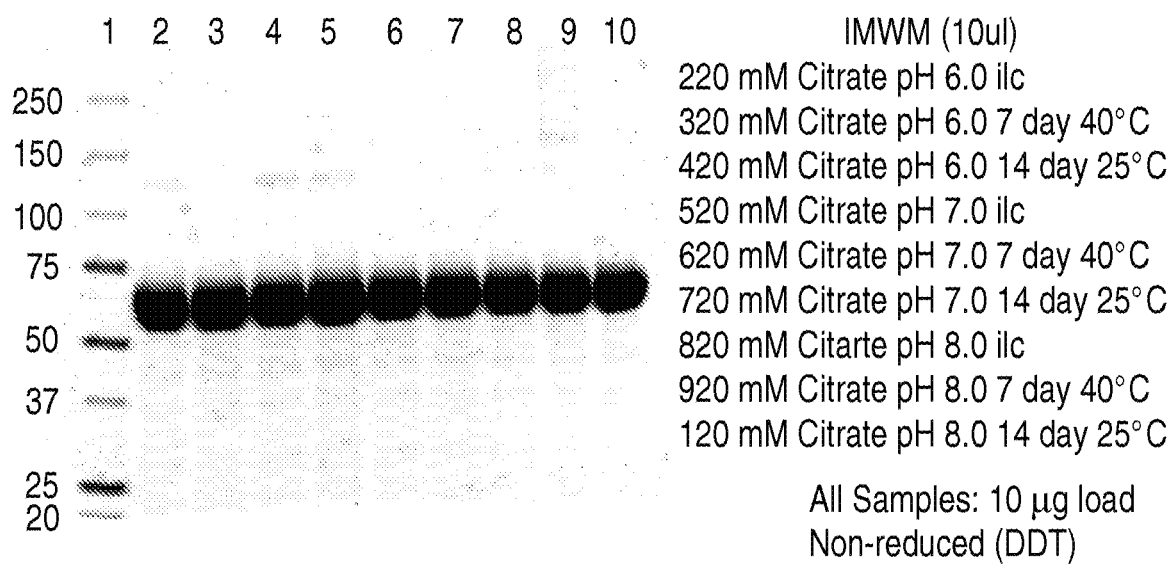
Figure 3C:
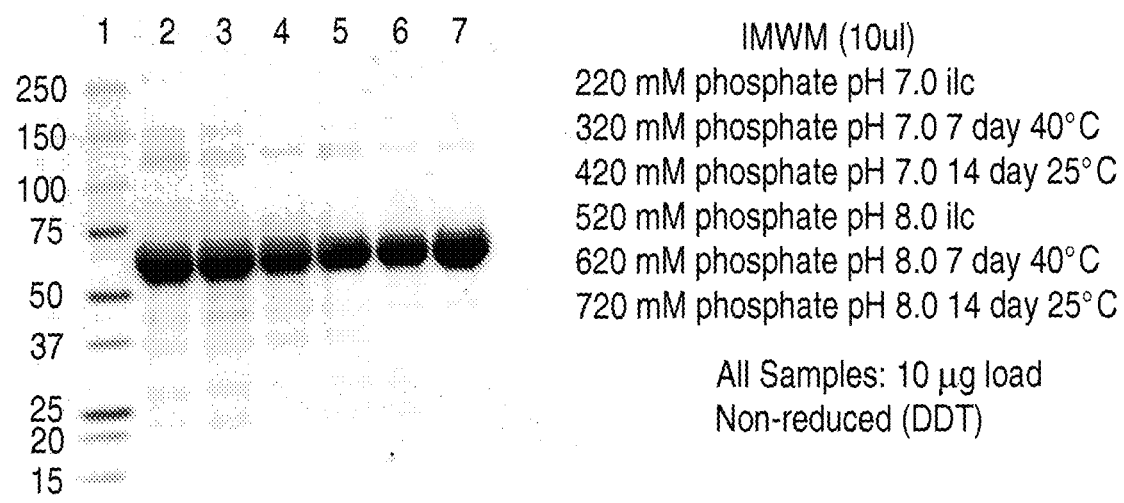

Exemplary SDS-PAGE gels are shown in FIG. 2 and FIG. 3. Reduced gels from the pH study are shown in FIG. 2, and show fragmentation bands in the formulation containing citrate at pH 3. All other formulations of pH 4-8 were similar and show only a major (monomer) band at ~60 kDa, except some high MW aggregates shown in the pH 8.0 citrate buffer after 7 days at 40° C. FIG. 3 shows the non-reduced gels from the pH study. Again, the fragmentation could be seen with the rhHNS formulation containing citrate pH 3.

Based upon these results, it was apparent that the rhHNS native dimer is primarily non-covalently bound since the presence or absence of a reducing agent doesn't affect the position of the main band. A faint 125 kDa dimer band, however, was present primarily in the non-reduced samples suggesting that this band is a covalently bound non-native dimer. The non-native dimer band was more pronounced in the ILC and 25° C. samples than in the 40° C. samples.

DSC Data from pH Study

Figure 4:
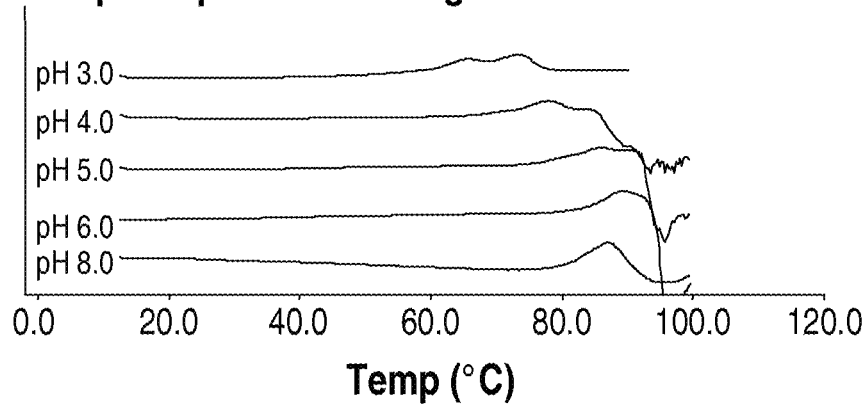
FIG. 4 depicts exemplary pH-dependent thermal stability in citrate as determined by DSC. The highest melting temperature of rhHNS in citrate was 90° C. at pH 6.0. The melting temperature of rhHNS at every pH examined exceeds 70° C.
Figure 4:
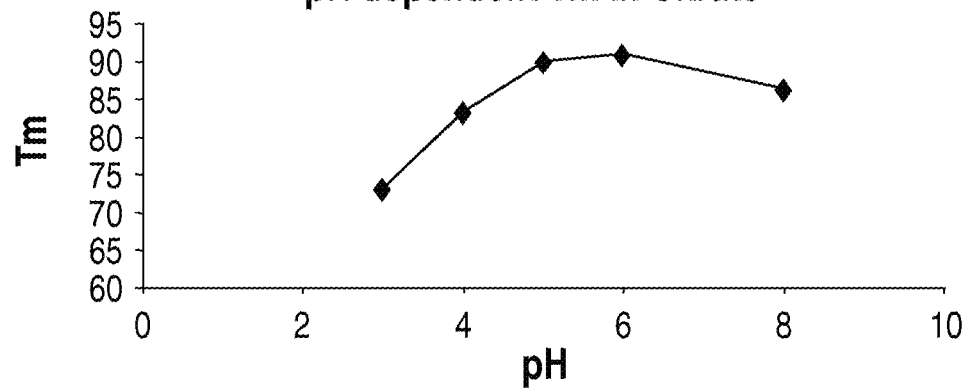
Figure 5:
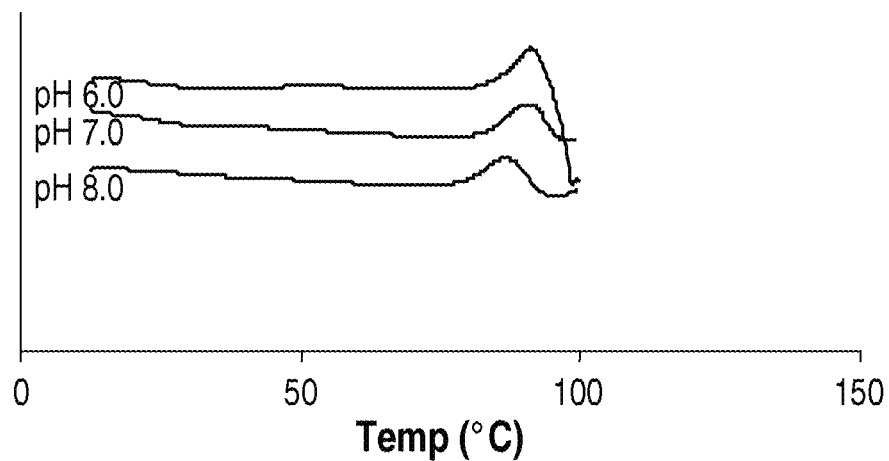
FIG. 5 depicts exemplary pH-dependent thermal stability in phosphate as determined by DSC. rhHNS formulations containing phosphate showed greatest thermal stability at pH 6-7. The melting temperature of rhHNS at every pH examined exceeds 70° C.
Figure 5:
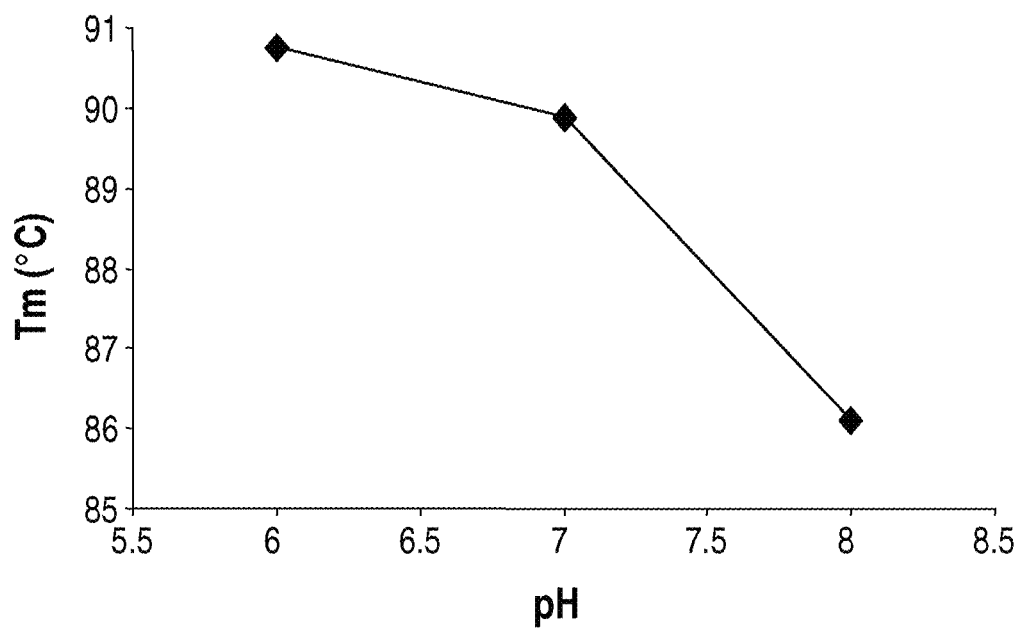

FIG. 4 shows the pH dependant thermal stability of citrate as determined by DSC. The highest melting temperature of rhHNS in citrate was 90° C. at pH 6.0. rhHNS formulations containing phosphate showed greatest thermal stability at pH 6-7. The melting temperature of rhHNS at every pH examined exceeded 70° C.

Ionic Strength Effect on rhHNS Stability

Turbidity and Appearance

The summary of OD320 values are shown below in Table 13. There was no observed change in turbidity of the samples over time, and no temperature dependant change in values. The appearance of the samples remained unchanged at each time point. All samples appeared clear, colorless, and no visible particulates

TABLE 13

OD320 of Ionic Effect

| Sample | Formulation | OD 320 |
|---|---|---|
| ILC | 10 mM Citrate pH 6.0 | 0.001 |
| 50° C. 7 day | 10 mM Citrate pH 6.0 | 0.006 |
| 25° C. 14 day | 10 mM Citrate pH 6.0 | 0.005 |
| 5° C. 28 day | 10 mM Citrate pH 6.0 | 0.003 |
| ILC | 10 mM Citrate pH 6.0 100 mM NaCl | 0.002 |
| 50° C. 7 day | 10 mM Citrate pH 6.0 100 mM NaCl | 0.009 |
| 25° C. 14 day | 10 mM Citrate pH 6.0 100 mM NaCl | 0.004 |
| 5° C. 28 day | 10 mM Citrate pH 6.0 100 mM NaCl | 0.001 |
| ILC | 10 mM Citrate pH 6.0 150 mM NaCl | 0.001 |
| 50° C. 7 day | 10 mM Citrate pH 6.0 150 mM NaCl | 0.007 |
| 25° C. 14 day | 10 mM Citrate pH 6.0 150 mM NaCl | 0.003 |
| 5° C. 28 day | 10 mM Citrate pH 6.0 150 mM NaCl | 0.001 |
| ILC | 10 mM Citrate pH 6.0 300 mM NaCl | 0.001 |
| 50° C. 7 day | 10 mM Citrate pH 6.0 300 mM NaCl | 0.006 |
| 25° C. 14 day | 10 mM Citrate pH 6.0 300 mM NaCl | 0.006 |
| 5° C. 28 day | 10 mM Citrate pH 6.0 300 mM NaCl | 0.003 |
| ILC | 10 mM Phosphate pH 7.0 | 0.002 |
| 50° C. 7 day | 10 mM Phosphate pH 7.0 | 0.009 |
| 25° C. 14 day | 10 mM Phosphate pH 7.0 | 0.005 |
| 5° C. 28 day | 10 mM Phosphate pH 7.0 | 0.002 |
| ILC | 10 mM Phosphate pH 7.0 50 mM NaCl | 0.001 |
| 50° C. 7 day | 10 mM Phosphate pH 7.0 50 mM NaCl | 0.009 |
| 25° C. 14 day | 10 mM Phosphate pH 7.0 50 mM NaCl | 0.003 |
| 5° C. 28 day | 10 mM Phosphate pH 7.0 50 mM NaCl | 0.002 |
| ILC | 10 mM Phosphate pH 7.0 100 mM NaCl | 0.002 |
| 50° C. 7 day | 10 mM Phosphate pH 7.0 100 mM NaCl | 0.009 |
| 25° C. 14 day | 10 mM Phosphate pH 7.0 100 mM NaCl | 0.004 |
| 5° C. 28 day | 10 mM Phosphate pH 7.0 100 mM NaCl | 0.002 |
| ILC | 10 mM Phosphate pH 7.0 150 mM NaCl | 0.002 |
| 50° C. 7 day | 10 mM Phosphate pH 7.0 150 mM NaCl | 0.004 |
| 25° C. 14 day | 10 mM Phosphate pH 7.0 150 mM NaCl | 0.002 |
| 5° C. 28 day | 10 mM Phosphate pH 7.0 150 mM NaCl | 0.001 |
| ILC | 10 mM Phosphate pH 7.0 300 mM NaCl | 0.002 |
| 50° C. 7 day | 10 mM Phosphate pH 7.0 300 mM NaCl | 0.010 |
| 25° C. 14 day | 10 mM Phosphate pH 7.0 300 mM NaCl | 0.005 |
| 5° C. 28 day | 10 mM Phosphate pH 7.0 300 mM NaCl | 0.003 |

SEC-HPLC

Table 14 shows the SEC-HPLC data summary from the ionic effect study. After 7 days at 50° C., all the formulations had little changes except the 16 min peak. In the citrate buffer, the 16 minute peak area percent was between 0.1 and 0.3% with no particular increasing or decreasing trend with NaCl level. In phosphate buffer, however, there was an increase in the 16 minute peak percent to ~0.5% for ionic strengths from 50 to 150 mM. At lower and higher ionic strengths, the 16 minute peak went down to ~0.1%.

TABLE 14

SEC-HPLC Data Summary of Ionic Strength Effect

| Storage Condition | Formulation Description | % 16 Min Peak | % Dimer |
|---|---|---|---|
| ILC | Citrate pH 6.0 | 0 | 99.3 |
| 7 day 50° C. | Citrate pH 6.0 | 0.24 | 99.2 |
| 14 day 25° C. | Citrate pH 6.0 | 0 | 99.4 |
| 1 mo. 5° C. | Citrate pH 6.0 | 0 | 99.5 |
| ILC | Citrate pH 6.0 100 mM NaCl | 0 | 99.3 |
| 7 day 50° C. | Citrate pH 6.0 100 mM NaCl | 0.10 | 99.3 |
| 14 day 25° C. | Citrate pH 6.0 100 mM NaCl | 0 | 99.1 |
| 1 mo. 5° C. | Citrate pH 6.0 100 mM NaCl | 0 | 99.4 |
| ILC | Citrate pH 6.0 150 mM NaCl | 0 | 99.8 |
| 7 day 50° C. | Citrate pH 6.0 150 mM NaCl | 0.22 | 99.5 |
| 14 day 25° C. | Citrate pH 6.0 150 mM NaCl | 0 | 99.2 |
| 1 mo. 5° C. | Citrate pH 6.0 150 mM NaCl | 0 | 99.5 |
| ILC | Citrate pH 6.0 300 mM NaCl | 0 | 99.5 |
| 7 day 50° C. | Citrate pH 6.0 300 mM NaCl | 0.04 | 99.6 |
| 14 day 25° C. | Citrate pH 6.0 300 mM NaCl | 0 | 99.4 |
| 1 mo. 5° C. | Citrate pH 6.0 300 mM NaCl | 0 | 99.3 |
| ILC | Phosphate pH 7.0 | 0 | 99.3 |
| 7 day 50° C. | Phosphate pH 7.0 | 0.11 | 99.1 |
| 14 day 25° C. | Phosphate pH 7.0 | 0 | 99.2 |
| 1 mo. 5° C. | Phosphate pH 7.0 | 0 | 99.4 |
| ILC | Phosphate pH 7.0 50 mM NaCl | 0 | 99.4 |
| 7 day 50° C. | Phosphate pH 7.0 50 mM NaCl | 0.57 | 98.9 |
| 14 day 25° C. | Phosphate pH 7.0 50 mM NaCl | 0 | 99.3 |
| 1 mo. 5° C. | Phosphate pH 7.0 50 mM NaCl | 0 | 99.5 |
| ILC | Phosphate pH 7.0 100 mM NaCl | 0 | 99.3 |
| 7 day 50° C. | Phosphate pH 7.0 100 mM NaCl | 0.53 | 98.9 |
| 14 day 25° C. | Phosphate pH 7.0 100 mM NaCl | 0 | 99.2 |
| 1 mo. 5° C. | Phosphate pH 7.0 100 mM NaCl | 0 | 99.3 |
| ILC | Phosphate pH 7.0 150 mM NaCl | 0 | 99.4 |
| 7 day 50° C. | Phosphate pH 7.0 150 mM NaCl | 0.52 | 98.9 |
| 14 day 25° C. | Phosphate pH 7.0 150 mM NaCl | 0 | 99.2 |
| 1 mo. 5° C. | Phosphate pH 7.0 150 mM NaCl | 0 | 99.4 |
| ILC | Phosphate pH 7.0 300 mM NaCl | 0 | 99.4 |
| 7 day 50° C. | Phosphate pH 7.0 300 mM NaCl | 0.06 | 99.3 |
| 14 day 25° C. | Phosphate pH 7.0 300 mM NaCl | 0 | 99.3 |
| 1 mo. 5° C. | Phosphate pH 7.0 300 mM NaCl | 0 | 99.1 |

Enzymatic Activity

Table 15 shows the activity data summary of ionic effect on rhHNS stability under accelerated conditions of 7 days at 50° C. rhHNS formulations containing citrate retained only 8-30% activity, regardless of ionic strength under accelerated conditions. rhHNS formulations containing phosphate with 0-300 mM NaCl all showed higher overall activity retained under accelerated conditions, 45-70%.

TABLE 15

Activity Summary of Ionic Strength Effect Study

| Storage Condition | Formulation Description | Activity nmol/mg/hr |
|---|---|---|
| ILC | Citrate pH 6.0 | 1725 |
| 7 day 50° C. | Citrate pH 6.0 | 144 |
| ILC | Citrate pH 6.0 100 mM NaCl | 1715 |
| 7 day 50° C. | Citrate pH 6.0 100 mM NaCl | 303 |
| ILC | Citrate pH 6.0 150 mM NaCl | 1475 |
| 7 day 50° C. | Citrate pH 6.0 150 mM NaCl | 250 |
| ILC | Citrate pH 6.0 300 mM NaCl | 2059 |
| 7 day 50° C. | Citrate pH 6.0 300 mM NaCl | 619 |
| ILC | Phosphate pH 7.0 | 1661 |
| 7 day 50° C. | Phosphate pH 7.0 | 766 |
| ILC | Phosphate pH 7.0 50 mM NaCl | 1441 |
| 7 day 50° C. | Phosphate pH 7.0 50 mM NaCl | 784 |
| ILC | Phosphate pH 7.0 100 mM NaCl | 1290 |
| 7 day 50° C. | Phosphate pH 7.0 100 mM NaCl | 875 |
| ILC | Phosphate pH 7.0 150 mM NaCl | 1297 |
| 7 day 50° C. | Phosphate pH 7.0 150 mM NaCl | 839 |
| ILC | Phosphate pH 7.0 300 mM NaCl | 1338 |
| 7 day 50° C. | Phosphate pH 7.0 300 mM NaCl | 693 |

SDS-PAGE

Figure 6A:
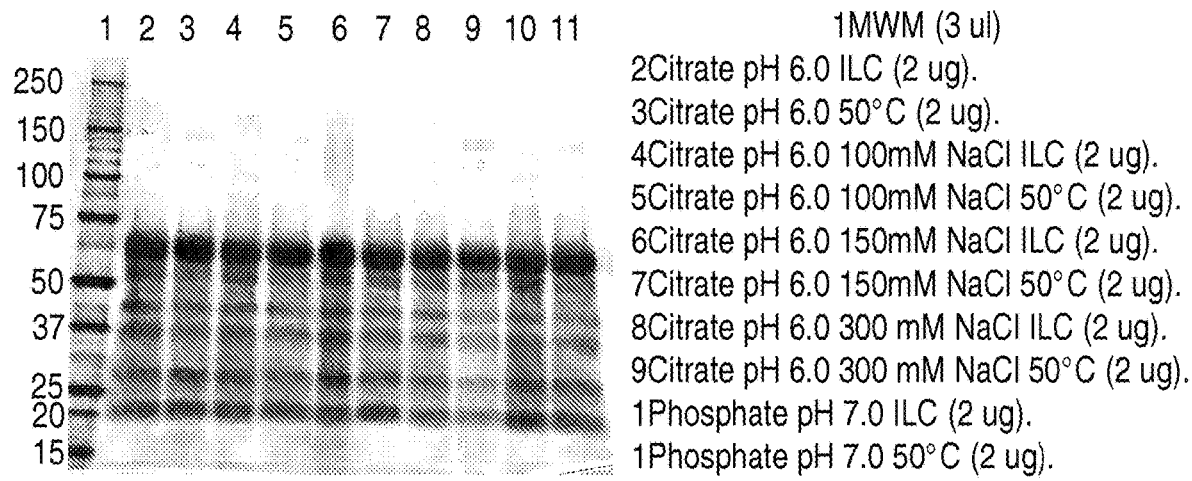
FIG. 6A-B depicts exemplary silver stained SDS-PAGE gels of rhHNS formulations from ionic effects study after 7 days at 50° C. Gels were run using samples which were boiled for 10 minutes.
Figure 6B:
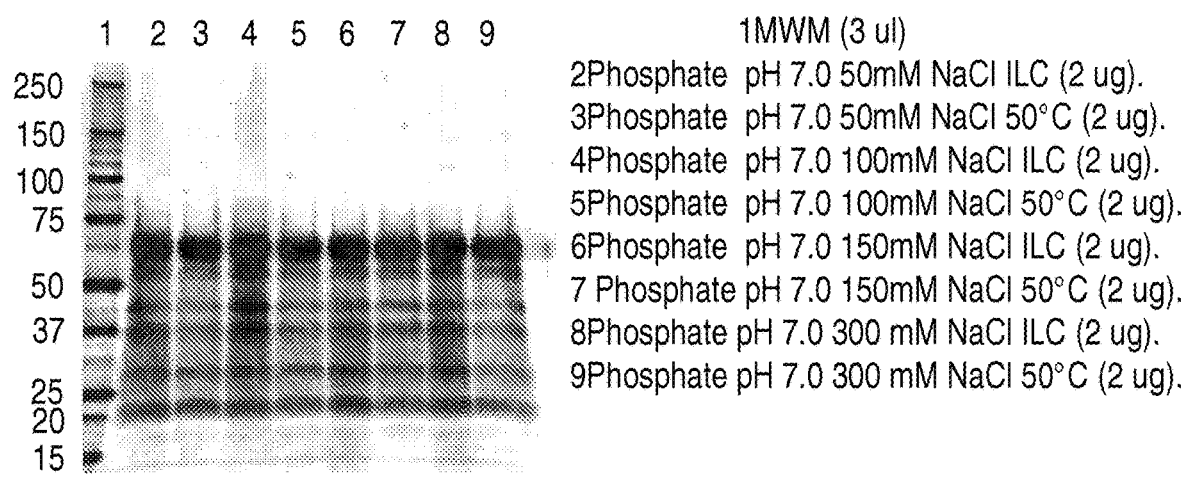

FIG. 6 shows silver stained SDS-PAGE gels of rhHNS formulations from the ionic effects study after 7 days at 50° C. These gels were run using the samples which were boiled for 10 minutes, so the fragmentation seen on the gels could be due to 10 min boiling, since in the subsequent studies, fragmentation was not observed when rhHNS was boiled for 5 minutes.

The citrate formulations with 0-300 mM NaCl and phosphate formulations with 0-300 mM NaCl all showed a primary monomer band at 60 kDa. The internal lot controls (stored at −80° C.) of rhHNS formulations appeared to show more pronounced fragment banding than samples held at 50° C. for 7 days. Overall, the ionic strength did not affect banding pattern on SDS gels.

Conclusions

The results from the studies demonstrate that the primary stability indicating assays for the formulation screening are enzymatic activity and HPLC-SEC. DSC data showed that rhHNS has the greatest thermal stability with a Tm value of ~90° C. at pH 6-7. rhHNS in the citrate buffers showed a significant loss of activity under accelerated conditions at all pH's and ionic strengths, suggesting that citrate is an unacceptable formulation buffer. Results for phosphate were considerably better, retaining maximal activity under accelerated conditions at pH 6-7. Furthermore, phosphate formulations containing 100-150 mM NaCl showed the greatest retention of activity under accelerated conditions. The high molecular weight (16 minute) peak in SEC-HPLC, however, is maximal at pH 6-8 and at ionic strengths of 50-150 mM, under accelerated conditions.

Additional formulation experiments are ongoing to better understand the causes of the 16 minute peak. Furthermore, studies are ongoing to compare the stability of phosphate formulations with un-buffer saline formulations, and the stability of low versus high protein concentration.

Example 2: Liquid Formulation for rhHNS

The experiments in this example were designed to optimize solubility of rhHNS formulations intended for intrathecal delivery. As described herein, intrathecal drug delivery requires a small amount of injected liquid volume, and consequently, a highly concentrated protein solution is needed. However, rhHNS typically has a heterogeneous charge profile with an isoelectric point range from 5.1 to 6.5, which impacts its solubility. The studies in the present example provide information on the effect of pH and sodium chloride concentration on solubility of the rhHNS product.

Figure 7A:
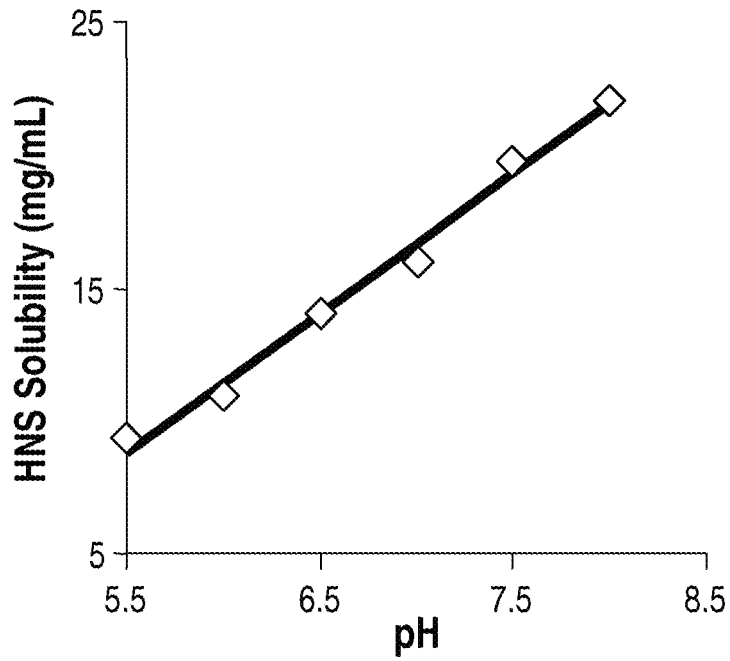
FIG. 7A-B depicts an exemplary rhHNS solubility study.
Figure 7B:
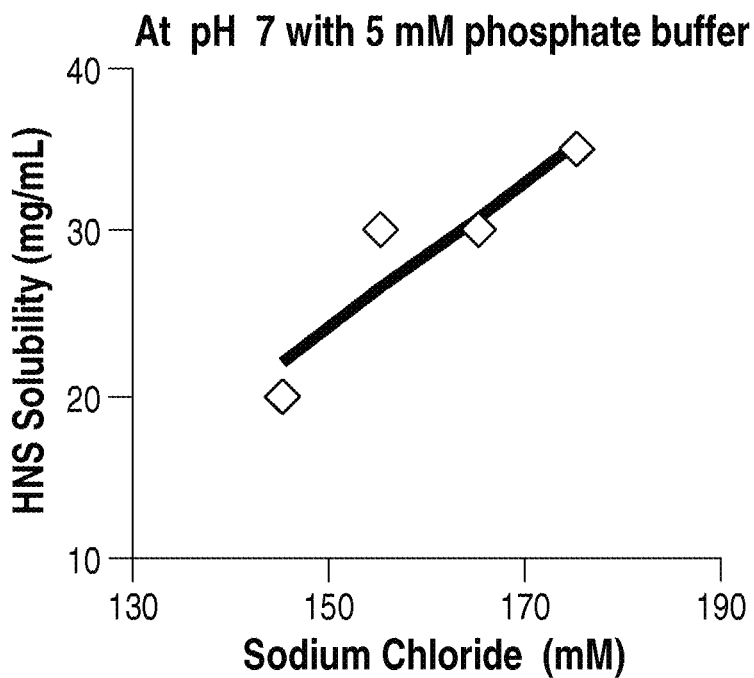
Figure 8A:
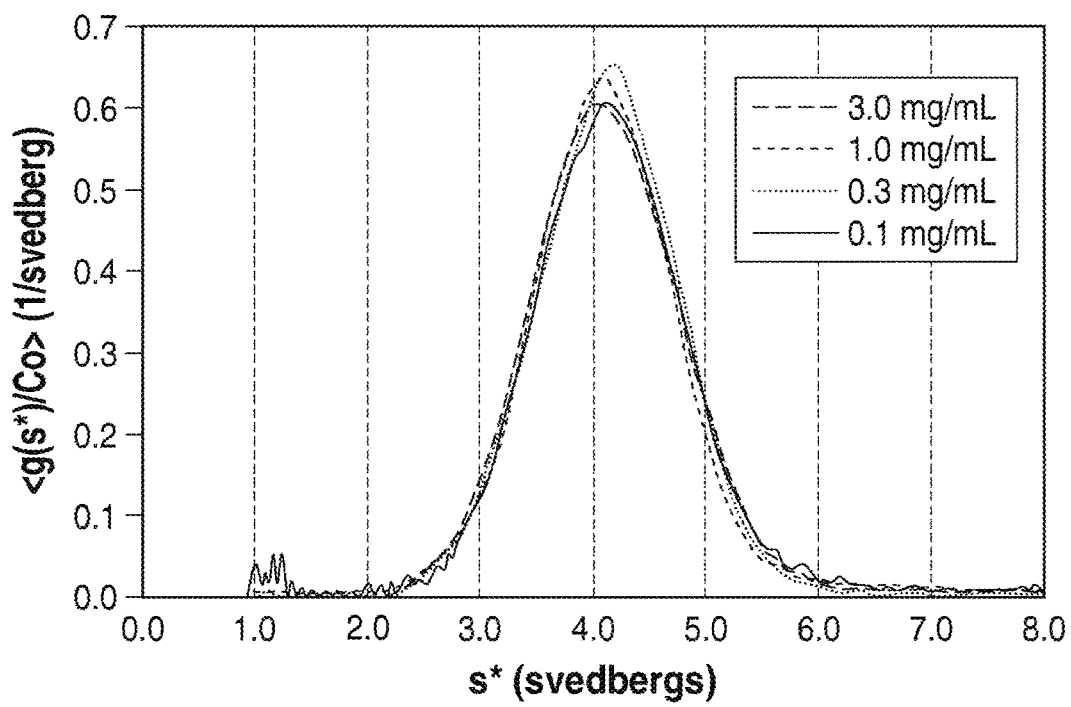
FIG. 8A-B depicts an exemplary study of the effect of salt on native state of rhHNS using AUC.
Figure 8B:
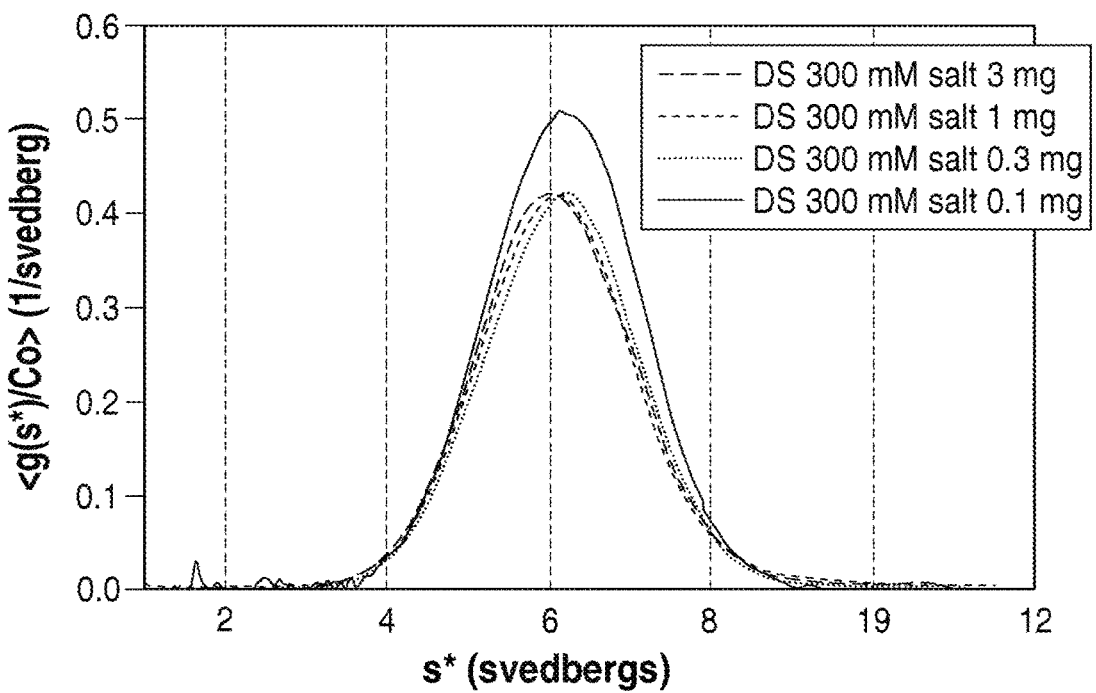

As can be seen in FIG. 7, increasing pH or salt concentration (e.g., sodium chloride) resulted in increased rhHNS solubility. rhHNS native state was analyzed by analytical ultracentrifugation (AUC) of rhHNS formulated with varying salt concentration (145 mM or 300 mM). As can be seen in FIG. 8, rhHNS contains homogenous molecules and maintains the same structure from 145 mM to 300 mM salt concentration at pH 7. Taken together, these results indicated that increasing NaCl concentration leads to increased solubility of rhHNS.

Two liquid formulations were identified for further study, including a high salt liquid formulation (15 mg/mL rhHNS, 175 mM NaCl, 5 mM phosphate, 0.005% polysorbate 20, pH 7.0); and a sucrose-containing formulation (15 mg/mL rhHNS, 2% sucrose, 145 mM NaCl, 5 mM phosphate, 0.005% polysorbate 20, pH 7.0).

Example 3: Lyophilized Formulation for rhHNS

The experiments in this example were designed to optimize lyophilization formulations and conditions for rhHNS. In particular, these studies provide information on the effect of formulation on the stability of the product, including appearance of the lyophilized cake, rhHNS enzyme activity, and chemical integrity of the lyophilized product.

rhHNS was formulated into various phosphate based lyophilized formulations. The following formulation parameters were examined: (1) Stabilizing Agent: Glucose (0.5-1%) or Sucrose (1-1.5%); and (2) Surfactant: Polysorbate 20 (0.02-0.005%). The following parameters were used in all the formulations tested: (3) 15 mg/mL rhHNS; (4) 145 mM NaCl; (5) 5 mM phosphate; (6) pH 7.0.

Exemplary formulations were lyophilized according to the conditions in Table 16:

TABLE 16

Exemplary Lyophilization Cycle
Total Lyo Time-4 days

| Freezing/Annealing | |
|---|---|
| Freezing | 0.25 C./min to −20 C. |
| Hold | −20 C. for 5 hrs. |
| Continue Freezing | −50 C. at 0.25 C./min |
| Hold | −50 for 3 hrs. |

| Primary Drying | |
|---|---|
| Ramp | 0.5 C./min to −25 C. and vacuum to 60 mT |
| Hold | −25 C. and 60 mT for 50 hrs. |

| Secondary Drying | |
|---|---|
| Ramp | 0.3 C./min to 20 C. and N2 pressure to 150 mT |
| Hold | 20 C. and 150 mT for 6 hrs. |

It was observed that glucose containing formulations had long reconstitution times (>30 minutes), although chemical stability was maintained (data not shown).

rhHNS lyo-formulations containing 1% sucrose had 15 month data at 2-8° C. and 3 month data at 25° C./40° C. (as shown below in Table 17), showing ≤1% change in SEC, RP, and SDS-PAGE.

TABLE 17

1% Sucrose Lyo-formulation Stability

| Test | Pre-Lyo | Post-Lyo | 5 ± 3° C. 3 M | 5 ± 3° C. 15 M | 25 ± 2° C. 3 M | 40 ± 2° C. 0.5 M |
|---|---|---|---|---|---|---|
| Cake Appearance | NA | White, solid cake | White, solid cake | White, solid cake | White, solid cake | White, solid cake |
| Moisture Content | NA | 0.5% | NA | NA | NA | NA |
| Recon Time | NA | <60 sec | <60 sec | <60 sec | <60 sec | <60 sec |
| Appearance of Recon solution | Opalescent, colorless w/o particles | Opalescent, colorless w/o particles | Opalescent, colorless w/o particles | Opalescent, colorless w/o particles | Opalescent, colorless w/o particles | Opalescent, colorless w/o particles |
| pH | 7.2 | 7.2 | 7.3 | NA | 7.2 | 7.2 |
| Protein Conc. (mg/mL) | 14.8 | 14.8 | NA | 15.3 | 14.6 | 14.0 |
| Specific Activity (U/mg) | 71 | 62 | NA | 78 | 85 | 78 |
| SEC main peak % | 99.9% | 99.8% | 99.6% | 99.5% | 99.6% | 99.5% |
| RP-HPLC Main peak % | 99.0% | 98.9% | 98.4% | 98.5% | 98.7% | 98.5% |
| SDS-PAGE | Conforms | Conforms | Conforms | Slight increase in lower band (<1%) | Conforms | Conforms | rhHNS lyo-formulations containing 1.5% sucrose had 14 month data at 2-8° C. and 3 month data at 25° C. (as shown below in Table 18), showing ≤0.2% change in SEC, RP, and SDS-PAGE.

Taken together, these data demonstrate that an increase in sucrose concentration in rhHNS lyo-formulations correlated with an increase in stability as well as an increase in lyophilized cake shrinkage.

TABLE 18

1.5% Sucrose Lyo-formulation Stability

| Test | Pre-Lyo | Post-Lyo | 5 ± 3° C. 3 M | 25 ± 2° C. 3 M | 40 ± 2° C. 1 M | 40 ± 2° C. 3 M |
|---|---|---|---|---|---|---|
| Cake Appearance | NA | White, solid cake | White, solid cake | White, solid cake | White, solid cake | White, solid cake |
| Moisture Content | NA | 0.5% | NA | NA | NA | NA |
| Recon Time | NA | <60 sec | <60 sec | <60 sec | <60 sec | <60 sec |
| Appearance of Recon solution | Opalescent, colorless w/o particles | Opalescent, colorless w/o particles | Opalescent, colorless w/o particles | Opalescent, colorless w/o particles | Opalescent, colorless w/o particles | Opalescent, colorless w/o particles |
| pH | 6.9 | 6.9 | 6.9 | 6.9 | 6.9 | 6.9 |
| Protein Conc. (mg/mL) | 16.1 | 14.2 | 15.7 | 15.4 | 16.6 | 15.4 |
| Specific Activity (U/mg) | 176 | 210 | 149 | 122 | 169 | 139 |
| SEC main peak % | 99.9% | 99.8% | 99.8% | 99.6% | 99.6% | 99.0% |
| RP-HPLC Main peak % | 99.2% | 99.0% | 98.8% | 98.5% | 98.0% | 97.7% |
| SDS-PAGE | Conforms | Conforms | Conforms | Slight increase in lower band (<1%) | Conforms | Slight increase in lower band (~1%) |

Figure 9A:
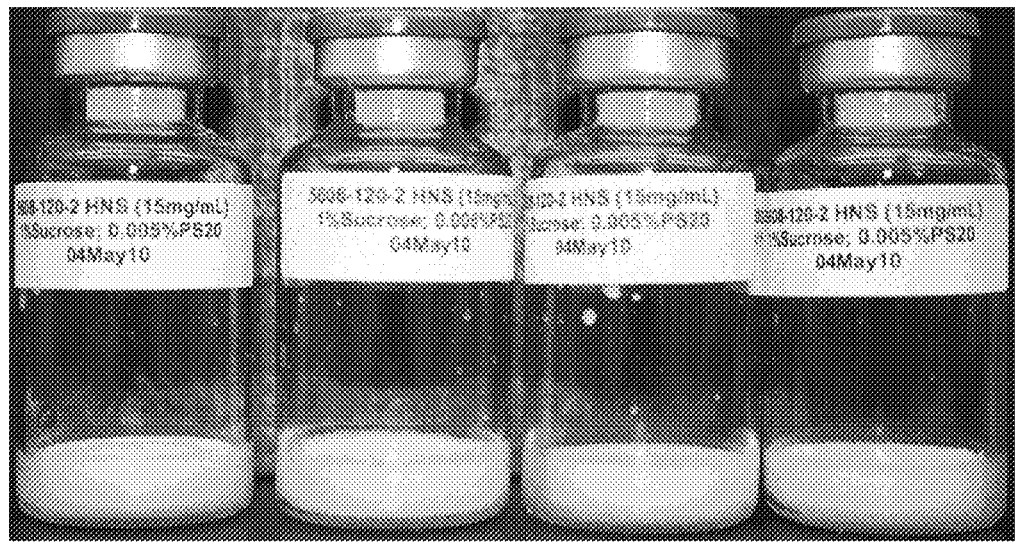
FIG. 9A and FIG. 9B depicts an exemplary study on the effect of sucrose level and lyophilization unit on cake appearance of lyophilized rhHNS formulations.
Figure 9A:
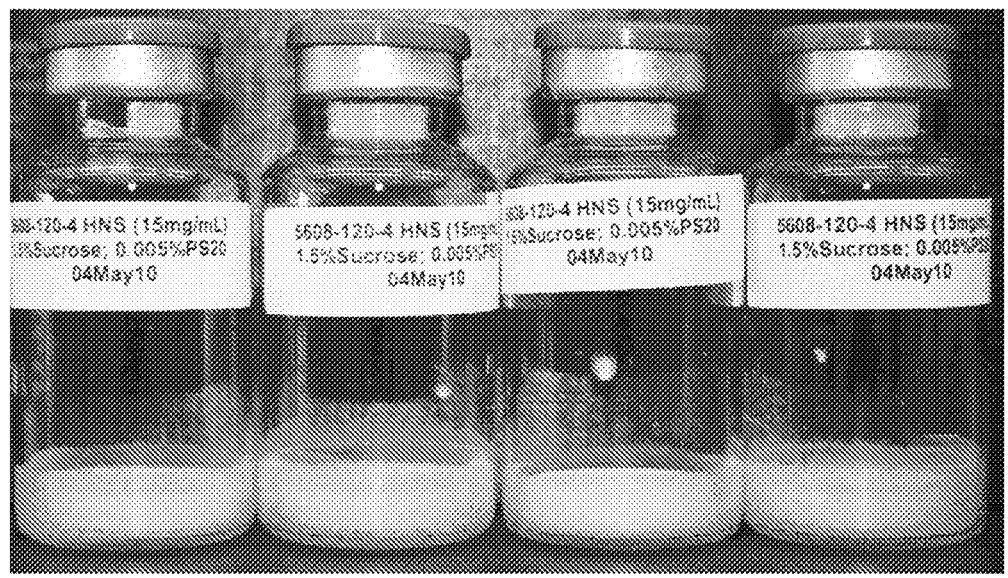
Figure 9B:
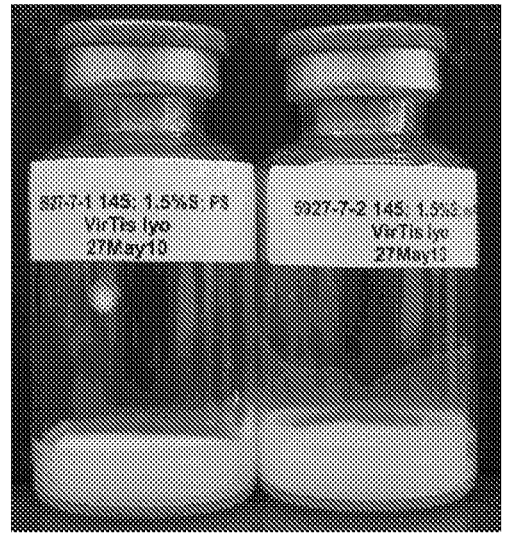
Figure 9B:
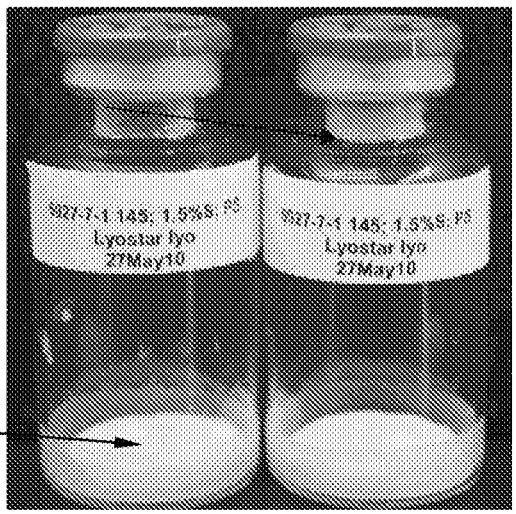

Lyophilized cakes were observed for cake appearance and integrity (e.g., melt-back). As can be seen in FIG. 9A, lyophilized cakes formulated with 1.5% sucrose had more cake shrinkage than those formulated with 1.0% sucrose. Lyophilized cakes formulated with 1.5% sucrose were also more sensitive to different lyophilization units, such as the VirTis unit vs the LyoStar unit (FIG. 9B).

A separate set of experiments confirms that increasing sucrose causes increased cake shrinkage, as indicated in Table 19 below.

TABLE 19

Comparison of rhHNS Stability and Cake Appearance at Various Sucrose

| Testing | Changes From the Baseline | | | | | |
|---|---|---|---|---|---|---|
| | 1% Sucrose | | 1.25% Sucrose | 1.5% Sucrose | | |
| Long Term (5 C.) | 22M | 12M | 6M | 21M | 5M | |
| SEC | 0.4% | 0.2% | 0.1% | 0.1% | 0% | |
| RP | 0.5% | 0.5% | 0.5% | 0.3% | 0.5% | |
| SDS-PAGE | <1% | <1% | <1% | 0% | 0% | |
| Accelerated (25 C.) | 20M | 12M | 6M | 21M | 12M | |
| SEC | 0.5% | 0.2% | 0.1% | 0.1% | 0% | |
| RP | 1.5% | 0.5% | 0.5% | 0.5% | 0% | |
| SDS-PAGE | <1% | 1% | 1% | 0% | 0% | |
| Stress Data (40 C.) | 0.5M | 1M | 3M | 1M | 0.5M | 1M |
| SEC | 0.5% | 0.4% | 1% | 0.1% | 0.1% | 0.2% |
| RP | 0.5% | 0.5% | 1.5% | 0.1% | 0.5% | 0.2% |
| SDS-PAGE | <1% | <1% | >1% | 1% | 0% | 0% |
| Cake Appearance | Slight shrinkage | | Some shrinkage | More shrinkage | | |

Figure 10:
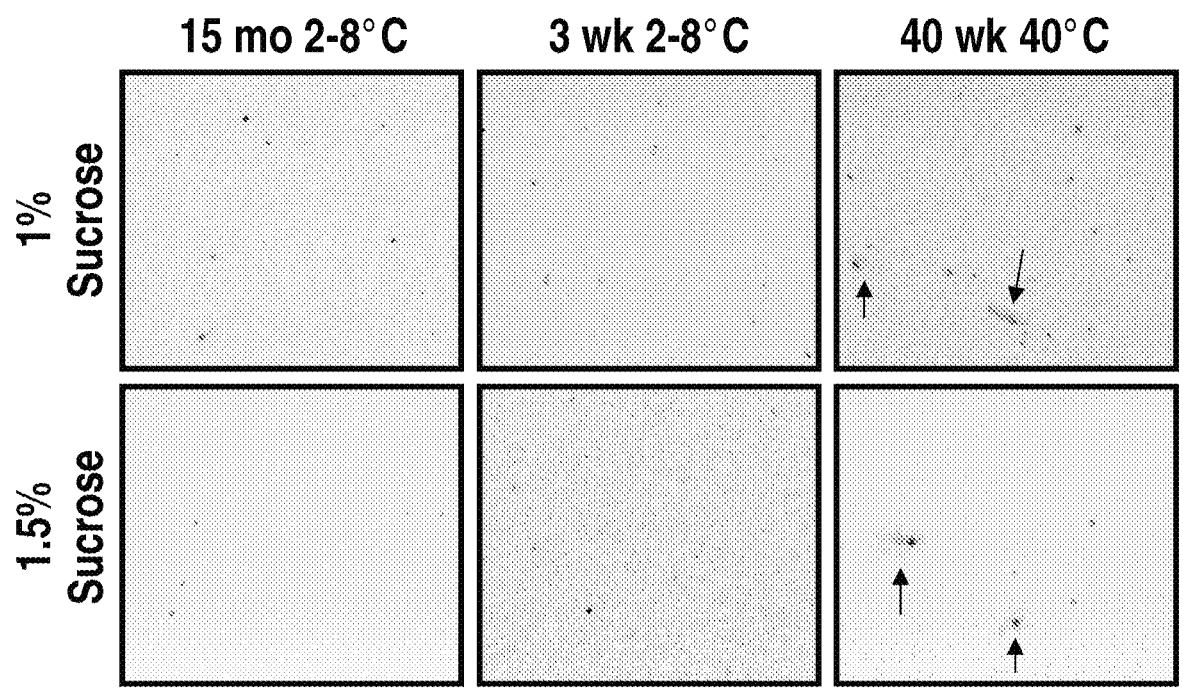
FIG. 10 depicts exemplary particulate images by Micro-Flow Imaging (MFI) for lyophilized rhHNS samples.

Reconstituted lyo-formulations were observed for the presence of particulates by Micro-Flow Imaging (MFI). Exemplary particulate images are depicted in FIG. 10. As can be seen in FIG. 10, large particles were observed after reconsistution of lyo-formulations containing either 1% and 1.5% sucrose after storage.

Figure 11:
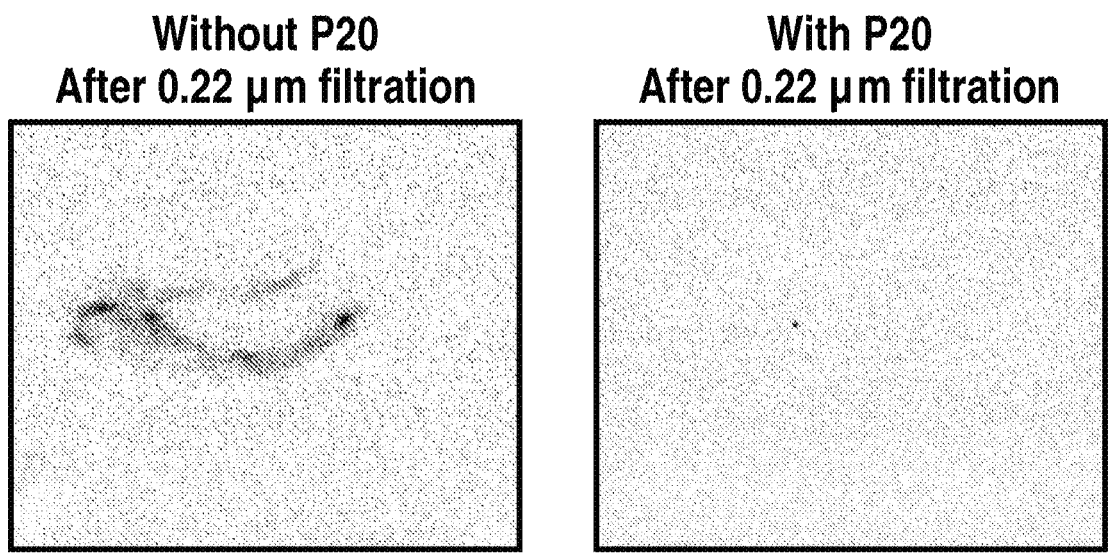
FIG. 11 depicts exemplary images of a study of the effect of polysorbate 20 on particulates detected by MFI for pre-lyophilized rhHNS samples containing 1.5% sucrose after 0.22 μm filtration.

Prelyophilized formulations were observed for the presence of particulates after 0.22 um filtration. As can be seen in FIG. 11, the presence of polysorbate 20 (P20) prevents protein-like flocculants that were generated without P20 upon 0.22 μm filtration. Thus, P20 is effective in preventing particulate formation and/or protecting rhHNS protein during filtration. Further studies showed that the presence of P20 was effective in reducing the presence of freeze-thaw induced particulates as well as lyophilization-induced particulates in rhHNS formulations (data not shown).

Lyophilization Conditions

Lyophilization cycle conditions were studied to determine the effect on rhHNS lyophilized formulations. For example, primary drying temperatures were varied from −38 C to −20 C, and stability of rhHNS lyo-formulations were determined by enzyme activity, SEC, RP, and cake appearance. Exemplary results of these analyses are shown in Table 20 below.

TABLE 20

Effect of Primary Drying on 1.5% Sucrose Lyo-formulations

| | | (-38° C.) | | (-30° C.) | | (-25° C.) | | (-23° C.) | | (-20° C.) | |
|---|---|---|---|---|---|---|---|---|---|---|---|
| Test | Pre-Lyo | Post-Lyo | 40° C. 0.5 M | Post-Lyo | 40° C. 1 M | Post-Lyo | 40° C. 0.5 M | Post-Lyo | 40° C. 0.5 M | Post-Lyo | 40° C. 0.5 M |
| Activity | 246 | 285 | 236 | 227 | 125 | 141 | 124 | 160 | 128 | 249 | 157 |
| SEC | 99.8 | 99.8 | 99.7 | 99.7 | 99.7 | 99.7 | 99.7 | 99.7 | 99.7 | 99.6 | 99.8 |
| RP | 98.8 | 98.8 | 98.5 | 98.8 | NT | 99.2 | NT | 99.1 | 98.8 | 98.9 | 99.0 |
| 2-10 μm | NT | 2958 | 1395 | 7593 | 4013 | 1550 | 3188 | 869 | 942 | 1235 | 4650 |
| Cake Shrinkage | NA | — | — | — | — | — | — | — | — | — | — |

As can be seen, no significant difference in stability profile was observed within a range of primary drying temperature from -38 C to -20 C. Lyophilized cake appearance showed increased cake shrinkage at a primary drying temperature of -20 C. Similar results were also observed in lyo-formulations containing 1.25% and 1.0% sucrose (data not shown).

Example 4. Chronic Intrathecal Administration of Heparan N-Sulfatase

This example demonstrates that intrathecal administration can be used to effectively deliver a lysosomal enzyme, such as recombinant human heparan N-sulfatase (rhHNS), into brain tissues for the treatment of the neurologic symptoms of mucopolysaccharidosis IIIA (MPS IIIA; Sanfilippo syndrome), the defining clinical feature of this disorder. Experiments described in this example demonstrate that chronic IT administration of rhHNS was well tolerated with dose-related enzyme activity detected in the brain, spinal cord and liver.

In summary, an intrathecal (IT) formulation of recombinant human heparan N-sulfatase (rhHNS) has been developed for the treatment of the neurologic symptoms of mucopolysaccharidosis IIIA (MPS IIIA; Sanfilippo syndrome), the defining clinical feature of this disorder. Since the average age of MPS IIIA patients is 4.5 years, the pivotal toxicology studies for rhHNS were conducted in juvenile cynomolgus monkeys to evaluate the effects on the developing brain. Monkeys were implanted with an intrathecal (IT)-lumbar drug delivery device and dosed every other week by short-term infusion (1.5, 4.5, or 8.3 mg/dose rhHNS for 6 months; 12 doses), with device and vehicle controls receiving phosphate-buffered saline or vehicle, respectively. Eight animals per group (4/sex) were necropsied at 3 and 6 months (device-control group necropsied at 3 months), and 8 animals from the vehicle group and the 3 rhHNS dose groups were necropsied 1 month after the final IT dose. No rhHNS-related clinical signs or gross central nervous system lesions were observed. Compared to controls, there were cellular infiltrates of slight-to-minimal mean severity in the meninges/perineurium surrounding the brain/spinal cord correlating with transient increases in cerebrospinal fluid (CSF) leukocytes, predominantly eosinophils, which largely resolved 1-month post-final dose. These changes were not associated with any adverse morphologic changes in the brain or spinal cord. There appeared to be a dose related trend toward higher mean CSF rhHNS levels and in tissue rhHNS activity levels in the brain, spinal cord, and liver. The no-observed-adverse-effect-level was 8.3 mg/dose given every other week, the highest dose administered, indicating that rhHNS may be safely administered intrathecally at various concentration including concentrations higher than 8.3 mg/dose.

Sanfilippo A Disease

Mucopolysaccharidosis type IIIA (MPS IIIA; Sanfilippo A disease), a rare lysosomal storage disorder affecting approximately 1 in 100,000 people worldwide, results from the absence or defective function of heparan N-sulfatase (HNS) (Neufeld E F, et al. The Metabolic and Molecular Bases of Inherited Disease (2001) pp. 3421-3452), an exosulfatase involved in the lysosomal catabolism of glycosaminoglycan (GAG) heparan sulfate. In the absence of this enzyme, GAG heparan sulfate accumulates in lysosomes of neurons and glial cells, with lesser accumulation outside the brain. The defining clinical feature of this disorder is central nervous system (CNS) degeneration, which results in loss of, or failure to attain, major developmental milestones. The progressive cognitive decline culminates in dementia and premature mortality.

IT Delivery of rhHNS

Since the average age of MPS IIIA patients is 4.5 years, the pivotal toxicology studies for rhHNS were conducted in juvenile cynomolgus monkeys (species selection based upon genetic and anatomic similarity to humans) to evaluate the effects on the developing brain. The age equivalence of monkeys to humans as cited in the literature ranges from 7.6 months to 12.1 months for children 30 to 40 months old (Hood R D, Developmental and Reproductive Toxicology: A practical approach (2006) p. 276). As part of this effort, a 6-month toxicology study was conducted in juvenile cynomolgus monkeys to evaluate IT lumbar administration of rhHNS. The data obtained from a prior 1-month juvenile cynomolgus monkey toxicity study guided the dose level selection and design of the 6-month repeated-dose juvenile monkey study. Based upon data known to date, this is the first study involving the chronic IT administration of ERT in juvenile nonhuman primates.

Fifty-six male and 56 female juvenile cynomolgus monkeys (*Macaca fascicularis*) approximately 6 to 9 months old and weighing 0.82 to 1.81 kg were used in this study. Monkeys were fed 15 biscuits of PMI-Certified Primate Diet 5048 (Richmond, Ind.) daily. Water was provided ad libitum via a filtered automatic water system and was withheld during urine collection periods. Monkeys were group-housed (two per cage) for 2 to 4 weeks in stainless steel cages upon arrival with the exception of the 3-month monkeys; these were individually housed in stainless steel cages. For the duration of the study, all monkeys were housed in individual stainless steel cages in rooms with controlled temperature and humidity with a cycle of 12 hours of light and 12 hours of darkness.

Prior to study initiation, all monkeys were implanted surgically with SC ports and IT catheters. Prednisolone sodium succinate (IV, 30 mg/kg) and flunixin meglumine (intramuscular [IM], 2 mg/kg) were administered prior to surgery. The monkeys were pretreated with SC atropine sulfate (0.04 mg/kg), sedated with IM ketamine HCl; 8 mg/kg), intubated, and maintained on approximately 1 L/min of oxygen and 2.0% isoflurane. An incision was made over the dorsal processes of the lumbar spine ($L_4$, $L_5$, or $L_6$), and a hemilaminectomy was made for the insertion of a tapered polyurethane catheter (25 cm in length, 0.9 mm outer diameter×0.5 mm inner diameter, with six side holes of 0.33 mm diameter) at $L_3$, $L_4$, or $L_5$. The catheter was inserted through a small dural incision and was advanced approximately 10 cm anterograde to the area of the thoracolumbar junction. A titanium SC port was attached to the IT catheter and implanted in the SC tissue. Proper catheter placement was confirmed by myelogram using Isovue-300 (0.8 ml; Bracco Diagnostics, Inc., Princeton, N.J.). After recovering from surgery, monkeys received butorphanol tartrate (IM, 0.05 mg/kg) and ceftiofur sodium (IM, 5.0 mg/kg twice daily for 2 days).

In this example, rhHNS was provided in an IT formulation vehicle including 5 mM sodium phosphate, 145 mM sodium chloride, and 0.005% polysorbate 20 (pH 7.0). EOW doses of rhHNS were administered as a short-term infusion over approximately eleven minutes: 0.6 mL (4 minutes) followed with a flush of 0.5 mL phosphate-buffered saline (PBS) (7 minutes). Monkeys in the vehicle-control group received the IT formulation alone; DC monkeys received PBS (pH 7.2) IT.

Morbidity and Mortality

There were no rhHNS-related deaths or early sacrifices. There were no rhHNS-related clinical signs noted at dosing or during the daily observations. Misplacement, pruritus, tremors, and ataxia observed during and after dosing resolved within a few minutes to approximately 4 hours of administration, and were considered a volume-related response rather than a reaction to rhHNS or the vehicle. Clinical signs observed during and immediately after dosing were seen at a comparable incidence in control groups (DC and/or vehicle-dosed group); there was no evidence of a dose response. In general, the incidence of clinical signs at dosing decreased with each subsequent dose. There were no rhHNS-related changes in body weight, food consumption, and physical and neurologic findings, or alterations in ECG or ophthalmology examinations.

Clinical Pathology

There were no changes considered related to rhHNS in hematology, serum chemistry, coagulation, or urinalysis parameters at any interval.

CSF Cell Counts and Chemistry

There were dose-related increases in mean CSF leukocyte counts for all groups, including DC and 0 mg/dose groups, 24 hours postdose. There was a general increase in leukocyte counts with each dose administered. Collection of CSF from approximately one half of the monkeys prior to dosing showed that these effects had abated in the 2 weeks since the previous dose. After dose 5, in addition to an increase in leukocytes, higher group mean CSF total protein and albumin were observed for the rhHNS-dosed males in the 4.5 and 8.3 mg/dose groups (up to 4- to 5-fold) compared with the predose mean ($P \leq 0.05$ versus the DC and the 0 mg/dose group); less of a trend was evident in the female rhHNS-dosed groups.

rhHNS Concentrations and Antibody Analysis

Figure 12A:
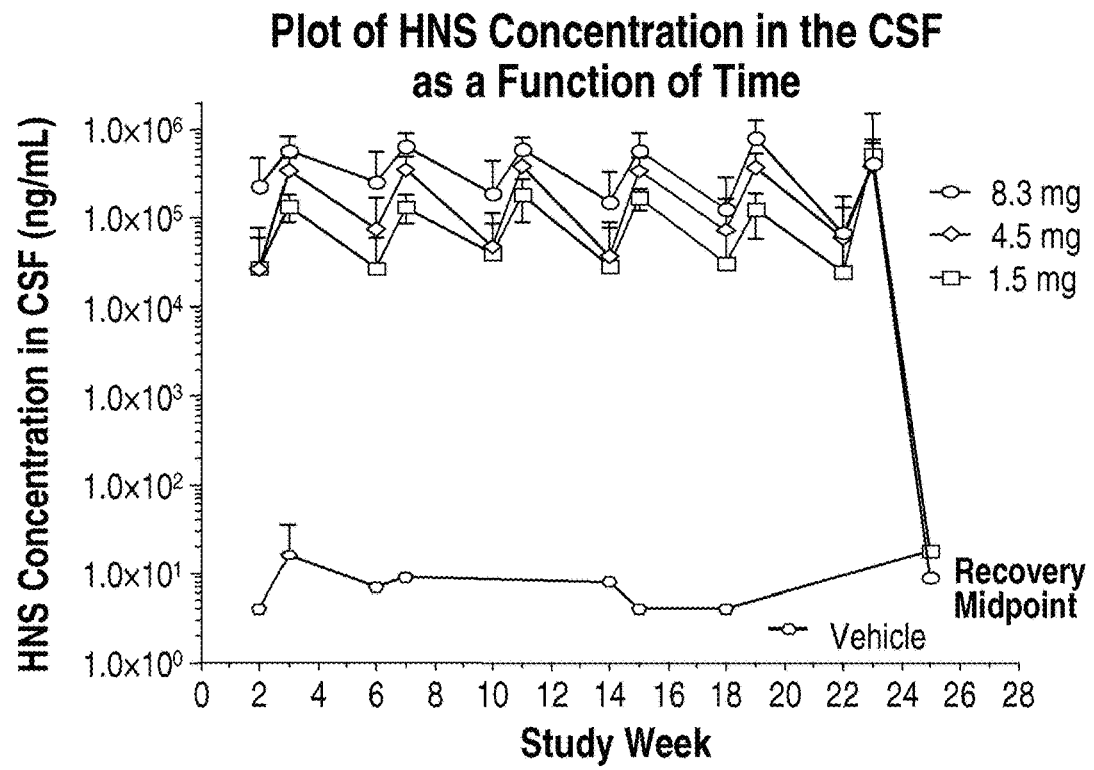
FIG. 12A depicts an exemplary result illustrating CSF concentrations of rhHNS as a function of time at 1.5, 4.5 and 8.3 mg doses following 6 months of dosing.

Typically, the mean rhHNS levels in serum were <limit of detection (LOD) for all test groups for all time points. The rhHNS concentration in CSF from monkeys in the DC- and vehicle-dosed control group was generally below the limit of quantification (LOQ). Although no statistical analyses were performed, there appeared to be a dose-related trend towards higher mean rhHNS levels in CSF in the 1.5, 4.5, and 8.3 mg/dose groups. The predose CSF mean rhHNS levels were significantly lower than the postdose CSF levels. The mean rhHNS concentrations for the 6-month cohort (both sexes) at study termination (main and recovery necropsy) are sumarized in Table 21. At a given dose level, mean concentrations of rhHNS in the CSF appeared to be maintained in the same range (FIG. 12A) despite the anti-HNS antibody levels in the serum and CSF, which continued to rise throughout the study.

TABLE 21

CSF rhHNS concentrations at study termination (main and recovery necropsies).

| | Main Necropsy | | Recovery Necropsy | |
|---|---|---|---|---|
| Group | n | Mean ± SD[a] (ng/mL) | n | Mean ± SD (ng/mL) |
| Vehicle | 8 | — | 8 | NA |
| 1.5 mg IT | 8 | 516,366 ± 1,024,084 | 8 | NA |
| 4.5 mg IT | 7 | 377,460 ± 304,996 | 7 | NA |
| 8.3 mg IT | 8 | 419,492 ± 345,975 | 8 | NA |

CSF, cerebrospinal fluid;
HNS, human heparan N-sulfatase;
n = number of samples above the LOQ;
IT, intrathecal;
SD, standard deviation.
[a] = samples collected approx. 24 hours postdose.
NA = no samples available for analysis or samples below the LOQ.

In the 6-month/recovery cohort, none of the monkeys in the device control group (PBS only) or those dosed with vehicle developed anti-HNS antibodies in serum or CSF at any time point tested. All monkeys in the 1.5, 4.5, and 8.3 mg/dose groups tested negative (<LOD) for anti-HNS antibodies in serum and CSF samples collected prestudy (for CSF) and at predose 2. By the end of the study, all monkeys tested positive for anti-HNS antibodies in serum.

All monkeys in the 1.5 mg/dose and 8.3 mg/dose groups and six of eight monkeys in the 4.5 mg/dose group tested positive for anti-HNS antibodies in the CSF at one or more time points. Since two monkeys in the 4.5 mg group had no sample collected at any time point including necropsy, these results would appear to indicate that all monkeys dosed with rhHNS produced an antibody response.

Figure 12B:
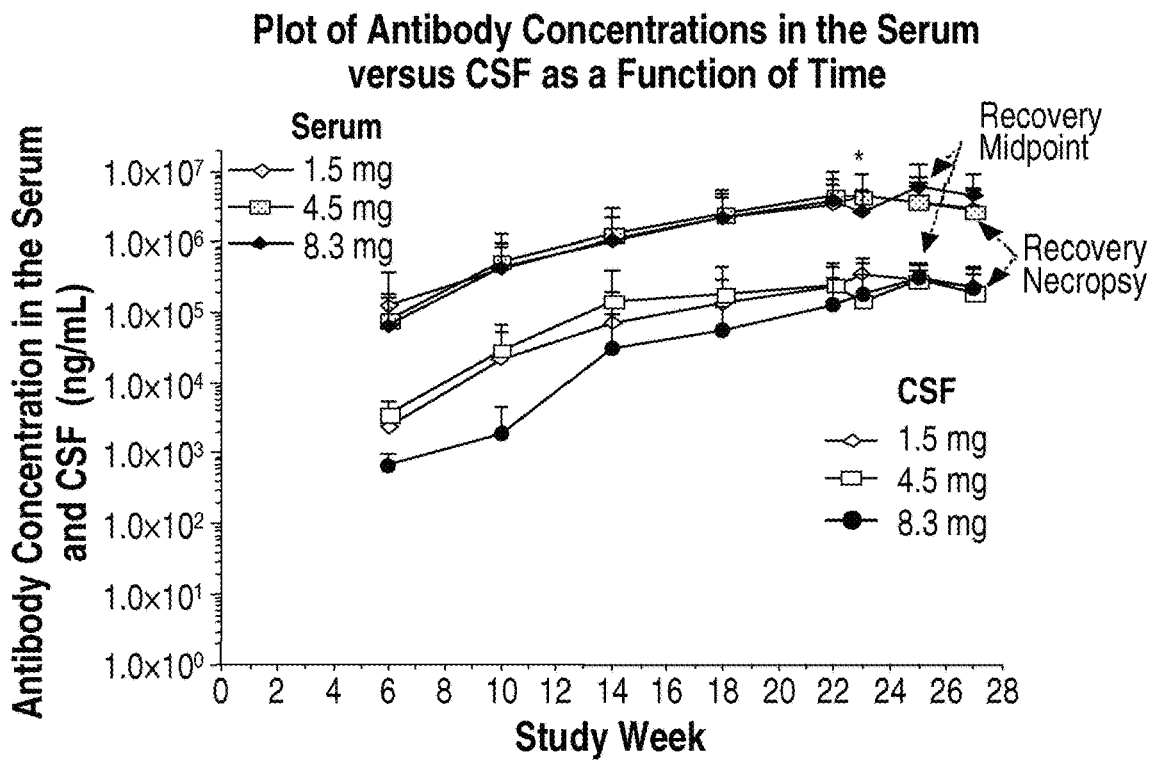
FIG. 12B details an exemplary result illustrating Anti-HNS antibody concentrations in the CSF after 6 months of IT administration of 1.5, 4.5 and 8.3 mg doses in monkeys. Data are shown for male and females combined.

At all three dose levels, anti-HNS antibody concentrations in serum were detected after dose 2, and levels increased markedly after dose 4. Although no statistical analyses were performed, there appeared to be a dose-related trend towards higher serum antibody concentration; by the end of the study, levels were comparable across the 3 rhHNS dose groups (FIG. 12B). Anti-HNS antibody levels in the serum were always higher than in the CSF over the time course of this study (from 9 to 236-fold serum/CSF antibody concentrations); the highest ratios of serum to CSF concentrations (98 and 236-fold) were seen at 8.3 mg dose level in the earlier course of dosing (6 and 10 weeks).

Anti-HNS antibody concentrations in the serum increased 9-, 16-, and 16-fold at 1.5 mg, 4.5 mg, and 8.3 mg/dose levels, respectively, in the early time of dosing (from week 6 to week 14). During the same time period, CSF antibody concentrations increased 30-, 41-, and 52-fold at 1.5 mg, 4.5 mg, and 8.3 mg/dose levels, respectively (FIG. 12B); substantial levels remained after the 1-month dose-free recovery phase (Table 22).

TABLE 22

CSF anti-HNS antibody concentrations at study termination (main and recovery necropsies).

| | Main Necropsy[a] | | Recovery Necropsy | |
|---|---|---|---|---|
| Group | n | Mean ± SD (ng/mL) | n | Mean ± SD (ng/mL) |
| Vehicle | 8 | — | 8 | — |
| 1.5 mg IT | 8 | 351,456 ± 244,171 | 8 | 299,512 ± 226,654 |
| 4.5 mg IT | 7 | 147,187 ± 213,095 | 7 | 193,045 ± 157,896 |
| 8.3 mg IT | 8 | 185,227 ± 315,858 | 8 | 238,727 ± 185,785 |

CSF, cerebrospinal fluid;
HNS, human heparan N-sulfatase;
IT, intrathecal;
n, number of sample above the limit of quantification;
SD, standard deviation.
[a]Samples collected approximately 1 week prior to dosing.

Figure 12C:
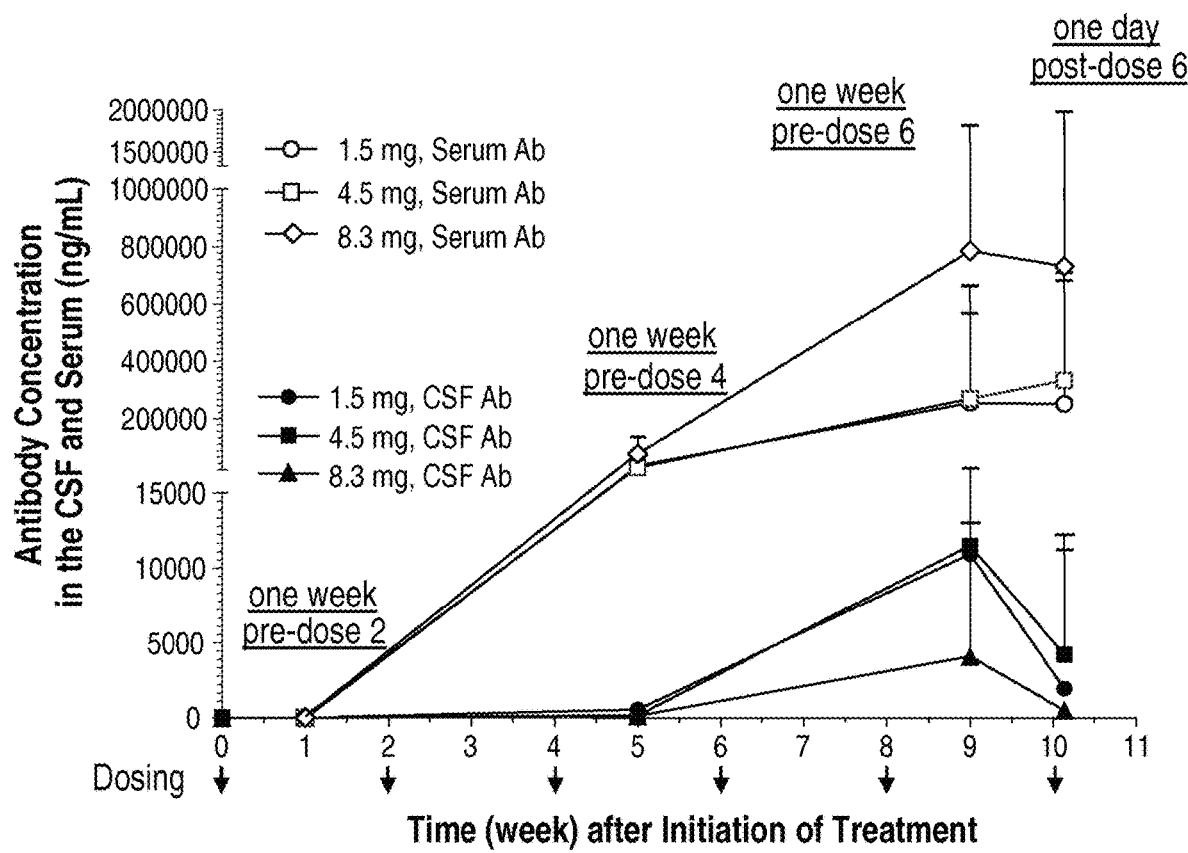
FIG. 12C details an exemplary result illustrating Anti-HNS antibody concentrations in the CSF after 6 months of IT administration of 1.5, 4.5 and 8.3 mg doses in monkeys following 6 months of dosing. Data are shown for male and females combined. The two highest concentrations (32,205 ng/mL and 15,467 ng/mL) post IT dose 6 at 8.3 mg of rhHNS were excluded from the plot because no CSF samples were taken predose 6.

Anti-HNS antibodies appeared later in the CSF than in serum (FIG. 12C). No apparent dose-related differences of antibody concentrations in the serum or CSF were observed (statistical analysis was not done due to small sample sizes); there was no observable difference between males and females in antibody responses.

In the presence of anti-HNS antibody in the CSF, the mean concentrations of rhHNS in the CSF appeared to be maintained, suggesting that the presence of anti-HNS antibodies in the serum and CSF did not alter the concentration level of the IT-dosed rhHNS. The 6-month/recovery cohort analyses of the 6-month repeat-dose administration of rhHNS indicated that the anti-HNS antibody concentrations for the 3-month interim and 6-month cohort sacrifice monkeys were comparable (FIG. 12C).

Gross and Histopathologic Findings

At all dose levels (although not at all sacrifice intervals, gender-specific, nor in a dose-related manner), eosinophilic infiltrates were present in the parenchyma of the brain (predominantly gray matter), spinal cord (gray and white matter), dorsal spinal nerve roots/ganglia and the trigeminal ganglia (mid-dose males only) (FIGS. 13A-E). The infiltrates appeared to be secondary to the meningeal/perineurium infiltrates and/or to the presence of (penetration by) rhHNS within the parenchyma of the tissue. Although there were numerous inflammatory type changes, the monkeys appeared to tolerate administration of rhHNS and none of the infiltrates were considered related to or causing adverse morphologic changes in the nervous system parenchyma. Specifically, there was no evidence of neuronal necrosis/degeneration and no glial response related to rhHNS administration.

Figure 13A:
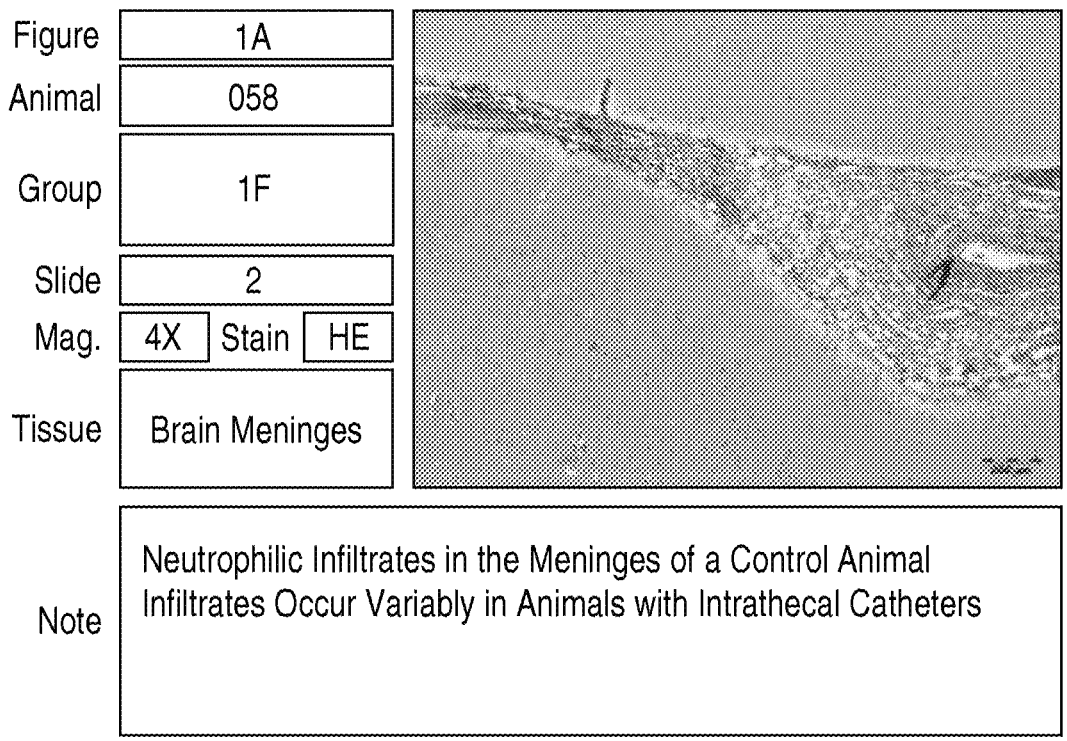
FIG. 13A-F depicts exemplary representative images of tissue sections from the meninges and parenchyma of the brain stained with hematoxylin and eosin.
Figure 13B:
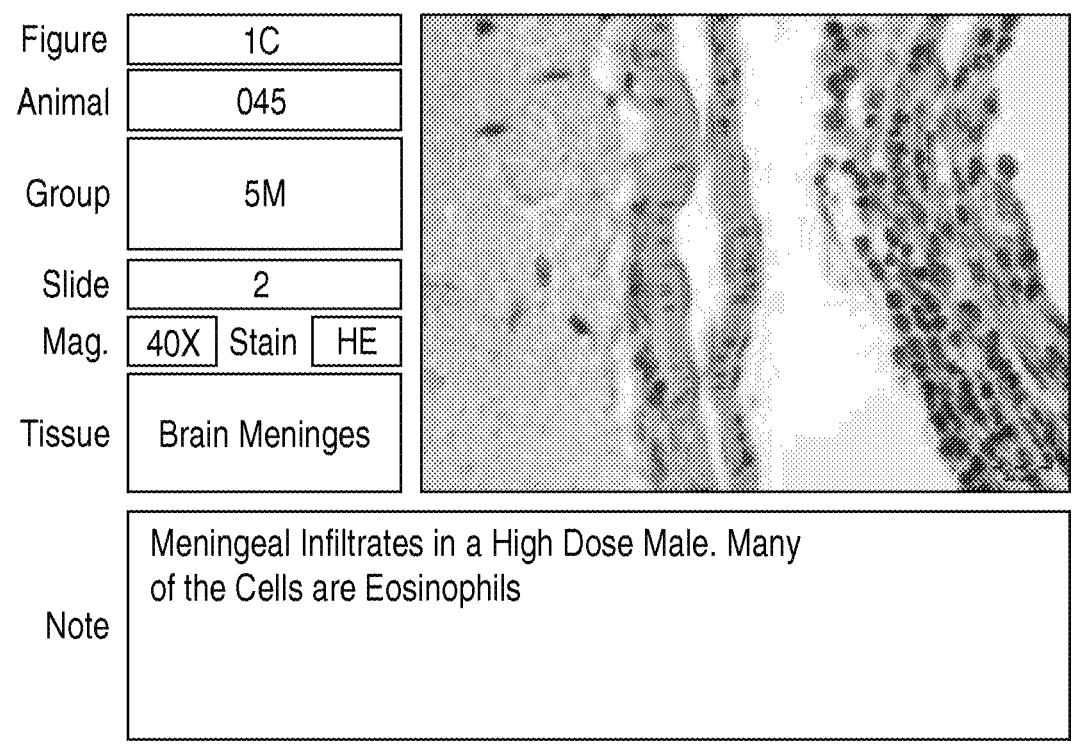
Figure 13C:
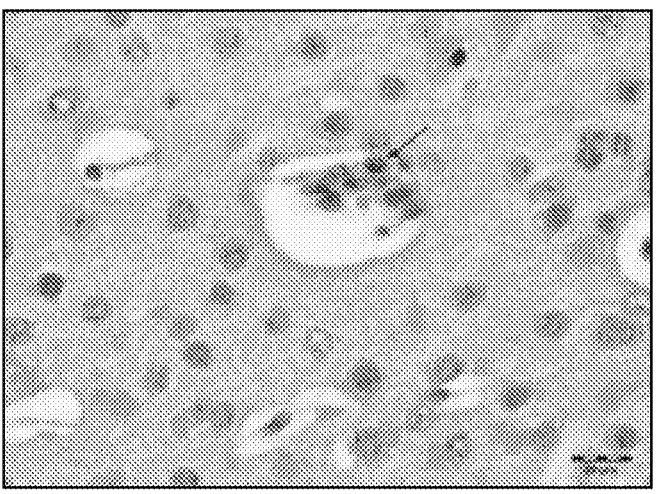
Figure 13D:
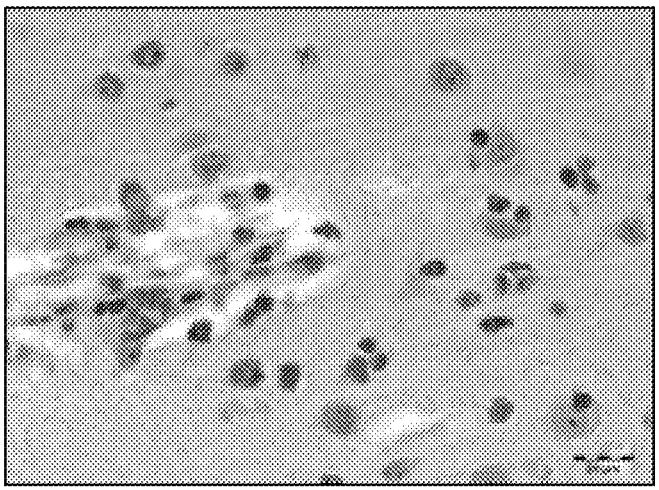
Figure 13E:
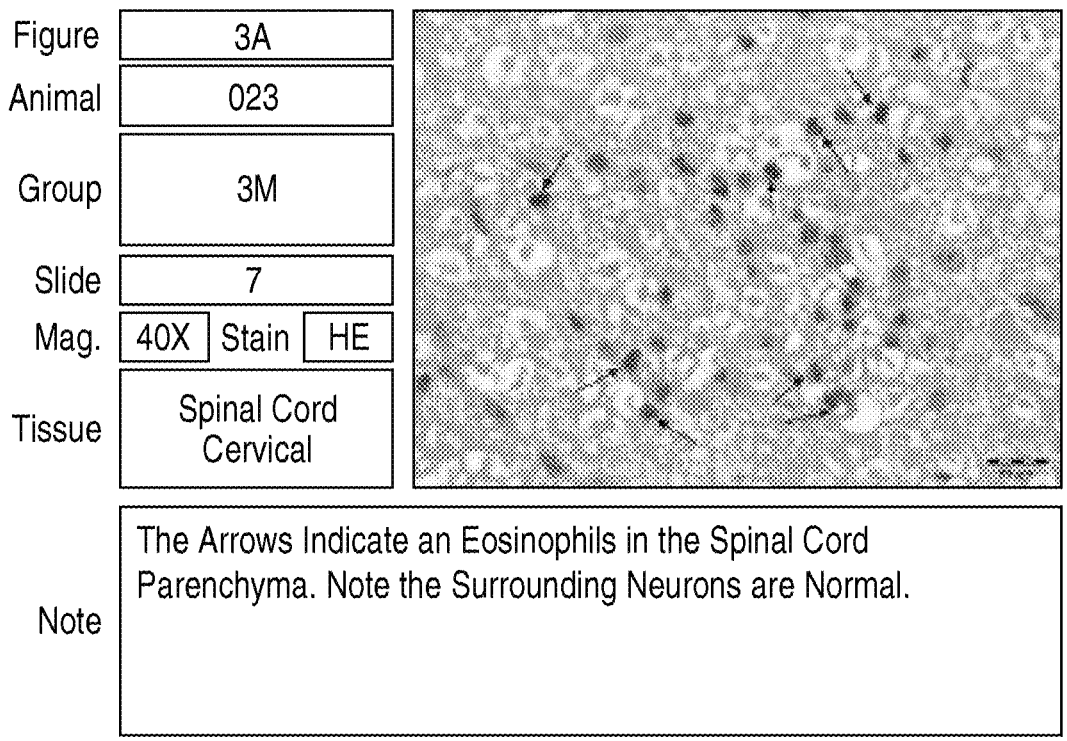
Figure 13F:
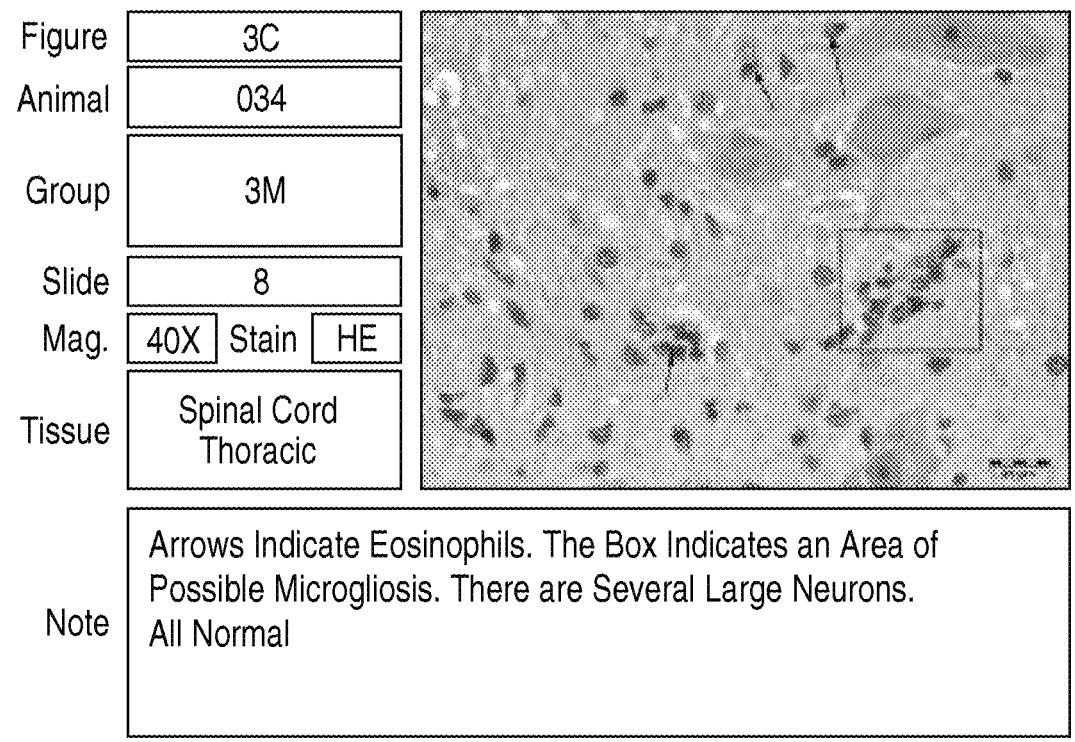

Microgliosis in the gray matter of the brain and spinal cord, in association with cellular infiltrates, predominantly eosinophilic, was relatively common in a previously performed 1-month juvenile monkey toxicity study; these changes were relatively uncommon by the 3-month interim sacrifice in the 6-month study, but residual evidence of such a response could still seen in the 6-month cohort (FIG. 13F). Microglial reactions tend to be a relatively early event in the reaction to some (typically protein-based) centrally administered (or centrally-reactive) test articles. The eosinophilic infiltrates did correlate with increased number of eosinophils in the CSF of rhHNS-dosed monkeys, although the cells were not present in sufficient numbers to elicit an adverse reaction.

At all dose levels, eosinophilic infiltrates were observed in the dorsal spinal nerve roots/ganglia for most rhHNS-dosed groups, regardless of gender. The infiltrates in the various nervous system tissues appeared to be secondary to the meningeal/perineurium infiltrates and/or to the presence of (penetration by) rhHNS within the parenchyma of the tissue. In the recovery sacrifice monkeys, rhHNS-related effects were generally either absent or reduced to control levels. Some changes, such as microgliosis in the spinal cord, were completely resolved after the recovery period. None of the rhHNS-related changes appeared to be associated with any adverse structural microscopic changes in the brain or spinal cord. There was no neuronal necrosis noted in the brain, spinal cord, or ganglia.

Nerve fiber degeneration and gliosis in the spinal cord appeared to be secondary to the placement and/or presence of the IT catheter. These changes were relatively similar between the control and rhHNS-dosed groups. In the spinal nerve roots, Schwann cell (the myelinating cell of the peripheral nervous system) hyperplasia and nerve fiber degeneration were present in both control and rhHNS-dosed monkeys. These changes were due to damage to one or more spinal nerve roots at the time of catheter placement.

HNS Enzyme Activity

Figure 14A:
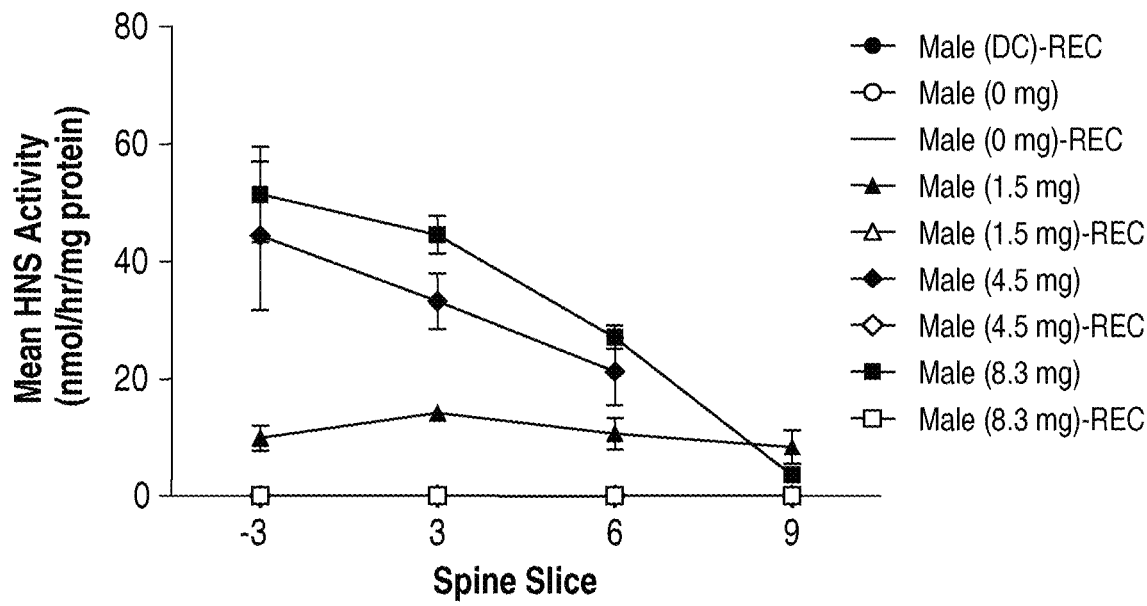
FIG. 14A-D depicts an exemplary result illustrating rhHNS enzyme activity in monkey spinal cords and brains.
Figure 14B:
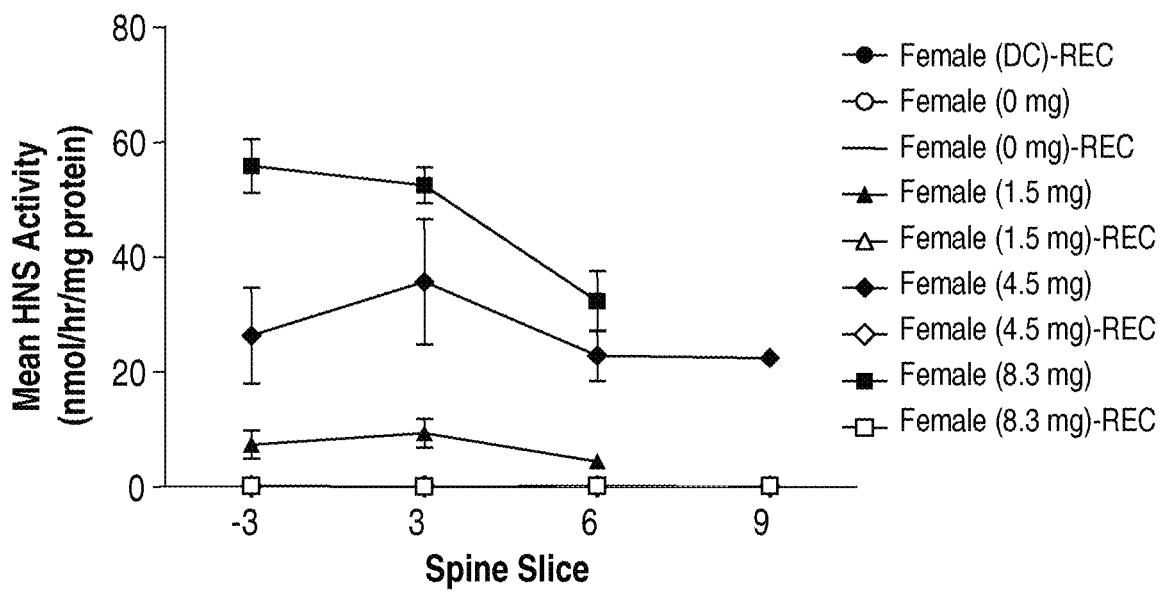

In the 6-month/recovery cohorts, rhHNS enzyme activity in the spinal cord and brain of the vehicle-dosed group (0.0-0.154 nmol/hr/mg protein) were similar to levels shown in tissues from the 3-month interim cohort (0.0-0.0.154 nmol/hr/mg protein). Enzyme activity levels in the spine were higher (approximately an order of magnitude higher in the lumbar spine) than levels measured in brain or liver, the 4.5 mg and 8.3 mg/dose groups having similar levels. The rhHNS enzyme activity in spinal cord slices ranged from 3.9-18.6, 13.1-67.1, and 3.6-69.2 nmol/hr/mg protein in males (FIG. 14A) and 1.8-16.2, 4.5-61.2, and 21.1-66.0 nmol/hr/mg protein in females (FIG. 14B) for the 1.5, 4.5, and 8.3 mg/dose groups, respectively. In spinal tissue after a 1-month recovery period, enzyme activity levels returned to levels consistent with vehicle control values.

Figure 14C:
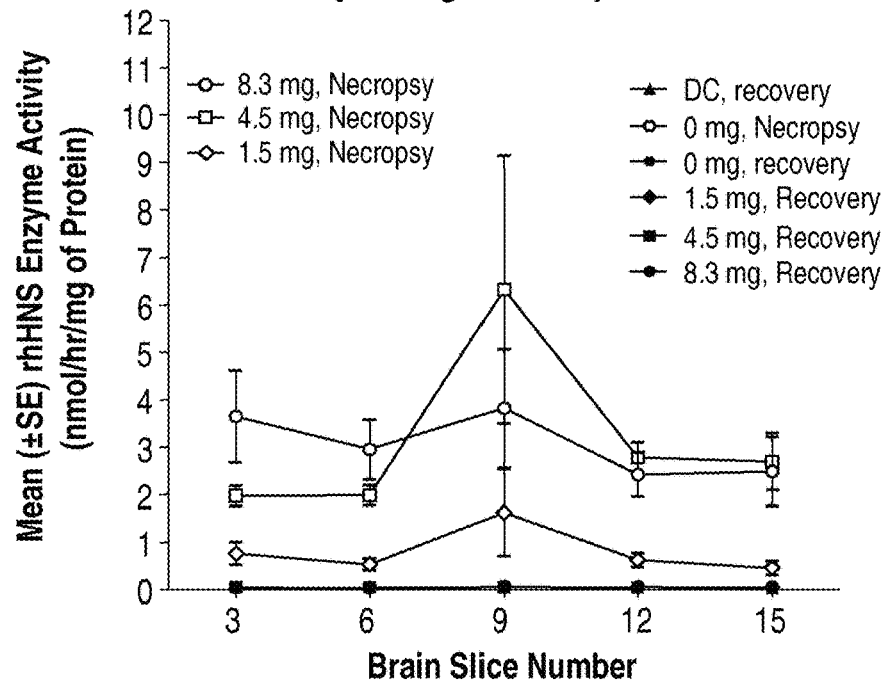
Figure 14D:
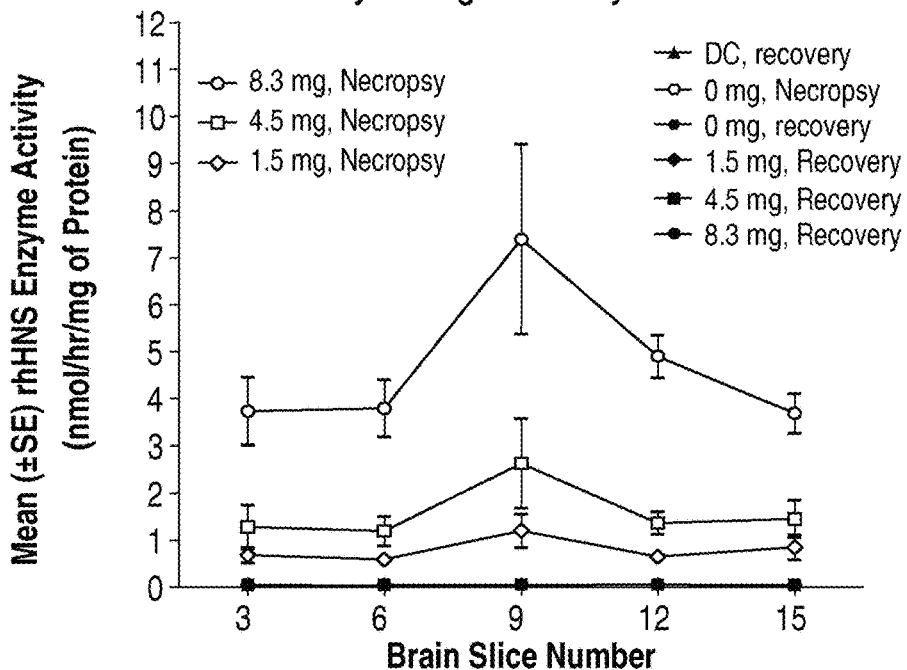

The rhHNS enzyme activity in brain slices ranged from 0.03-16.0, 0.30-55.7, and 0.15-21.2 nmol/hr/mg protein in males (FIG. 14C), and 0.04-5.1, 0.0-14.4 and 0.9-33.2 nmol/hr/mg protein in females (FIG. 14D) for the 1.5, 4.5, and 8.3 mg/dose groups, respectively. In brain tissue after recovery, enzyme activity levels returned to levels consistent with control values.

Figure 15A:
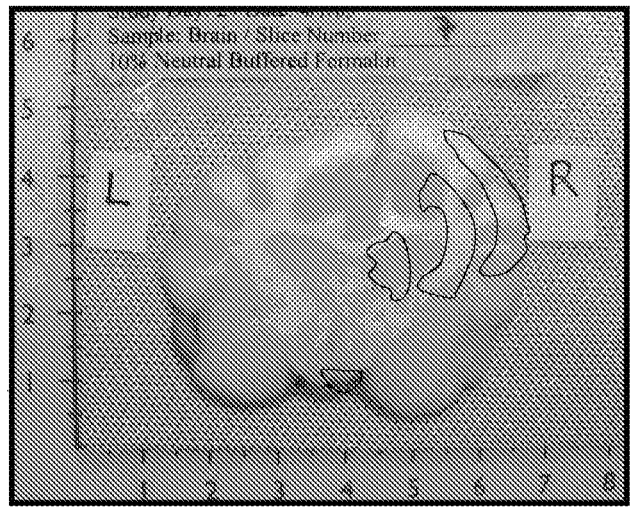
FIGS. 15A and 15B depicts an exemplary result illustrating enzyme activity in monkey brain and liver.
Figure 15A:
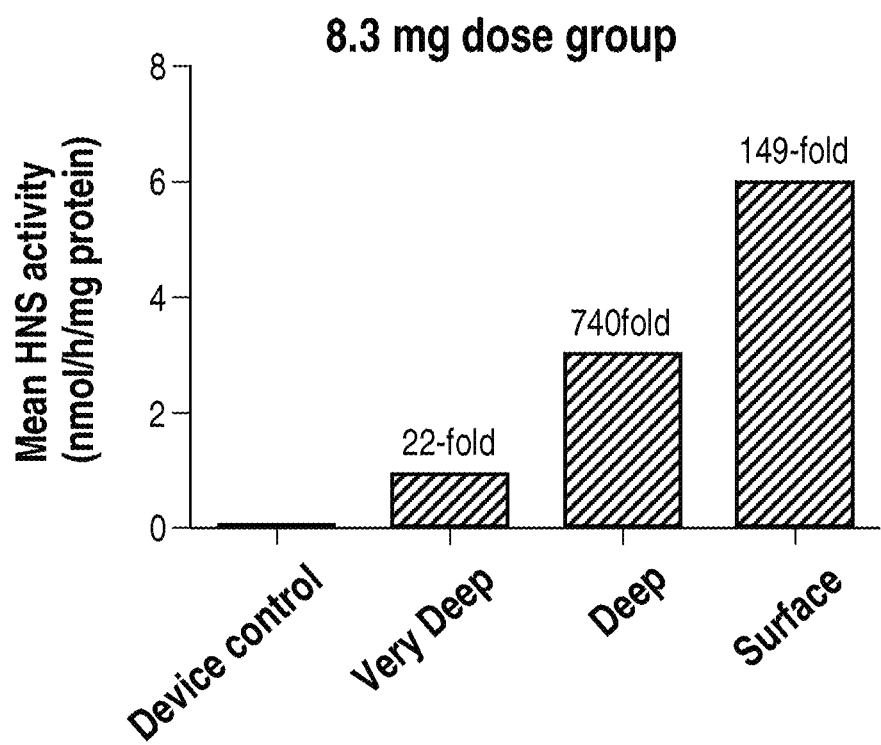

The fold-change in activity for different areas of the brain compared with endogenous levels (DC group) is shown in FIG. 15A. Although a trend toward increased distribution was noted in surface samples, lumbar-IT administered rhHNS could be shown to penetrate to periventricular areas of the brain.

Figure 15B:
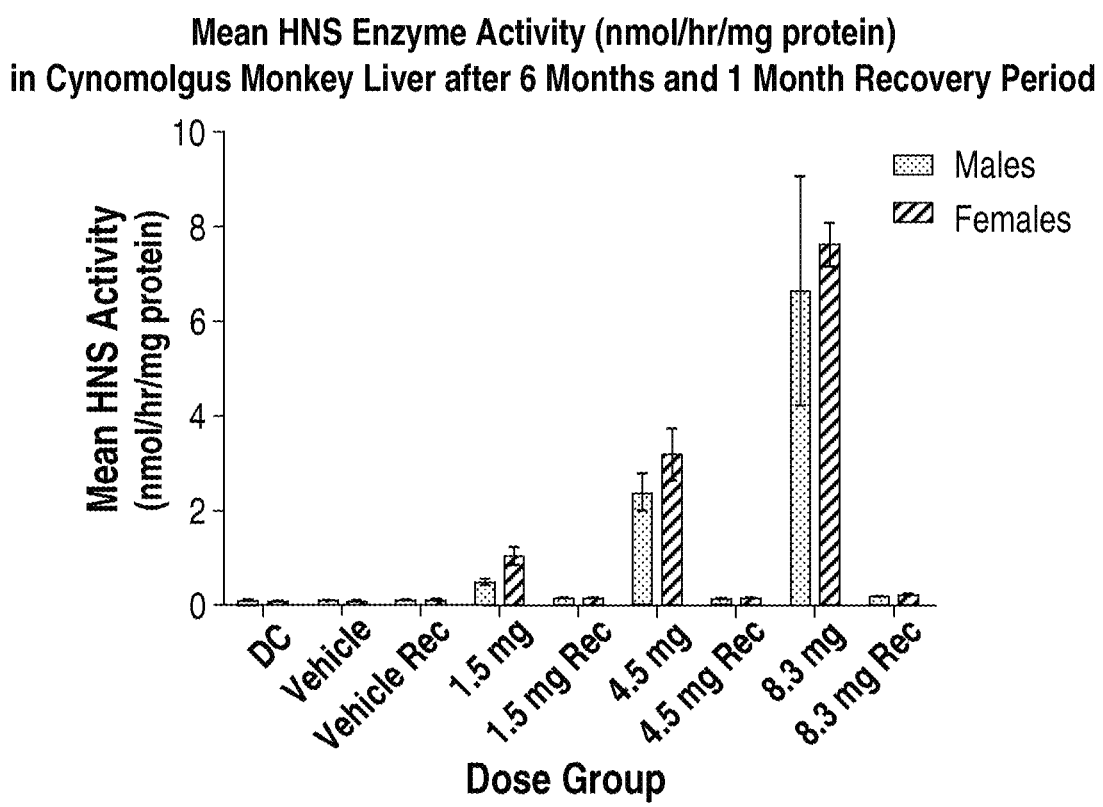

In the 6-month cohort/recovery cohorts, mean activity levels in liver were 0.50, 2.41, and 6.65 nmol/hr/mg protein in males and 1.04, 4.15, and 7.62 nmol/hr/mg protein in females for the 1.5, 4.5, and 8.3 mg/dose groups, respectively (FIG. 15B). Levels in vehicle control monkeys were 0.089 nmol/hr/mg protein for males and 0.083 nmol/hr/mg protein for females. Following the recovery period, rhHNS activity levels in liver were comparable to baseline control levels for all dose groups.

Figure 16A:
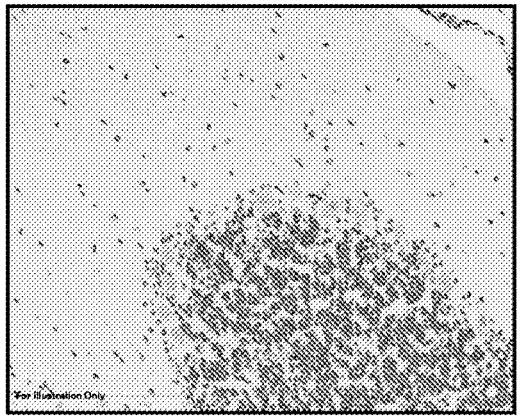
FIG. 16A-D depicts an exemplary result illustrating rhHNS localization in juvenile cynomolgus monkey cerebellum: 3-month interim cohort.
Figure 16B:
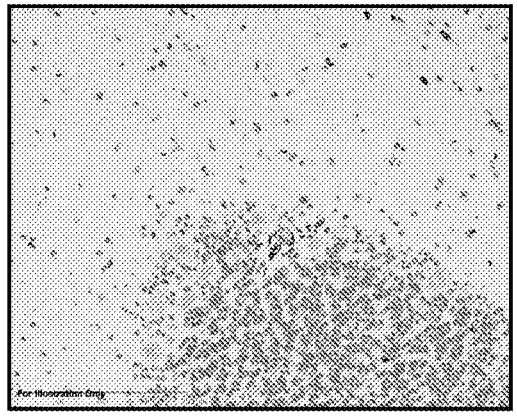
Figure 16C:
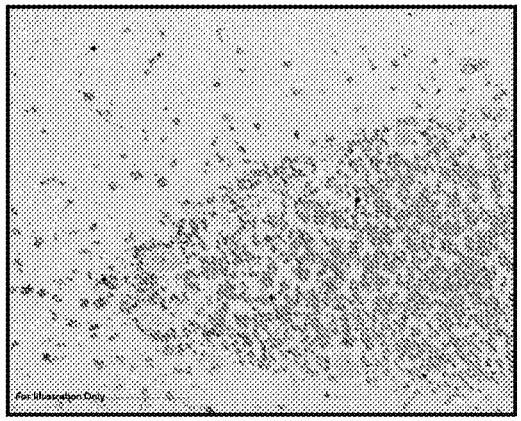
Figure 16D:
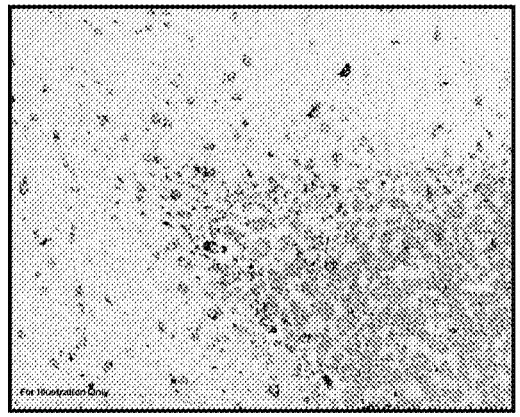

Immunohistochemistry rhHNS delivery to the CNS via bolus IT injection in the 3-month interim and 6-month/recovery cohorts resulted in delivery of immunoreactive test article to the pia-arachnoid tissues of the spinal cord and brain. In the monkeys that received IT rhHNS, the immunoreactive material was consistently present in meningeal and perivascular macrophages (brain/spinal cord) and variably present in the adjacent glial and neuronal cell populations. The lack of staining in vehicle-dosed control monkeys (FIG. 16A) demonstrated the specificity of the antibody to human HNS. Generally, the immunoreactivity was dose related (i.e., using a semiquantitative grading scale, increased immunohistochemical staining was noted in a generally dose-dependent manner). rhHNS delivery to the CNS via bolus IT resulted in positive immunostaining in the cerebral cortex and cerebellum (FIGS. 16B-D); however, immunoreactivity was not consistently evident in the caudate/putamen region, midbrain, or deeper regions of the pons or medulla. Immunoreactivity was evident in the livers (in sinusoidal lining cells including Kupffer cells, but not in hepatocytes) of all monkeys administered rhHNS. Immunoreactivity was not evident in the one female sacrificed early (4.5 mg/dose group) because of a leaking catheter that could not be repaired.

In the 1.5 mg/dose group, essentially full recovery was evident with the exception of liver and the meninges of the brain and spinal cord where some residual immunoreactivity was evident. At higher doses (4.5 and 8.3 mg/dose), the intensity and incidences of immunoreactivity were lower than at the end of dosing. At all dose levels, the levels of rhHNS in spinal cord, brain, and liver approximated those seen in vehicle-dosed controls after the 1-month recovery period.

Discussion

In this study, EOW delivery of rhHNS administered IT for 6 months was generally well tolerated. No remarkable changes were observed in body weight, clinical status, ophthalmologic/neurologic/physical examinations, ECGs, organ weights, or gross organ appearance. Findings were limited to transient changes in CSF clinical pathology accompanied by slight to mild meningeal infiltrates and epidural inflammation, with nearly complete reversal in all but the highest dose group following the recovery period. Widespread distribution of rhHNS throughout the brain and spinal cord was observed.

IT administration of rhHNS EOW elicited an inflammatory response characterized by residual leukocyte infiltration and effusion of albumin noted at 24 hours postdose and at necropsy. Without wishing to be bound by any particular theory, this presumably reflects a transient, localized, and incomplete opening of the BBB related to changes in the tight junctions near the catheter tip, resulting in entry of leukocytes and plasma proteins into the CSF (Simard J M, et al. Lancet Neurol. (2007) 6, 258-268; Stamatovic S M, et al. Curr. Neuropharmacol. (2008) 6, 179-192). This may be the result of two components: one related to the dose administration procedures or volume and another related to IT administration of a protein.

The transient changes in BBB permeability (no significant differences between dose groups and controls 24 hours postdose at the main necropsy), were not accompanied by any clinical signs.

There appeared to be a dose-related trend for higher mean CSF rhHNS levels; at a given dose level, mean concentrations of rhHNS in the CSF appeared to be maintained in the same range despite the increasing anti-HNS antibody levels in the serum and CSF.

Meningeal cellular infiltration of slight-to-minimal mean severity was observed in the brains and spinal cords of rhHNS-dosed juvenile monkeys. This microscopic change was also noted in vehicle-dosed controls, indicating some of the response was related to IT catheter placement, as well as a nonspecific inflammatory response to foreign protein. The introduction of a biologic/protein into the IT space, especially one that penetrates the CNS, nearly always elicits some degree of an inflammatory response (Hovland D N, et al. Toxicol. Pathol. (2007) 35, 1013-1029; Butt M T, Toxicol. Pathol. (2011) 39, 213-219), which, if present in numbers that damage adjacent tissue, would represent an adverse effect. In the current study, however, these cells (predominantly eosionophils) appeared to represent a marker of tissue reaction/penetration and were not found in sufficient quantities to qualify as an adverse effect. None of the rhHNS-related changes appeared to be associated with any adverse structural microscopic changes in the brain or spinal cord. There was no neuronal necrosis noted in the brain, spinal cord, or ganglia.

There were changes in the dorsal tracts of the spinal cord associated with the drug delivery device in some monkeys that included nerve fiber degeneration, catheter tract fibrosis, and compression of the spinal cord; none of these changes were considered to be rhHNS-related in that they occurred in proximity to the IT catheter. The IT lumbar drug delivery device was not specifically designed for IT implantation in juvenile monkeys, which have a smaller IT space than humans. A retrospective analysis of microscopic evaluation data from control (device and/or saline-dosed) animals in IT studies concluded that some minimal degree of meningeal infiltration and catheter tract-associated inflammation, fibrosis, and gliosis, and spinal cord nerve fiber degeneration is seen (Butt M T, Toxicol. Pathol. (2011) 39, 213-219).

Evaluation of anti-test article antibodies is an important aspect of the toxicity studies because of the potential impact of neutralizing or binding antibodies on the clearance or biodistribution of test article (Ponce R P, et al. Regul. Toxicol. Pharmacol. (2009) 54, 164-182). In this study, since dose-related and quantitatively similar levels of rhHNS enzyme activity were noted in the brain and spinal cord of the 3-month interim and 6-month cohorts, and mean concentrations of rhHNS in the CSF appeared to be maintained in the same range despite the increasing anti-HNS antibody levels in the serum and CSF, we concluded that no neutralizing activity was seen.

There appeared to be a dose-related trend toward higher levels of rhHNS enzyme activity in spinal cord, brain, and liver, that was highest near the injection site in the lumbar region of the spinal cord and uniform in the brain, with no significant differences rostral to caudal and between right and left hemispheres. No evidence for rhHNS accumulation was noted in the brain and spinal cord tissue of the 6-month cohort as compared with the 3-month interim cohort. Although a trend toward increased distribution was noted in surface samples, lumbar-IT administered rhHNS penetrated to deep, periventricular areas of the brain. The rhHNS enzyme activity in the liver suggested the rhHNS redistributed systemically after IT delivery; no rhHNS-related adverse effects were observed in the liver after evaluation of clinical and anatomic pathology parameters in the pivotal toxicity studies.

In general, the immunohistochemistry results corroborated the tissue enzyme activity in that dose-related immunoreactivity was observed in the spinal cord and brain pia-arachnoid meninges and in the nervous tissues (neurons, glial cells) in the immediate proximity of the meninges. There was good gray matter penetration of the cerebrum and cerebellum after bolus IT injection or short-term IT infusion. Although immunoreactivity was not evident in deeper structures such as the basal ganglia or the central regions of the thalamus/hypothalamus, midbrain or the pons/medulla, enzyme activity results indicate that lumbar-IT administered rhHNS penetrated to deep, periventricular areas of the brain. Thus, immunohistochemistry may be less sensitive technique for detecting biodistribution of a test article. Immunoreactivity was evident in Kupffer cells and the endothelial cells (cells capable of phagocytosis) of the liver, but not parenchymal cells (hepatocytes).

The 6-month/recovery cohort analyses of the 6-month repeated-dose IT toxicity study in juvenile monkeys indicated that rhHNS-related changes in the 3-month interim and 6-month sacrifice monkeys were comparable, including in-life parameters, clinical and anatomic pathology, concentrations of rhHNS and anti-HNS antibodies in CSF and serum, and distribution/subcellular location of rhHNS in spinal cord, brain, and liver. In the recovery sacrifice monkeys, rhHNS effects were either absent or significantly reduced. Thus, the no-observed-adverse-effect-level for the 6-month juvenile monkey study was 8.3 mg/dose, the highest dose administered.

Monitoring changes in CSF cellularity and protein concentrations appears to be a reliable correlate of the morphological changes noted on histopathologic evaluation and may be useful in patients treated IT with rhHNS; these changes were considered to be an expected reaction to an IT-administered protein and were largely resolved after the recovery period. These data from animal models provide confidence for pursuing IT therapy as a treatment strategy for the neurological manifestations of lysosomal storage diseases. This juvenile nonhuman primate toxicology study demonstrates the feasibility and tolerability of administering rhHNS via an IT lumbar drug delivery device to pediatric patients. The nonadverse CNS pathology and lack of adverse clinical signs have supported the recent investigational medical product dossier approval and indicated that IT-administered rhHNS can safely and effectively treat CNS symptoms of Sanfillippo A syndrome.

Exemplary materials and methods used in various experiments described in this example are provided below.

Study Design and rhHNS Dosing

The monkeys were randomized into five treatment groups; group 1 was untreated (implant device control [DC], port and catheter) and was not dosed with the vehicle or test article. Groups 2 through 5 received 0.6 mL of 0, 2.5, 7.5 or 13.8 mg/mL rhHNS IT, (i.e., a total dose of 0, 1.5, 4.5, or 8.3 mg) EOW. Four monkeys/sex/group were necropsied at 3 months (interim necropsy; 24 hours after the 6$^{th}$ dose), four monkeys/sex/group (except the DC group, which were necropsied at 3 months) were necropsied at 6 months of dosing (main necropsy; 24 hours after the 12$^{th}$ dose), and the remaining four monkeys/sex/group were necropsied at the end of a 1-month recovery period. At necropsy, selected tissues were harvested, processed, and examined microscopically.

rhHNS was provided in an IT formulation vehicle consisting of 5 mM sodium phosphate, 145 mM sodium chloride, and 0.005% polysorbate 20 (pH 7.0). Every other week doses of rhHNS were administered as a short-term infusion over approximately eleven minutes: 0.6 mL (4 minutes) followed with a flush of 0.5 mL phosphate-buffered saline (PBS) (7 minutes). Monkeys in the vehicle-control group received the IT formulation alone; DC monkeys received PBS (pH 7.2) IT.

Clinical Evaluation

Clinical signs and morbidity and mortality observations were recorded at least twice daily starting at the first dose. Body weights were measured prior to surgery, on the day of surgery, weekly during the study, and at necropsy. Food consumption was monitored daily starting before surgery. Physical (heart rate, respiration, body temperature, auscultation, gait, disposition, abdominal palpation, lymph nodes, and general appearance) and neurologic (level of consciousness, tracking) examinations were performed before the study was initiated, each month during the study, and before necropsy. Motor functions, cerebral reflexes (pupillary, blink, and corneal reflex), and spinal reflexes (sensory foot, knee jerk, cutaneous, proprioceptive, and tail reflex) were also assessed. Electrocardiographic (ECG; leads I, II, and III) and ophthalmologic examinations were completed prior to the first dose of rhHNS and in the week before the interim (3-month) or the main (6-month) necropsy. Ophthalmic examinations were performed by indirect ophthalmoscope, the monkeys were sedated with ketamine HCl (IM, 8 mg/kg), and eyes were dilated with 1% tropicamide.

Clinical Pathology

Blood samples were collected from fasted monkeys for hematology and serum chemistry prior to the study start, after IT doses 1, 3, 5, 7, 9 and 11, mid-recovery, and at necropsy. Urine samples were collected via pan catch predose, once monthly during the dosing and recovery period, and prior to necropsy. CSF samples were collected via the lumbar catheter for total cell count and chemistry analysis at the time of surgery, and 24 hours following IT doses 1, 3, 5, 7, 9, 11, mid-recovery, and at necropsy; on occasion, samples were not collected due to partial catheter obstruction. Because higher than expected CSF leukocyte counts were noted, the 3-month dose 5 CSF samples were collected from half the monkeys in each group before dosing and from the remaining monkeys 24 hours after dosing. The predose sample collection occurred at least 1 day prior to dosing so as not to significantly alter the CSF volume just prior to dosing. For the 6-month and recovery monkeys, CSF for total cell count and chemistry was collected from half the monkeys in each group before dosing and from the remaining monkeys 24 hours after dosing. If a monkey had a nonsampling catheter due to an obstruction, a spinal tap (cisterna magna) was performed at the necropsy.

rhHNS Analysis

Blood samples for rhHNS analysis were collected from a peripheral vein prior to and 24 hours post IT doses 2, 4, 6, 8, 10, 12; mid-recovery, and at necropsy. CSF samples were collected via the lumbar catheter prior to and 24 hours post IT doses 2, 4, 6, 8, 10, 12, mid-recovery, and at necropsy. rhHNS concentrations were determined by enzyme-linked immunosorbent assay. The capture antibody was a polyclonal rabbit anti-HNS IgG and the detection antibody was a horseradish peroxidase-conjugate of the same rabbit anti-HNS IgG. The LOD was 0.22 ng/mL; thus, the LOQ was calculated to be 0.66 ng/mL. Serum and CSF samples were screened in duplicate at 1:100 and 1:5 dilutions; samples exceeding the high end of the calibration curve were further diluted and retested.

Anti-HNS Antibody Analysis

Blood for antibody analysis was collected from a peripheral vein approximately 1 week prior to IT doses 2, 4, 6, 8, 10, 12; mid-recovery, and at necropsy. CSF samples for antibody analysis were collected at surgery, and via the lumbar catheter approximately 1 week prior to IT doses 2, 4, 6, 8, 10, 12; mid-recovery; and at necropsy. A Meso Scale Discovery (MSD®) technology electrochemiluminescent bridge test was used for detection of anti-HNS antibodies. The assay is a general, but sensitive, screening method for anti-HNS antibodies from any species and all immunoglobulin isotypes. The LOD was 5 ng/mL, and the samples were screened in duplicate at a 1:20 dilution, resulting in an effective assay sensitivity of 100 ng/mL. Samples exceeding the high end of the calibration curve were further diluted and retested.

Necropsy and Preparation of Tissues

Monkeys underwent a full necropsy either 24 hours after the final IT dose (main necropsy) or at the end of the 1-month recovery period (recovery necropsy). All monkeys were sedated with ketamine HCl (IM, 8 mg/kg), were maintained on an isoflurane/oxygen mixture, and received an IV bolus of heparin sodium (200 IU/kg). Monkeys were perfused via the left cardiac ventricle with room temperature 0.001% sodium nitrite in saline at a rate of 200 ml/min for 12 min (~2400 ml). After collection, tissue samples were then fixed in 10% neutral buffered formalin for histopathologic examination/immunohistochemical analysis or were frozen on dry ice and stored at −60° C. or lower for analysis of rhHNS activity.

The brain was cut in a brain matrix (MBM-2000C, ASI Instruments, Inc., Warren, Mich.) at 3-mm coronal slice thickness. The slices were numbered, with the most rostral slice designated as slice 1. Slices 1, 4, 7, 10, 13, and 16 were processed for histopathology and slices 2, 5, 8, 11, 14, and 17 (if available) were processed for immunohistochemistry. Slices 3, 6, 9, 12, and 15 were frozen for analysis of rhHNS activity. The spinal cords (cervical, thoracic, and lumbar portions) were cut into 1-cm sections. The first slice and every third slice thereafter were processed for histopathologic evaluation and the second slice and every third slice thereafter were processed for immunohistochemical analysis. The third slice and every third slice thereafter were frozen for rhHNS analysis. The distribution of slices was adjusted so that the slice containing the tip of the intrathecal catheter (slice 0) was fixed in formalin and analyzed for histopathology. Duplicate samples of ~5 g of the liver were taken from two separate lobes and frozen for rhHNS analysis and an additional sample of ~5 g was fixed for immunohistochemical analysis.

Histopathology

The brains, spinal cords, dorsal spinal nerve roots/ganglion, sciatic, tibial and sural nerves, a complete tissue list (typical for preclinical drug safety studies of this duration in this species), and any gross lesions were harvested at necropsy from all monkeys. Tissue sections were embedded in paraffin and stained with hematoxylin and eosin (in addition to any special staining/embedding procedures noted below) for comprehensive microscopic evaluation.

Brain sections from the prepared paraffin blocks from the device and vehicle-control groups, and the high-dose monkeys were stained with Fluoro-Jade B (a stain increasing the sensitivity of evaluating neuronal degeneration) and Bielschowsky's silver (a procedure that allows direct visualization of axons, dendrites, and neuronal filaments). The Fluoro-Jade B stained slides were examined under fluorescent lighting using a fluorescein isothiocyanate filter cube.

Spinal cords were sectioned serially, with a transverse and oblique sections taken at the cervical, thoracic, and lumbar regions (one slice examined at each level) including sections at the catheter tip; an additional transverse section was taken from the cauda equina region. Dorsal spinal roots and ganglia (midcervical, midthoracic, and midlumbar) were processed and examined. Peripheral nerves (sciatic, tibial, and sural) were sectioned longitudinally, embedded in paraffin and stained with hematoxylin and eosin (H&E). Cross sections were postfixed in osmium, embedded in Spurr's resin, sectioned (2 µm) and stained with toluidine blue.

Serial spinal cord sections, as well as dorsal spinal nerve roots and ganglia, from the device and vehicle control groups and the high-dose group were stained with Bielschowsky's silver. Spinal cord sections from these groups also were stained with anti-glial fibrillary acidic protein, an immunohistochemical stain that allows for direct visualization of astrocytes and their processes.

Preparation of Tissue Extracts for Quantitative Analysis

Frozen brain slices 3, 6, 9, 12, and 15 were dissected by separating the left and right hemispheres. Surface tissue was taken by measuring 4 mm from the surface, and the remaining tissue in each hemisphere was considered deep tissue. If present (e.g., slices 6 and 9), an additional periventricular sample was cut from the coronal slices. Since only one-half of the brain (the right side) was processed (the left side was retained frozen), the sectioning resulted in two to three samples per slice: right surface, right deep, and, if present, right periventricular (i.e., Ventricle deep; Vdeep). Cerebellar and brain stem tissues, when present, were isolated prior to separating the hemispheres and were processed independently. Spinal cord sections were prepared similarly, weighed, and homogenized.

Tissue samples were homogenized in lysis buffer (1 ml/0.25 g tissue) formulated with 10 mM Tris, 5 mM ethylenediaminetetracetic acid, 0.1% Igepal supplemented with Alpha Complete protease inhibitor minitablets (Roche Diagnostics, Indianapolis, Ind.) using TeenA Lysing Matrix A tubes or conical polypropylene tubes. Samples were processed for 40 seconds in the Fastprep-24 automated homogenizer (MP Biomedicals, Solon, Ohio) or PowerGen Model 125 powered homogenizer (Omni International, Kennesaw, Ga.). Once homogenized, samples were subjected to five freeze-thaw cycles using an ethanol/dry ice bath and a 37° C. water bath and then centrifuged at 4° C. to pellet tissue debris; supernatants were stored at −80° C. until assayed. rhHNS activity was determined using a specific substrate (4-methylumbelliferyl-α-D-N-sulphoglucosaminide) with a 2-step fluorometric assay.

Tissue Processing and Staining for Immunohistochemistry

Six formalin-fixed coronal brain slices (slice numbers 2, 5, 8, 11, 14, and 17) of 3-mm thickness from each monkey were numbered 1 to 6 rostral to caudal. Generally, slices 1 to 4 contained basal nuclei/thalamus/midbrain and cerebrum, and the caudal two slices contained cerebellum and brain stem (medulla oblongata) tissue. Brain, spinal cord and liver sections (from the same paraffin blocks as those used for H&E and the various special stains) were immunohistochemically stained for rhHNS. A specific mouse monoclonal antibody (clone 2C7; Maine Biotech, Portland, Me.) was used to detect intracellular uptake of IT-administered rhHNS; this reagent demonstrated no cross-reactivity with endogenous cynomolgus monkey rhHNS. Negative controls were performed using an irrelevant mouse IgG. Deparaffinized slides were incubated with primary mouse anti-HNS antibody overnight at 2 to 8° C. A secondary goat anti-mouse biotinylated immunoglobulin G was added and incubated for 30 minutes at 37° C. Avidin/biotinylated horseradish peroxidase complex was added and incubated for 30 minutes. Slides were incubated in peroxidase substrate diaminobenzidine solution until the desired stain intensity developed. Nuclei were counterstained with hematoxylin.

Statistical Analyses

Body weights, body weight changes, food consumption, respiratory rate, body temperature, heart rate, CSF cell count, CSF chemistry, clinical pathology data, urine data, and absolute and relative organ weights were analyzed by a one-way analysis of variance and a comparison of the device and vehicle control groups to each rhHNS-dosed group by Dunnett's test. In addition, the statistical analysis compared the two control groups to each other. Analysis was two-tailed for significance levels of 5% and 1%. All data are presented as mean±standard deviation.

Example 5. Heparan N-Sulfatase Biodistribution and Pharmacokinetic Studies

The experiments in this example were designed to determine tissue distribution of rhHNS in rats after a single intravenous or intrathecal dose (1 or 10 mg/kg) of rhHNS. For example, among other things, the purpose of these experiments were to characterize the biodistribution (BD) properties of rhHNS in rats using positron emission tomography (PET); to compare distribution patterns of rhHNS when given in different routes (IV or IT) and at different doses (1 or 10 mg/kg); and to determine pharmacokinetic properties of rhHNS in each of the interest organs in these dosing regimens.

Pharmacokinetic (PK) and biodistribution (BD) profiles of $^{124}$I-sulfamidase (rhHNS) were studied by tissue PET imaging in rats after single intravenous (IV) or intrathecal (IT) administration of 1 or 10 mg/kg of $^{124}$I-HNS. Radioactivity-time data in the region of interest were obtained from dynamic images in the first 20 min and from static images at 0.05 (only for IT administration), 1, 2, 4, 8, 24, 48, 96 and 192 hours post IV or IT dosing.

Four rats in each of four groups (1 mg/kg IV, 1 mg/kg IT, 10 mg/kg IV and 10 mg/kg IT) were used in this study. Radioactivity-time data were measured in the head, brain (including cerebrospinal fluid, CSF), spine and liver regions after IT administration; and in the blood, brain (including CSF), liver, kidney, heart (including lungs) and skin after IV administration. The data were corrected by the decay half-life of 124-iodine (100.2 hours), expressed as percentage of injected dose (% ID) of a region of interest or % ID per gram (% ID/g) of the imaged tissues, and then normalized for the body weight of 200 grams. The total amounts (ug) or concentrations (ug/g) of the dosed protein in the region of interest were calculated from the corresponding % ID or % ID/g data.

In the first 20 min after IT dosing, total amount of rhHNS in the head region was reduced at a constant rate of 0.002/min-0.011/min ($\lambda z$) at 1 and 10 mg/kg. Clearance rates and distribution volumes were not used for pharmacokinetic comparisons between the two doses and the two administration routes in this report (see Results section for more information). The constant rates of elimination from the brain were essentially the same at two test doses ($\lambda z$: 0.016/hr versus 0.014/hr for 1 and 10 mg/kg, respectively) with a similar half-life of about two days as determined by static imaging up to 192 hours after IT dosing. The values of Cmax and AUC (0-last or 0-infinite) were proportional to the administered doses. A linear PK behavior was indicated in the dose range of 1 to 10 mg/kg given in these IT single-dosing regimens. Concentration gradients were observed from the proximal to distal sections of the spine at both dose levels.

After IT dosing, rhHNS protein was measurable in the liver up to 96 hours at 1 mg/kg and up to 192 hours at 10 mg/kg of rhHNS. The concentrations in the liver reached the peak 2 hours at 1 mg/kg, and 7 hours at 10 mg/kg. The elimination was 0.030±0.011/hr (mean $\lambda z$) at 1 mg/kg, which was not significantly different from that at 10 mg/kg ($\lambda z$ 0.017±0/hr) (p=0.10), with a corresponding t1/2 (28 versus 42 hours at the doses of 1 and 10 mg/kg, respectively).

After IV dosing, the elimination half-lives in the liver, kidney, heart and skin were 47±10 and 38±13 hours for the liver, 54±25 and 29±16 hours for the kidney, 36±15 and 42±19 hours for the heart, and 40±21 and 31±13 hours for the skin at 1 and 10 mg/kg, respectively; while the half-lives in the brain were 71±23 and 60±53 hours. The mean values of Cmax for the liver, skin, kidney, heart and brain were 9.6, 0.30, 0.25, 0.22, and 0.08 ug/g at 1 mg/kg and 132, 7.9, 3.9, 3.7 and 1.8 ug/g at 10 mg/kg. After the Cmax values from individual animal were normalized for dose, the Cmax/dose values at 10 mg/kg were significantly higher than that at 1 mg/kg in all these organs (most p values <0.05, p=0.06 for the liver). The values of AUClast for the liver, skin, kidney, heart and brain were 525, 16, 14, 9 and 7 hr·ug/g at 1 mg/kg; and 6747, 276, 183, 201 and 86 hr·ug/g at 10 mg/kg. After normalization, the AUClast/dose values at 10 mg/kg were significantly higher than that at 1 mg/kg in the skin (p<0.01), marginally different in the heart (p=0.06), and not significantly different in the liver, brain and kidney (all p values >0.34).

When the same dose of rhHNS was injected, intrathecal administration resulted in a three-log greater brain exposure than that with intravenous administration. The elimination half-life in the brain was 2 days by IT and 3 days by IV administration. However, hepatic exposures after IT dosing were similar to that after IV dosing at the same dose of rhHNS. The exposure (Cmax and AUClast) for the liver by IT/IV at 1 mg/kg and 10 mg/kg were in a range of 0.4-1.2.

Experimental Design

The central nervous system (CNS) is vulnerable in most lysosome storage diseases and is seriously damaged in some types of these diseases, such as Sanfilippo (mucopolysaccharidosis III), Metachromatic Leukodystrophy (MLD) and Hunter Syndrome. As described herein, it is contemplated that, due to poor penetration through blood-brain barrier when administered peripherally, direct administration of enzymatic proteins into the CNS may increase their concentrations in the central nervous tissues and further enhance their therapeutic effects. Intrathecal (IT, or cisterna magna) administration was investigated and compared with IV administration at different dose levels in this study.

PET is a non-invasive, repeatable and quantitative technology to provide dynamic change of drug concentration over time in the organ of interest. The dynamic concentration-time data from target organs (active sites, rather than in blood circulation) are valuable, and are directly related to the biological activity of the dosed drug. Furthermore, the information on tissue exposures from PET study in animals can be used to guide the selection of the first-dose in human.

Materials and Methods

Test Articles

Heparin N-Sulfatase (rhHNS) was formulated at a concentration of 20 mg/mL of rhHNS in 5 mM sodium phosphates buffer with 145 mM sodium chloride at pH 7.0. The material was purified by RP-HPLC and contained 98.7% of Heparin N-Sulfatase with 99.9% of dimer. rhHNS was labeled with $^{124}$iodine.

Sample Source

Radioactivity images were from rats after IV and IT dosing $^{124}$I—H—N-sulfatase at 1 and 10 mg/kg.

Animals

Sixteen male Sprague-Dawley rats were purchased from Charles River Laboratories (190±60 g, n=16), and were separated into four groups (n=4). Single IV or IT injection at two different doses (1 mg/kg and 10 mg/kg) was given to each group of these rats (total 4 groups). The dose and injected volume were individualized based on the body weight of each animal. In two IV-treated groups, sedation was induced by IV injection of sodium pentobarbital at a dose of 35 mg/kg. Intravenous doses were injected in a bolus through a tail vein. In two IT-treated groups, animals were anesthetized by intra-peritoneal administration of sodium pentobarbital at a dose of 50 mg/kg. Intrathecal doses were administered over 1 min at cisterna magna level through the atlanto-occipital membrane. The actual administered radioactivity was measured by PET, and served as the injected dose.

Experimental and/or Assay Method(s)

Dynamic images (every 2 min) were obtained in the first 20 minutes in the regions of the heart (including the lungs), liver and kidneys post IV injection; and in the head region post IT administration of both doses. Static imaging was acquired in the regions including the brain (including cerebrospinal fluid, CSF), liver, kidney, heart (including the lungs), muscle, skin and bone in IV-treated group; and in the region of head, brain (including CSF) and liver of IT-treated animals at 0.05 (only available for IT groups), 1, 2, 4, 8, 24, 48, 96 and 192 hours post-dosing. The images were reconstructed and the three body sections were fused into one image.

Data Analyses

PET data were expressed in nanocurie (nCi) per mL (for fluid) or per gram (for tissue). Relative activity was obtained for the brain, liver, kidneys, skeletal muscle, stomach, heart (with lungs) and skin regions in static images. Absolute activity in the whole head or brain regions was obtained for the animals that received IT injections. Radioactivity per millimeter of spinal column was determined in the IT injected animals at three selected sections: the proximal (neck), mid (against upper edge of the liver), and distal (1 cm from the distal end of the protein containing compartment) spine.

All data were corrected by the decay half-life of $^{124}$I (100.2 hours) and normalized for registration efficacy based on calibration with a $^{124}$I source with externally measured activity. The data were then expressed as percentage of injected dose (% ID) of a whole region (the head and brain) or % ID per gram (% ID/g) of a tissue, and then normalized for a body weight of 200 grams [data normalization: (% ID or % ID/g)/body weight of the animal×200]. The normalization was adopted to reduce the variability of the data, as only four animals were used in each group.

In this example, rhHNS protein concentrations or amount were calculated using the injected protein dose to each animal: protein concentration (ug/g)=(% ID/g)×(mg/kg of injected dose×1000×0.2); total amount of the dosed protein (ug) in a region of interest=% ID×(mg/kg of injected dose× 1000×0.2), here the injected dose was 1 mg/kg or 10 mg/kg and 0.2 is the normalizing factor for body weight. Group mean and standard deviation of each PK parameter were calculated based on the individual non-compartmental data in each of the four groups. A Student t-test was performed to compare the values of λz, t1/2, Cmax and AUC between the two test doses and the two administration routes. Statistical significance was defined as a p-values less that 0.05 (p<0.05).

Results

The amounts (ug) or concentrations (ug/g) of rhHNS in the following tables, figures and PK analyses were calculated by multiplying the injected protein dose (1 mg/kg or 10 mg/kg) with the corresponding values of % ID or % ID/g.

Intrathecal Treatment with $^{124}$I-HNS at Doses of 1 and 10 mg/kg

Figure 17:
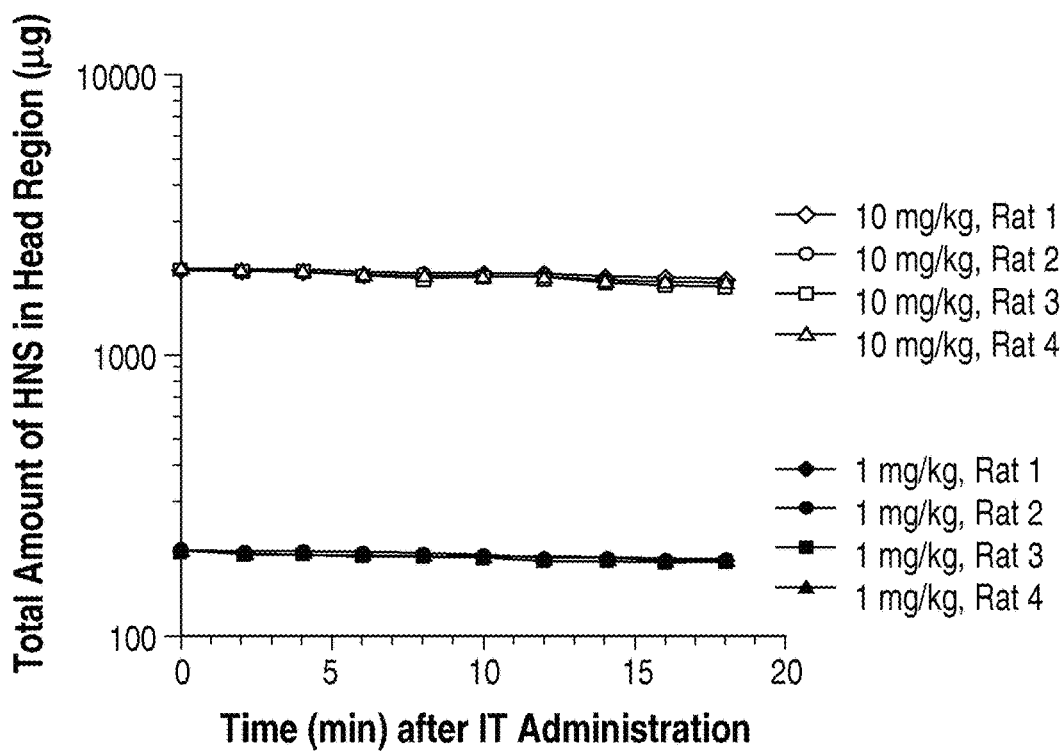
FIG. 17 depicts an exemplary study of the concentration of rhHNS in the head region plotted with time in the first 20 minutes after IT dosing of $^{124}$I-HNS at 1 and 10 mg/kg.
Figure 21:
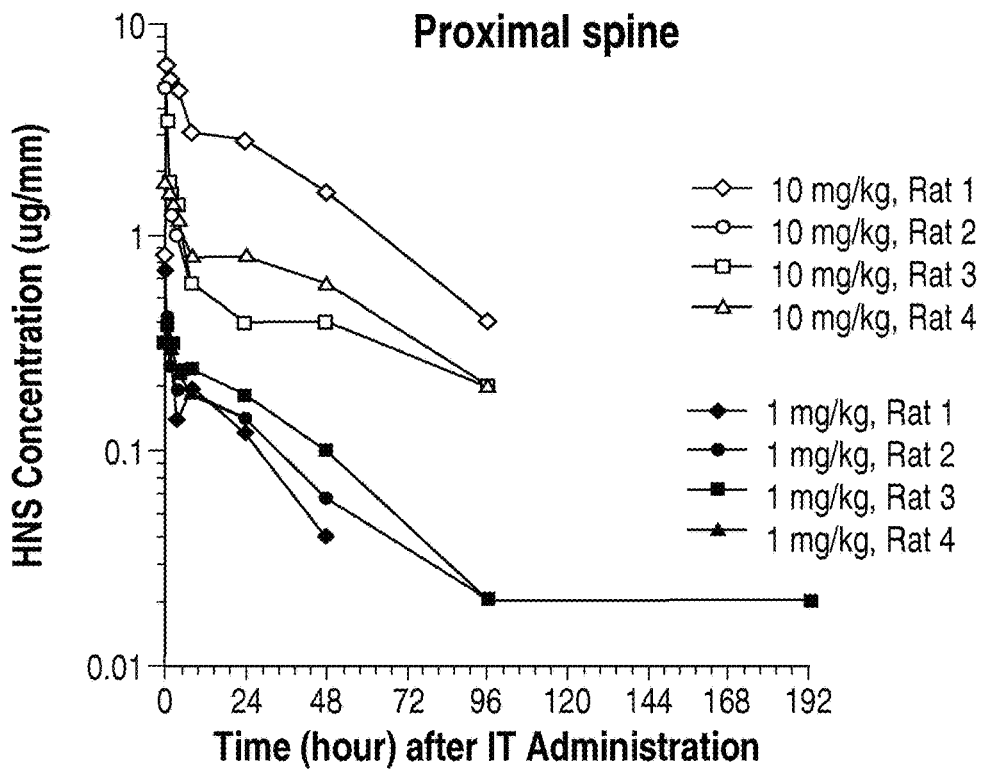
FIG. 21 depicts an exemplary study of the concentration of rhHNS in the proximal spine plotted with time after IT dosing of $^{124}$I-HNS at 1 and 10 mg/kg.
Figure 22:
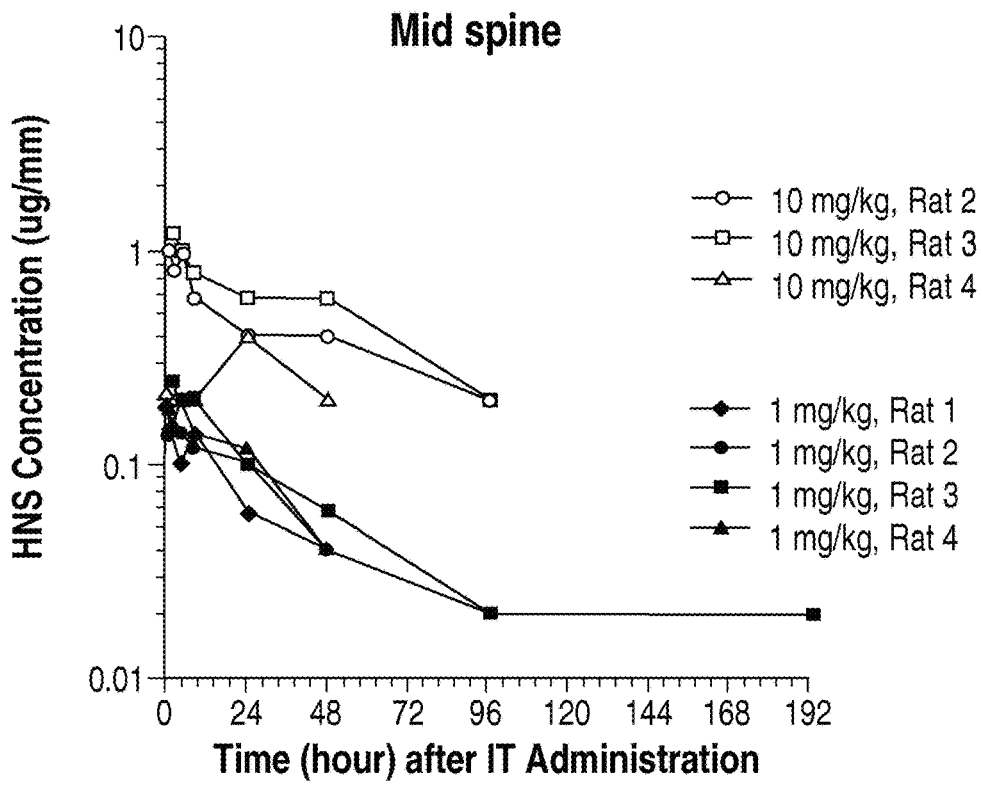
FIG. 22 depicts an exemplary study of the concentration of rhHNS in the mid-spine plotted with time after IT dosing of $^{124}$I-HNS at 1 and 10 mg/kg.
Figure 23:
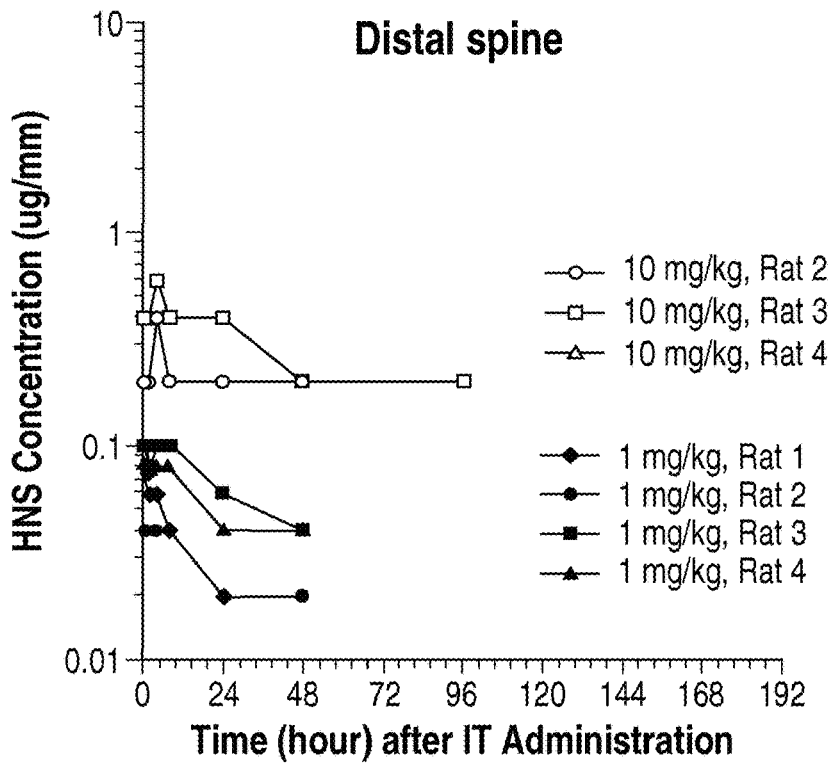
FIG. 23 depicts an exemplary study of the concentration of rhHNS in the distal spine plotted with time after IT dosing of $^{124}$I-HNS at 1 and 10 mg/kg.
Figure 24:
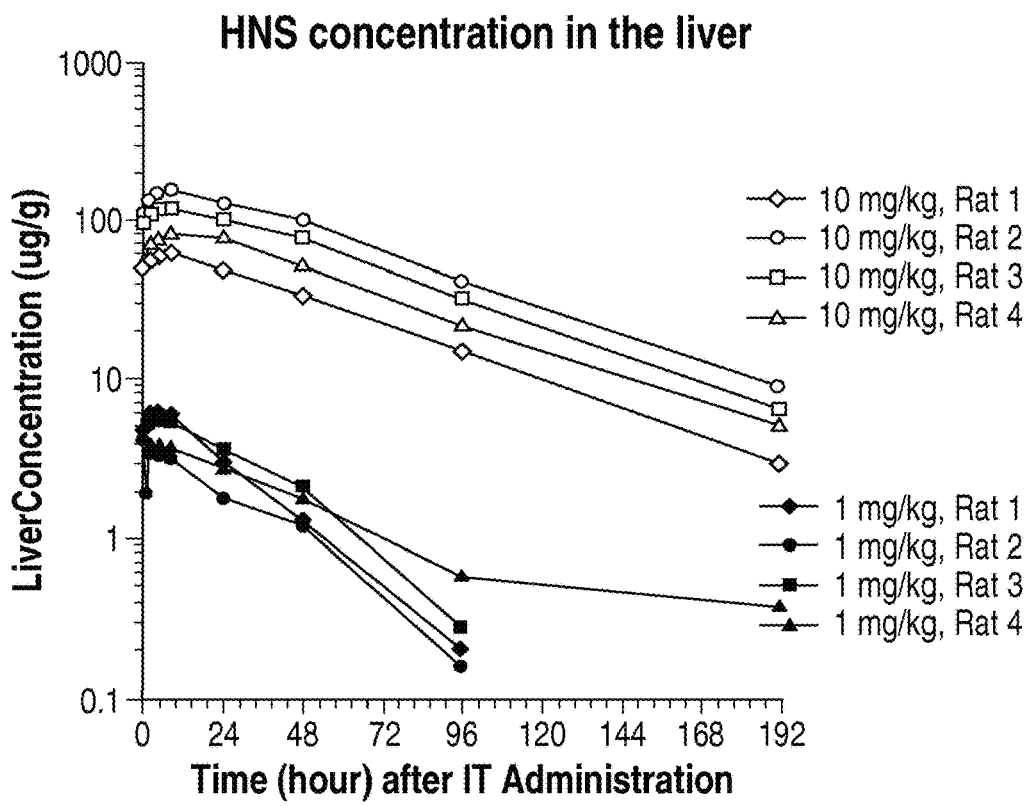
FIG. 24 depicts an exemplary study of the concentration of rhHNS in the liver plotted with time after IT dosing of $^{124}$I-HNS at 1 and 10 mg/kg.
Figure 25:
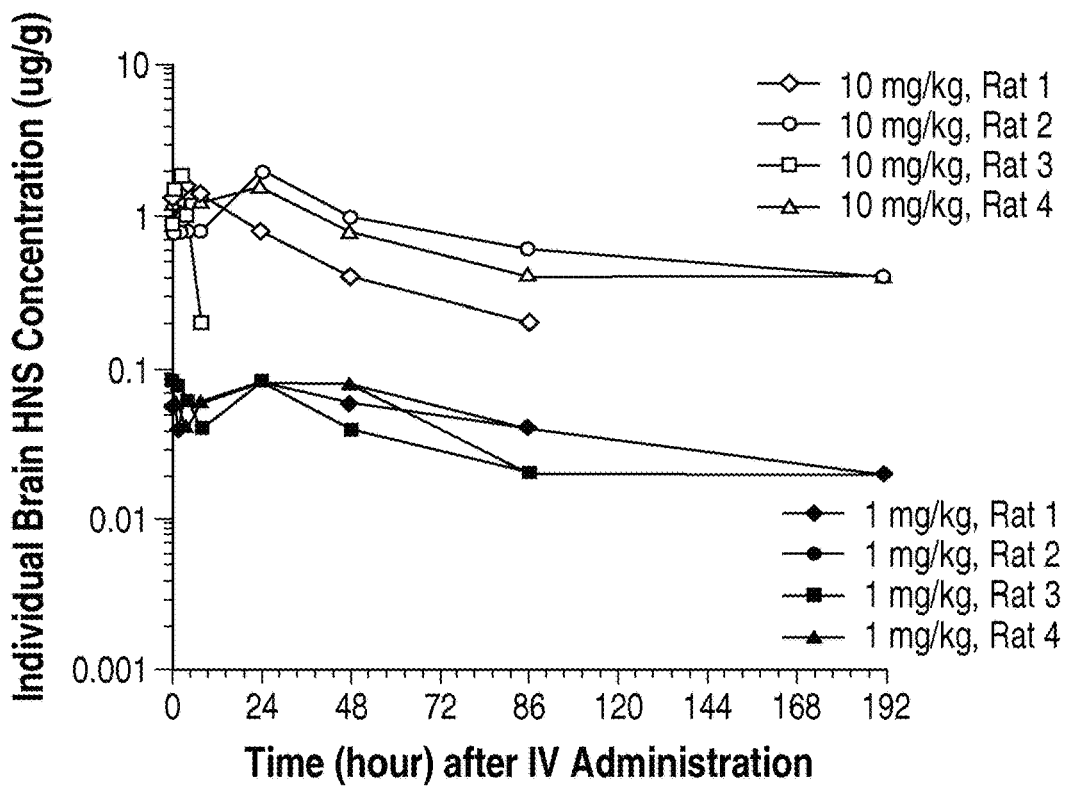
FIG. 25 depicts an exemplary study of the concentration of rhHNS in the brain plotted with time after IT dosing of $^{124}$I-HNS at 1 and 10 mg/kg, individual (top) and mean±SD (bottom).
Figure 25:
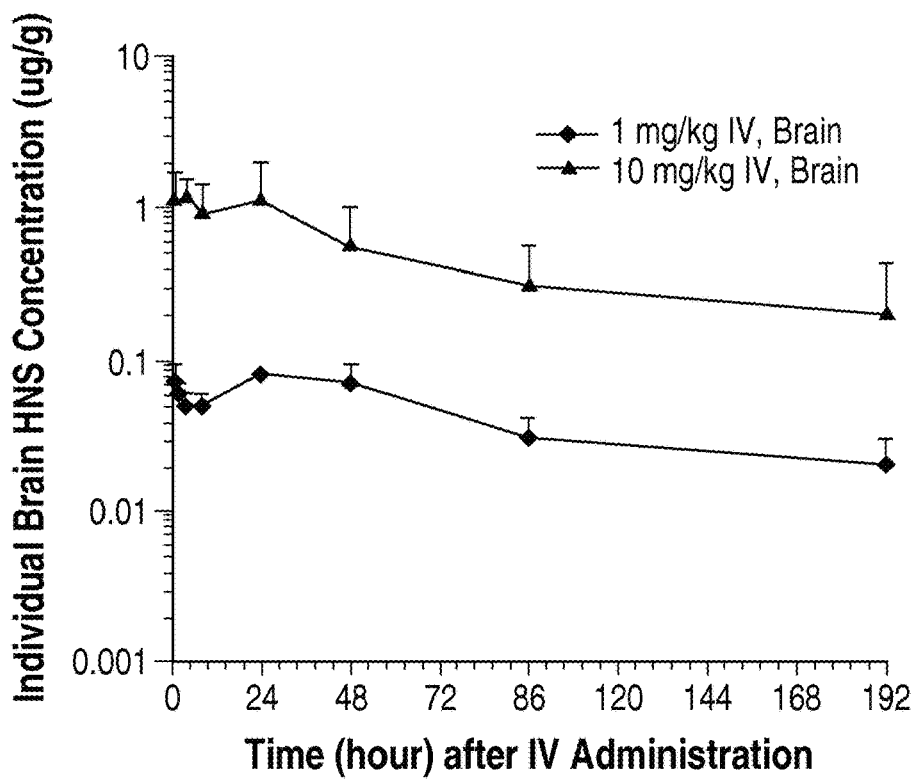
Figure 26:
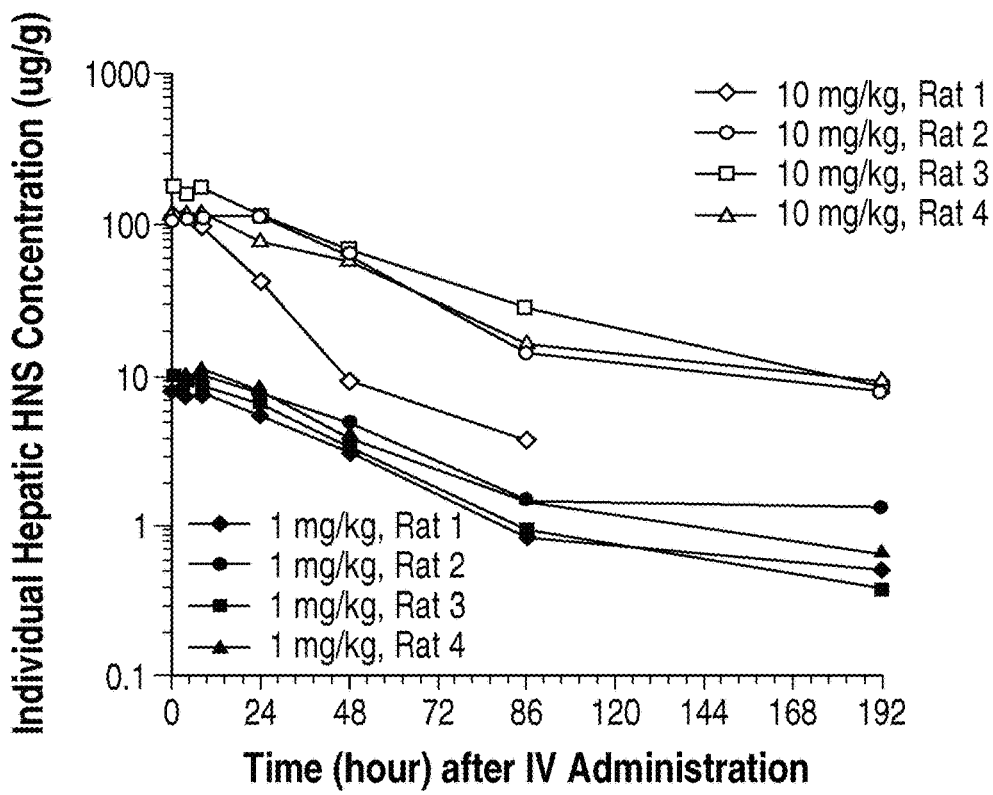
FIG. 26 depicts an exemplary study of the hepatic concentration of rhHNS plotted with time after IT dosing of $^{124}$I-HNS at 1 and 10 mg/kg, individual (top) and mean±SD (bottom).
Figure 26:
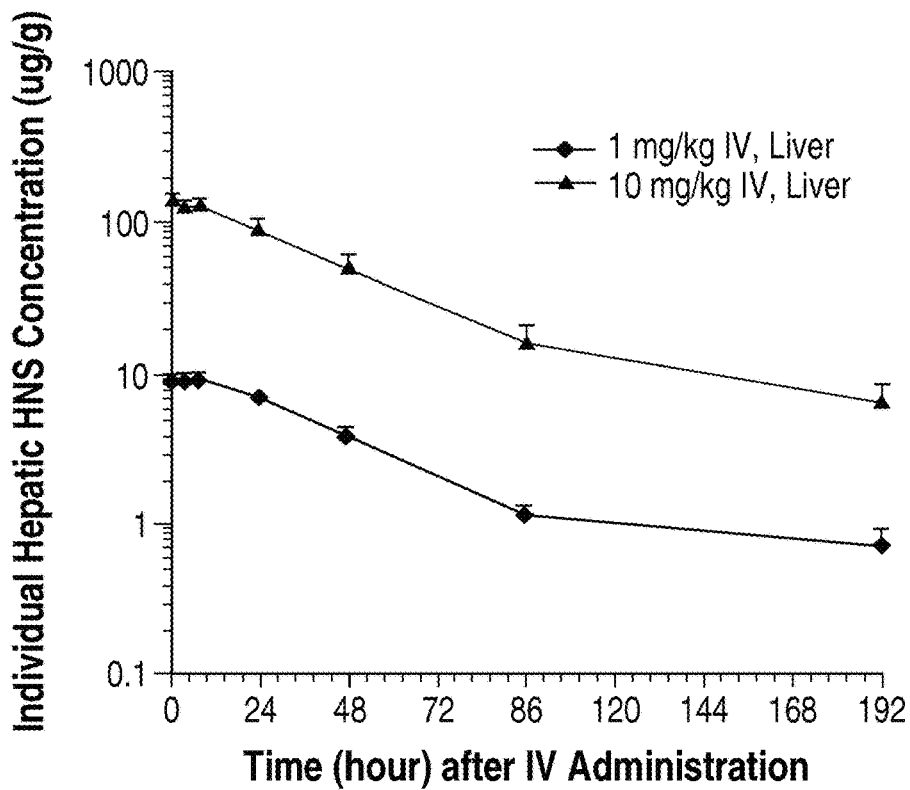
Figure 27:
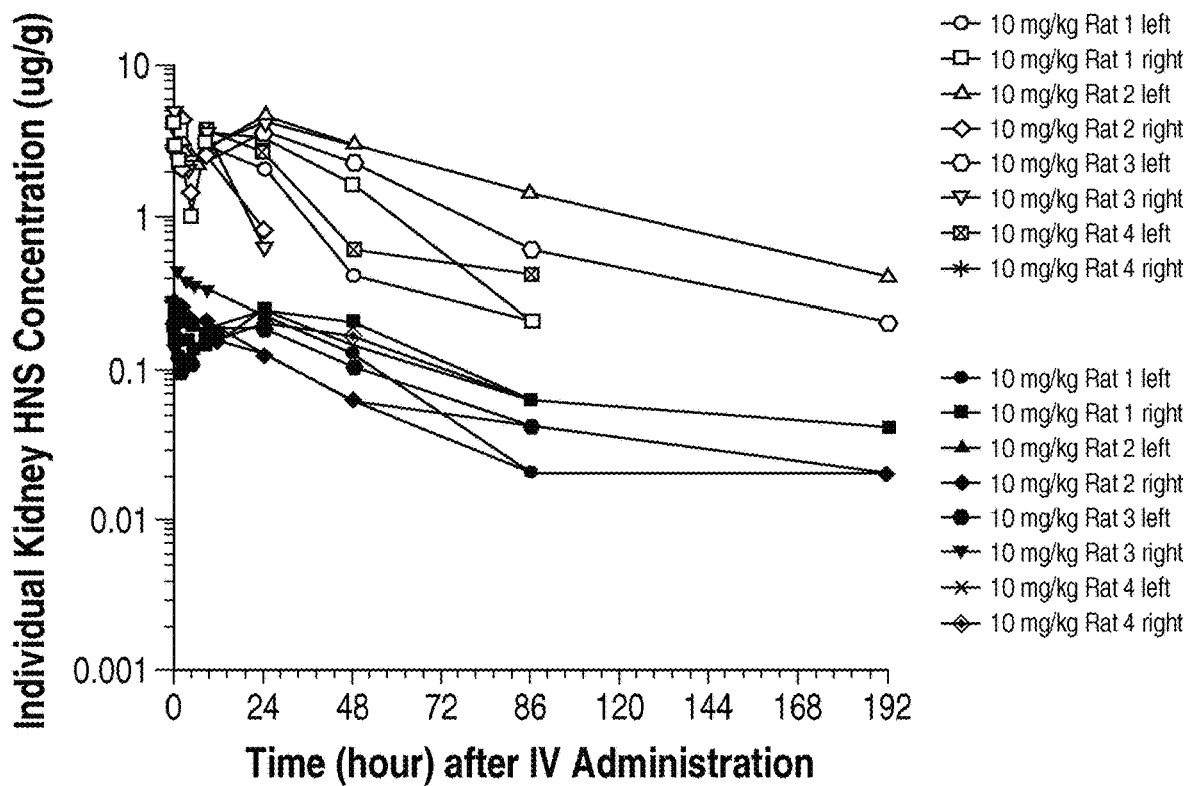
FIG. 27 depicts an exemplary study of the renal concentration of rhHNS plotted with time after IT dosing of $^{124}$I-HNS at 1 and 10 mg/kg, individual (top) and mean±SD (bottom).
Figure 27:
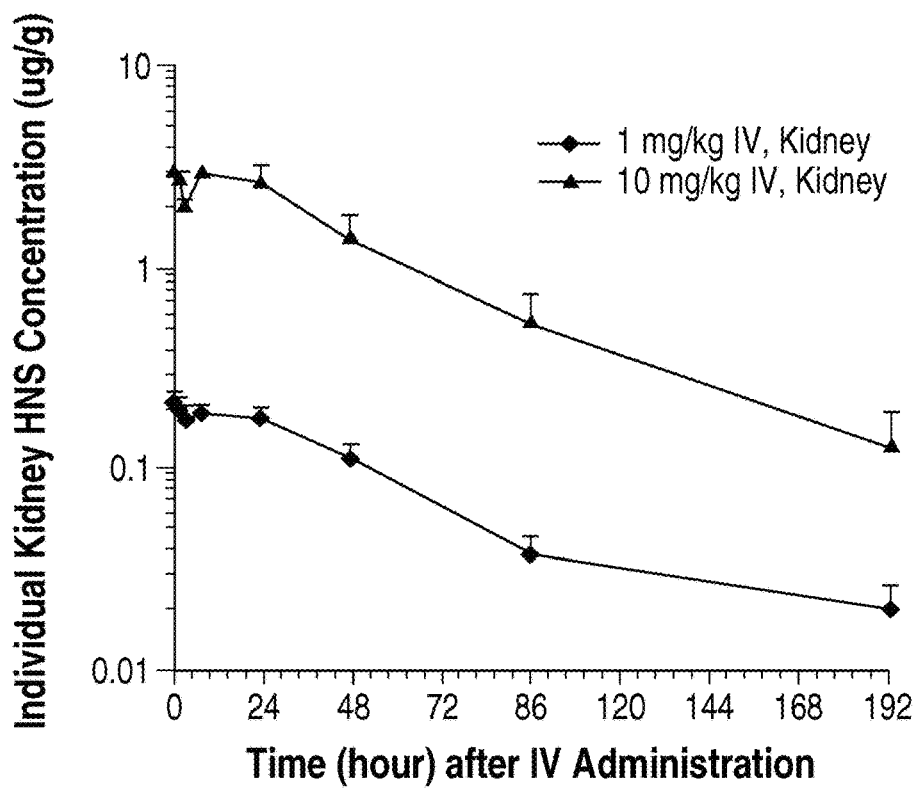
Figure 28:
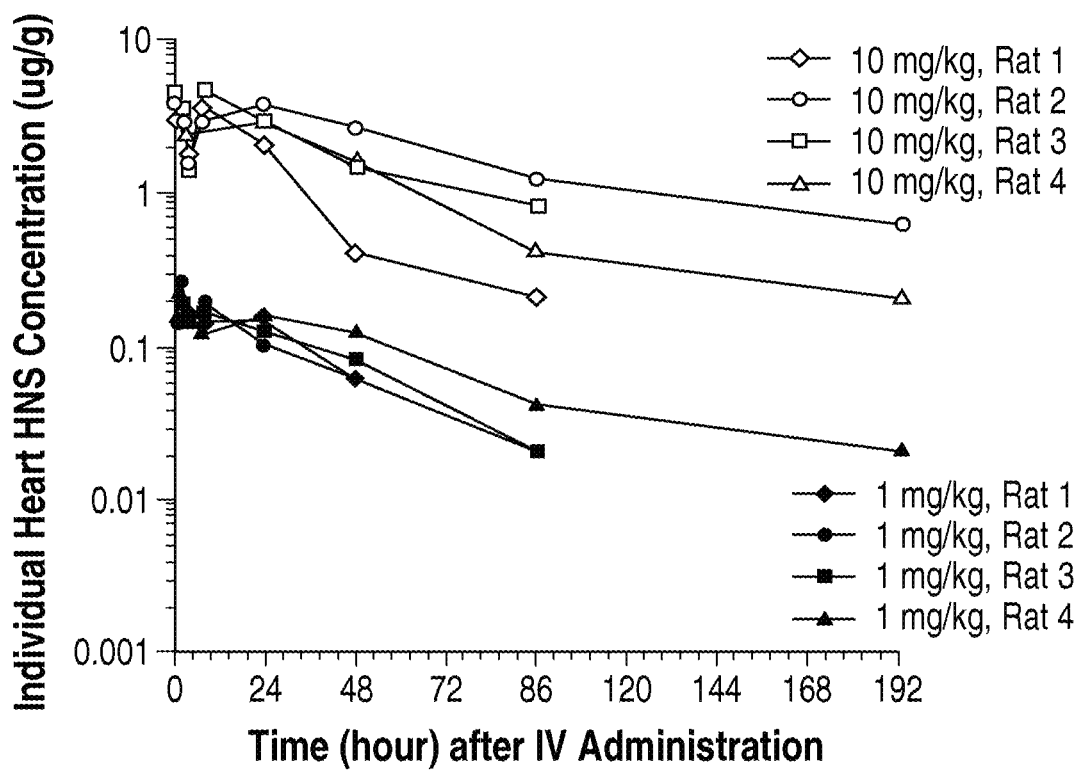
FIG. 28 depicts an exemplary study of the heart concentration of rhHNS plotted with time after IT dosing of $^{124}$I-HNS at 1 and 10 mg/kg, individual (top) and mean±SD (bottom).
Figure 28:
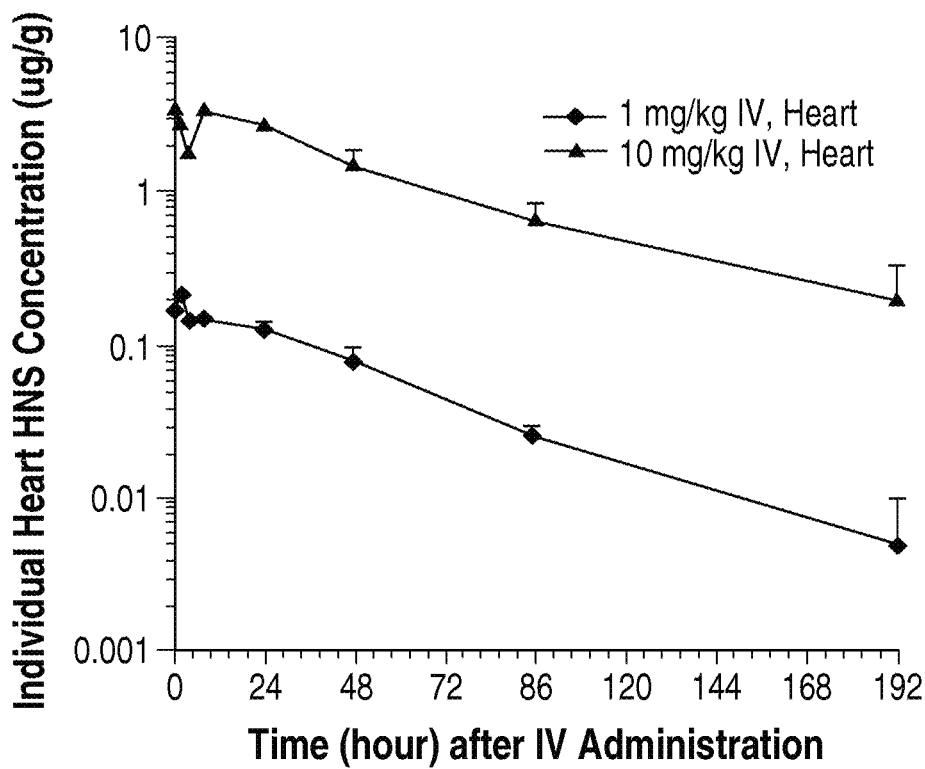
Figure 29:
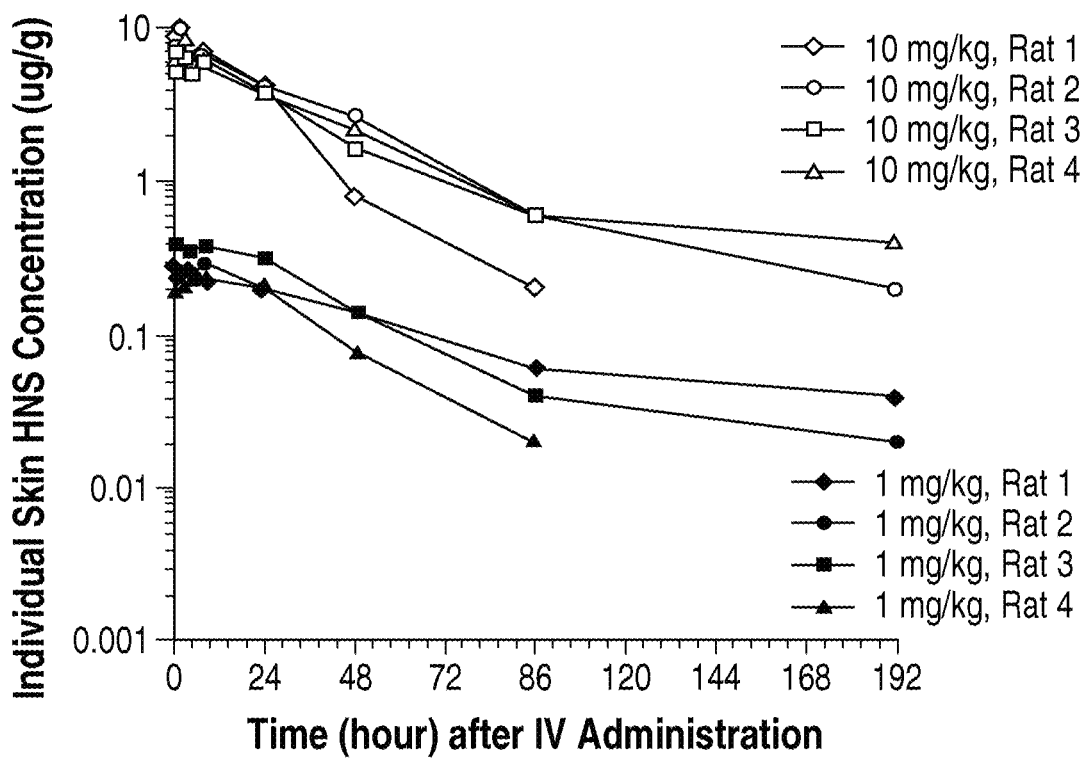
FIG. 29 depicts an exemplary study of the skin concentration of rhHNS plotted with time after IT dosing of $^{124}$I-HNS at 1 and 10 mg/kg, individual (top) and mean±SD (bottom).
Figure 29:
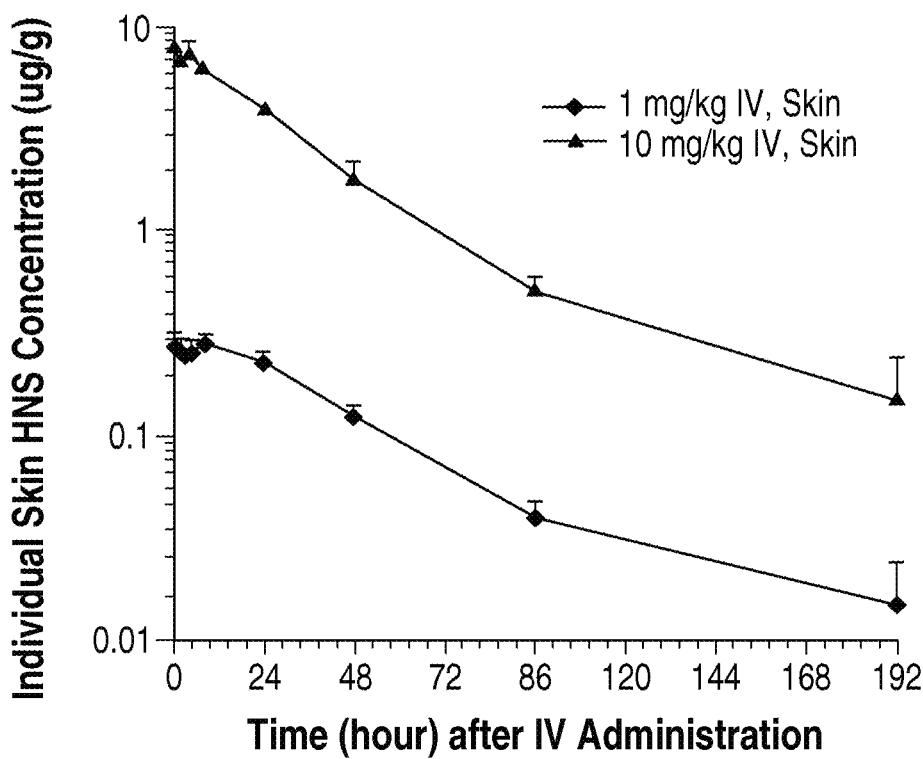

The amount of the dosed protein (ug) in the head region from dynamic images was plotted as a function of time in FIG. 17. The concentration (ug/g) in the brain regions from static images was plotted as a function of time in FIG. 18. The total amount of injected protein (ug) in the brain and head regions from static images were plotted with time in FIG. 19 and FIG. 20 respectively. Concentration-time curves (ug/mm) at the proximal, mid and distal spine were shown in FIG. 21 to FIG. 23. FIG. 24 shows the changes of rhHNS concentration (ug/g) in the liver with time after IT administration of $^{124}$I-HNS at 1 and 10 mg/kg.

The total amount-time (ug) or concentration-time (ug/g) data were analyzed by non-compartmental models (WinNonlin 5.2, Pharsight, Mountain View, Calif.). The PK parameters, such as the constant rate of elimination (λz), peak concentration (Cmax), terminal half-life (t1/2), area under curve (AUClast and AUC0-inf) and others were estimated from the data of each individual animal.

Clearance rates and distribution volumes were estimated (see Appendix 3), however, they were not used for PK comparisons between the two doses and the two administration routes in this report for two reasons (1) this study focused on biodistribution of rhHNS in solid tissues, rather than on blood PK; and (2) the radioactivity in the brain region was the sum of those from the brain tissue (solid) and CSF (liquid), which could not be separated from each other in the study. The λz was evaluated, and used for comparison, because it indicated a percentage of the injected dose eliminated per unit of time.

The group means and standard deviations (SD) were calculated and compared between two test doses. These PK parameters are tabulated in Table 23 below:

TABLE 23

Summary of non-compartmental PK parameters (group mean ± SD) in various organs after IT and IV dosing 1 and 10 mg/kg of $^{124}$I-HNS.

| Parameter | Brain (ug/g)* | | Liver | | Brain (ug)# | | Head (ug)# |
|---|---|---|---|---|---|---|---|
| | Mean | SD | Mean | SD | Mean | SD | Mean |
| 1 mg/kg IT | | | | | | | |
| λz | 0.016 | 0.003 | 0.030 | 0.011 | 0.017 | 0.002 | 0.016 |
| $t_{1/2}$ | 45 | 7 | 28 | 16 | 42 | 5 | 45 |
| $T_{max}$ | 0.1 | 0.0 | 2.3 | 1.3 | 2.0 | 4.0 | 0.1 |
| $C_{max}$ | 257.0 | 89.9 | 4.9 | 1.3 | 68.6 | 8.0 | 200.1 |
| $AUC_{last}$ | 8393 | 2457 | 204 | 50 | 3809 | 622 | 8216 |
| $AUC_{inf.}$ | 8942 | 2416 | 216 | 57 | 4030 | 643 | 8904 |
| $MRT_{last}$ | 46 | 6 | 32 | 13 | 44 | 5 | 46 |

TABLE 23-continued

Summary of non-compartmental PK parameters (group mean ± SD) in various organs after IT and IV dosing 1 and 10 mg/kg of $^{124}$I-HNS.

| | | | 10 mg/kg IT | | | | |
|---|---|---|---|---|---|---|---|
| $\lambda z$ | 0.014 | 0.001 | 0.017 | 0.000 | 0.014 | 0.001 | 0.010 |
| $t_{1/2}$ | 49 | 4 | 42 | 1 | 51 | 5 | 70 |
| $T_{max}$ | 0.1 | 0.0 | 7.0 | 2.0 | 0.1 | 0.0 | 0.1 |
| $C_{max}$ | 2628 | 265 | 105 | 41 | 836 | 117 | 1844 |
| $AUC_{last}$ | 83962 | 10083 | 7987 | 3276 | 59115 | 8624 | 128751 |
| $AUC_{inf.}$ | 89460 | 12098 | 8345 | 3424 | 63836 | 9466 | 151405 |
| $MRT_{last}$ | 56 | 1 | 51 | 1 | 58 | 2 | 65 |

| | Head (ug)# | | Proximal | | Mid | | Distal | |
|---|---|---|---|---|---|---|---|---|
| Parameter | | SD | Mean | SD | Mean | SD | Mean | SD |
| | | | | 1 mg/kg IT | | | | |
| $\lambda z$ | | 0.002 | 0.025 | 0.012 | 0.020 | 0.008 | 0.028 | 0.016 |
| $t_{1/2}$ | | 7 | 32 | 13 | 39 | 16 | 30 | 12 |
| $T_{max}$ | | 0.0 | 0.3 | 0.5 | 1.8 | 1.5 | 1.0 | 0.0 |
| $C_{max}$ | | 0.0 | 0.5 | 0.1 | 0.2 | 0.0 | 0.1 | 0.0 |
| $AUC_{last}$ | | 782 | 9 | 3 | 7 | 3 | 2 | 1 |
| $AUC_{inf.}$ | | 1069 | 11 | 3 | 8 | 3 | 3 | 2 |
| $MRT_{last}$ | | 5 | 31 | 17 | 34 | 20 | 16 | 5 |
| | | | | 10 mg/kg IT | | | | |
| $\lambda z$ | | 0.001 | 0.018 | 0.008 | 0.014 | — | 0.006 | — |
| $t_{1/2}$ | | 9 | 45 | 18 | 50 | — | 123 | — |
| $T_{max}$ | | 0.0 | 0.3 | 0.5 | 8.7 | 13.3 | 8.0 | — |
| $C_{max}$ | | 314 | 6 | 4 | 1 | 0 | 1 | — |
| $AUC_{last}$ | | 15723 | 83 | 67 | 35 | 20 | 38 | — |
| $AUC_{inf.}$ | | 15123 | 98 | 66 | 60 | — | 73 | — |
| $MRT_{last}$ | | 3 | 31 | 2 | 32 | 7 | 61 | — |

| | Brain (ug/g)* | | Liver | | Kidney | | Heart | | Skin | |
|---|---|---|---|---|---|---|---|---|---|---|
| | | | | | 1 mg/kg IV | | | | | |
| $\lambda z$ | 0.011 | 0.005 | 0.015 | 0.003 | 0.016 | 0.009 | 0.021 | 0.006 | 0.021 | 0.010 |
| $t_{1/2}$ | 71 | 23 | 47 | 10 | 54 | 25 | 36 | 15 | 40 | 21 |
| $T_{max}$ | 7 | 12 | 5 | 4 | 10 | 12 | 2 | 1 | 5 | 4 |
| $C_{max}$ | 0.1 | 0.0 | 9.6 | 1.5 | 0.2 | 0.1 | 0.2 | 0.0 | 0.3 | 0.1 |
| $AUC_{last}$ | 7 | 2 | 525 | 104 | 14 | 5 | 9 | 3 | 16 | 4 |
| $AUC_{inf.}$ | 9 | 3 | 576 | 138 | 16 | 6 | 10 | 3 | 18 | 5 |
| $MRT_{last}$ | 61 | 16 | 47 | 5 | 47 | 18 | 36 | 13 | 41 | 16 |
| | | | | | 10 mg/kg IV | | | | | |
| $\lambda z$ | 0.102 | 0.180 | 0.021 | 0.012 | 0.035 | 0.024 | 0.020 | 0.010 | 0.026 | 0.012 |
| $t_{1/2}$ | 60.5 | 53.1 | 37.8 | 13.4 | 28.4 | 16.4 | 41.6 | 18.6 | 31.0 | 12.7 |
| $T_{max}$ | 13 | 12 | 2 | 1 | 12 | 11 | 16 | 9 | 3 | 1 |
| $C_{max}$ | 1.8 | 0.2 | 131.6 | 26.8 | 3.9 | 0.7 | 3.7 | 0.7 | 7.9 | 2.3 |
| $AUC_{last}$ | 86 | 66 | 6747 | 2837 | 183 | 123 | 201 | 89 | 276 | 40 |
| $AUC_{inf.}$ | 118 | 98 | 7171 | 3029 | 198 | 131 | 230 | 110 | 292 | 43 |
| $MRT_{last}$ | 43 | 32 | 40 | 14 | 33 | 21 | 41 | 18 | 33 | 13 |

In the first 20 min after dosing, total amount (ug) of rhHNS in the head region was reduced at a constant rate of 0.002-0.011 per min ($\lambda z$, 0.005±0.004/min) at 1 mg/kg and 0.003-0.010 per min (0.007±0.003/min) at 10 mg/kg. These constant rates of elimination were not significantly different at these two dose levels (p=0.57, FIG. 17).

Figure 18:
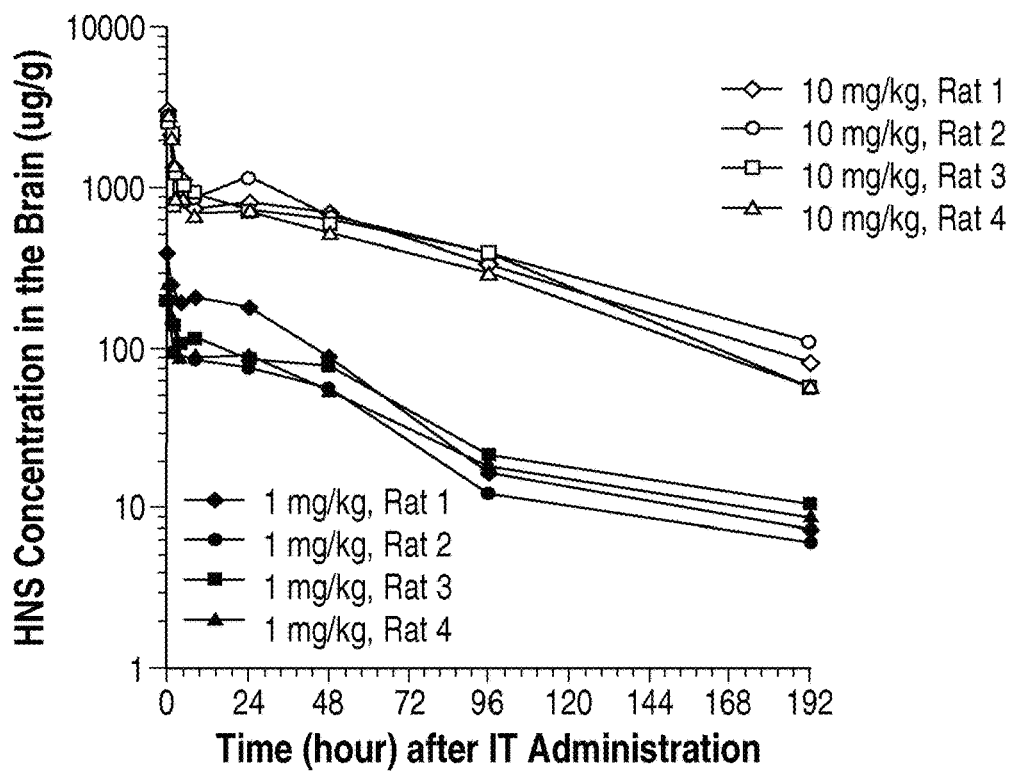
FIG. 18 depicts an exemplary study of the concentration of rhHNS in the brain plotted with time after IT dosing of $^{124}$I-HNS at 1 and 10 mg/kg.

The concentration-time curve (ug/g from 0.05 to 192 hours) for the brain indicated a bi-phasic profile (FIG. 18). The early phase lasts for about two hours. The terminal phase follows first-order kinetics. The constant rates of elimination from the brain were very similar at two tested doses (0.0016±0.003 and 0.014±0.001 per hour) with a similar half-life of about two days (45±7 and 49±4 hours at 1 and 10 mg/kg, respectively). The values of peak concentrations (257±90 and 2628±265 ug/g) and AUClast (8393±2457 and 83962±10083 hr·ug/g at 1 and 10 mg/kg, respectively) increase approximately ten-fold when the dose was increased from 1 to 10 mg/kg. These observations indicated a linear PK behavior in the dose range of 1 to 10 mg/kg given in these IT single dosing regimens. The peak concentration appeared in the brain 3 min (Tmax) after IT dosing.

Figure 19:
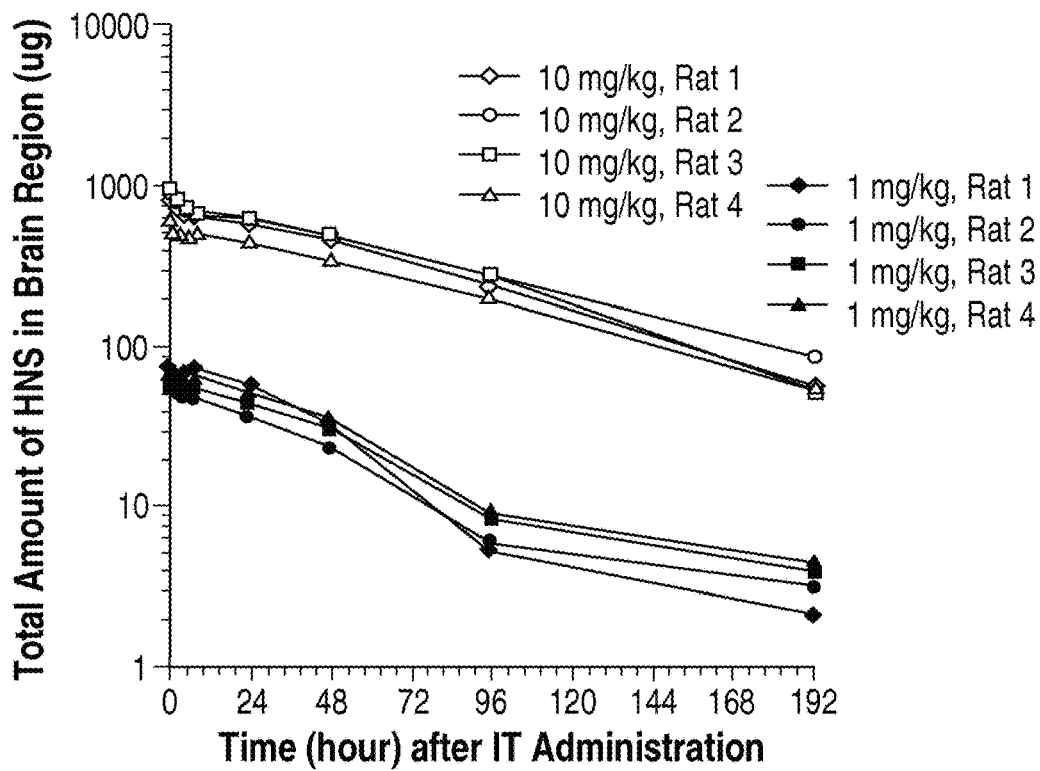
FIG. 19 depicts an exemplary study of the concentration of rhHNS in the brain region plotted with time after IT dosing of $^{124}$I-HNS at 1 and 10 mg/kg.
Figure 20:
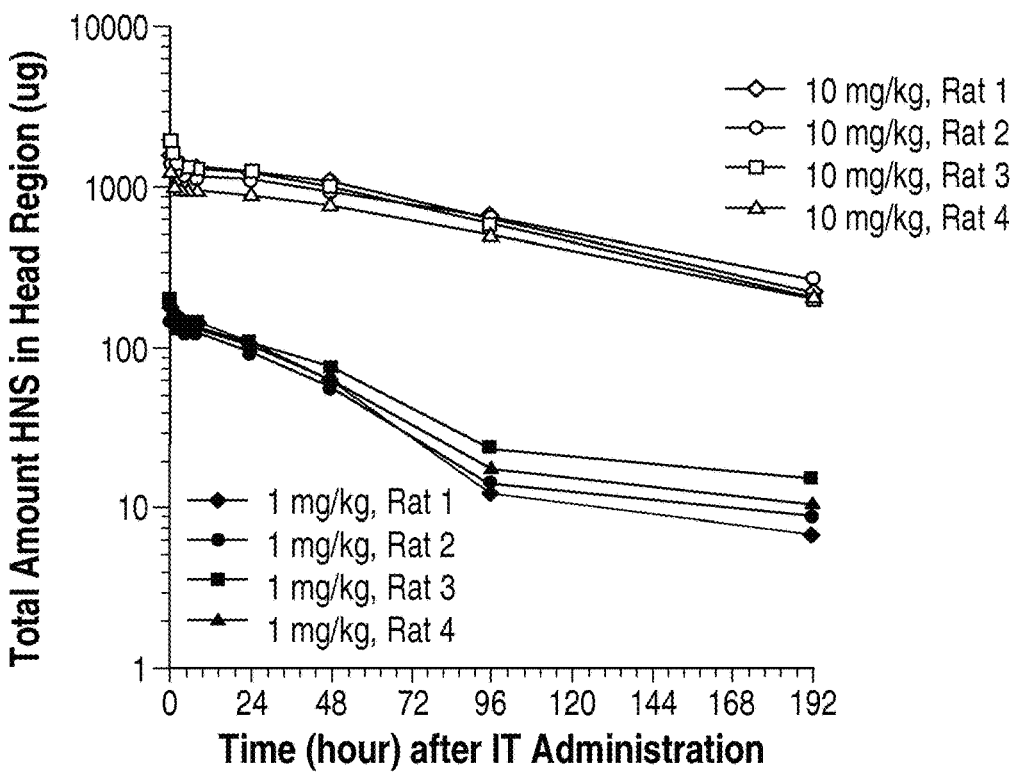
FIG. 20 depicts an exemplary study of the concentration of rhHNS in the head region plotted with time after IT dosing of $^{124}$I-HNS at 1 and 10 mg/kg.

The total amount-time curve (ug from 0.05 to 192 hours) in the brain and head regions followed the same bi-phasic pattern as seen with concentration-time curves (ug/g) in the brain (FIG. 19 and FIG. 20). The values of Cmax in the brain region were significantly lower than that in the head region (69±8 versus 200±0 at 1 mg/kg, p<0.01; and 836±117 versus 1844±314 ug, p<0.01 at 10 mg/kg, respectively). The constant rates of elimination were 0.017±0.002/hr and 0.014±0.001/hr for the brain, and 0.016±0.002 and 0.010±0.001/hr for the head region at 1 and 10 mg/kg, respectively. The values of mean residual time were 42±5 versus 51±5 hours for the brain (p=0.048), and 45±7 versus 70±9 hours for the head (p<0.01) at 1 and 10 mg/kg, respectively. These observations suggested that the dosed protein was eliminated from both regions more rapidly at lower dose than at higher doses. The mean half-lives were in a range of 42 to 70 hours in these regions after IT dosing 1 mg/kg and 10 mg/kg of rhHNS.

A concentration gradient was observed from the proximal, to the mid and to the distal sections of the spine at both dose levels (data not shown). After IT dosing, the peak concentration (ug/mm of spine column) was seen around 30 min (0 to 1 hour) at the proximal, 1 to 4 hours at the mid (except of one rat being 24 hours) and 1 to 8 hours at the distal section. The half-lives in these sections were variable (mean t1/2: 32±13 and 45±18 hours for the proximal, 39±16 and about 50 hours for the mid, and 30±12 and about 123 hours for the distal sections of spine at 1 mg/kg and 10 mg/kg, respectively). The mean values of peak concentrations were roughly proportional to the doses at each of these three sections at 1 and 10 mg/kg of $^{124}$I-HNS (0.5 versus 6.0, 0.2 versus 0.9 and 0.1 versus 0.5 ug/mm at the proximal, mid and distal sections of the spine, respectively). The mean values of AUClast followed the same proportional pattern as seen in the peak concentration (9.5 versus 83, 6.8 versus 35, and 2 versus 38 hr·ug/mm at the proximal, mid and distal sections, respectively).

Even though rhHNS was not detectable in most peripheral organs, it was measurable in the liver from as early as 1 hour (the first imaging time point after dosing) to 96 hours (three of four animals) at 1 mg/kg and to 192 hours (all four rats) at 10 mg/kg after IT dosing (FIG. 24). The concentrations in the liver reached the peak 2 hours after IT dosing of 1 mg/kg, and 7 hours after IT dosing of 10 mg/kg, which was followed by an elimination phase with first-order kinetics. The constant rate of elimination was faster at 1 mg/kg ($\lambda z$ 0.030±0.011/hr) than that at 10 mg/kg ($\lambda z$ 0.017±0/hr) (p=0.10), with a corresponding shorter t1/2 (28±16 versus 42±1 hours at the doses of 1 and 10 mg/kg, respectively, p=0.76). The value of AUClast at 1 mg/kg reduced about 40-fold in comparison with that at 10 mg/kg (204±50 versus 7987±3276 ug/g, respectively).

Intravenous Treatment with $^{124}$I-HNS at Doses of 1 and 10 mg/kg

The concentration in the brain, liver, kidney, heart (including lung tissue) and skin were plotted as a function of time after IV dosing 1 and 10 mg/kg of rhHNS as shown in FIG. 25 through FIG. 29, respectively. Since the first static imaging time point for these organs was one hour after dosing, the initial phase of these concentration-time curves cannot be observed in this study. The concentration-time curves for the liver, kidney, heart and skin showed a flat phase from 1 to 8 hours after IV dosing. This flat phase lasted for 24 hours in the brain post-dosing, suggesting that the brain took up the IV dosed protein slower than that by the peripheral organs. The remaining data indicated a terminal elimination phase with approximately first-order kinetics.

The elimination half-lives in the liver, kidney, heart and skin 47±10 and 38±13 hours for the liver, 54±25 and 29±16 hours for the kidney, 36±15 and 42±19 hours for the heart and 40±21 and 31±13 hours for the skin at 1 and 10 mg/kg, respectively; while the half-lives in the brain were 71±23 and 60±53 hours (Rat 3 in 10 mg/kg group was excluded for insufficient data to determine t1/2) at 1 and 10 mg/kg, respectively. No statistical differences were seen between the half-lives at 1 and 10 mg/kg in these organs, with an exception of p value <0.03 for kidney.

The mean values of Cmax for the liver, skin, kidney, heart and brain were 9.6, 0.3, 0.25, 0.22, and 0.08 ug/g at 1 mg/kg and 132, 7.9, 3.9, 3.7 and 1.8 ug/g at 10 mg/kg. The ratios of Cmax at 10 mg/kg to the corresponding values at 1 mg/kg were 14, 26, 16, 17 and 23 for these organs. After the Cmax values from individual animal were normalized for dose, the Cmax/dose values at 10 mg/kg were significantly higher than that at 1 mg/kg in all these organs (most p values <0.05, p=0.06 for the liver). The values of AUClast for the liver, skin, kidney, heart and brain were 525, 16, 14, 9.3 and 7 hr·ug/g at 1 mg/kg; and 6747, 276, 183, 201 and 86 hr·ug/g at 10 mg/kg. The ratios of AUClast at 10 mg/kg to the corresponding values of AUClast at 1 mg/kg were 13, 17, 13, 22 and 12 for these organs, respectively. After normalization, the AUClast/dose values at 10 mg/kg were significantly higher than that at 1 mg/kg in the skin (p<0.01), marginally different in the heart (p=0.06), and not significantly different in the liver, brain and kidney (all p values >0.34).

These observations suggested (1) the half-lives in most organs were about 2 days, with the exception of the brain (about 3 days); (2) the exposure per gram in the liver was larger than that of the skin, heart and kidney, which are larger than that of the brain; (3) with a ten-fold increase in dose (10/1 mg/kg), the values of Cmax at 10 mg/kg from all tested organs increased more than 10 times than that at 1 mg/kg.

The peak concentration in the brain was reached 1-24 hours (Tmax) after IV dosing.

Comparison of IV Versus IT Treatments

Figure 30:
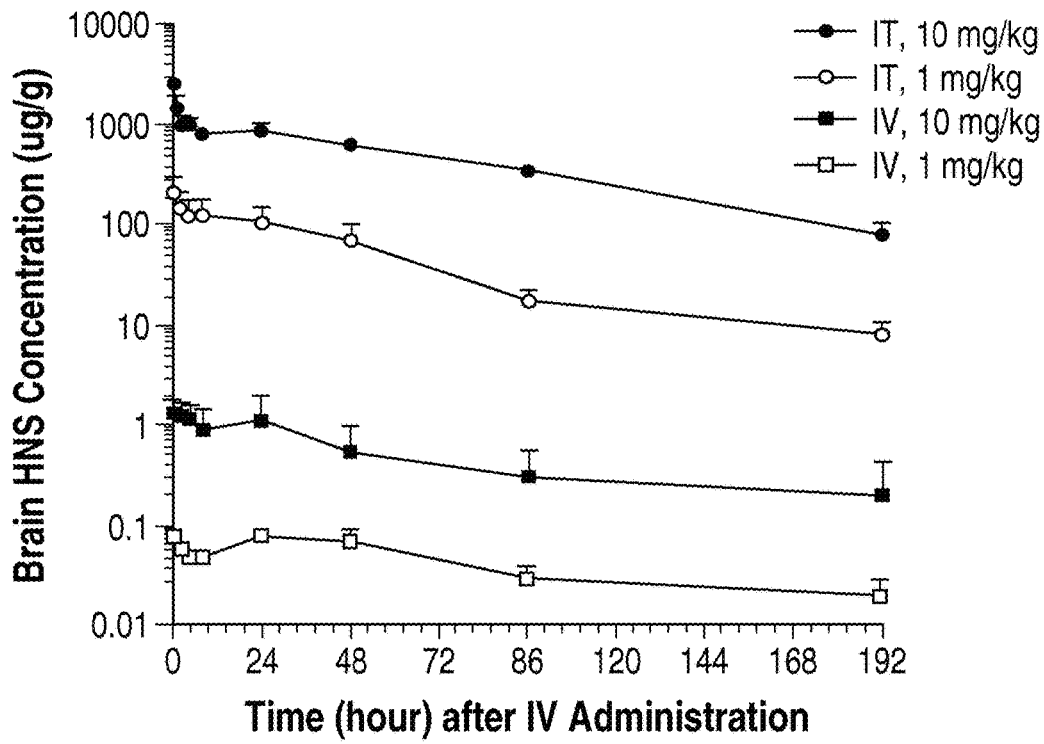
FIG. 30 depicts an exemplary study of the brain concentration of rhHNS plotted with time after IT dosing of $^{124}$I-HNS at 1 and 10 mg/kg (top), and a comparison of the non-compartmental PK parameters in the brain (bottom).
Figure 31:
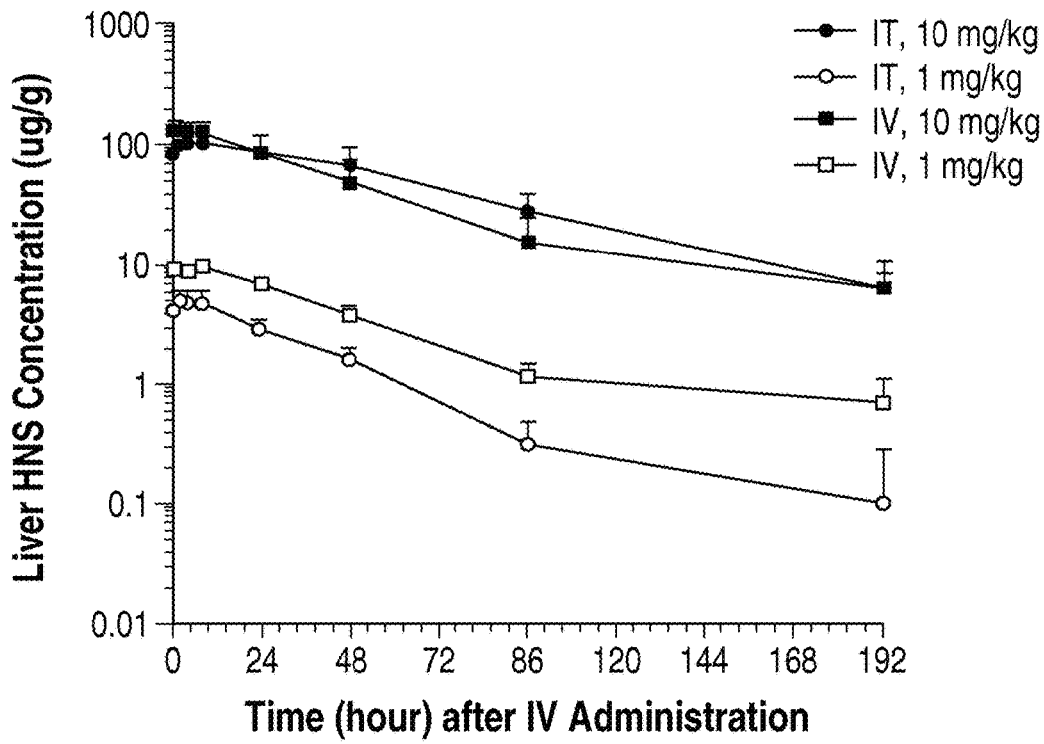
FIG. 31 depicts an exemplary study of the liver concentration of rhHNS plotted with time after IT dosing of $^{124}$I-HNS at 1 and 10 mg/kg (top), and a comparison of the non-compartmental PK parameters in the liver (bottom).
Figure 32:
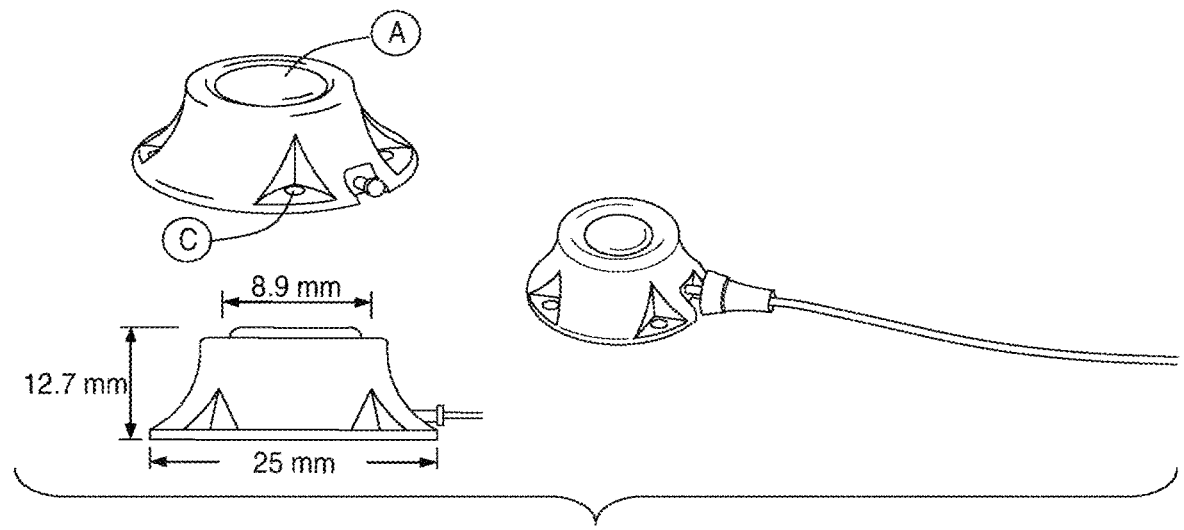
FIG. 32 depicts an exemplary intrathecal drug delivery device (IDDD).
Figure 33:
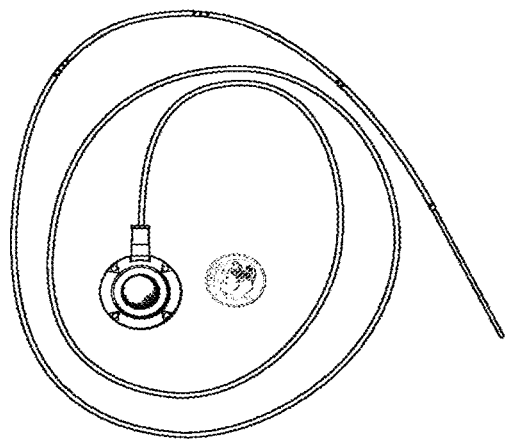
FIG. 33 depicts an exemplary port-a-cath low profile intrathecal implantable access system.
Figure 34:
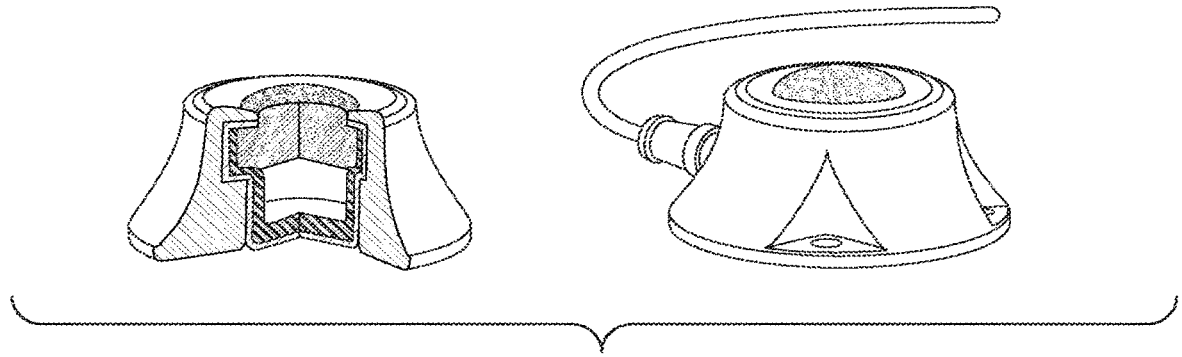
FIG. 34 depicts an exemplary intrathecal drug delivery device (IDDD).
Figure 35:
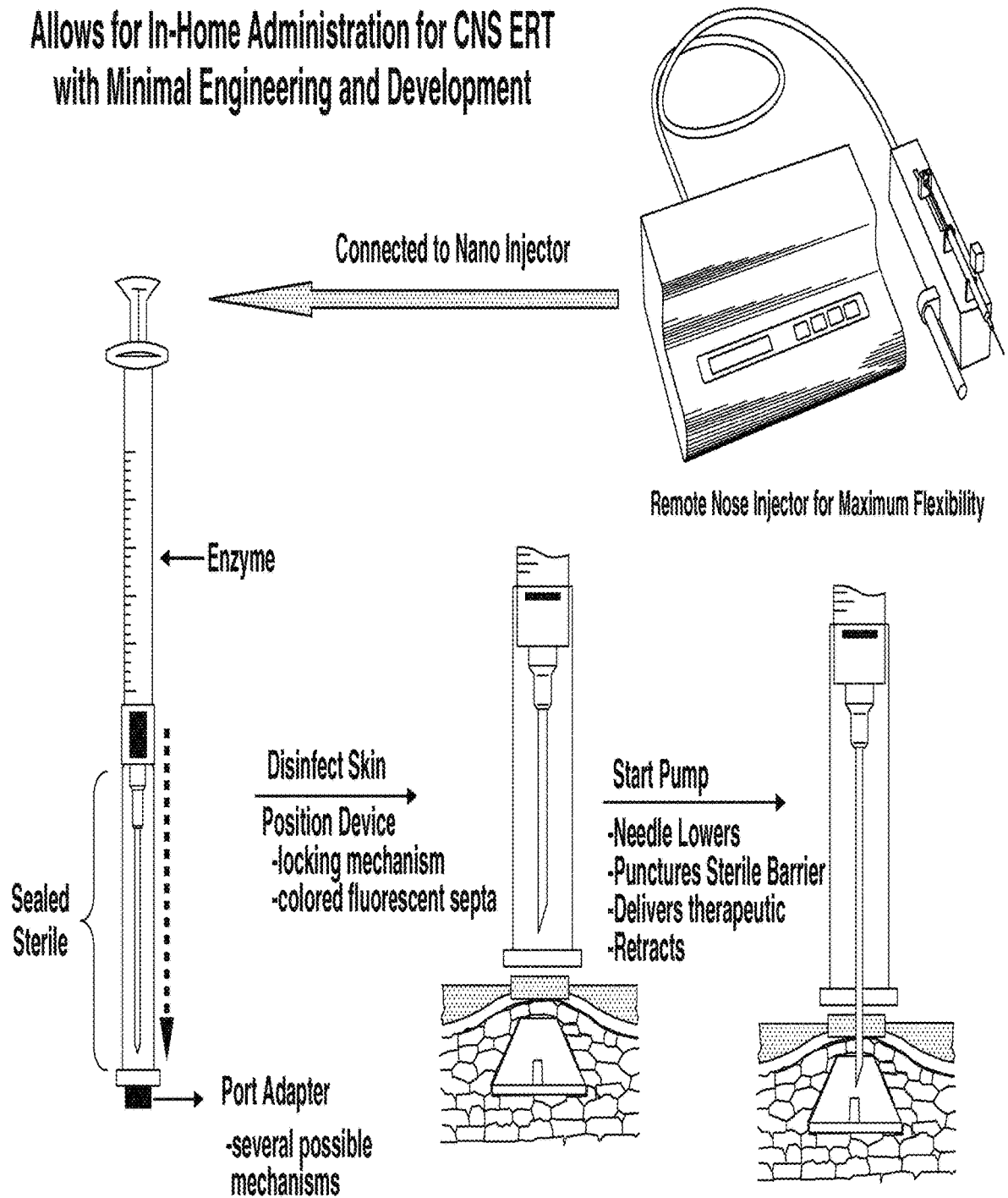
FIG. 35 depicts an exemplary intrathecal drug delivery device (IDDD), which allows for in-home administration for CNS enzyme replacement therapy (ERT).

The concentration-time curves in the brain and liver after IV and IT administration at 1 and 10 mg/kg are compared in FIG. 30 and FIG. 31, respectively. The ratios of Cmax in the brain by IT/IV at 1 and 10 mg/kg were 3212 and 1501, respectively. These ratios of AUC0-192 hr were 1136 and 978. These observations indicated that, when the same dose of rhHNS was injected, intrathecal administration resulted in an approximately three-log greater exposure of the brain than that with intravenous administration. The elimination half-life in the brain was 2 days (45 and 49 hours at 1 and 10 mg/kg) by IT and 3 days (71 and 60 hours at 1 and 10 mg/kg) by IV administration at both dose levels.

However, hepatic exposures after IT dosing were similar to that after IV dosing at the same dose of rhHNS. The ratios of Cmax in the liver by IT/IV at 1 mg/kg and 10 mg/kg were 0.5 and 0.8, and the ratios of AUClast were 0.4 and 1.2, respectively.

Conclusions

Pharmacokinetic and biodistribution profiles of $^{124}$I-sulfamidase (rhHNS) were studied by tissue PET images in rats after single intravenous or intrathecal administration of 1 or 10 mg/kg of $^{124}$I-sulfamidase. Concentration-time data were obtained both dynamically (the first 20 min) and statically in the regions of interest at 0.05, 1, 2, 4, 8, 24, 48, 96 and 192 hours post dosing. By dynamic imaging after IT dosing, total amount of rhHNS in the head region was reduced at a similar constant rate of 0.005/min-0.007/min (mean $\lambda z$) in the first 20 min. By static imaging, the rates of elimination from the brain were essentially the same at two tested doses ($\lambda z$: 0.016/hr versus 0.014/hr for 1 and 10 mg/kg, respectively) with a similar half-life about two days.

The values of Cmax and AUClast were proportional to the administered doses, and a linear PK behavior was indicated in the dose range of 1 to 10 mg/kg given in these IT single dosing regimens.

Concentration gradients were observed from the proximal to distal spine at both dose levels.

After IT dosing, the peak concentration was seen around 20 min at the proximal, 1 to 4 hours at the mid and 1 to 8 hours at the distal sections. Linear PK behavior was also indicated in the different sections of the spine.

After IT dosing, rhHNS protein was measurable in the liver from very early time up to 96 hours at 1 mg/kg and 192 hours at 10 mg/kg. The rate of elimination was faster at 1 mg/kg ($\lambda z$ 0.030/hr) than that at 10 mg/kg ($\lambda z$ 0.017/hr), with a corresponding shorter t1/2 at the lower dose (28±16 versus 42±1 hours at the doses of 1 and 10 mg/kg, respectively).

After IV dosing, the elimination half-lives in the liver, kidney, heart and skin 47±10 and 38±13 hours for the liver, 54±25 and 29±16 hours for the kidney, 36±15 and 42±19 hours for the heart and 40±21 and 31±13 hours for the skin at 1 and 10 mg/kg, respectively; while the halflives in the brain were 71±23 and 60±53 hours. The mean values of Cmax for the liver, skin, kidney, heart and brain were 9.6, 0.30, 0.25, 0.22, and 0.08 ug/g at 1 mg/kg and 132, 7.9, 3.9, 3.7 and 1.8 ug/g at 10 mg/kg. After the Cmax values from individual animal were normalized for dose, the Cmax/dose values at 10 mg/kg were significantly higher than that at 1 mg/kg in all these organs (most p values <0.05, p=0.06 for the liver). The values of AUClast for the liver, skin, kidney, heart and brain were 525, 16, 14, 9.3 and 7 hr·ug/g at 1 mg/kg; and 6747, 276, 183, 201 and 86 hr·ug/g at 10 mg/kg. After normalization, the AUClast/dose values at 10 mg/kg were significantly higher than that at 1 mg/kg in the skin (p<0.01), marginally different in the heart (p=0.06), and not significantly different in the liver, brain and kidney (all p values >0.34).

Example 6. Treatment of Sanfilippo A (San A) Patients with rhHNS

Direct CNS administration through, e.g., IT delivery can be used to effectively treat San A patients. This example illustrates a multicenter dose escalation study designed to evaluate the safety of up to 3 dose levels every other week (EOW) for a total of 40 weeks of rhHNS administered via an intrathecal drug delivery device (IDDD) to patients with San A. Various exemplary intrathecal drug delivery devices suitable for human treatment are depicted in FIGS. 32-35.

In one particular example, up to 16 patients will be enrolled:
Cohort 1: 4 patients (Lowest Dose—10 mg)
Cohort 2: 4 patients (Intermediate Dose—30 mg)
Cohort 3: 4 patients (Highest Dose—100 mg)
4 patients will be randomized to no treatment or use of device.

Sanfilippo Syndrome Type A patients generally demonstrate cognitive and neurodevelopmental impairment including delay of early development milestones (e.g., walking, speech, toilet training), intellectual deficit, hyperactivity, hearing loss, impaired speech development, deficits in motor skills, hyperactivity, aggressiveness and/or sleep disturbances, among others. All of the indications can be part of the criteria for trials. Patients are selected for the study based on inclusion of the following criteria: (1) 3-18 years of age; (2) intelligence quotient of less than 77 or a decline of 15 to 30 IQ points in past 3 years; (3) no CSF shut or poorly controlled seizure disorder and (4) no co-morbidities presenting anesthesia and/or surgical risks.

Safety of ascending doses of rhHNS administered by IT injection for 6 months in children with late infantile Sanfilippo Syndrome Type A is determined. Enrollment and escalation will be very slow to provide full assessments of patient safety. In addition, the clinical activity of rhHNS on gross motor function, and single and repeated-dose pharmacokinetics in serum and concentrations in cerebrospinal fluid (CSF) are assessed.

Objectives of the study will be to evaluate the safety and tolerability of ascending doses of rhHNS, as well as the safety, tolerability and long term patency of the IDDD. Additionally, the concentration of rhHNS after single and repeated IT doses in both CSF and blood, as well as the effects of rhHNS on CF biomarkers and urinary GAG. Further evaluation will include effects of rhHNS on clinical parameters such as physiological and neurocognitive assessments, neuro function and brain structure volumes. Additionally, the effects of treatment on daily living and relationships between biomarkers and symptoms can be evaluated.

Typically, treatment of Sanfilippo Syndrome Type A patients by IT delivery of rhHNS results in reduction of accumulation of GAG in various tissues (e.g., the nervous system, kidneys, gallbladder, and other organs).

While certain compounds, compositions and methods described herein have been described with specificity in accordance with certain embodiments, the following examples serve only to illustrate the compounds of the invention and are not intended to limit the same.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications, websites and other reference materials referenced herein to describe the background of the invention and to provide additional detail regarding its practice are hereby incorporated by reference.

The invention claimed is:

1. A method of treating Sanfilippo A Syndrome comprising a step of
administering intrathecally to a subject in need of treatment a formulation comprising a heparan N-sulfatase (HNS) protein at a concentration at or greater than 5 mg/ml, and no greater than 50 mM phosphate.

2. The method of claim 1, wherein the intrathecal administration of the formulation results in reduction of lysosomal storage in the brain target tissues, spinal cord neurons and peripheral target tissues.

3. The method of claim 1, wherein the intrathecal administration of the formulation results in reduced intensity, severity, or frequency, or delayed onset of at least one symptom or feature of the Sanfilippo A Syndrome.

4. The method of claim 1, wherein the intrathecal administration is used in conjunction with intravenous administration.

5. The method of claim 1, wherein the intrathecal administration is used in absence of concurrent immunosuppressive therapy.

* * * * *